(12) United States Patent
Kim et al.

(10) Patent No.: US 8,507,512 B2
(45) Date of Patent: Aug. 13, 2013

(54) SOLUBLE GUANYLATE CYCLASE ACTIVATORS

(75) Inventors: Ronald M. Kim, Summit, NJ (US); Emma R. Parmee, Scotch Plains, NJ (US); Christopher Joseph Sinz, Cranford, NJ (US); Olga A. Ziouzina, Teaneck, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 447 days.

(21) Appl. No.: 12/711,854

(22) Filed: Feb. 24, 2010

(65) Prior Publication Data

US 2010/0216764 A1 Aug. 26, 2010

Related U.S. Application Data

(60) Provisional application No. 61/208,648, filed on Feb. 26, 2009.

(51) Int. Cl.
| | | |
|---|---|---|
| A01N 43/54 | (2006.01) |
| A01N 43/40 | (2006.01) |
| A61K 31/505 | (2006.01) |
| A61K 31/44 | (2006.01) |
| C07D 239/02 | (2006.01) |
| C07D 401/00 | (2006.01) |

(52) U.S. Cl.
USPC ......... 514/275; 514/341; 544/297; 546/275.4

(58) Field of Classification Search
USPC ............... 514/275, 341; 544/297; 546/275.4
See application file for complete search history.

(56) References Cited

U.S. PATENT DOCUMENTS

| | | | |
|---|---|---|---|
| 6,162,819 A | 12/2000 | Schindler et al. |
| 7,674,825 B2 | 3/2010 | Alonso-Alija et al. |
| 7,985,876 B2 | 7/2011 | Hahn et al. |
| 8,183,271 B2 | 5/2012 | Bartel et al. |
| 8,217,063 B2 | 7/2012 | Hahn et al. |
| 2001/0044445 A1 | 11/2001 | Bamaung et al. |
| 2008/0004301 A1 | 1/2008 | Tamaki et al. |
| 2010/0075964 A1 | 3/2010 | Busch et al. |
| 2010/0216764 A1 | 8/2010 | Kim et al. |
| 2010/0331295 A1 | 12/2010 | Busch et al. |
| 2011/0028493 A1 | 2/2011 | Matsunaga et al. |
| 2011/0118282 A1* | 5/2011 | Bittner et al. ............ 514/255.05 |

FOREIGN PATENT DOCUMENTS

| | | |
|---|---|---|
| CA | 2039770 | 8/1991 |
| DE | 19744026 | 4/1999 |
| DE | 19744027 | 4/1999 |
| EP | 0908456 | 4/1999 |
| WO | 00/27394 | 5/2000 |
| WO | WO 00/27394 | * 5/2000 |
| WO | 02/074753 | 9/2002 |
| WO | 03/031435 | 4/2003 |
| WO | 2004/047730 | 6/2004 |
| WO | 2004/092140 | 10/2004 |
| WO | 2006/134459 | 12/2006 |
| WO | 2006/134468 | 12/2006 |
| WO | 2007/002559 | 1/2007 |
| WO | 2008/045484 | 4/2008 |
| WO | 2009/032249 | 3/2009 |
| WO | 2009/068652 | 6/2009 |
| WO | 2009/071504 | 6/2009 |
| WO | 2009/123316 | 8/2009 |
| WO | 2010/015652 | 2/2010 |
| WO | 2010/015653 | 2/2010 |
| WO | 2012/058132 | 5/2012 |

OTHER PUBLICATIONS

PCT International Search Report in PCT/US2010/024853, mailed Aug. 18, 2010.
PCT International Preliminary Report on Patentability in PCT/US2010/024853, mailed Sept 9, 2011.
Office Action for U.S. Appl. No. 12/674,795, dated Apr. 12, 2012, cover page and p. 7.
Boerrigter et al., Handbook of Experim. Pharmacol. (2009), vol. 191, "Modulation of cGMP in Heart Failure:. . . ", pp. 485-506.
Ghofrani et al., Eur. Respiratory Rev. (2009). vol. 18, "Soluable guanylate cyclase stimulation:. . . ", pp. 35-41.
Frey et al., BMC Pharmacol., "BAY 58-2667, a soluble guanylate cyclase activator, . . . " (published Jul. 25, 2007) pp. 1-2.
Bayer AG Investor Conference Call (edited transcript), dated Oct. 24, 2012, pp. 1-19.

* cited by examiner

*Primary Examiner* — Erich A Leeser
(74) *Attorney, Agent, or Firm* — Carol S. Quagliato; Catherine D. Fitch

(57) ABSTRACT

This inventions relates to compounds having the structure Formula I

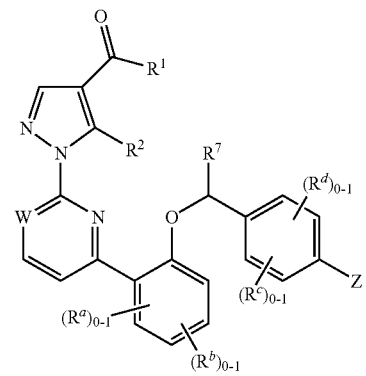

and pharmaceutically acceptable salts thereof which are soluble guanylate cyclase activators. The compounds are useful for treatment or prevention of cardiovascular diseases, endothelial dysfunction, diastolic dysfunction, atherosclerosis, hypertension, pulmonary hypertension, angina pectoris, thromboses, restenosis, myocardial infarction, strokes, cardiac insufficiency, pulmonary hypertonia, erectile dysfunction, asthma bronchiale, chronic kidney insufficiency, diabetes, or cirrhosis of the liver.

23 Claims, No Drawings

SOLUBLE GUANYLATE CYCLASE ACTIVATORS

CROSS REFERENCE TO RELATED APPLICATIONS

This application claims the benefit of U.S. Provisional Application No. 61/208,648, filed Feb. 26, 2009.

BACKGROUND OF THE INVENTION

Cyclic GMP (cGMP) is an important intracellular messenger which triggers a multitude of different effects via the modulation of cGMP-dependent protein kinases, phosphodiesterases and ion channels. Examples are the relaxation of smooth muscles, the inhibition of thrombocyte activation and the inhibition of the proliferation of smooth-muscle cells and of leukocyte adhesion. cGMP is produced by particulate and soluble guanylate cyclases as a response to a number of extracellular and intracellular stimuli. In the case of the particulate guanylate cyclases, stimulation is essentially effected by peptidic messengers, such as the atrial natriuretic peptide or the cerebral natriuretic peptide. The soluble guanylate cyclases ("sGC"), which are cytosolic heterodimeric heme proteins, in contrast, are essentially regulated by a family of low-molecular-weight factors which are formed enzymatically. The most important stimulant is nitrogen monoxide ("NO") or a closely related species. The function of other factors such as carbon monoxide or the hydroxyl radical is still largely unclear. The binding of NO to the heme with formation of a penta-coordinate heme-nitrosyl complex is proposed as the mechanism of the activation by NO. The associated release of the histidine which is bound in the basal state to the iron converts the enzyme into the active conformation.

Under pathologic conditions, the formation of guanylate-cyclase-activating factors can be reduced, or their degradation may be promoted owing to the increased occurrence of free radicals. The resulting reduced activation of the sGC leads, via a weakening of the respective cGMP-mediated cellular response, for example to an increase of the blood pressure, to platelet activation or to increased cell proliferation and cell adhesion. As a consequence, formation of endothelial dysfunction, atherosclerosis, hypertension, stable or unstable angina pectoris, thromboses, myocardial infarction, strokes or erectile dysfunction results. Pharmacological stimulation of sGC offers a possibility to normalize cGMP production and therefore makes possible the treatment and/or prevention of such disorders.

For the pharmacological stimulation of the sGC, use has been made of compounds whose activity is based on an intermediate NO release, for example organic nitrates.

The drawback of this treatment is the development of tolerance and a reduction of activity, and the higher dosage which is required because of this.

Various sGC stimulators which do not act via NO release were described by Vesely in a series of publications. However, the compounds, most of which are hormones, plant hormones, vitamins or natural compounds such as, for example, lizard poisons predominantly only have weak effects on the cGMP formation in cell lysates. D. L. Vesely, Eur. J. Clin. Invest., vol. 15, 1985, p. 258; D. L. Vesely, Biochem. Biophys. Res. Comm., vol. 88, 1979, p. 1244. A stimulation of heme-free guanylate cyclase by protoporphyrin IX was demonstrated by Ignarro et al., Adv. Pharmacol., vol. 26, 1994, p. 35. Pettibone et al., Eur. J. Pharmacol., vol. 116, 1985 p. 307, described an antihypertensive action of diphenyliodonium hexafluorophosphate and attributed this to a stimulation of sGC. According to Yu et al., Brit. J. Pharmacol, vol. 114, 1995, p. 1587, isoliquiritigenin, which has a relaxing action on isolated rat aortas, also activates sGC. Ko et al., Blood vol. 84, 1994, p. 4226, Yu et al., Biochem. J. vol. 306, 1995, p. 787, and Wu et al., Brit. J. Pharmacol. vol. 116, 1995, p. 1973, demonstrated a sGC-stimulating activity of 1-benzyl-3-(5-hydroxymethyl-2-furyl)indazole and demonstrated an antiproliferative and thrombocyte-inhibiting action. Pyrazoles and fused pyrazoles which exhibit a sGC-stimulating activity are described in European Patent Application No. 908,456 and German Patent Application No. 19,744,027.

A series of 2-sulfonylaminobenzoic acid N-arylamides, the N-aryl group of which carries a thio substituent, have been mentioned in the literature. These compounds in which the N-aryl group generally carries as further substituents groups which are readily oxidizable such as, for example, two hydroxy groups being in para position with respect to one another and which in this case can be regarded as hydroquinone derivatives, are auxiliaries for the preparation of photographic materials (see, for example, Chemical Abstracts 119, 105757; 120, 41858; 123, 70224; or 126, 257007). British patent publication No. 876,526 (Chemical Abstracts 56, 15432e) discloses 3,5-dichloro-2-methylsulfonylaminobenzoic acid N-(5-chloro-2-(4-chlorophenylmercapto)-phenyl)-amide which can be used for the protection of wool against moths.

It has now been found that the compounds of the present invention effect a strong activation of guanylate cyclase and are therefore useful for the therapy and prophylaxis of disorders which are associated with a low cGMP level.

SUMMARY OF THE INVENTION

The present invention relates to compounds of structural Formula I

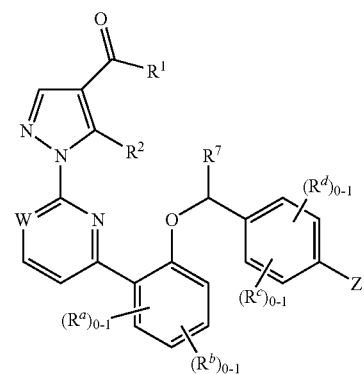

and the pharmaceutically acceptable salts thereof. The compounds activate soluble guanylate cyclase and are valuable pharmaceutically active compounds for the therapy and prophylaxis of diseases, for example for cardiovascular diseases such as hypertension, angina pectoris, diabetes, cardiac insufficiency, thromboses or atherosclerosis. The compounds of Formula I are capable of modulating the body's production of cyclic guanosine monophosphate ("cGMP") and are useful for the therapy and prophylaxis of diseases which are associated with a disturbed cGMP balance. The invention furthermore relates to processes for preparing compounds of Formula I, to their use for the therapy and prophylaxis of the abovementioned diseases and for preparing pharmaceuticals for this purpose, and to pharmaceutical preparations which comprise compounds of Formula I.

DETAILED DESCRIPTION OF THE INVENTION

The invention concerns compounds of Formula I which activate soluble guanylate cyclase (SGC):

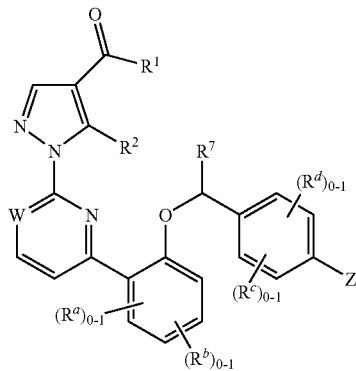

I and pharmaceutically acceptable salts thereof, wherein:
W is selected from the group consisting of CH and N;
Z is selected from the group consisting of:

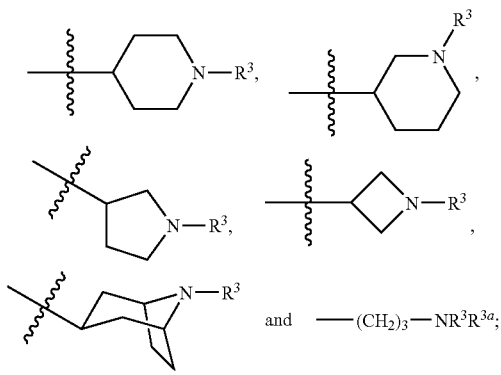

and —(CH$_2$)$_3$—NR$^3$R$^{3a}$;

R$^1$ is selected from the group consisting of —OH, —OC$_{1-6}$ alkyl and —N(R$^5$)$_2$;
R$^2$ is selected from the group consisting of —C$_{1-2}$ perfluoroalkyl and —NH$_2$;
R$^3$ is selected from the group consisting of:
1) —C$_{1-6}$ alkyl substituted with 1-3 of —F,
2) COR$^4$ and
3) —SO$_2$R$^6$;
R$^{3a}$ is selected from the group consisting of —H; —C$_{1-3}$ alkyl; C$_{3-6}$ cycloalkyl optionally mono- or di-substituted with one or more substituents selected from the group consisting of —CH$_3$ and —F; and —CH$_2$—C$_{3-6}$cycloalkyl optionally mono- or di-substituted with one or more substituents selected from the group consisting of —CH$_3$ and —F;
R$^4$ is selected from the group consisting of:
1) —H,
2) —C$_{1-3}$ alkyl,
3) —OC$_{1-3}$ alkyl
4) —C$_{3-6}$ cycloalkyl optionally mono- or di-substituted with one or more substituents selected from the group consisting of —CH$_3$ and —F,
5) —CH$_2$—C$_{3-6}$cycloalkyl optionally mono- or di-substituted with one or more substituents selected from the group consisting of —CH$_3$ and —F,
6) —OC$_{3-6}$ cycloalkyl optionally mono- or di-substituted with one or more substituents selected from the group consisting of —CH$_3$ and —F, and
7) —N(R$^5$)$_2$;
R$^5$ is independently selected at each occurrence from —H and —C$_{1-3}$ alkyl;
R$^6$ is selected from the group consisting of —C$_{1-3}$alkyl; —C$_{3-6}$cycloalkyl optionally mono- or di-substituted with one or more substituents selected from the group consisting of —CH$_3$ and —F; and —CH$_2$—C$_{3-6}$cycloalkyl optionally mono- or di-substituted with one or more substituents selected from the group consisting of —CH$_3$ and —F;
R$^7$ is selected from the group consisting of —H and —CH$_3$;
R$^a$ and R$^b$ are independently selected at each occurrence from —F, and —C$_{1-3}$ alkyl optionally substituted with 1-3 of —F; and
R$^c$ and R$^d$ are independently selected at each occurrence from —F, and —C$_{1-3}$ alkyl optionally substituted with 1-3 of —F.

In an embodiment of this invention are compounds of Formula I wherein W is CH, having structural Formula II and the pharmaceutically acceptable salts thereof:

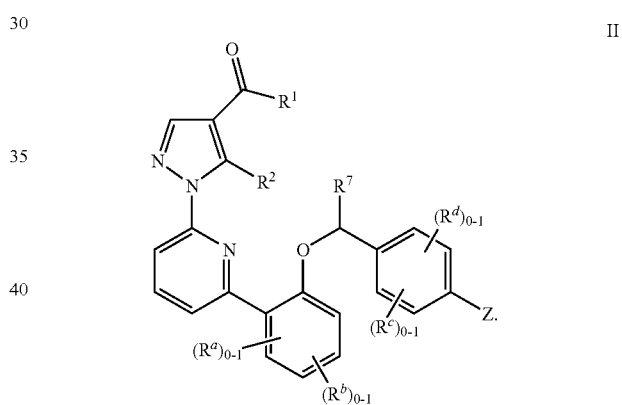

II

In another embodiment are compounds of Formula I wherein W is N, having structural Formula III and the pharmaceutically acceptable salts thereof:

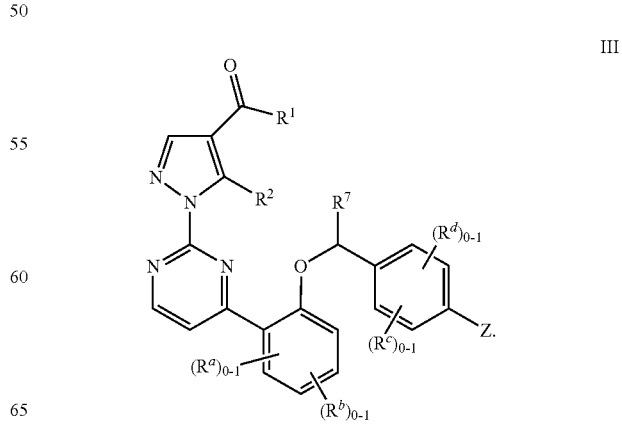

III

In another embodiment, referred to as Embodiment A herein, are compounds of Formula I, II, III or VI wherein Z is selected from the group consisting of:

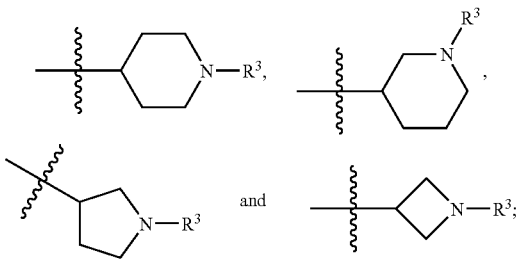

and more particularly it is selected from the group consisting of:

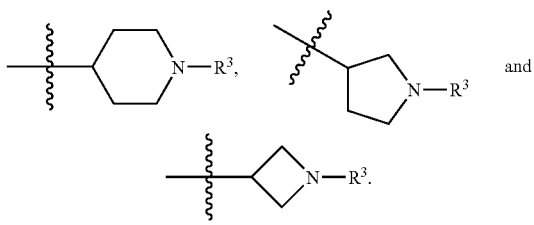

In a preferred embodiment are compounds of Formula I having structural Formula IV and the pharmaceutically acceptable salts thereof:

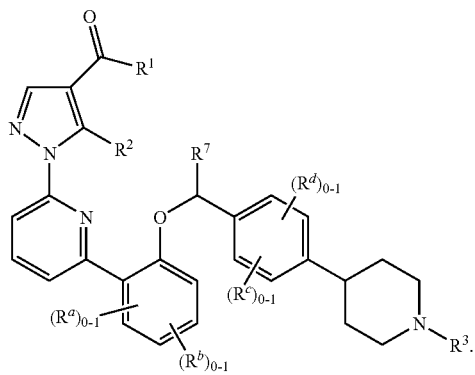

IV

In another embodiment of this invention are compounds of Formula I, II, III, IV or VI or Embodiment A wherein $R^1$ is —OH.

In another embodiment of this invention are compounds of Formula I, II, III, IV or VI or Embodiment A wherein $R^2$ is —$C_{1-2}$ perfluoroalkyl, and preferably it is —$CF_3$.

In another embodiment of this invention are compounds of Formula I, II, III, IV, V or VI or Embodiment A wherein $R^3$ is —$C_{1-4}$ alkyl substituted with 1-3 of —F, and particularly wherein the terminal carbon is —$CF_3$. Preferably $R^3$ is —$CH_2CF_3$.

In another embodiment of this invention are compounds of Formula I, II, III, IV, V or VI or Embodiment A wherein $R^3$ is —$COR^4$ and $R^4$ is selected from the group consisting of —$C_{1-3}$ alkyl, particularly —$CH_3$, —$CH_2CH_3$ and -i-propyl; —$OC_{1-3}$ alkyl, particularly —$OCH_3$; —$OCH_2CH_3$ and —O-i-propyl; —$C_{3-4}$ cycloalkyl optionally mono- or di-substituted with one or more substituents selected from the group consisting of —$CH_3$ and —F; and —$N(R^5)_2$ wherein $R^5$ is independently selected each occurrence from —H, —$CH_3$ and —$CH_2CH_3$.

In another embodiment of this invention are compounds of Formula I, II, III, IV, V or VI or Embodiment A wherein $R^3$ is —$SO_2R^6$ and $R^6$ is selected from the group consisting of —$C_{1-3}$ alkyl, particularly —$CH_3$, —$CH_2CH_3$ and i-propyl; and cyclopropyl.

In another embodiment of this invention are compounds of Formula I, II, III or VI wherein $R^{3a}$ is selected from the group consisting of —H, —$CH_3$ and —$CH_2$-cyclopropyl.

In another embodiment of this invention are compounds of Formula I, II, III, IV or VI or Embodiment A wherein $R^7$ is —H.

In a further embodiment of this invention, referred to herein as Embodiment B, are compounds of Formula I, II, III, IV or VI or Embodiment A and pharmaceutically acceptable salts thereof wherein:

$R^1$ is —OH;
$R^2$ is —$C_{1-2}$ perfluoroalkyl, and preferably it is —$CF_3$;
$R^3$ is selected from the group consisting of:
(a) —$C_{1-4}$ alkyl substituted with 1-3 of —F, and preferably wherein the terminal carbon is —$CF_3$, and most preferably wherein $R^3$ is —$CH_2CF_3$;
(b) —$COR^4$ wherein $R^4$ is selected from the group consisting of —$C_{1-3}$ alkyl, particularly —$CH_3$, —$CH_2CH_3$ and i-propyl; —$OC_{1-3}$ alkyl, particularly —$OCH_3$, —$OCH_2CH_3$ and —O-i-propyl; —$C_{3-4}$ cycloalkyl optionally mono- or di-substituted with one or more substituents selected from the group consisting of —$CH_3$ and —F; and —$N(R^5)_2$ wherein $R^5$ is independently selected each occurrence from —H, —$CH_3$ and —$CH_2CH_3$; and
(c) —$SO_2R^6$ wherein $R^6$ is selected from the group consisting of —$C_{1-3}$ alkyl, particularly —$CH_3$, —$CH_2CH_3$ and i-propyl; and cyclopropyl;
$R^{3a}$ is selected from the group consisting of —H, —$CH_3$ and —$CH_2$-cyclopropyl (except that $R^{3a}$ is
not present in compounds of Formula IV or Embodiment A);
$R^7$ is —H;
$R^a$ and $R^b$ are independently selected at each occurrence from —F, —Cl and —$C_{1-3}$ alkyl optionally substituted with 1-3 of —F; and
$R^c$ and $R^d$ are independently selected at each occurrence from —F, —Cl and —$C_{1-3}$ alkyl optionally substituted with 1-3 of —F.

In another embodiment of this invention are compounds of Formula I having structural Formula V and the pharmaceutically acceptable salts thereof:

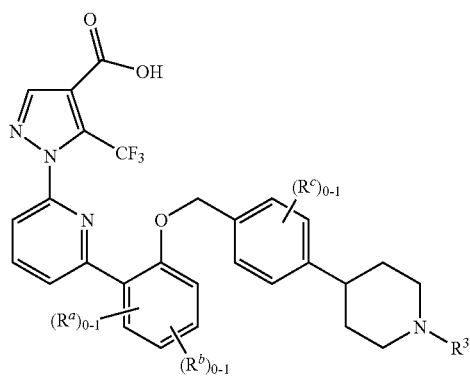

V wherein $R^3$ is selected from the group consisting of: —$C_{1-3}$ alkyl substituted with 1-3 of —F; —CO—$C_{1-3}$ alkyl; —CO—$C_{3-4}$ cycloalkyl optionally mono- or di-substituted with one or more substituents selected from the group consisting of —$CH_3$ and —F; and —$COOC_{1-3}$ alkyl.

In another embodiment of this invention, referred to herein as Embodiment C, are compounds of Formula I, II, III, IV or V or Embodiment A or B and the pharmaceutically acceptable salts thereof, wherein the substituents $R^a$, $R^b$, $R^c$ and $R^d$ are at the positions on the rings as shown in Formula VIa. That is, the substituents $R^a$ and $R^c$ are each optionally present at the fixed positions shown in Formula VIa and the substituents $R^b$ and $R^d$ are each optionally present on any available carbon in the ring to which each is attached, as depicted in Formula VIa. With regard to $R^a$ and $R^b$, preferably $R^b$, when present, is bonded to one of the ring carbons denoted with an asterisk (C*) or double asterisk (C**), and more particularly: (a) $R^a$ and $R^b$ are both absent, or (b) $R^a$ is absent and $R^b$ is bonded to C* or C**, or (c) $R^a$ is present and $R^b$ is either absent or bonded to C*. With regard to the $R^c$ and $R^d$ substituents, preferably $R^d$ is optionally present only when $R^c$ is present, or more particularly: (a) $R^c$ and $R^d$ are both absent, or (b) $R^c$ is present and $R^d$ is either absent or present at another available position on the ring and more preferably $R^d$ is absent. When an $R^a$, $R^b$, $R^c$ or $R^d$ substituent is present, the substituent replaces the hydrogen that would otherwise be bonded to the relevant ring carbon.

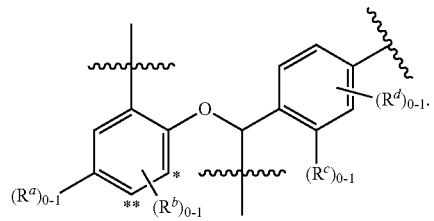

VIa

An example of this embodiment with respect to Formula I is shown as structural Formula VI:

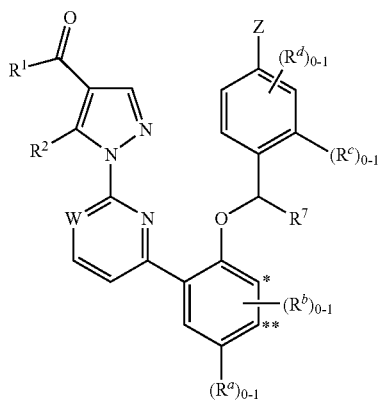

VI and the pharmaceutically acceptable salts thereof.

As used herein except if noted otherwise, "alkyl" is intended to include both branched- and straight-chain saturated aliphatic hydrocarbon groups having the specified number of carbon atoms. Commonly used abbreviations for alkyl groups are used throughout the specification. For example the term "$C_{1-6}$ alkyl" (or "$C_1$-$C_6$ alkyl"), means linear or branched chain alkyl groups, including all isomers, having the specified number of carbon atoms and includes all of the hexyl and pentyl isomers as well as n-, iso-, sec- and tert-butyl (n-butyl, s-butyl, i-butyl, t-butyl; Bu=butyl), n- and i-propyl (Pr=propyl), ethyl (Et) and methyl (Me).

"Cycloalkyl" is a cyclized alkyl ring having the indicated number of carbon atoms. Examples of cycloalkyl include cyclopropyl, cyclobutyl, cyclopentyl and cyclohexyl. The cycloalkyl ring may be substituted on any available carbon which results in the creation of a stable structure, including the ring carbon which serves as the point of attachment to the rest of the molecule.

The phrase "optionally mono- or di-substituted with one or more substituents" means that each carbon and heteroatom (when present) available for substitution in the given moiety may be independently unsubstituted or mono- or di-substituted with one or two substituents that are the same or different at each occurrence and which result in the creation of a stable structure as is understood to be reasonable by one skilled in the art, provided that the total number of substituents on the optionally substituted moiety is zero, one or two.

In some instances the number of substituents which may be optionally present on a moiety is specified, for example but not limited to, 1 to 3 of —F (fluoro). For example, an alkyl group that can be optionally substituted with 1-3 of —F includes, but is not limited to, —$CH_3$, —$CH_2F$, —$CHF_2$, —$CF_3$, —$CH_2CH_3$, —$CH_2$—$CH_2F$, —$CH_2$—$CHF_2$, —$CHF$—$CH_2F$, —$CH_2CF_3$, —$CHF$—$CHF_2$, —$(CH_2)_2CH_3$, —$CH(CF_3)$—$CH_3$, —$(CH_2)_3$—$CF_3$, —$(CH_2)_2CH(CF_3)$$CH_3$, and —$(CH_2)_5$—$CF_3$, as appropriate for the defined number of carbon atoms for the given alkyl group.

Unless expressly depicted or described otherwise (as for example in Formula VI and VIa), each of substituents $R^a$, $R^b$, $R^c$ and $R^d$, when present, are permitted on any available carbon atom in the ring to which each is attached when depicted with a "floating" bond, e.g.,

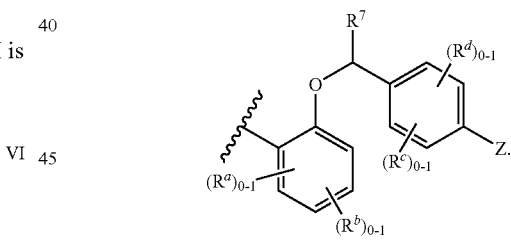

The present invention encompasses all stereoisomeric forms of the compounds of Formula I. Centers of asymmetry that are present in the compounds of Formula I can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

Reference to the compounds of this invention as those of a specific formula or embodiment, e.g., Formula I (which includes the compounds of Formulas II-VI and embodiments thereof) or any other generic structural formula or specific compound described or claimed herein, is intended to encompass the specific compound or compounds falling within the scope of the formula or embodiment, including salts thereof, particularly pharmaceutically acceptable salts, solvates of such compounds and solvated salt forms thereof, where such forms are possible unless specified otherwise. For example, an embodiment wherein $R^1$ is —OH includes compounds having the resulting free acid moiety —COOH as well as the pharmaceutically acceptable salts that can be formed from the resulting —COOH moiety.

When the compounds of Formula I contain one or more acidic or basic groups the invention also includes the corresponding physiologically or toxicologically acceptable salts, in particular the pharmaceutically utilizable salts. Thus, the compounds of Formula I which contain acidic groups can be used according to the invention, for example, as alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids. Compounds of Formula I which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of physiologically (i.e., pharmaceutically) acceptable salts.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with un-solvated and anhydrous forms.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

The compounds of Formula I according to the invention effect an increase of the cGMP concentration via the activation of soluble guanylate cyclase (sGC), and they are therefore useful agents for the therapy and prophylaxis of disorders which are associated with a low or decreased cGMP level or which are caused thereby, or for whose therapy or prophylaxis an increase of the present cGMP level is desired. Accordingly, an object of the instant invention is to provide a method for activating soluble guanylate cyclase in a patient in need thereof, comprising administering a compound of Formula I to the patient in an amount effective to activate soluble guanylate cyclase in the patient. An additional object is to provide a method for increasing the cGMP level in a patient in need thereof, comprising administering a compound of Formula I to the patient in an effective amount for increasing the patient's cGMP level. The activation of sGC by the compounds of Formula I can be examined, for example, in the activity assays described below.

Disorders and pathological conditions which are associated with a low cGMP level or for which an increase of the cGMP level is desired are, for example, cardiovascular diseases, such as endothelial dysfunction, diastolic dysfunction, atherosclerosis, hypertension, pulmonary hypertension, stable and unstable angina pectoris, thromboses, restenosis, myocardial infarction, stroke (ischemic and hemorrhagic), cardiac insufficiency (including acute and congestive heart failure) and/or pulmonary hypertonia, or, for example, erectile dysfunction, asthma bronchiale, chronic kidney insufficiency and/or diabetes. Compounds of Formula I can additionally be used in the therapy of cirrhosis of the liver and also for improving a restricted memory performance or ability to learn. Accordingly, the instant invention provides a method for treating or preventing the above-described medical conditions comprising administering a therapeutically or prophylactically effective, as appropriate, amount of a compound of Formula I to a patient in need of such treatment or prevention.

In general, compounds that are sGC activators can be identified as those compounds which have an Inflection Point/maximum fold induction over DMSO control in the sGC Cell-Based Assay of less than or equal to about 10 µM/equal to or greater than about 4-fold; preferably less than or equal to about 200 nM/equal to or greater than about 20-fold; and most preferably less than or equal to about 100 nM/equal to or greater than about 50-fold, in the Cell-based sGC Functional Assay described below.

The dosage amount of the compound to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula I. A consideration of these factors is well within the purview of the ordinarily skilled clinician for the purpose of determining the therapeutically effective or prophylactically effective dosage amount needed to prevent, counter, or arrest the progress of the condition. It is expected that the compound will be administered chronically on a daily basis for a length of time appropriate to treat or prevent the medical condition relevant to the patient, including a course of therapy lasting days, months, years or the life of the patient.

In general, a daily dose of approximately 0.001 to 100 mg/kg, preferably 0.001 to 30 mg/kg, in particular 0.001 to 10 mg/kg (in each case mg per kg of bodyweight) is appropriate for administration to an adult weighing approximately 75 kg in order to obtain the desired results. The daily dose is preferably administered in a single dose or, in particular when larger amounts are administered, can be divided into several, for example two, three or four individual doses, and may be, for example but not limited to, 0.1 mg, 0.25 mg, 0.5 mg, 0.75 mg, 1 mg, 1.25 mg, 2.5 mg, 5 mg, 10 mg, 20 mg, 40 mg, 50 mg, 75 mg, 100 mg, etc., on a daily basis. In some cases, depending on the individual response, it may be necessary to deviate upwards or downwards from the given daily dose.

The term "patient" includes animals, preferably mammals and especially humans, who use the instant active agents for the prevention or treatment of a medical condition. Administering of the drug to the patient includes both self-administration and administration to the patient by another person. The patient may be in need of treatment for an existing disease or medical condition, or may desire prophylactic treatment to prevent or reduce the risk of said disease or medical condition.

The term therapeutically effective amount is intended to mean that amount of a drug or pharmaceutical agent that will elicit the biological or medical response of a tissue, a system, animal or human that is being sought by a researcher, veterinarian, medical doctor or other clinician. A prophylactically effective amount is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. It is understood that a specific daily dosage amount can simultaneously be both a therapeutically effective amount, e.g., for treatment of hypertension, and a prophylactically effective amount, e.g., for prevention of myocardial infarction.

In the methods of treatment of this invention, the sGC activators may be administered via any suitable route of administration such as, for example, orally, parenterally, or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. Oral formulations are preferred, particularly solid oral dosage units such as pills, tablets or capsules.

Accordingly, this invention also provides pharmaceutical compositions comprised of a compound of Formula I and a pharmaceutically acceptable carrier. For oral use, the pharmaceutical compositions of this invention containing the active ingredient may be in forms such as pills, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients, which are suitable for the manufacture of tablets. These excipients may be for example, inert diluents, such as calcium carbonate, sodium carbonate, lactose, mannitol, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc.

Pharmaceutical compositions may also contain other customary additives, for example, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

Oral immediate-release and time-controlled release dosage forms may be employed, as well as enterically coated oral dosage forms. Tablets may be uncoated or they may be coated by known techniques for aesthetic purposes, to mask taste or for other reasons. Coatings can also be used to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an anti-oxidant such as ascorbic acid. Syrups and elixirs may be formulated with sweetening agents, for example glycerol, propylene glycol, sorbitol or sucrose.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier. The carrier is comprised of one or more pharmaceutically acceptable excipients. Furthermore, a therapeutically effective amount of a compound of this invention can be used for the preparation of a medicament useful for activating soluble guanylate cyclase, for normalizing a disturbed cGMP balance, or for treating or preventing any of the medical conditions described herein, in dosage amounts described herein.

The amount of active compound of Formula I and/or its pharmaceutically acceptable salts in the pharmaceutical composition may be, for example but not limited to, from 0.1 to 200 mg, preferably from 0.1 to 50 mg, per dose on a free acid/free base weight basis, but depending on the type of the pharmaceutical composition and potency of the active ingredient it could also be lower or higher. Pharmaceutical compositions usually comprise 0.5 to 90 percent by weight of the active compound on a free acid/free base weight basis.

The compounds of Formula I activate soluble guanylate cyclase. On account of this property, apart from use as pharmaceutically active compounds in human medicine and veterinary medicine, they can also be employed as a scientific tool or as aid for biochemical investigations in which such an effect on soluble guanylate cyclase is intended, and also for diagnostic purposes, for example in the in vitro diagnosis of cell samples or tissue samples. The compounds of Formula I can also be employed as intermediates for the preparation of other pharmaceutically active compounds.

One or more additional pharmacologically active agents may be administered in combination with a compound of Formula I. An additional active agent (or agents) is intended to mean a pharmaceutically active agent (or agents) different from the compound of Formula I. Generally, any suitable additional active agent or agents, including but not limited to anti-hypertensive agents, anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), angiotensin II receptor antagonists (e.g., losratan, valsartan, candesartan, olmesartan, telmesartan) neutral endopeptidase inhibitors (e.g., thiorphan and phosphoramidon), aldosterone antagonists, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891, SQ 34017, aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635), endothelin receptor antagonists, vasodilators, calcium channel blockers (e.g., amlodipine, nifedipine, verapamil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, peripheral vasodilators (e.g. hydralazine), lipid lowering agents (e.g., simvastatin, lovastatin, pravastatin, atorvastatin rosuvastatin, ezetimibe); niacin in immediate-release or controlled release forms, and particularly in niacin in combination with a DP antagonist such as laropiprant (TREDAPTIVE®) and/or with an HMG-CoA reductase inhibitor; niacin receptor agonists such as acipimox and acifran, as well as niacin receptor partial agonists; metabolic altering agents including insulin sensitizing agents and related compounds (e.g., muraglitazar, glipizide, metformin, rosiglitazone); or with other drugs beneficial for the prevention or the treatment of the above-mentioned diseases including nitroprusside and diazoxide.

The compounds of the present invention can be prepared according to the procedures of the following Schemes using appropriate materials and are further exemplified by the specific Examples which follow. Moreover, by utilizing the procedures described herein, one of ordinary skill in the art can readily prepare additional compounds of the present invention claimed herein. In the general schemes provided below, the variables (e.g., $R^1$, $R^2$, $R^3$, $R^4$, $R^5$, $R^6$, $R^7$, W, $R^a$, $R^b$, $R^e$, $R^d$ and Z) are defined as in Formula I, taking into account the specific examples that are provided.

Throughout the synthetic schemes, abbreviations are used with the following meanings unless otherwise indicated: Ac=acetate; aq, aq.=aqueous; Ar=aryl; BOC, Boc=t-butyloxycarbonyl; Bn=benzyl; Bu=butyl, t-Bu=tert-butyl; BuLi, n-BuLi=n-butyllithium; CBZ, Cbz=Benzyloxycarbonyl;

conc, conc.=concentrated; cPr=cyclopropyl; DAST=(diethylamino)sulfur trifluoride; dba=dibenzylideneacetone; DCM=dichloromethane; DIAD=diisopropylazodicarboxylate; DIBAL, DIBAL-H=diisobutylaluminum hydride; DIEA=diisopropylethylamine; DMAC, DMA=dimethylacetamide; DME=1,2-dimethoxyethane; DMAP=4-dimethylaminopyridine; DMF=N,N-dimethylformamide; DMSO=dimethylsulfoxide; eq.=equivalent(s); ESI=electrospray ionization; Et=ethyl; EtOAc=ethyl acetate; EtOH=ethanol; h, hr=hour; HOAc=acetic acid; HPLC=High pressure liquid chromatography; IPA, i-PrOH=isopropanol; iPr=isopropyl; LAH=Lithium aluminum hydride; LCMS=liquid chromatography–mass spectroscopy; LHMDS=lithium bis(trimethylsilyl)amide; Me=methyl; MeOH=methanol; min, min.=minute; NMP=N-methylpyrrolidinone; NMR=nuclear magnetic resonance; OMs, mesyl=methanesulfonyl; Pd$_2$ dba$_3$=tris(dibenzylidineacetone)dipalladium; Pd/C=palladium on activated carbon; Ph=phenyl; Pr=propyl; Py=pyridyl; RT, rt=room temperature; sat.=saturated; TBAI=tetrabutylammonium iodide; TFA=trifluoroacetic acid; THF=tetrahydrofuran; TLC=thin layer chromatography; prep TLC=preparative thin layer chromatography; Tosyl=toluenesulfonyl; triflate, OTf=trifluoromethanesulfonate; triflic=trifluoromethanesulfonic; Xantphos=4,5-bis(diphenylphosphino)-9,9-dimethylxanthene.

Pyrazole esters may be readily prepared by those skilled in the art. One such procedure is shown in Scheme 1, involving reaction of a pyridyl hydrazine 1 with β-keto ester derivative 2 in the presence of a base such as Et$_3$N in a solvent such as acetonitrile at elevated temperatures to provide pyrazole 3 (*J. Comb. Chem.* 2003, 5, 465; *Heterocycles* 1992, 34, 791).

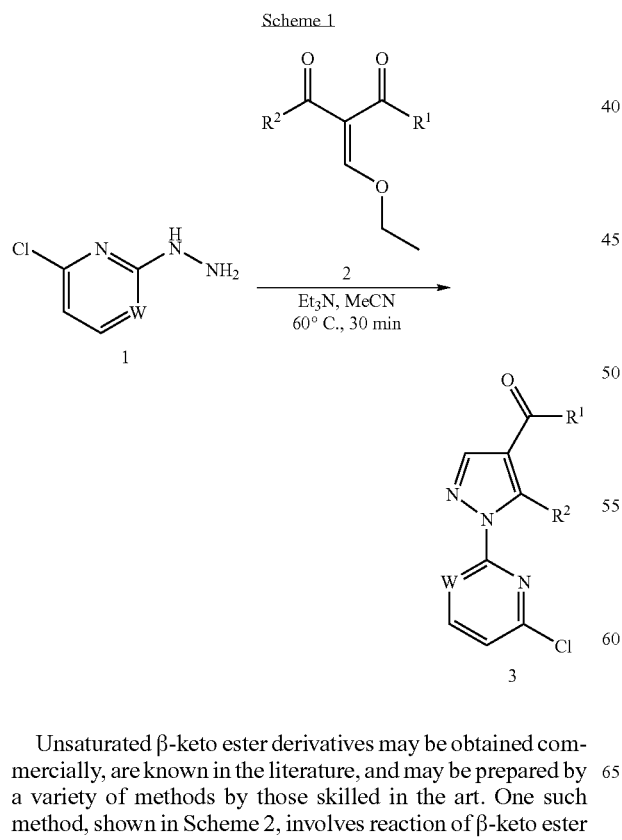

Unsaturated β-keto ester derivatives may be obtained commercially, are known in the literature, and may be prepared by a variety of methods by those skilled in the art. One such method, shown in Scheme 2, involves reaction of β-keto ester 4 with acetic anhydride and triethylorthoformate at elevated temperature to provide enol ether 5. Enol ethers such as 5 may be converted to the corresponding pyrazole ester 6 (wherein R$^1$=OEt) by the same method as that described in Scheme 1.

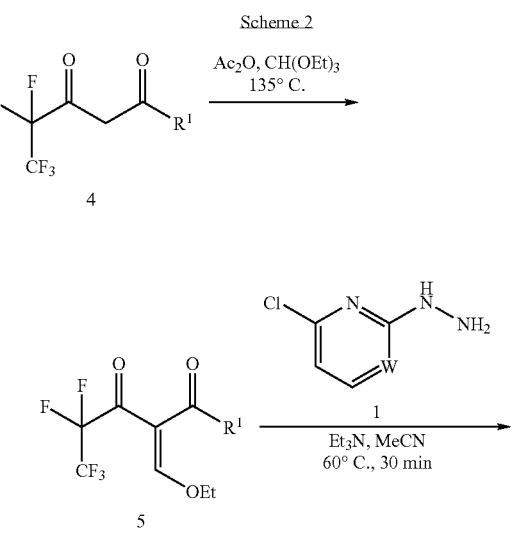

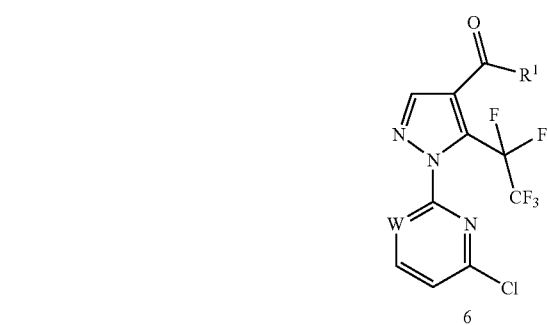

Where R$^2$=NH$_2$, such pyrazole esters may be obtained commercially, are known in the literature, and may be prepared by a variety of methods by those skilled in the art. One such method, shown in Scheme 3, involving reaction of pyridyl hydrazine 1 with commercially available α-cyano ester derivative 7 in a solvent such as ethanol at elevated temperature provides pyrazole esters such as 8.

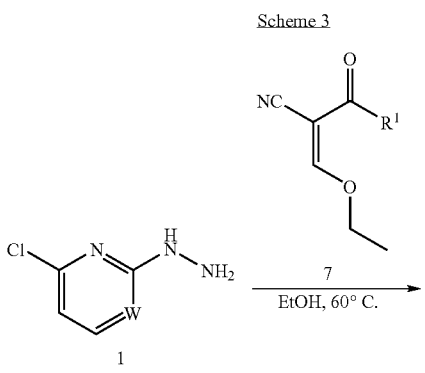

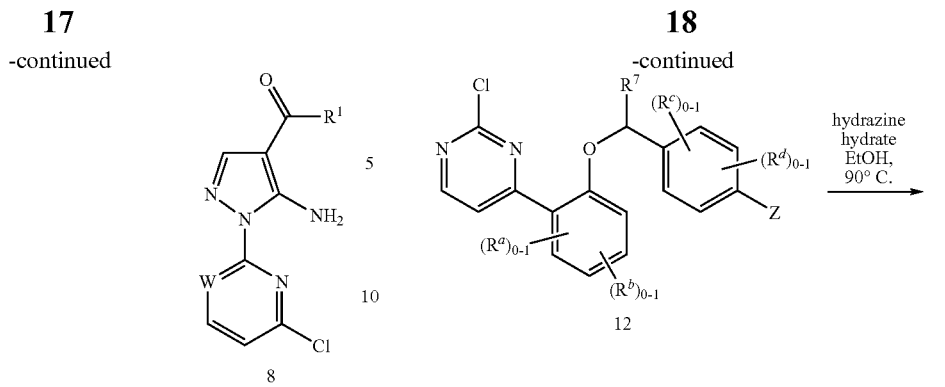

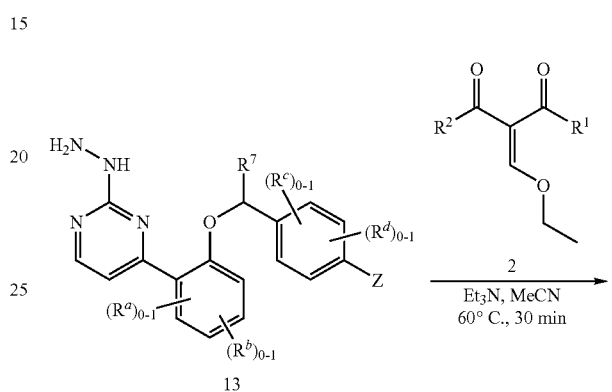

Pyrimidine containing analogs may be synthesized according to the route depicted in Scheme 4, beginning with cross coupling of boronic acid 9 with 2,4-dichloropyrimidine in the presence of a catalyst such as PdCl$_2$(PPh$_3$)$_2$ and a base such as sodium carbonate in a mixed solvent system such as acetonitrile and water at elevated temperature to provide phenol derivative 10 (*Heterocycles*, 2003, 60, 1891). The phenol may then be alkylated with benzylic alcohol derivative 11 (vide infra) in the presence of triphenylphosphine, an azodicarboxylate such as diisopropyl azodicarboxylate in a solvent such as DCM at room temperature to provide ether derivative 12 (*Synthesis* 1981, p. 1). Chloropyrimidine 12 may also be converted to the corresponding pyrimidinyl hydrazine 13 by reaction with hydrazine hydrate in a solvent such as ethanol at elevated temperatures. Condensation of hydrazine 13 with β-keto ester derivative 2 as described in Scheme 1 provides pyrazole 14.

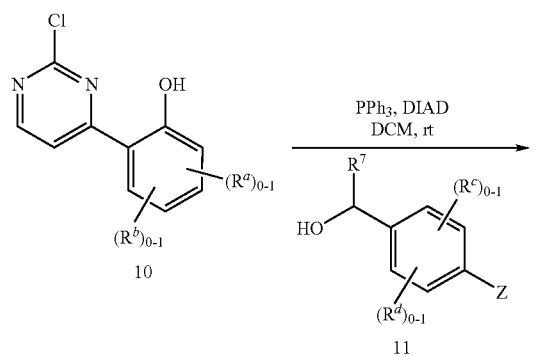

Appropriately substituted chloropyridines can be modified via cross coupling reactions. One such example is shown in Scheme 5, wherein chloropyridine 15 is reacted with 2-hydroxyphenyl boronic acid derivative 9 in the presence of a metal catalyst such as dichlorobis(triphenylphosphine)palladium(II), a base such as sodium carbonate, and a mixture of solvents such as acetonitrile and water, often at elevated temperature. Alternatively, 2-methoxyphenylboronic acid derivative 17 may be used, under similar reaction conditions, as shown in Scheme 6. Reaction of compound 18 with a Lewis acid such as boron tribromide in a solvent such as DCM at low temperature or, where appropriate, at ambient temperature, provides phenol derivative 16.

Scheme 5

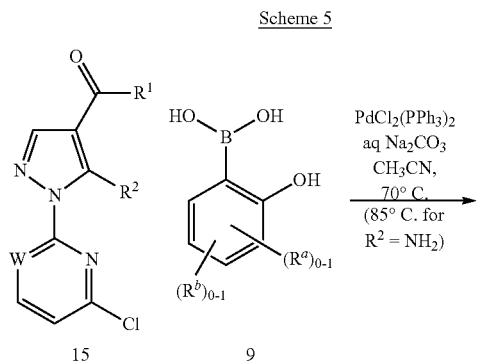

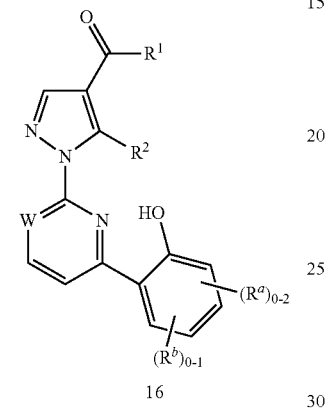

Scheme 6

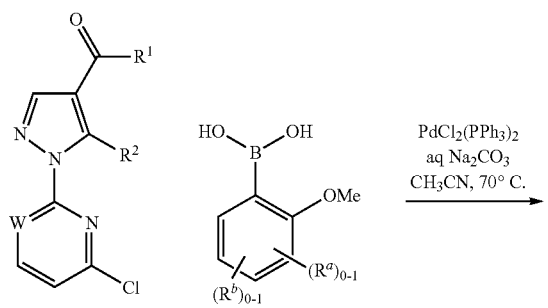

11 (vide infra) in the presence of triphenylphosphine, an azodicarboxylate such as diisopropyl azodicarboxylate in a solvent such as DCM at room temperature to provide ether derivative 19

Scheme 7

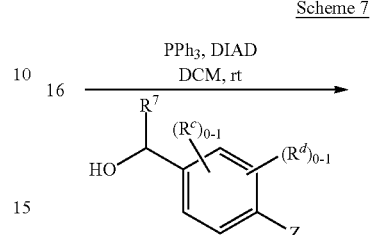

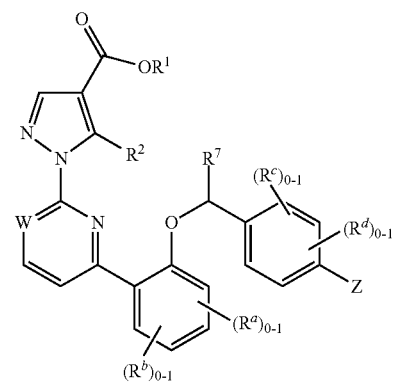

Scheme 8 depicts another protocol, in which phenol derivative 16 may be alkylated with a substituted benzylic halide such as bromide 20 in a polar solvent such as DMF in the presence of an inorganic base such cesium carbonate to provide aryl bromide 21. This aryl bromide may then be further functionalized to introduce the Z substituent (vide infra). Alternatively, Mitsunobu coupling of phenol 16 with an appropriately substituted benzylic alcohol 22 according to the conditions described above, provides aryl bromide 21.

Scheme 8

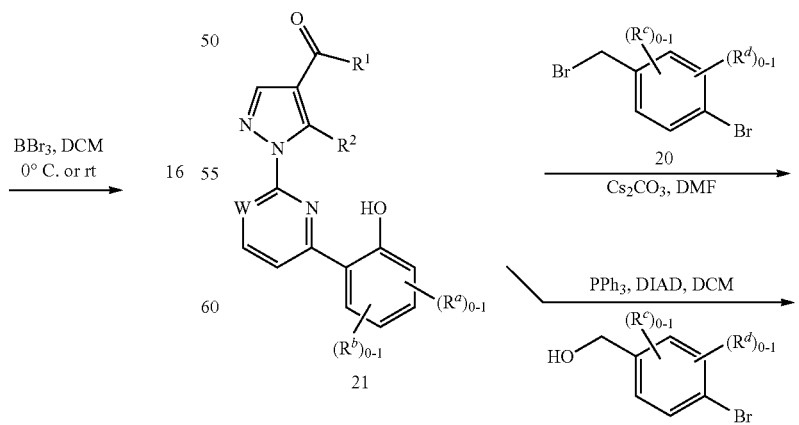

As shown in Scheme 7, phenol derivative 16 can be reacted with an appropriately substituted benzylic alcohol derivative

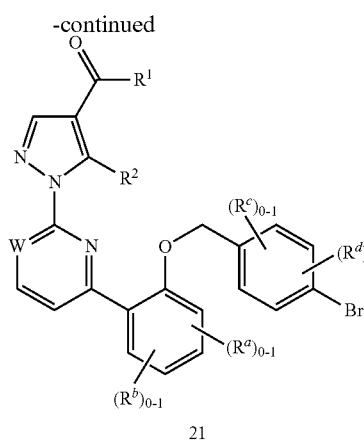

As depicted in Scheme 9, if desired a difluoromethyl $R^a/R^b$ substituent may be introduced by reaction of a suitably substituted aldehyde such as 23 with DAST, in the presence of a catalytic quantity of ethanol, in a solvent such as THF to provide difluoromethyl analog 24.

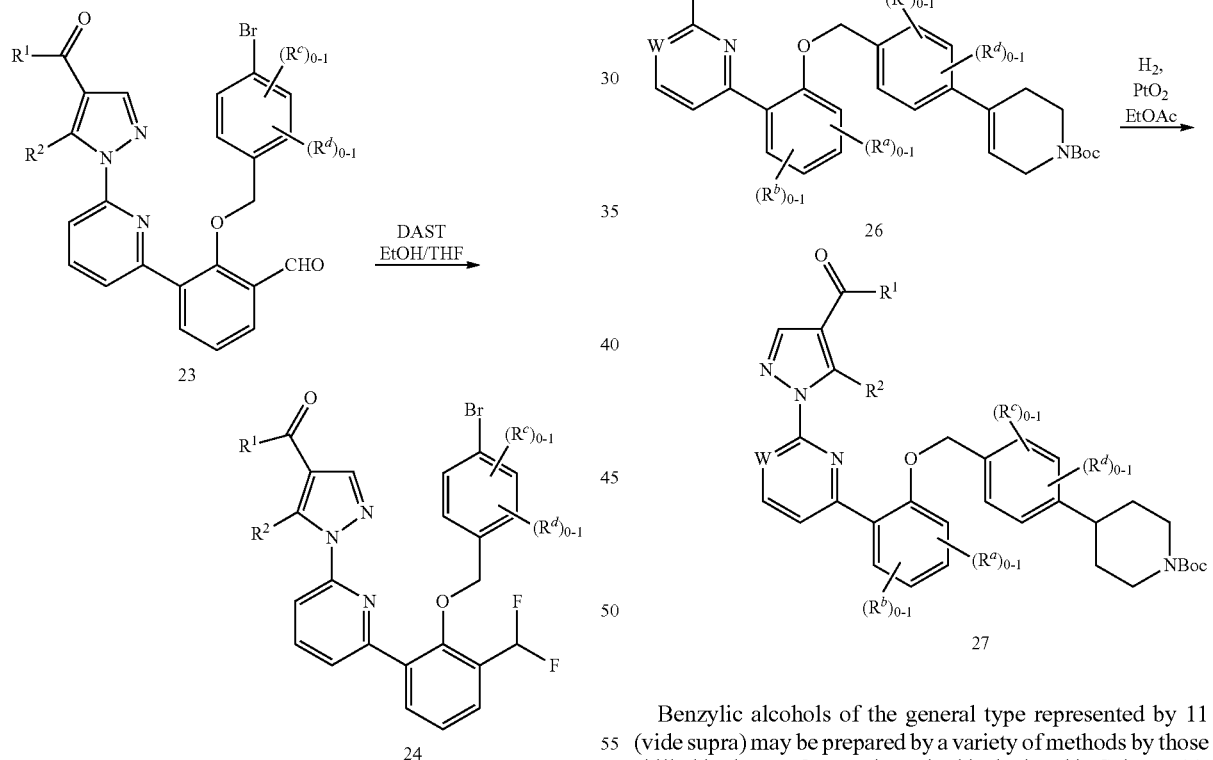

Introduction of the Z substituent to aryl bromide containing compounds such as 21 may be accomplished using cross coupling conditions, as is well known to those skilled in the art. As depicted in Scheme 10, reaction of aryl bromide 21 with boronate ester 25 (*Tetrahedron Lett,* 2000, 41, 3705-3708) using a metal catalyst such as dichlorobis(triphenylphosphine)palladium (II), a base such as sodium carbonate, and a mixture of solvents such as acetonitrile and water at elevated temperature provides tetrahydropyridine derivative 26. Reduction of the tetrahydropyridine to generate piperidine 27 may be accomplished under hydrogenation conditions, using a catalyst such as platinum (IV) oxide in a solvent such as EtOAc, under a hydrogen atmosphere.

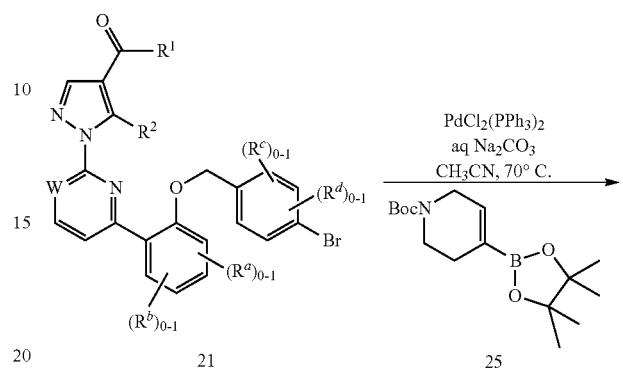

Benzylic alcohols of the general type represented by 11 (vide supra) may be prepared by a variety of methods by those skilled in the art. One such method is depicted in Scheme 11. Enol triflates such as 29, where n=0 or 1, are known in the literature (*Heterocycles,* 1996, 43, 2131-2138) and may be readily prepared. Cross coupling of phenyl boronic acid derivate 28 and enol triflate 29 in the presence of a catalyst such as $PdCl_2(PPh_3)_2$ and a base such as sodium carbonate in the mixed solvent system such as acetonitrile and water at elevated temperature provides olefin derivative 30. Reduction of the olefin by hydrogenation using a metal catalyst such as platinum oxide in a solvent such as ethyl acetate under a hydrogen atmosphere provides piperidine and pyrrolidine derivatives such as 31. Treatment with a reducing agent such as DIBAL-H in a solvent such as THF at low temperature provides benzylic alcohols such as 32.

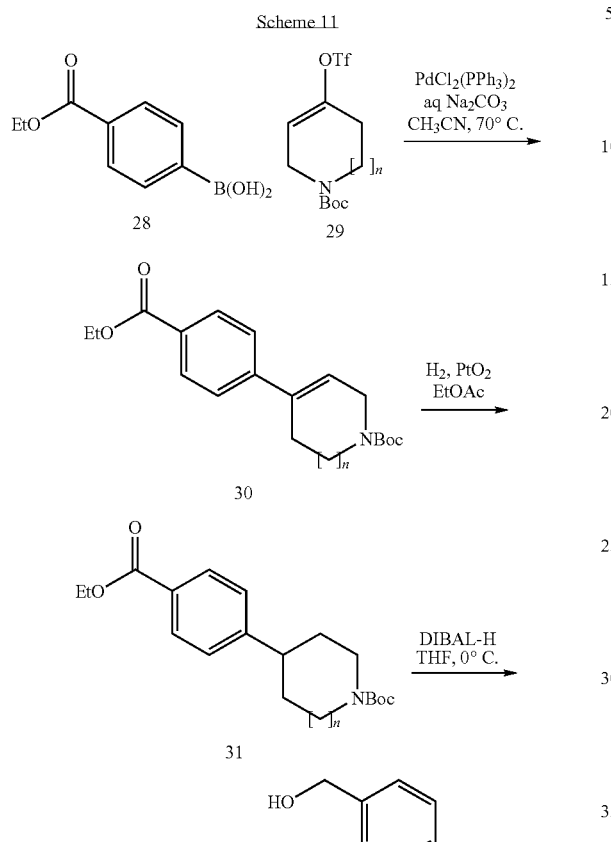

In instances where $R^c/R^d$ substituents are desired, substituted phenylboronic acids and their corresponding boronate ester derivatives are commercially available, or may be prepared by a variety of methods. One such method is shown in Scheme 12. Conversion of benzoic acid derivative 33 to the corresponding boronate ester 34 may be accomplished by reaction with bis(pinacolato)diboron using a catalyst such as Pd(dppf)Cl$_2$ in the presence of a base such as potassium acetate and an appropriate solvent such as DMSO at elevated temperatures (*J. Org Chem.* 1995, 60, 7508).

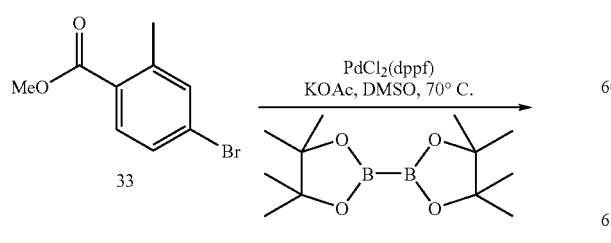

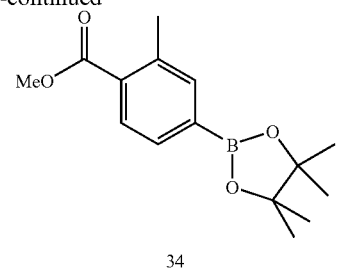

Alternatively, benzylic alcohols such as 39 may be generated from appropriately substituted aryl triflate or aryl bromide derivatives. One such example, depicted in Scheme 13, involves conversion of phenol derivative 35 to the corresponding triflate 36, using a trifluoromethanesulfonic anhydride, and a base such as pyridine in a solvent such as DCM. Metal catalyzed cross coupling with boronate ester 25 (*Tetrahedron Lett,* 2000, 41, 3705-3708) according to conditions described in Scheme 11 (vide supra), provides tetrahydropyridine derivative 37. A series of standard functional group manipulations, as described in Scheme 11 (vide supra) provides the benzylic alcohol 39.

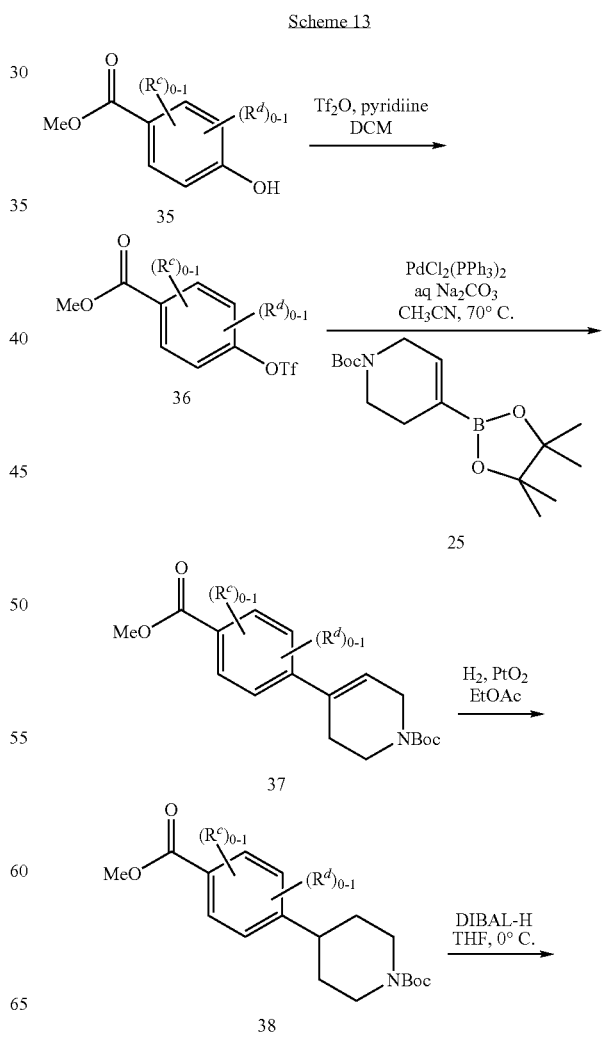

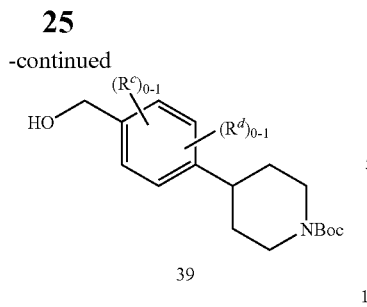

39

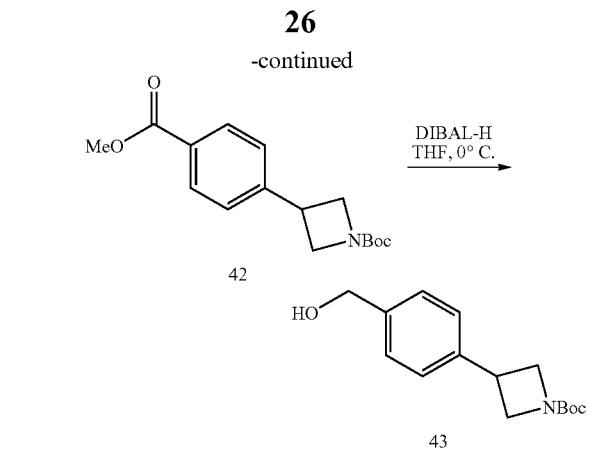

Azetidine analogs may be synthesized by cross-coupling of iodoarene derivative 40 with the alkyl zinc reagent 41 (*Synlett*, 1998, 379-380), itself generated by treatment of the corresponding iodoazetidine derivative with zinc metal, trimethylsilyl chloride and 1,2-dibromoethane at elevated temperature in THF. Cross couplings of this type to generate aryl azetidines such as 42 may be accomplished using a metal catalyst such as tris(dibenzylidene)acetone palladium (0) and tri-(2-furyl)phosphine as a ligand, in THF as solvent at elevated temperature. Reduction of the ester moiety with a hydride-reducing agent such as DIBAL-H in a solvent such as THF at reduced temperature provides benzylic alcohol 43.

Scheme 14

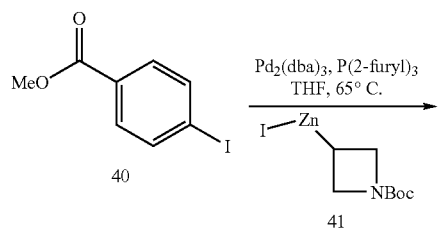

If desired, a pyrazole acid compound bearing a substituent $R^7$ may be synthesized, as depicted in Scheme 15. Metal catalyzed cross coupling of acetophenone derivative 44 with boronate ester 25 according to conditions described in Scheme 10 (vide supra) provides tetrahydropyridine 45. Reduction to piperidine 46 may be accomplished under hydrogenation conditions, using a catalyst such as platinum (IV) oxide in a solvent such as EtOAc under a hydrogen atmosphere. Deprotection of the N-Boc piperidine via reaction with TFA in DCM at ambient temperature allows for introduction of the $R^3$ substituent. Thus, reaction with a selected acylating agent such as cyclopropanecarbonyl chloride in the presence of a base such as DIEA in an aprotic solvent such as DCM provides amide 47. Reduction of the ketone moiety may be accomplished by reaction with a hydride reducing agent such as sodium borohydride in a protic solvent such as ethanol, at ambient temperature. Alkylation of phenol 16 with the substituted benzylic alcohol 48 may be accomplished under Mitsunobu conditions, as described in Scheme 7 (vide supra).

Scheme 15

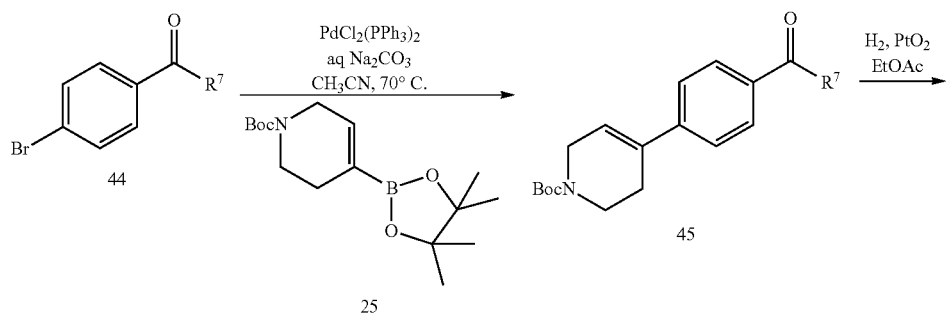

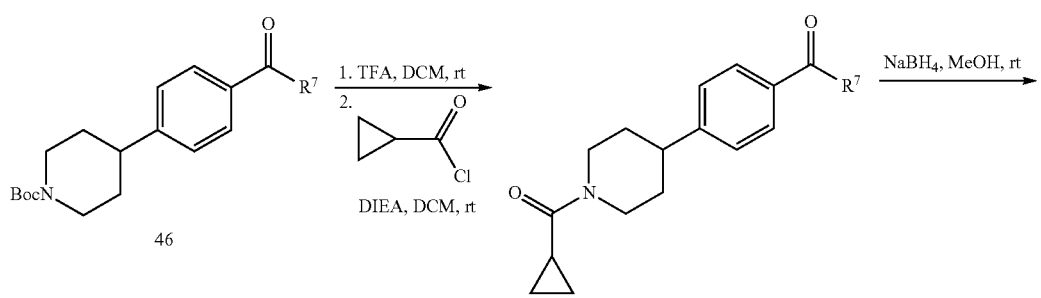

-continued

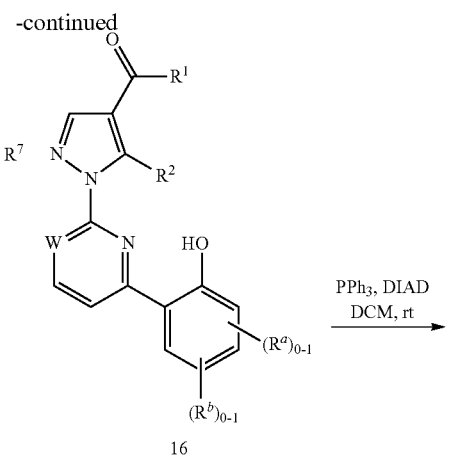

48

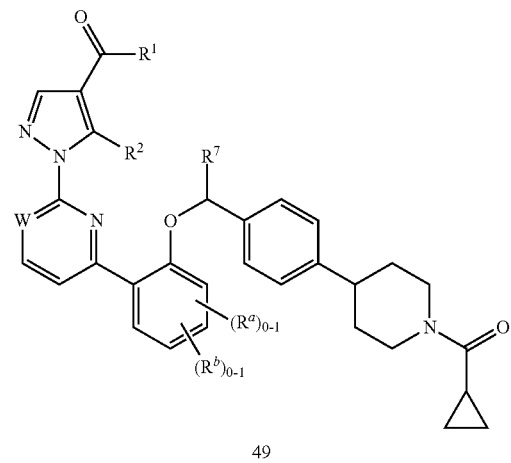

49

N-Boc protected piperidines such as 27 may be deprotected under a variety of conditions, as is well known to those skilled in the art. As shown in Scheme 16, reaction of 27 with a strong acid such as trifluoroacetic acid in an aprotic solvent such as DCM at ambient temperature provides 50 as the TFA-salt. Alternatively, use of a mixed solvent system of acetic acid and water at elevated temperature provides 50 as the acetic acid salt.

Scheme 16

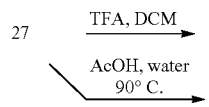

-continued

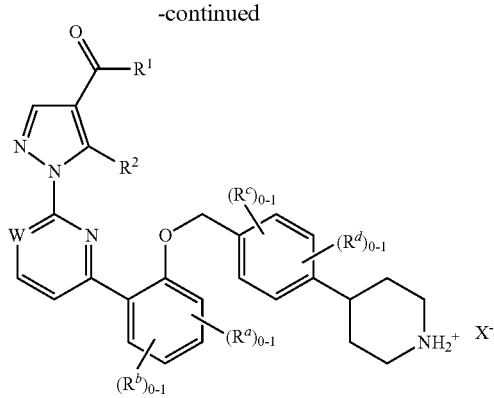

50

The amine-HX salts obtained as described in Scheme 16 may be derivatized in a variety of ways, as desired. As shown in Scheme 17, reaction with electrophilic agents such as sulfonyl chlorides, acyl chlorides, alkyl chloroformates, and carbamyl chlorides using a base such as DIEA in an aprotic solvent such as DCM at ambient temperature provides piperidines such as 51.

Scheme 17

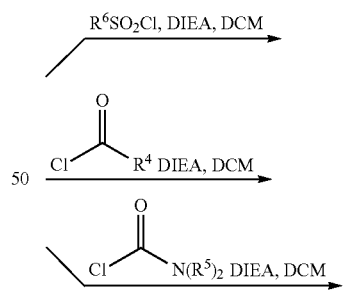

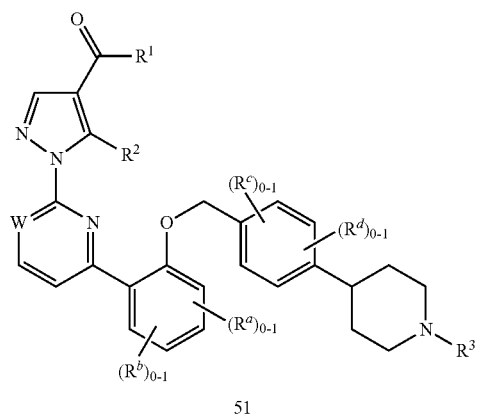

50

51

As depicted in Scheme 18, the amine-HX salts or the corresponding amine free bases may be alkylated with a suitable aliphatic electrophile such as trifluoroethyl trifluoromethanesulfonate in the presence of an inorganic base such as cesium carbonate in a polar aprotic solvent such as acetonitrile, at ambient temperature; alternatively, alkylations may be conducted with an amine base such as DIEA, in a polar aprotic solvent such as acetonitrile, at elevated temperature. Similarly, reaction with alkyl halides such as 3,3,3-trifluoro-1-bromopropane may be achieved in the presence of an amine base such as DIEA, in a polar aprotic solvent such as acetonitrile, often at elevated temperatures, as depicted in Scheme 19.

Scheme 18

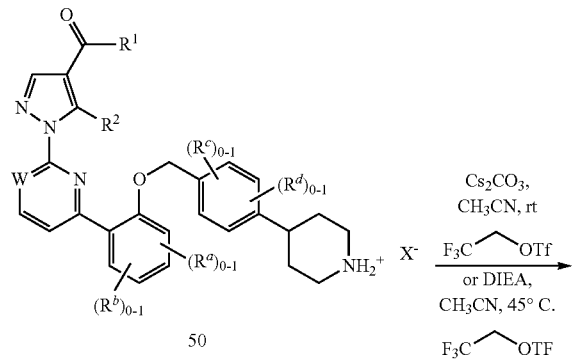

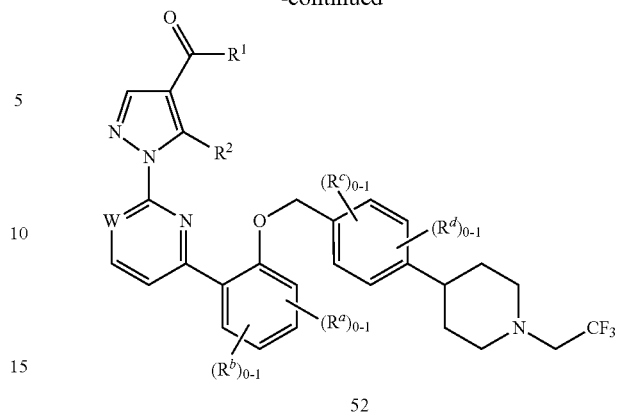

52

Scheme 19

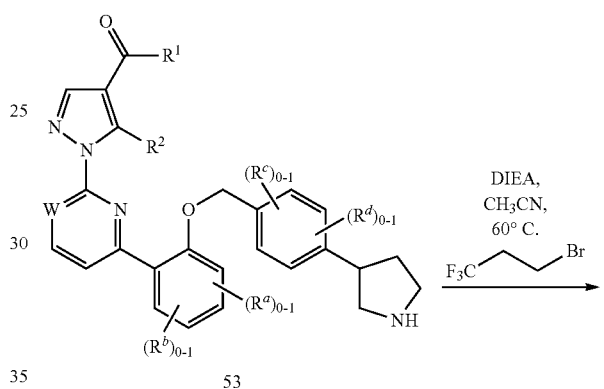

53

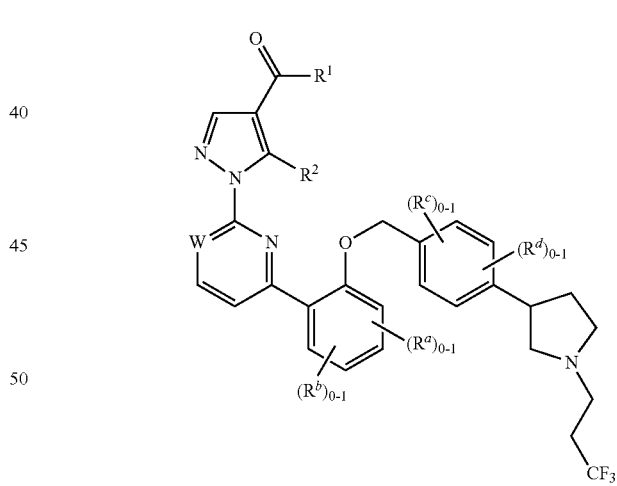

54

Additionally, in cases wherein the Z substituent is acyclic, tertiary amine products may be obtained employing standard alkylation and reductive amination protocols, as are well known to those skilled in the art. As depicted in Scheme 20, secondary amine 55 may be further elaborated by reaction with an appropriate aldehyde (RCHO wherein R is a precursor to $R^{3a}$) in the presence of a hydride reducing agent such as sodium (triacetoxy)borohydride and a protic acid such as acetic acid in an aprotic solvent such as DCM to provide tertiary amine 56.

Scheme 20

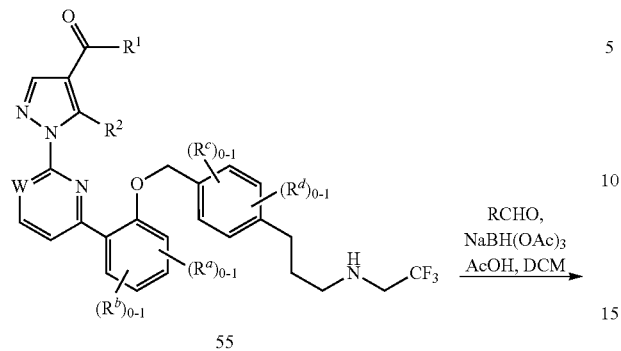

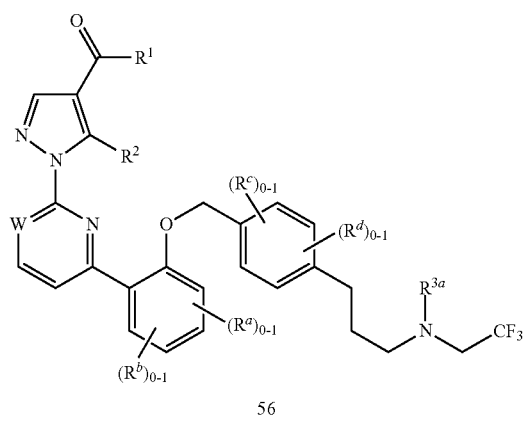

As depicted in Scheme 21, the pyrazole products wherein $R^1$ generates an ester obtained by methods described above may be converted to their corresponding carboxylic acids under standard aqueous hydrolysis conditions. Reaction of ester 57 with lithium hydroxide in a mixed solvent of dioxane and water, often at elevated temperature, provides the pyrazole acid 58.

Scheme 21

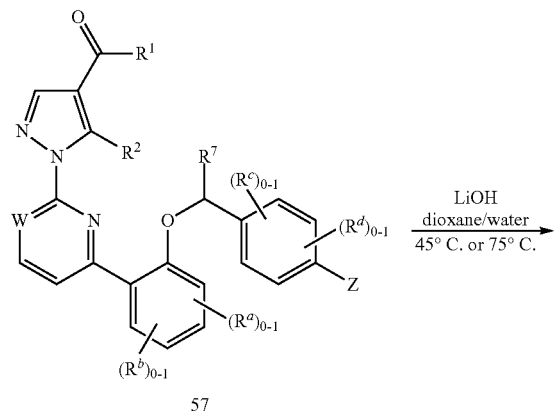

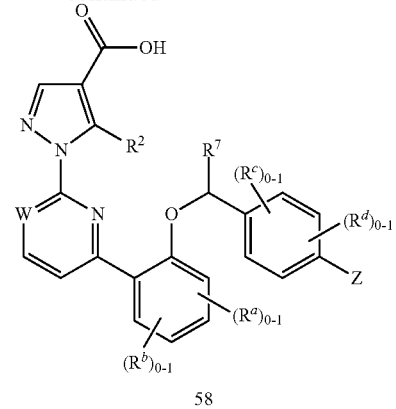

If desired, pyrazole acids such as 58 may be converted to the corresponding primary amides using a variety of conditions known to those skilled in the art. As shown in Scheme 22, reaction of carboxylic acid 58 with a standard coupling agent such as EDC in the presence of HOBt in an aprotic solvent such as DCM provides an activated ester intermediate. Reaction of the activated ester with concentrated ammonium hydroxide in dioxane then provides primary amide 59.

Scheme 22

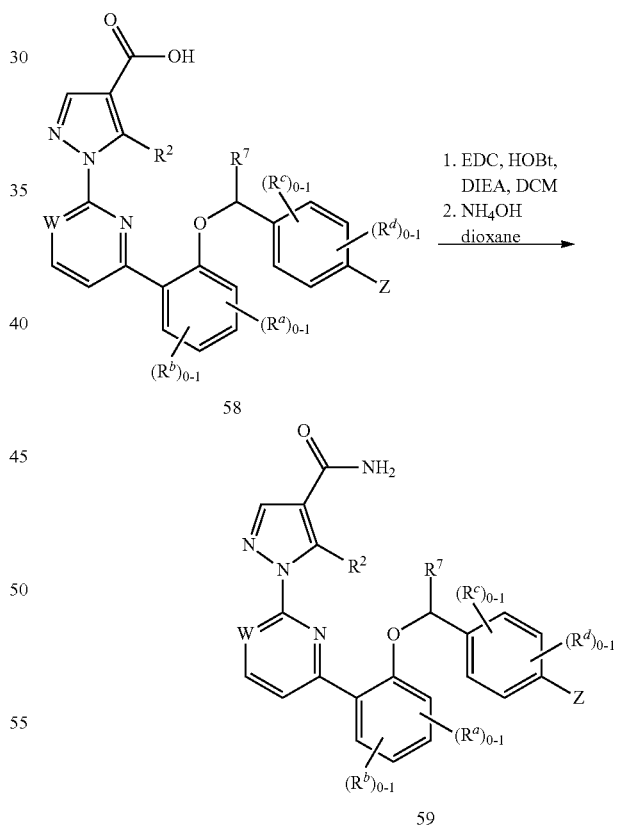

As will be known to those skilled in the art, in all schemes, the products of Formula I and all synthetic intermediates may be purified from unwanted side products, reagents and solvents by recrystallization, trituration, preparative thin layer chomatography, flash chomatography on silica gel as described by W. C. Still et al, J. Org. Chem. 1978, 43, 2923, or reverse-phase HPLC. Compounds purified by HPLC may be isolated as the corresponding salt.

Additionally, in some instances the final compounds of Formula I and synthetic intermediates may be comprised of a mixture of cis and trans isomers, enantiomers or diastereomers. As will be known to those skilled in the art, such cis and trans isomers, enantiomers and diastereomers may be separated by various methods including crystallization, chomatography using a homochiral stationary phase and, in the case of cis/trans isomers and diastereomers, normal-phase and reverse-phase chomatography.

Chemical reactions were monitored by LCMS, and the purity and identity of the reaction products were assayed by LCMS (electrospray ionization) and NMR. $^1$H NMR spectra are internally referenced to residual protio solvent signals. Data for $^1$H NMR are reported with chemical shift (δ ppm), multiplicity (s=singlet, d=doublet, t=triplet, q=quartet, m=multiplet, br s=broad singlet, br m=broad multiplet), coupling constant (Hz), and integration. Unless otherwise noted, all LCMS ions listed are [M+H]. All temperatures are degrees Celsius unless otherwise noted.

In the Examples, some intermediates and final compounds having a chiral carbon were prepared as racemates, and some chiral intermediates were resolved and the enantiomers were used separately to synthesize enantiomeric downstream intermediates and final products. In some cases racemic final products may have been resolved. In the instances where chiral compounds were separated by chiral HPLC purification, the term "enantiomer A" or "ent A" refers to the first eluting enantiomer and the downstream compounds derived from this enantiomer. The term "enantiomer B" or "ent B" refers to the second eluting enantiomer and the downstream compounds derived from this enantiomer. The term "rac" refers to a racemic mixture. As a result, the chemical nomenclature may indicate that an S and/or an R enantiomer was obtained, but the absolute stereochemistry of the separate enantiomers A and/or B was not determined.

Preparative HPLC was performed on either a Kromasil 100-100 8 column (100×30 mm i.d.) or a Phenomenex Luna 5 μm C18 column (100×21.2 mm i.d.) either at an initial flow rate of 4 mL/min for 1.35 min, followed by 20 mL/min for 13.6 min, or at an initial flow rate of 4 mL/min for 1.45 min, followed by 20 mL/min for 10.5 min. The gradients employed during the faster part of the run are described, and all runs were followed with 100% organic at 20 mL/min for 0.5 min.

Flash chromatography on silica gel was performed using pre-packed silica gel columns on Biotage Horizon or Biotage SP-1 instruments equipped with UV detectors.

The following examples are provided so that the invention might be more fully understood. They should not be construed as forming the only genus that is considered as the invention nor limiting the invention in any way.

EXAMPLE 1

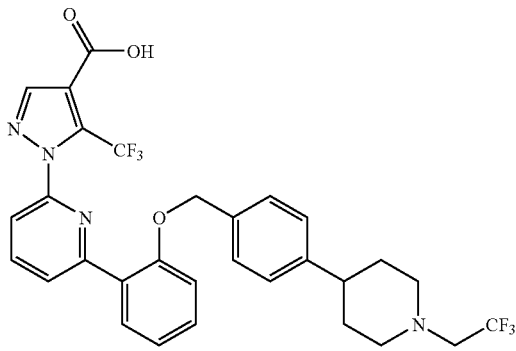 [SMILES: O=C(O)c1cnn(-c2cccc(-c3ccccc3OCc3ccc(C4CCN(CC(F)(F)F)CC4)cc3)n2)c1C(F)(F)F]

Step A. tert-Butyl 4-(4-(ethoxycarbonyl)phenyl)-3,6-dihydropyridine-1(2H)-carboxylate Preparation of 1,1-dimethylethyl 4-(((trifluoromethyl)sulfonyl)oxy)-3,6-dihydropyridine-1(2H)-carboxylate: To a cooled (−78° C.) solution of 1-Boc-4-piperidinone (30.22 g, 152 mmol) in THF (200 mL), was added LHMDS (174 mL, 1.0 M in THF, 174 mmol) dropwise over 40 min. After 2 h, a solution of 2-[N,N-bis(trifluoromethylsulfonyl)amino]-5-chloropyridine (61.3 g, 156 mmol) in THF (100 mL) was added dropwise via cannula over 30 min. The cooling bath was allowed to warm slowly to ambient temperature over 15 h, at which point the reaction mixture was concentrated in vacuo. Purification by silica gel chromatography (0 to 15% EtOAc in hexanes, then 15 to 100% EtOAc in hexanes; TLC plates visualized using potassium permanganate stain) provided the enol triflate: $^1$H NMR (500 MHz, CDCl$_3$) δ 5.77 (br m, 1H), 4.05 (br m, 2H), 3.63 (br m, 2H), 2.44 (br m, 2H), 1.48 (s, 9H).

Preparation of tert-Butyl 4-(4-(ethoxycarbonyl)phenyl)-3,6-dihydropyridine-1 (2H)-carboxylate: To a flask containing a portion of the enol triflate prepared above (8.00 g, 24.2 mmol) were added 4-ethoxycarbonylphenylboronic acid (6.09 g, 31.4 mmol) and trans-dichlorobis(triphenylphosphine) palladium (II) (1.693 g, 2.42 mmol). Acetonitrile (100 mL) and sodium carbonate (60 mL, 1.0 M aqueous, 60.0 mmol) were added, and the resulting mixture was degassed via nitrogen sparge. The reaction mixture was stirred at 70° C. for 18 h, then was allowed to cool to ambient temperature and was poured into water. The mixture was extracted with EtOAc, and the organic phase was concentrated in vacuo. Purification by chromatography on silica gel (0 to 10% EtOAc in hexanes, then 10 to 100% EtOAc in hexanes) provided the title compound: LCMS m/z 231.9 [M-Boc]$^+$; $^1$H NMR (500 MHz, CDCl$_3$) δ 8.00 (d, J=8.5 Hz, 2H), 7.43 (d, J=8.5 Hz, 2H), 6.20-6.10 (m, 1H), 4.37 (q, J=7.0 Hz, 2H), 4.10 (br m, 2H), 3.66-3.64 (m, 2H), 2.54 (br m, 2H), 1.50 (s, 9H), 1.40 (t, J=7.0 Hz, 3H).

Step B. tert-Butyl 4-(4-(ethoxycarbonyl)phenyl)piperidine-1-carboxylate

To a degassed solution of the title compound from Example 1 Step A (3.97 g, 12.0 mmol) in EtOAc (100 mL) was added platinum oxide (800 mg). The reaction flask was fitted with a hydrogen balloon attached to a 3-way adapter. The reaction mixture was then evacuated and back-filled with hydrogen. After this process was repeated three times, the reaction mixture was placed under a hydrogen atmosphere, and was stirred vigorously. After 45 min, the reaction mixture was filtered though Celite, rinsing with EtOAc. The mixture was dried over anhydrous sodium sulfate, filtered, and concentrated in vacuo: $^1$H NMR (500 MHz, CDCl$_3$) δ 7.98 (d, J=8.0 Hz, 2H), 7.26 (d, J=8.0 Hz, 2H), 4.36 (q, J=7.0 Hz, 2H), 4.32-4.20 (m, 2H), 2.84-2.70 (m, 2H) 2.74-2.67 (m, 1H), 1.84-1.81 (m, 2H), 1.67-1.59 (m, 2H), 1.49 (s, 9H), 1.39 (t, J=7.0 Hz, 3H).

Step C. tert-Butyl 4-(4-(hydroxymethyl)phenyl)piperidine-1-carboxylate

The title compound from Example 1 Step B (~12.0 mmol) was dissolved in benzene (50 mL) and concentrated in vacuo. This process was repeated, and the resulting azeotropically dried compound was dissolved in THF (100 mL) and was cooled to 0° C. To the cooled reaction mixture was added DIBAL-H (47.9 mL, 1.0 M in hexanes, 47.9 mmol). After 1 h, the reaction mixture was quenched by addition of MeOH (10 mL). The resulting mixture was diluted with dichloromethane and saturated aqueous sodium/potassium tartrate, and the mixture was stirred vigorously until a clear phase separation was achieved. The organic phase was then separated, dried over anhydrous sodium sulfate, and concentrated in vacuo to provide the title compound, which was used without further purification: LCMS m/z 291.9 [M+H]$^+$; $^1$H NMR (500 MHz, CDCl$_3$) δ 7.31 (d, J=8.0 Hz, 2H), 7.20 (d, J=8.0 Hz, 2H), 4.66 (s, 2H), 4.28-4.16 (br m, 2H), 2.84-2.76 (br m, 2H), 2.67-2.61 (m, 1H), 1.83-1.78 (m, 2H), 1.65-1.57 (m, 2H), 1.48 (s, 9H).

Step D. Ethyl-1-(6-chloropyridin-2-yl)-5-trifluoromethyl-1H-pyrazole-4-carboxylate To a solution of 2-chloro-6-hydrazinopyridine (5.00 g, 34.8 mmol) and triethylamine (4.85 mL, 34.8 mmol) in acetonitrile (174 mL) was added ethyl 2-(ethoxymethylene)-4,4,4-trifluoro-3-oxobutyrate (6.77 mL, 34.8 mmol). After 20 min, the reaction mixture was placed in a 60° C. oil bath. After 30 min, the reaction mixture was allowed to cool to ambient temperature, then was concentrated in vacuo. Purification by flash chromatography on silica gel (0 to 30% EtOAc in hexanes, then 30 to 100% EtOAc in hexanes) gave the title compound: LCMS m/z 319.9 [M+H]$^+$; $^1$H NMR (500 MHz, CDCl$_3$) δ 8.10 (s, 1H), 7.88 (t, J=7.5 Hz, 1H), 7.58 (d, J=8.0 Hz, 1H), 7.47 (d, J=8.0 Hz, 1H), 4.38 (q, J=7.0 Hz, 2H), 1.38 (t, J=7.0 Hz, 3H).

Step E. Ethyl 1-[6-(2-hydroxyphenyl)pyridine-2-yl]-5-trifluoromethyl-1H-pyrazole-4-carboxylate To a flask containing a portion of the title compound from Example 1 Step D (7.50 g, 23.5 mmol) were added 2-hydroxyphenylboronic acid (4.85 g, 35.2 mmol) and trans-dichlorobis(triphenylphosphine)palladium (II) (1.65 g, 2.35 mmol). Acetonitrile (100 mL) and sodium carbonate (59 mL, 1.0 M aqueous, 59 mmol) were added, and the resulting mixture was degassed via nitrogen sparge. The reaction mixture was stirred at 70° C. for 24 h, then was allowed to cool to ambient temperature and was poured into water. The mixture was extracted with EtOAc, and the organic phase was concentrated in vacuo. Purification by chromatography on silica gel (0 to 30% EtOAc in hexanes, then 30 to 100% EtOAc in hexanes) provided the title compound: LCMS m/z 378.5 [M+H]$^+$; $^1$H NMR (500 MHz, CDCl$_3$) δ 12.02 (s, 1H), 8.18 (s, 1H), 8.09-8.04 (m, 2H), 7.82 (dd, J=8.0, 1.5 Hz, 1H), 7.50 (dd, J=7.5, 1.5 Hz, 1H), 7.38-7.34 (m, 1H), 7.06-7.03 (m, 1H), 6.99-6.95 (m, 1H), 4.40 (q, J=7.0 Hz, 2H), 1.40 (t, J=7.0 Hz, 3H).

Step F. tert-Butyl 4-(4-((2-(6-(4-(ethoxycarbonyl)-5-(trifluoromethyl)-1H-pyrazol-1-yl)pyridin-2-yl)phenoxy)methyl)phenyl)piperidine-1-carboxylate To a solution of the title compound from Example 1 Step E (3.80 g, 10.07 mmol), the title compound from Example 1 Step C (4.40 g, 15.11 mmol), and triphenylphosphine (3.96 g, 15.11 mmol) in DCM (100 mL) was added diisopropyl azodicarboxylate (2.94 mL, 15.11 mmol), and the resulting mixture was stirred at ambient temperature. After 4 h, the reaction mixture was concentrated in vacuo. Purification by flash chromatography on silica gel (0 to 40% EtOAc in hexanes, then 40 to 100% EtOAc in hexanes) provided the title compound: LCMS m/z 651.0 [M+H]$^+$; $^1$H NMR (500 MHz, CDCl$_3$) δ 8.15 (d, J=8.0 Hz, 1H), 8.12 (s, 1H), 7.96 (dd, J=7.5, 2.0 Hz, 1H), 7.87 (app t, J=8.0 Hz, 1H), 7.53 (d, J=8.0 Hz, 1H), 7.39-7.36 (m, 1H), 7.31 (d, J=8.0 Hz, 2H), 7.19 (d, J=8.0 Hz, 2H), 7.13-7.10 (m, 1H), 7.07 (d, J=8.0 Hz, 1H), 5.13 (s, 2H), 4.38 (q, J=7.0 Hz, 2H), 4.32-4.18 (br m, 2H), 2.84-2.76 (br m, 2H), 2.68-2.62 (m, 1H), 1.83-1.81 (m, 2H), 1.66-1.58 (m, 2H), 1.49 (s, 9H), 1.39 (t, J=7.0 Hz, 3H).

Step G. Ethyl 1-(6-(2-((4-(1-(2,2,2-trifluoroethyl)piperidin-4-yl)benzyl)oxy)phenyl)pyridin-2-yl)-5-(trifluoromethyl)-1H-pyrazole-4-carboxylate To a solution of the title compound from Example 1 Step F (3.53 g, 5.43 mmol) in DCM (20 mL) was added TFA (10 mL), and the resulting mixture was stirred at ambient temperature. After 10 min, the reaction mixture was concentrated in vacuo, to yield a TFA-salt.

This crude salt was dissolved in DCM, then was washed with K$_2$CO$_3$ (1 M aq, 2×250 mL) to yield a free base which was used without further purification: LCMS m/z 551.0 [M+H]$^+$. To a solution of the product obtained above in acetonitrile (50 mL) was added DIEA (4.74 mL, 27.1 mmol), followed by 2,2,2-trifluoroethyl trifluoromethanesulfonate (2.24 mL, 13.6 mmol), and the resulting mixture was stirred at 45° C. After 35 min, the reaction mixture was poured into sat aq NaHCO$_3$ then was extracted with DCM. The organic phase was separated and concentrated in vacuo. Purification by flash chromatography on silica gel (0 to 40% EtOAc in hexanes, then 40 to 100% EtOAc in hexanes) provided the title compound: LCMS m/z 633.0 [M+H]$^+$; $^1$H NMR (500 MHz, CDCl$_3$) δ 8.15 (d, J=8.0 Hz, 1H), 8.12 (s, 1H), 7.97 (dd, J=8.0, 2.0 Hz, 1H), 7.87 (app t, J=8.0 Hz, 1H), 7.53 (d, J=8.0 Hz, 1H), 7.39-7.36 (m, 1H), 7.31 (d, J=8.0 Hz, 2H), 7.21 (d, J=8.0 Hz, 2H), 7.11 (t, J=8.0 Hz, 1H), 7.07 (d, J=8.0 Hz, 1H), 5.13 (s, 2H), 4.38 (q, J=7.0 Hz, 2H), 3.10-3.07 (br m, 2H), 3.02 (t, $^3J_{H-F}$=10 Hz, 2H), 2.54-2.46 (m, 3H), 1.84-1.80 (m, 4H), 1.39 (t, J=7.0 Hz, 3H).

Step H. 1-[6-[2-[[4-[1-(2,2,2-Trifluoroethyl)-4-piperidinyl]phenyl]methoxy]phenyl]-2-pyridinyl]-5-(trifluoromethyl)-1H-pyrazole-4-carboxylic acid To a solution of the title compound from Example 1 Step G (2.18 g, 3.45 mmol) in 1,4-dioxane (20 mL) was added lithium hydroxide (10 mL, 2N aqueous, 20 mmol), and the resulting mixture was stirred at 45° C. After 2 h, the reaction mixture was allowed to cool to ambient temperature, then rendered acidic by addition of TFA, diluted with acetonitrile and purified by reverse phase HPLC (20 to 100% acetonitrile/water, both 0.1% v/v formic acid). To remove residual formic acid, the purified product was then crystallized from acetonitrile and water to yield the title compound: LCMS m/z 605.0 [M+H]$^+$; $^1$H NMR (500 MHz, d$_6$-DMSO) δ 13.4 (s, 1H), 8.30 (s, 1H), 8.15 (t, J=8.0 Hz, 1H), 8.10 (d, J=8.0 Hz, 1H), 7.74 (d, J=8.0 Hz, 1H), 7.71 (d, J=8.0 Hz, 1H), 7.45-7.41 (m, 1H), 7.35 (d, J=8.0 Hz, 2H), 7.28 (d, J=8.5 Hz, 1H), 7.24 (d, J=8.0 Hz, 2H), 7.09 (t, J=7.5 Hz, 1H), 5.21 (s, 2H), 3.19 (q, $^3J_{H-F}$=10 Hz, 2H), 3.01-2.99 (m, 2H), 2.50-2.41 (m, 3H), 1.72-1.61 (m, 4H).

EXAMPLE 2

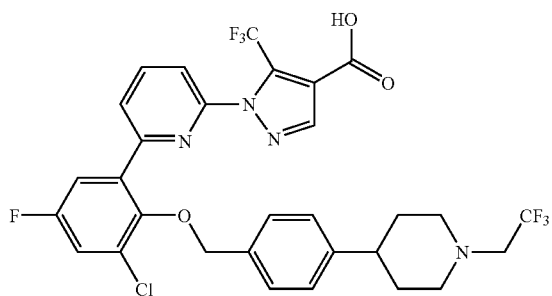 [SMILES: O=C(O)c1cnn(-c2cccc(-c3cc(F)cc(Cl)c3OCc3ccc(C4CCN(CC(F)(F)F)CC4)cc3)n2)c1C(F)(F)F]

Step A. Ethyl 1-(6-(5-fluoro-2-methoxyphenyl)pyridin-2-yl)-5-(trifluoromethyl)-1H-pyrazole-4-carboxylate To a flask containing the title compound from the Example 1 Step D (2.50 g, 7.82 mmol) were added 2-methoxy-5-fluoro-phenylboronic acid (1.595 g, 9.38 mmol) and trans-dichlorobis(triphenylphosphine)palladium (II) (548 mg, 0.782 mmol). Acetonitrile (25 mL) and sodium carbonate (19.6 mL, 1.0 M aqueous, 19.6 mmol) were added, and the resulting mixture was degassed via nitrogen sparge. The reaction mixture was stirred at 70° C. for 4 h, then was allowed to cool to ambient temperature and was poured into water. The mixture was extracted with EtOAc, and the organic phase was concentrated in vacuo. Purification by chromatography on silica gel (0 to 35% EtOAc in hexanes, then 35 to 100% EtOAc in hexanes) provided the title compound: LCMS m/z 409.9 [M+H]$^+$; $^1$H NMR (500 MHz, CDCl$_3$) δ 8.16 (d, J=8.0 Hz, 1H), 8.12 (s, 1H), 7.94 (t, J=8.0 Hz, 1H), 7.73 (dd, J=9.5, 3.0 Hz, 1H), 7.58 (d, J=8.0 Hz, 1H), 7.10-7.06 (m, 1H), 6.95 (dd, J=9.0, 5.0 Hz, 1H), 4.39 (q, J=7.0 Hz, 2H), 3.89 (s, 3H), 1.40 (t, J=7.0 Hz, 3H).

Step B. Ethyl 1-(6-(5-fluoro-2-hydroxyphenyl)pyridin-2-yl)-5-(trifluoromethyl)-1H-pyrazole-4-carboxylate To a cooled (0° C.) solution of the title compound from Example 2 Step A (2.89 g, 7.06 mmol) in DCM (30 mL) was added dropwise BBr$_3$ (21.2 mL, 1.0 M in DCM, 21.2 mmol). After addition was complete, the cooling bath was removed, and the reaction mixture was allowed to stir at room temperature. After 1.5 h, the mixture was cooled to 0° C., then was quenched by careful addition (exothermic, gas evolution) of sat aq NaHCO$_3$ (100 mL). The resulting mixture was diluted with DCM, the phases were separated, and the organic phase was concentrated in vacuo. Purification by chromatography on silica gel (0 to 35% EtOAc in hexanes, then 35 to 100% EtOAc in hexanes) provided the title compound: LCMS m/z 395.8 [M+H]$^+$; $^1$H NMR (500 MHz, CDCl$_3$) δ 11.79 (s, 1H), 8.18 (s, 1H), 8.10 (t, J=8.0 Hz, 1H), 7.95 (d, J=8.0 Hz, 1H), 7.54 (d, J=8.0 Hz, 1H), 7.49 (dd, J=10.0, 3.0 Hz, 1H), 7.09-7.06 (m, 1H), 6.98 (dd, J=9.0, 5.0 Hz, 1H), 4.39 (q, J=7.0 Hz, 2H), 1.39 (t, J=7.0 Hz, 3H).

Step C. Ethyl 1-(6-(3-chloro-5-fluoro-2-hydroxyphenyl)pyridin-2-yl)-5-(trifluoromethyl)-1H-pyrazole-4-carboxylate To a solution of the title compound from Example 2 Step B (1.50 g, 3.79 mmol) in acetonitrile (9.5 mL) was added N-chlorosuccinimide (760 mg, 5.69 mmol), and the resulting mixture was placed in a pre-heated oil bath (90° C.). After 1 h, the reaction mixture was allowed to cool to room temperature, then was diluted with DCM, and the resulting mixture was washed with brine. The organic phase was then concentrated in vacuo. Purification by chromatography on silica gel (0 to 30% EtOAc in hexanes, then 30 to 100% EtOAc in hexanes) provided the title compound: LCMS m/z 429.9 [M+H]$^+$; $^1$H NMR (500 MHz, CDCl$_3$) δ 12.50 (s, 1H), 8.18 (s, 1H, 8.14 (t, J=8.0 Hz, 1H), 7.99 (d, J=8.0 Hz, 1H), 7.58 (d, J=8.0 Hz, 1H), 7.46 (dd, J=9.0, 3.0 Hz, 1H), 7.25 (dd, J=9.0, 3.0 Hz, 1H), 4.40 (q, J=7.0 Hz, 2H), 1.40 (t, J=7.0 Hz, 3H).

Step D. ten-Butyl 4-(4-((2-(6-(4-(ethoxycarbonyl)-5-(trifluoromethyl)-1H-pyrazol-1-yl)pyridin-2-yl)phenoxy)methyl)phenyl)piperidine-1-carboxylate To a solution of the title compound from Example 2 Step C (230 mg, 0.535 mmol), the title compound from Example 1 Step C (234 mg, 0.803 mmol), and triphenylphosphine (211 mg, 0.803 mmol) in DCM (2 mL) was added diisopropyl azodicarboxylate (0.156 mL, 0.803 mmol), and the resulting mixture was stirred at ambient temperature. After 15 h, the reaction mixture was concentrated in vacuo. Purification by flash chromatography on silica gel (0 to 50% EtOAc in hexanes, then 50 to 100% EtOAc in hexanes) provided the title compound: LCMS m/z 647.0 [M-C$_4$H$_9$]$^+$; $^1$H NMR (500 MHz, CDCl$_3$) δ 8.15 (s, 1H), 8.14 (d, J=8.0 Hz, 1H), 7.91 (d, J=8.0 Hz, 1H), 7.64 (d, J=8.0 Hz, 1H), 7.54 (dd, J=9.0, 3.0 Hz, 1H), 7.26-7.24 (m, 1H), 7.17 (d, J=8.0 Hz, 2H), 7.12 (d, J=8.0 Hz, 2H), 4.68 (s, 2H), 4.40 (q, J=7.5 Hz, 2H), 4.28-4.18 (m, 2H), 2.82-2.74 (m, 2H), 2.64-2.58 (m, 1H), 1.78 (app d, J=8.0 Hz, 2H), 1.63-1.54 (m, 2H), 1.49 (s, 9H), 1.40 (t, J=7.5 Hz, 3H).

Step E. 1(6-(3-Chloro-5-fluoro-2-((4-(1-(2,2,2-trifluoroethyl)piperidin-4-yl)benzyl)oxy)phenyl)pyridin-2-yl)-5-(trifluoromethyl)-1H-pyrazole-4-carboxylic acid The title compound from Example 2 Step D (262 mg, 0.53 mmol) was dissolved in acetic acid (2 mL) and water (0.5 mL), and the resulting mixture was heated at 90° C. After 15 h, the reaction mixture was allowed to cool to ambient temperature, and then was concentrated in vacuo. The crude reaction mixture was azeotroped with benzene to remove acetic acid, and the acetic acid salt was used without further purification: LCMS m/z 602.9 [M+H]$^+$. To a solution of the acetic acid-salt obtained above in acetonitrile (4 mL) was added cesium carbonate (0.978 g, 3.00 mmol), followed by 2,2,2-trifluoroethyl trifluoromethanesulfonate (149 µL, 0.300 mmol), and the resulting mixture was stirred at ambient temperature. After 1 h, the reaction mixture was poured into sat aq NaHCO$_3$ then was extracted with DCM. The organic phase was separated and concentrated in vacuo, and the crude alkylation product was used without further purification: LCMS m/z 685.0 [M+H]$^+$. To a solution of the alkylation product obtained above in 1,4-dioxane (4 mL) was added lithium hydroxide (2 mL, 2N aqueous, 4 mmol), and the resulting mixture was stirred at 60° C. After 1 h, the reaction mixture was rendered acidic by addition of TFA, then was diluted with acetonitrile and purified by reverse phase HPLC (20 to 100% acetonitrile/water, both 0.1% v/v TFA). To remove residual TFA, a portion of the purified product was dissolved in a minimum amount of acetonitrile and then was added to an excess of water, whereupon the product precipitated and was isolated by filtration: LCMS m/z 656.0 [M+H]$^+$; $^1$H NMR (500 MHz, d$_6$-DMSO) δ 8.32 (s, 1H), 8.17 (t, J=8.0 Hz, 1H), 8.06 (d, J=8.0 Hz, 1H), 7.83 (d, J=8.0 Hz, 1H), 7.69 (dd, J=8.0, 3.0 Hz, 1H), 7.45 (dd, J=9.0, 3.0 Hz, 1H), 7.11 (d, J=8.0 Hz, 2H), 7.06 (d, J=8.0 Hz, 2H), 4.71 (s, 2H), 3.16-3.14 (m, 2H), 2.70-2.62 (m, 2H), 2.54-2.50 (m, 3H), 1.71-1.64 (m, 4H).

EXAMPLE 3

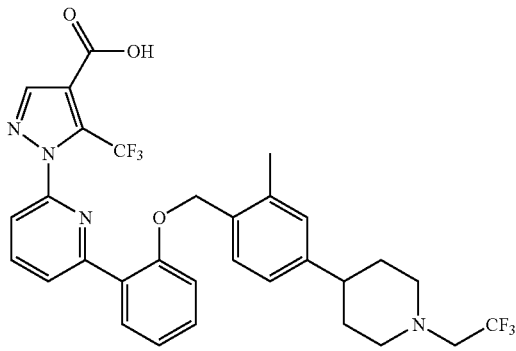

Step A. Methyl 2-methyl-4-(4,4,5,5-tetramethyl-1,3,2-dioxaborolan-2-yl)benzoate A round bottomed flask was charged with methyl 4-bromo-2-methylbenzoate (3.98 g, 17.37 mmol), bis(pinacolato)diboron (4.85 g, 19.11 mmol), potassium acetate (5.12 g, 52.1 mmol), and dichloro [1,1'-bis(diphenylphosphino) ferrocene] palladium (II) dichloromethane adduct (0.426 g, 0.521 mmol). The flask was purged with nitrogen. Anhydrous DMSO (100 mL) was added, and the resulting suspension was degassed via nitrogen sparge. The mixture was then placed in a pre-heated oil bath (80° C.), and was held at this temperature for 2 h, whereupon it was allowed to cool to ambient temperature, then was poured into water. The aqueous phase was extracted with ether, and the organic phase was washed with brine. The organic phase was then separated, dried over anhydrous sodium sulfate, filtered, and concentrated in vacuo. Purification by flash chromatography on silica gel (0 to 10% EtOAc in hexanes, then 10 to 100% EtOAc in hexanes) provided the title compound: LCMS m/z 277.6 [M+H]$^+$; $^1$H NMR (500 MHz, CDCl$_3$) δ 7.87 (d, J=7.5 Hz, 1H), 7.68 (s, 1H), 7.66 (d, J=7.5 Hz, 1H), 3.89 (s, 3H), 2.59 (s, 3H), 1.35 (s, 12H).

Step B. tert-Butyl-4-(4-(methoxycarbonyl)-3-methylphenyl)-3,6-dihydropyridine-1(2H)-carboxylate To a flask containing 1,1-dimethylethyl 4-(((trifluoromethyl)sulfonyl)oxy)-3,6-dihydropyridine-1(2H)-carboxylate (3.80 g, 11.5 mmol, prepared according to Heterocycles, 1996, 43, 2131-2138) were added the title compound from Example 3 Step A (3.80 g, 13.8 mmol) and trans-dichlorobis(triphenylphosphine)palladium (II) (804 mg, 1.15 mmol). Acetonitrile (57 mL) and sodium carbonate (28.7 mL, 1.0 M aqueous, 28.7 mmol) were added, and the resulting mixture was degassed via nitrogen sparge. The reaction mixture was stirred at 70° C. for 3 h, then was allowed to cool to ambient temperature and was poured into water. The mixture was extracted with EtOAc, and the organic phase was concentrated in vacuo. Purification by chromatography on silica gel (0 to 10% EtOAc in hexanes, then 10 to 100% EtOAc in hexanes) provided the title compound: LCMS m/z 276.0 [M-C$_4$H$_9$]$^+$; $^1$H NMR (500 MHz, CDCl$_3$) δ 7.89 (d, J=9.0 Hz, 1H), 7.24-7.22 (m, 2H), 6.12 (br s, 1H), 4.09 (br m, 2H), 3.88 (s, 3H), 3.65-3.62 (m, 2H), 2.61 (s, 3H), 2.52 (br m, 2H), 1.49 (s, 9H).

Step C. tert-Butyl 4-(4-hydroxymethyl)-3-methylphenyl)piperidine-1-carboxylate To a degassed solution of the title compound from Example 3 Step B (3.20 g, 9.66 mmol) in EtOAc (100 mL) was added platinum oxide (700 mg). The reaction flask was fitted with a hydrogen balloon attached to a 3-way adapter. The reaction mixture was then evacuated and back-filled with hydrogen. After this process was repeated three times, the reaction mixture was placed under a hydrogen atmosphere, and was stirred vigorously. After 15 min, the reaction mixture was filtered though Celite, rinsing with EtOAc. The mixture was dried over anhydrous sodium sulfate, filtered, concentrated in vacuo and used without further purification: LCMS m/z 234.0 [M-Boc]$^+$; $^1$H NMR (500 MHz, CDCl$_3$) δ 7.86 (d, J=9.0 Hz, 1H), 7.08-7.06 (m, 2H), 4.30-4.18 (br m, 2H), 3.87 (s, 3H), 2.83-2.75 (m, 2H), 2.68-2.61 (m, 1H), 2.59 (s, 3H), 1.82-1.79 (m, 2H), 1.66-1.58 (m, 2H), 1.48 (s, 9H)

Step D. tert-Butyl 4-(4-hydroxymethyl)-3-methylphenyl)piperidine-1-carboxylate The title compound from Example 3 Step C (~9.6 mmol) was dissolved in THF (100 mL) and was cooled to 0° C. To the cooled reaction mixture was added DIBAL-H (33.0 mL, 1.0 M in hexanes, 33.0 mmol). After 1 h, the reaction mixture was quenched by addition of MeOH (10 mL). The resulting mixture was diluted with dichloromethane and saturated aqueous sodium/potassium tartrate, and the mixture was stirred vigorously until a clear phase separation was achieved. The organic phase was then separated, dried over anhydrous sodium sulfate, and concentrated in vacuo to provide the title compound, which was used without further purification.

Step E. tert-Butyl 4-(4-((2-(6-(4-(ethoxycarbonyl)-5-(trifluoromethyl)-1H-pyrazol-1-yl)pyridin-2-yl)phenoxy)methyl)-3-methylphenyl)piperidine-1-carboxylate To a solution of the title compound from Example 1 Step E (300 mg, 0.795 mmol), the title compound from Example 3 Step D (364 mg, 1.193 mmol), and triphenylphosphine (313 mg, 1.193 mmol) in DCM (6 mL) was added diisopropyl azodicarboxylate (0.232 mL, 1.193 mmol), and the resulting mixture was stirred at ambient temperature. After 3 h, the reaction mixture was concentrated in vacuo. Purification by flash chromatography on silica gel (0 to 50% EtOAc in hexanes, then 50 to 100% EtOAc in hexanes) provided the title-compound: LCMS m/z 665.1 [M+H]$^+$; $^1$H NMR (500 MHz, CDCl$_3$) δ 8.12 (s, 1H), 8.11 (d, J=8.0 Hz, 1H), 7.84 (t, J=8.0 Hz, 1H), 7.52 (d, J=8.0 Hz, 1H), 7.41-7.38 (m, 1H), 7.30 (d, J=8.0 Hz, 1H), 7.14-7.10 (m, 2H), 7.03-7.01 (m, 2H), 5.10 (s, 2H), 4.40 (q, J=7.5 Hz, 2H), 4.31-4.20 (m, 2H), 2.85-2.75 (m, 2H), 2.65-2.59 (m, 1H), 2.28 (s, 3H), 1.83-1.80 (m, 2H), 1.66-1.58 (m, 2H), 1.49 (s, 9H), 1.40 (t, J=7.5 Hz, 3H).

Step F. 1-(6-2-((2-Methyl-4-(1-(2,2,2-trifluoroethyl)piperidin-4-yl)benzyl)phenyl)pyridin-2-yl)-5-(trifluoromethyl)-1H-pyrazole-4-carboxylic acid To a solution of the title compound from Example 3 Step E (75 mg, 0.264 mmol) in DCM (3 mL) was added TFA (1 mL), and the resulting mixture was stirred at room temperature. After 10 min, the reaction mixture was concentrated in vacuo, to yield a TFA-salt which was used without further purification: LCMS m/z 565.0 [M+H]+. Approximately half of the crude TFA-salt was taken forward as follows: To a solution of the TFA-salt obtained above in acetonitrile (1 mL) was added cesium carbonate (0.215 g, 0.66 mmol), followed by 2,2,2-trifluoroethyl trifluoromethanesulfonate (27 μL, 0.17 mmol), and the resulting mixture was stirred at 50° C. After 90 min, the reaction mixture was poured into sat aq NaHCO$_3$ then was extracted with DCM. The organic phase was separated and concentrated in vacuo, and the crude alkylation product was used without further purification: LCMS m/z 647.1 [M+H]+. To a solution of the alkylation product obtained above in 1,4-dioxane (2 mL) was added lithium hydroxide (1 mL, 2N aqueous, 2 mmol), and the resulting mixture was stirred at 45° C. After 1 h, the reaction mixture was rendered acidic by addition of TFA, then was diluted with acetonitrile and purified by reverse phase HPLC (20 to 100% acetonitrile/water, both 0.1% v/v TFA). To remove residual TFA, a portion of the purified product was dissolved in a minimum amount of acetonitrile and then was added to an excess of water, whereupon the product precipitated and was isolated by filtration: LCMS m/z 619.0 [M+H]+; $^1$H NMR (500 MHz, d$_6$-DMSO) δ 13.43 (s, 1H), 8.29 (s, 1H), 8.07 (t, J=7.5 Hz, 1H), 8.05 (d, J=7.5 Hz, 1H), 7.72-7.68 (m, 2H), 7.77 (t, J=7.5 Hz, 1H), 7.32 (d, J=8.0 Hz, 1H), 7.27 (d, J=7.5 Hz, 1H), 7.11-7.07 (m, 2H), 7.02 (d, J=7.5 Hz, 1H), 5.17 (s, 2H), 3.20-3.14 (m, 2H), 3.10-2.98 (m, 2H), 2.46-2.40 (m, 3H), 2.21 (s, 3H), 1.68-1.60 (m, 4H).

EXAMPLE 4

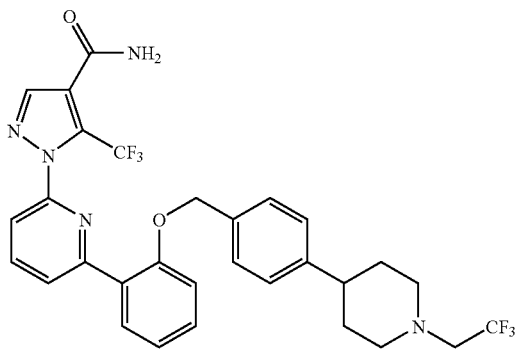

Step A. 1-(6-(2-((4-(1-(2,2,2-Trifluoroethyl)piperidin-4-yl)benzyl)oxy)phenyl)pyridin-2-yl)-5-(trifluoromethyl)-1H-pyrazole-4-carboxamide To a vial containing the title compound from Example 1 Step H (50 mg, 0.083 mmol) were added EDC (63 mg, 0.33 mmol), HOBt (51 mg, 0.33 mmol), and DCM (1 mL), and the resulting mixture was stirred at ambient temperature. After 1 h, the reaction mixture was poured into sat aq NH$_4$Cl and was extracted with EtOAc. The organic phase was separated, dried over sodium sulfate, and concentrated in vacuo. The activated ester intermediate was used directly: LCMS m/z 722.1 [M+1-1]+. To the crude product obtained above were added dioxane (1 mL) and concentrated ammonium hydroxide (0.5 mL), and the resulting mixture was stirred at room temperature. After 18 h, the reaction mixture was poured into sat aq NH$_4$Cl, and the mixture was extracted with EtOAc. The organic phase was washed with 2N HCl, then was concentrated in vacuo, then was redissolved in dioxane and water. Purification by reverse phase HPLC (50 to 100% acetonitrile/water, both 0.1% v/v TFA) provided the title compound: LCMS m/z 604.1 [M+H]+; $^1$H NMR (500 MHz, d$_6$-DMSO) δ 8.17 (s, 1H), 8.13 (d, J=8.0 Hz, 1H), 8.08 (t, J=8.0 Hz, 1H), 8.02 (br s, 1H), 7.76 (dd, J=8.0, 2.0 Hz, 1H), 7.60 (br s, 1H), 7.44-7.41 (m, 1H), 7.35 (d, J=8.0 Hz, 2H), 7.26 (d, J=8.5 Hz, 1H), 7.24 (d, J=8.0 Hz, 2H), 7.09 (t, J=8.0 Hz, 1H), 5.21 (s, 2H), 3.53 (m, obscured by water peak, 2H), 3.38-3.28 (m, 2H), 3.08-3.05 (m, 2H), 2.53 (m, 1H), 1.74-1.64 (m, 4H).

EXAMPLE 5

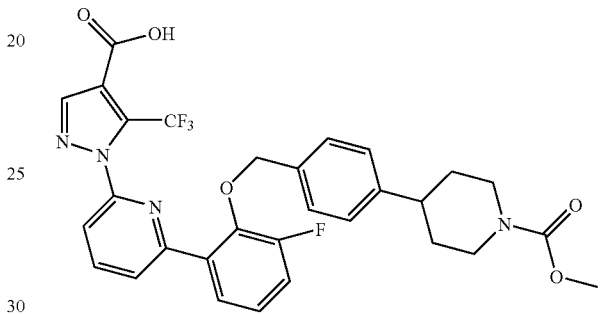

Step A. Ethyl 1-[6-(3-fluoro-2-hydroxyphenyl)pyridin-2-yl]-5-(trifluoromethyl)-1H-pyrazole-4-carboxylate To a flask containing the title compound from the Example 1 Step D (3.30 g, 10.32 mmol) were added 2-methoxy-3-fluoro-phenylboronic acid (1.93 g, 11.36 mmol) and trans-dichlorobis(triphenylphosphine)palladium (II) (548 mg, 0.782 mmol). Acetonitrile (52 mL) and sodium carbonate (26.8 mL, 1.0 M aqueous, 26.8 mmol) were added, and the resulting mixture was degassed via nitrogen sparge. The reaction mixture was stirred at 70° C. for 3 h, then was allowed to cool to ambient temperature and was poured into water. The mixture was extracted with EtOAc, and the organic phase was concentrated in vacuo. Purification by chromatography on silica gel (0 to 25% EtOAc in hexanes, then 25 to 100% EtOAc in hexanes) provided the Suzuki product precursor to the title compound: LCMS m/z 410.5 [M+H]+; $^1$H NMR (500 MHz, CDCl$_3$) δ 8.14 (s, 1H), 8.07 (d, J=8.0 Hz, 1H), 7.97 (t, J=8.0 Hz, 1H), 7.68-7.66 (m, 1H), 7.61 (d, J=7.5 Hz, 1H), 7.20-7.13 (m, 2H), 4.39 (q, J=7.0 Hz, 2H), 3.84 (s, 3H), 1.39 (t, J=7.0 Hz, 3H). To a cooled (0° C.) solution of a portion of the Suzuki product obtained above (1.50 g, 3.66 mmol) in DCM (18 mL) was added dropwise BBr$_3$ (11.0 mL, 1.0 M in DCM, 11.0. mmol). After 1.5 h, the mixture was quenched by careful addition (exothermic, gas evolution) of sat aq NaHCO$_3$. The resulting mixture was diluted with DCM, the phases were separated, and the organic phase was concentrated in vacuo. Purification by chromatography on silica gel (0 to 40% EtOAc in hexanes, then 40 to 100% EtOAc in hexanes) provided the title compound: LCMS m/z 395.8 [M+H]+; $^1$H NMR (500 MHz, CDCl$_3$) δ 12.18 (s, 1H), 8.18 (s, 1H), 8.10 (app t, J=7.5 Hz, 1H), 8.04 (d, J=8.5 Hz, 1H), 7.60 (dd, J=8.0, 1.0 Hz, 1H), 7.54 (d, J=7.5 Hz, 1H), 7.18 (dd, J=8.5, 1.5 Hz, 1H), 6.89 (ddd, J=8.0, 8.0, $^4J_{H-F}$=5.0 Hz, 1H), 4.40 (q, J=7.0 Hz, 2H), 1.40 (t, J=7.0 Hz, 3H).

Step B. tert-Butyl 4-{4-[(2-[6-{4-(ethoxycarbonyl)-5-(trifluoromethyl)-1H-pyrazol-1-yl]pyridin-2-yl}-6-fluorophenoxy)methyl]phenyl}piperidine-1-carboxylate To a solution of the title compound from Example 5 Step A (530 mg, 1.34 mmol), the title compound from Example 1 Step C (508 mg, 1.74 mmol), and triphenylphosphine (527 mg, 2.01 mmol) in DCM (7 mL) was added diisopropyl azodicarboxylate (0.39 mL, 2.01 mmol), and the resulting mixture was stirred at ambient temperature. After 2 h, the reaction mixture was concentrated in vacuo. Purification by flash chromatography on silica gel (0 to 40% EtOAc in hexanes, then 40 to 100% EtOAc in hexanes) provided the title compound: LCMS m/z 669.0 [M+H]$^+$; $^1$H NMR (500 MHz, CDCl$_3$) δ 8.13 (s, 1H), 8.05 (d, J=7.5, 1H), 7.87 (td, J=8.0, 2.0 Hz, 1H), 7.67-7.64 (m, 1H), 7.58 (d, J=8.0 Hz, 1H), 7.22-7.15 (m, 4H), 7.10 (d, J=8.0 Hz, 2H), 4.91 (s, 2H), 4.8 (q, doubled (rotamers), J=7.0 Hz, 2H), 4.32-4.14 (br m, 2H), 2.87-2.70 (br m, 2H), 2.62-2.57 (m, 1H), 1.76 (d, J=8.0 Hz, 2H), 1.60-1.53 (m, 2H), 1.48 (s, doubled (rotamers), 9H), 1.39 (t, doubled (rotamers), J=7.0 Hz, 3H).

Step C. Ethyl 1-[6-(3-fluoro-2-{[4-(piperidin-4-yl)benzyl]oxy}phenyl)pyridin-2-yl]-5-(trifluoromethyl)-1H-pyrazole-4-carboxylate A solution of the title compound from Example 5 Step B (800 mg, 1.20 mmol) in acetic acid (4 mL) and water (1 mL) was stirred at 90° C. for 14 h. The reaction mixture was allowed to cool to ambient temperature and evaporated in vacuo. The product was used in the subsequent step without further purification: LCMS m/z 568.8 [M+H]$^+$.

Step D. Methyl 4-{4-[(2-{6-[4-(ethoxycarbonyl)-5-(trifluoromethyl)-1H-pyrazol-1-yl]pyridin-2-yl}-6-fluorophenoxy)methyl]phenyl}piperidine-1-carboxylate To a solution of the title compound from Example 5 Step C (194 mg, 0.34 mmol) in DCM (2 mL) were added diisopropyl ethyl amine (0.60 mL, 3.41 mmol) and methyl chloroformate (0.08 mL, 1.02 mmol). The reaction mixture was stirred for 1 h at ambient temperature, then was diluted with sat. aq. NaHCO$_3$ and extracted with DCM. The organic phase was separated, dried over sodium sulfate, filtered, and concentrated in vacuo. The product was used in the subsequent step without further purification: LCMS m/z 626.9 [M+H]$^+$.

Step E. 1-{6-[3-fluoro-2-({4-[1-methoxycarbonyl)piperidin-4 yl]benzyl}oxy)phenyl]pyridin-2-yl}-5-(trifluoromethyl)-1H-pyrazole-4-carboxylic acid To a solution of the title compound from Example 5 Step D (214 mg, 0.34 mmol) in 1,4-dioxane (2 mL) was added lithium hydroxide (1.0 mL, 2.0 M in water, 2.00 mmol), and the resulting mixture was stirred at 50° C. After 2 h, the reaction mixture was rendered acidic by addition of aqueous hydrochloric acid (1.5 mL), then was diluted with 1,4-dioxane and passed though a 0.45 micron syringe filter. Purification by reverse phase HPLC (40 to 100% acetonitrile in water, each with 0.1% v/v TFA) provided the title compound: LCMS m/z 599.0 [M+H]$^+$; $^1$H NMR (500 MHz, d$_6$-DMSO) δ 8.32 (s, 1H), 8.15 (t, J=7.5 Hz, 1H), 7.99 (d, J=8.0 Hz, 1H), 7.78 (d, J=8.0 Hz, 1H), 7.48 (d, J=7.5 Hz, 1H), 7.45-7.41 (m, 1H), 7.27 (ddd, J=8.0, 8.0, $^4$J$_{H-F}$=5.5 Hz, 1H), 7.07 (dd, J=15.5, 8.0 Hz, 4H), 4.94 (s, 2H), 4.15-3.98 (br m, 2H), 3.61 (s, 3H), 2.96-2.70 (br m, 2H), 2.64-2.59 (m, 1H), 1.65 (d, J=13.0 Hz, 2H), 1.47-1.38 (m, 2H).

EXAMPLE 6

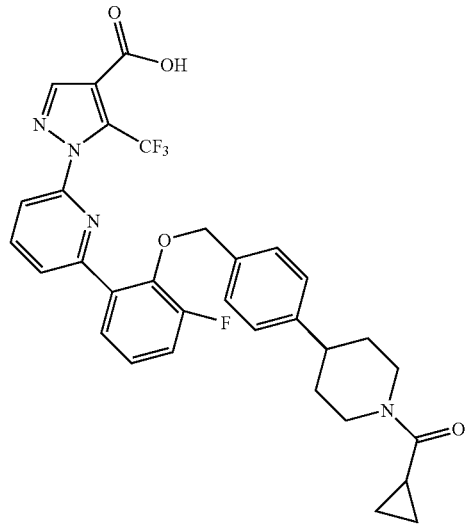 [SMILES: O=C(O)c1cnn(-c2cccc(-c3cccc(F)c3OCc3ccc(C4CCN(C(=O)C5CC5)CC4)cc3)n2)c1C(F)(F)F]

Step A. Ethyl 1-{6-[2-({4-[1-(cyclopropylcarbonyl)piperidin-4-yl]benzyl}oxy)-3-fluorophenyl]pyridin-2-yl}-5-(trifluoromethyl)-1H-pyrazole-4-carboxylate To a solution of the title compound from Example 5 Step C (40 mg, 0.07 mmol) in DCM (1 mL) were added diisopropyl ethyl amine (0.12 mL, 0.70 mmol) and cyclopropanecarbonyl chloride (0.02 mL, 0.21 mmol). The reaction mixture was stirred for 1 h at ambient temperature, then was diluted with sat. aq. NaHCO$_3$ and extracted with DCM. The organic phase was separated, dried over sodium sulfate, filtered, and concentrated in vacuo. The product was used in the subsequent step without further purification: LCMS m/z 636.8 [M+H]$^+$.

Step B. 1-{6-[2-({4-[1-(cyclopropylcarbonyl)piperidin-4-yl]benzyl}oxy)-3-fluorophenyl]pyridin-2-yl}-5-(trifluoromethyl)-1H-pyrazole-4-carboxylic acid To a solution of the title compound from Example 6 Step A (44 mg, 0.07 mmol) in 1,4-dioxane (2 mL) was added lithium hydroxide (1.0 mL, 2.0 M in water, 2.00 mmol), and the resulting mixture was stirred at 50° C. After 2 h, the reaction mixture was rendered acidic by addition of aqueous hydrochloric acid (1.5 mL), then was diluted with 1,4-dioxane and passed though a 0.45 micron syringe filter. Purification by reverse phase HPLC (40 to 100% acetonitrile in water, each with 0.1% v/v TFA) provided the title compound: LCMS m/z 608.9 [M+H]$^+$; $^1$H NMR (500 MHz, d$_6$-DMSO) δ 8.33 (s, 1H), 8.15 (t, J=8.0 Hz, 1H), 7.99 (d, J=8.0 Hz, 1H), 7.78 (d, J=8.0 Hz, 1H), 7.49 (d, J=8.0 Hz, 1H), 7.45-7.41 (m, 1H), 7.27 (ddd, J=8.0, 8.0, $^4$J$_{H-F}$=5.5 Hz, 1H), 7.08 (dd, J=16.5, 8.0 Hz, 4H), 4.95 (s, 2H), 4.56-4.30 (m, 2H), 3.22-3.04 (m, 1H), 2.78-2.68 (m, 1H), 2.68-2.56 (m, 1H), 2.24-1.94 (m, 1H), 1.82-1.62 (br m, 2H), 1.56-1.30 (br m, 2H), 0.82-0.64 (m, 4H).

EXAMPLE 7

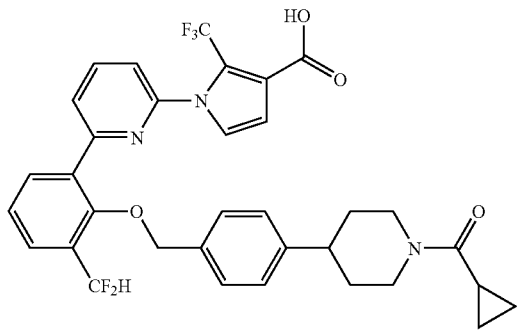 [SMILES: O=C(O)c1ccn(-c2cccc(-c3cccc(C(F)F)c3OCc3ccc(C4CCN(C(=O)C5CC5)CC4)cc3)n2)c1C(F)(F)F]

Step A. Ethyl 1-[6-(3-formyl-2-methoxyphenyl)pyridin-2-yl]-5-(trifluoromethyl)-1H-pyrazole-4-carboxylate To a flask containing the title compound from the Example 1 Step D (1.65 g, 5.16 mmol) were added (3-formyl-2-methoxyphenyl)boronic acid (1.02 g, 5.68 mmol) and trans-dichlorobis(triphenylphosphine)palladium (II) (0.36 g, 0.52 mmol). Acetonitrile (26 mL) and sodium carbonate (12.90 mL, 1.0 M aqueous, 12.90 mmol) were added, and the resulting mixture was degassed via nitrogen sparge. The reaction mixture was stirred at 70° C. for 3 h, then was allowed to cool to ambient temperature and was poured into water. The mixture was extracted with EtOAc, and the organic phase was concentrated in vacuo. Purification by chromatography on silica gel (0 to 30% EtOAc in hexanes, then 30 to 100% EtOAc in hexanes) provided the title compound: LCMS m/z 419.8 [M+H]$^+$; $^1$H NMR (500 MHz, CDCl$_3$) δ 10.48 (s, 1H), 8.18-8.10 (m, 3H), 8.03 (t, J=7.5 Hz, 1H), 7.95 (dd, J=7.5, 1.5 Hz, 1H), 7.67 (d, J=7.5 Hz, 1H), 7.38 (t, J=7.5 Hz, 1H), 4.39 (q, J=7.0 Hz, 2H), 3.68 (s, 3H), 1.40 (t, J=7.0 Hz, 3H).

Step B. Ethyl 1-[6-(3-formyl-2-hydroxyphenyl)pyridin-2-yl]-5-(trifluoromethyl)-1H-pyrazole-4-carboxylate To a cooled solution (0° C.) of the title compound from the Example 7 Step A (1.00 g, 2.30 mmol) in DCM (11 mL), tribromoborane (6.89 mL, 1 M solution in DCM, 6.89 mmol) was carefully added and the reaction mixture was held at 0° C. for 30 min. The reaction mixture was poured into saturated aq. NaHCO$_3$ and extracted with DCM. The organic phase was dried over Na$_2$SO$_4$ and concentrated in vacuo. Purification by chromatography on silica gel (0 to 25% EtOAc in hexanes, then 25 to 100% EtOAc in hexanes) provided the title compound: LCMS m/z 405.8 [M+H]$^+$; $^1$H NMR (500 MHz, CDCl$_3$) δ 12.26 (s, 1H), 10.12 (s, 1H), 8.36-8.28 (m, 2H), 8.15 (s, 1H), 8.03 (t, J=7.5 Hz, 1H), 7.73 (dd, J=8.0, 1.5 Hz, 1H), 7.61 (d, J=8.0 Hz, 1H), 7.16 (t, J=7.5 Hz, 1H), 4.40 (q, J=7.0 Hz, 2H), 1.40 (t, J=7.0 Hz, 3H).

Step C. Ethyl 1-(6-{2-[(4-bromobenzyl)oxy]-3-formylphenyl}pyridin-2-yl)-5-(trifluoromethyl)-1H-pyrazole-4-carboxylate To a solution of the title compound from the Example 7 Step B (310 mg, 0.77 mmol) in DMF (4 mL), were added 1-bromo-4-(bromomethyl)benzene (248 mg, 0.99 mmol) and cesium carbonate (498 mg, 1.53 mmol). The reaction mixture was stirred at 40° C. for 2 h, then was diluted with saturated aq. NaHCO$_3$ and extracted with EtOAc. The organic phase was dried over Na$_2$SO$_4$ and concentrated in vacuo. Purification by chromatography on silica gel (0 to 30% EtOAc in hexanes, then 30 to 100% EtOAc in hexanes) provided the title compound: LCMS m/z 575.8 [M+H]$^+$; $^1$H NMR (500 MHz, CDCl$_3$) δ 10.33 (s, 1H), δ 8.16 (s, 1H), 8.10 (dd, J=7.0, 2.0 Hz, 1H), 8.06 (d, J=7.5 Hz, 1H), 7.98-7.92 (m, 2H), 7.67 (d, J=8.0 Hz, 1H), 7.45-7.38 (m, 3H), 7.02 (d, J=8.5 Hz, 2H), 4.69 (s, 2H), 4.40 (q, J=7.0 Hz, 2H), 1.40 (t, J=7.0 Hz, 3H).

Step D. Ethyl 1-(6-{2-[(4-bromobenzyl)oxy]-3-(difluoromethyl)phenyl}pyridin-2-yl)-5-(trifluoromethyl)-1H-pyrazole-4-carboxylate To a Teflon vial containing a solution of the title compound from the Example 7 Step C (400 mg, 0.70 mmol) in DCM (3 mL) was added DAST reagent (0.16 mL, 1.12 mmol), followed by EtOH (0.01 mL, 0.14 mmol). The vial was then capped and the reaction mixture was allowed to stir at ambient temperature. After 12 h, the reaction mixture was poured into sat. aq. NaHCO$_3$ (25 mL) and extracted with DCM. The organic phase was dried over Na$_2$SO$_4$ and concentrated in vacuo. Purification by chromatography on silica gel (0 to 30% EtOAc in hexanes, then 30 to 100% EtOAc in hexanes) provided the title compound: LCMS m/z 597.7 [M+H]$^+$; $^1$H NMR (500 MHz, CDCl$_3$) δ 8.15 (s, 1H), 8.03 (d, J=8.0 Hz, 1H), 7.99-7.90 (m, 2H), 7.69 (d, J=7.5 Hz, 1H), 7.65 (d, J=7.5 Hz, 1H), 7.45 (d, J=8.0 Hz, 2H), 7.40 (t, J=7.5 Hz, 1H), 7.05 (d, J=8.0 Hz, 2H), 6.98 (t, $^2$J$_{H-F}$=55.5 Hz, 1H), 4.57 (s, 2H), 4.40 (q, J=7.0 Hz, 2H), 1.40 (t, J=7.0 Hz, 3H).

Step E. tert-Butyl 4-(4-{[2-(difluoromethyl)-6-[6-[4-(ethoxycarbonyl)-5-(trifluoromethyl)-1H-pyrazol-1-yl]pyridin-2-yl]phenoxy}methyl]phenyl)-3,6-dihydropyridine-1(2H)-carboxylate To a flask containing the title compound from the Example 7 Step D (166 mg, 0.28 mmol) were added tert-butyl 4-(4,4,5,5-tetramethyl-1,3,2-dioxaborolan-2-yl)-3,6-dihydropyridine-1(2H)-carboxylate (95 mg, 0.31 mmol; *Tetrahedron Lett*, 2000, 41, 3705-3708) and trans-dichlorobis(triphenylphosphine)palladium (II) (20 mg, 0.03 mmol). Acetonitrile (3 mL) and sodium carbonate (0.70 mL, 1.0 M aqueous, 0.70 mmol) were added, and the resulting mixture was degassed via nitrogen sparge. The reaction mixture was stirred at 70° C. for 3 h, then was allowed to cool to ambient temperature and was poured into water. The mixture was extracted with EtOAc, and the organic phase was concentrated in vacuo. Purification by chromatography on silica gel (0 to 30% EtOAc in hexanes, then 30 to 100% EtOAc in hexanes) provided the title compound: LCMS m/z 699.0 [M+H]$^+$; $^1$H NMR (500 MHz, CDCl$_3$) δ 8.08 (s, 1H), 8.03 (d, J=8.0 Hz, 1H), 7.93-7.83 (m, 2H), 7.60 (dd, J=11.5, 8.0 Hz, 2H), 7.32 (t, J=7.5 Hz, 1H), 7.26 (d, J=8.0 Hz, 2H), 7.08 (d, J=8.0 Hz, 2H), 6.87 (t, $^2$J$_{H-F}$=55.5 Hz, 1H), 6.04-5.89 (br m, 1H), 4.52 (s, 2H), 4.32 (q, J=7.0 Hz, 2H), 4.04-3.96 (m, 2H), 3.62-3.52 (m, 2H), 2.48-2.38 (m, 2H), 1.43 (s, 9H), 1.33 (t, J=7.0 Hz, 3H).

Step F. tert-Butyl 4-(4-{[2-(difluoromethyl)-6-{6-[4-(ethoxycarbonyl)-5-(trifluoromethyl)-1H-pyrazol-1-yl]pyridin-2-yl}phenoxy]methyl}phenyl)piperidine-1-carboxylate To a degassed solution of the title compound from Example 7 Step E (115 mg, 0.17 mmol) in EtOAc (5 mL) was added platinum oxide (22 mg). The reaction flask was fitted with a hydrogen balloon attached to a 3-way adapter. The reaction mixture was then evacuated and back-filled with hydrogen. After this process was repeated three times, the reaction mixture was placed under a hydrogen atmosphere, and was stirred vigorously. After 45 min, the reaction mixture was filtered though Celite, rinsing with EtOAc. The mixture was dried over anhydrous sodium sulfate, filtered, and concentrated in vacuo. Purification by chromatography on silica gel (0 to 30% EtOAc in hexanes, 30 to 100% EtOAc in hexanes) provided the title compound: LCMS m/z 701.0 [M+H]$^+$; $^1$H NMR (500 MHz, CDCl$_3$) δ 8.15 (s, 1H), 8.12 (d, J=8.0 Hz, 1H), 8.01-7.92 (m, 2H), 7.68 (dd, J=8.0, 6.0 Hz, 2H), 7.39 (t, J=8.0 Hz, 1H), 7.15 (dd, J=12.5, 8.5 Hz, 4H), 6.94 (t, $^2J_{H-F}$=55.5 Hz, 1H), 4.57 (s, 2H), 4.40 (q, J=7.0 Hz, 2H), 4.34-4.16 (br m, 2H), 2.90-2.72 (br m, 2H), 2.68-2.60 (m, 1H), 1.86-1.74 (m, 2H), 1.66-1.56 (m, 2H), 1.49 (s, 9H), 1.40 (t, J=7.0 Hz, 1H).

Step G. Ethyl 1-{6-[3-(difluoromethyl)-2-{[4-piperidin-4-yl)benzyl]oxy}phenyl]pyridin-2-yl}-5-(trifluoromethyl)-1H-pyrazole-4-carboxylate A solution of the title compound from Example 7 Step F (88 mg, 0.13 mmol) in acetic acid (2 mL) and water (0.5 mL) was stirred at 90° C. for 14 h. The reaction mixture was allowed to cool to ambient temperature and evaporated in vacuo. The product was used in the subsequent step without further purification: LCMS m/z 600.8 [M+H]$^+$.

Step H. Ethyl 1-{6-[2-({4-[1-(cyclopropylcarbonyl) piperidin-4-yl}benzyl}oxy)-3-(difluoromethyl)phenyl]pyridin-2-yl}-5-(trifluoromethyl)-1H-pyrazole-4-carboxylate To a solution of the title compound from Example 7 Step G (75 mg, 0.13 mmol) in DCM (2 mL) were added diisopropyl ethyl amine (0.22 mL, 1.25 mmol) and cyclopropanecarbonyl chloride (0.03 mL, 0.37 mmol). The reaction mixture was stirred for 1 h at ambient temperature, then was diluted with sat. aq. NaHCO$_3$ and extracted with DCM. The organic phase was separated, dried over sodium sulfate, filtered, and concentrated in vacuo. The product was used in the subsequent step without further purification: LCMS m/z 669.5 [M+H]$^+$.

Step I. 1-{6-[2-({4-[1-(Cyclopropylcarbonyl)piperidin-4-yl]benzyl}oxy)-3-[(difluoromethyl)phenyl] pyridin-2-yl]-5-(trifluoromethyl)-1H-pyrazole-4-carboxylic acid To a solution of the title compound from Example 7 Step H (122 mg, 0.18 mmol) in 1,4-dioxane (2 mL) was added lithium hydroxide (1.0 mL, 2.0 M in water, 2.00 mmol), and the resulting mixture was stirred at 50° C. After 2 h, the reaction mixture was rendered acidic by addition of aqueous hydrochloric acid (1.5 mL), then was diluted with 1,4-dioxane and passed though a 0.45 micron syringe filter. Purification by reverse phase HPLC (40 to 100% acetonitrile in water, each with 0.1% v/v TFA) provided the title compound: LCMS m/z 641.0 [M+H]$^+$; $^1$H NMR (500 MHz, d$_6$-DMSO) δ 8.32 (s, 1H), 8.19 (t, J=7.5 Hz, 1H), 8.05 (d, J=7.5 Hz, 1H), 7.84 (d, J=7.5 Hz, 2H), 7.70 (d, J=8.0 Hz, 1H), 7.46 (t, J=8.0 Hz, 1H), 7.18 (d, J=8.0 Hz, 2H), 7.14 (t, $^2J_{1-F}$=55.0 Hz, 1H), 7.07 (d, J=8.0 Hz, 2H), 4.55 (s, 2H), 4.54-4.46 (br m, 1H), 4.39-4.29 (br m, 1H), 3.18-3.06 (m, 1H), 2.80-2.68 (m, 1H), 2.66-2.52 (m, 1H), 2.02-1.94 (m, 1H), 1.84-1.64 (m, 2H), 1.58-1.30 (m, 2H), 0.79-0.64 (m, 4H).

EXAMPLE 8

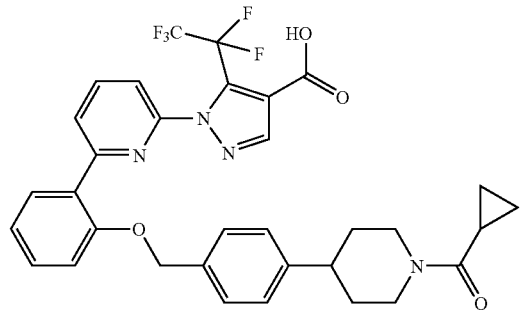 [SMILES: O=C(O)c1cnn(-c2cccc(-c3ccccc3OCc3ccc(C4CCN(C(=O)C5CC5)CC4)cc3)n2)c1C(F)(F)C(F)(F)F]

Step A. Ethyl-2-(ethoxymethylene)-4,4,5,5,5-pentafluoro-3-oxopentanoate

A sealable vial was charged with triethylorthoformate (1.07 mL, 6.41 mmol), acetic anhydride (3.22 mL, 34.2 mmol) and ethyl 4,4,5,5,5-pentafluoro-3-oxopentanoate (0.747 mL, 4.27 mmol), and the resulting mixture was capped and stirred at 135° C. After 2 h, the reaction mixture was allowed to cool to room temperature, and the volatiles were removed in vacuo to provide the title compound as a mixture of olefin isomers, which was used without further purification.

Step B. Ethyl 1-(6-chloropyridin-2-yl)-5-(pentafluoroethyl)-1H-pyrazole-4-carboxylate To a solution of the title compound from Example 8 Step A (706 mgs, 2.43 mmol) and 2-chloro-6-hydrazinopyridine (233 mgs, 1.62 mmol) in acetonitrile (8 mL) was added TEA (339 μL, 2.43 mmol), and the resulting mixture was stirred at 50° C. After 30 min, the reaction mixture was allowed to cool to room temperature, then was concentrated in vacuo. Purification by flash chromatography on silica gel (0 to 30% EtOAc in hexanes, then 30 to 100% EtOAc in hexanes) provided the title compound: LCMS m/z 369.7 [M+H]$^+$; $^1$H NMR (500 MHz, CDCl$_3$) δ 8.18 (s, 1H), 7.88 (t, J=8.0 Hz, 1H), 7.50 (d, J=7.5 Hz, 1H), 7.48 (d, J=7.5 Hz, 1H), 4.36 (q, J=7.0 Hz, 2H), 1.37 (t, J=7.0 Hz, 3H).

Step C. Ethyl 1-(6-(2-hydroxyphenyl)pyridin-2-yl)-5-(pentafluoroethyl)-1H-pyrazole-4-carboxylate To a flask containing the title compound from the Example 8 Step B (430 mg, 1.16 mmol) were added 2-hydroxy-phenylboronic acid (241 mg, 1.75 mmol) and trans-dichlorobis (triphenylphosphine)palladium (II) (82 mg, 0.116 mmol). Acetonitrile (6 mL) and sodium carbonate (3 mL, 1.0 M aqueous, 3 mmol) were added, and the resulting mixture was degassed via nitrogen sparge. The reaction mixture was stirred at 70° C. for 15 h, then was allowed to cool to ambient temperature and was poured into water. The mixture was extracted with EtOAc, and the organic phase was concentrated in vacuo. Purification by chromatography on silica gel (0 to 40% EtOAc in hexanes, then 40 to 100% EtOAc in hexanes) provided the title compound: LCMS m/z 427.7

[M+H]⁺; ¹H NMR (500 MHz, CDCl₃) δ 12.08 (s, 1H), 8.24 (s, 1H), 8.09-8.04 (m, 2H), 7.82 (dd, J=8.0, 1.5 Hz, 1H), 7.37-7.33 (m, 2H), 7.01 (dd, J=8.0, 1.5 Hz, 1H), 6.98-6.95 (m, 1H), 4.38 (q, J=7.0 Hz, 2H), 1.39 (t, J=7.0 Hz, 3H).

Step D. Ethyl 1-(6-(2-((4-bromobenzyl)oxy)phenyl) pyridin-2-yl)-5-(pentafluoroethyl)-1H-pyrazole-4-carboxylate To flask containing the title compound from Example 8 Step C (415 mg, 0.971 mmol) were added cesium carbonate (791 mg, 2.43 mmol), 4-bromobenzyl bromide (316 mg, 1.26 mmol), and DMF (6 mL), and the resulting mixture was stirred at 45° C. After 3 h, the reaction mixture was allowed to cool to room temperature, then was poured into brine and extracted with EtOAc. The organic phase was separated and concentrated in vacuo. Purification by chromatography on silica gel (0 to 25% EtOAc in hexanes, then 25 to 100% EtOAc in hexanes) provided the title compound: LCMS m/z 597.7 [M+H]⁺; ¹H NMR (500 MHz, CDCl₃) δ 8.21 (s, 1H), 8.05 (d, J=8.0 Hz, 1H), 7.86 (t, J=8.0 Hz, 1H), 7.82 (dd, J=8.0, 2.0 Hz, 1H), 7.49-7.47 (m, 2H), 7.38-7.35 (m, 2H), 7.23 (d, J=8.5 Hz, 2H), 7.11-7.08 (m, 1H), 7.02 (d, J=8.5 Hz, 1H), 5.09 (s, 2H), 4.37 (q, J=7.0 Hz, 2H), 1.38 (t, J=7.0 Hz, 3H).

Step E. tert-Butyl 4-(4-((2-(6-(4-(ethoxycarbonyl)-5-(pentafluoroethyl)-1H-pyrazol-1-yl)pyridin-2-yl) phenoxy)methyl)phenyl)-3,6-dihydropyridine-1(2H) carboxylate To a flask containing the title compound from the Example 8 Step D (550 mg, 0.92 mmol) were added tert-butyl 4-(4,4,5,5-tetramethyl-1,3,2-dioxaborolan-2-yl)-3,6-dihydropyridine-1(2H)-carboxylate (428 mg, 1.38 mmol; *Tetrahedron Lett*, 2000, 41, 3705-3708) and trans-dichlorobis(triphenylphosphine)palladium (II) (65 mg, 0.092 mmol). Acetonitrile (4 mL) and sodium carbonate (2.3 mL, 1.0 M aqueous, 2.3 mmol) were added, and the resulting mixture was degassed via nitrogen sparge. The reaction mixture was stirred at 70° C. for 18 h, then was allowed to cool to ambient temperature and was poured into water. The mixture was extracted with EtOAc, and the organic phase was concentrated in vacuo. Purification by chromatography on silica gel (0 to 40% EtOAc in hexanes, then 40 to 100% EtOAc in hexanes) provided the title compound: LCMS m/z 698.8 [M+H]⁺; ¹H NMR (500 MHz, CDCl₃) δ 8.21 (s, 1H), 8.12 (d, J=8.0 Hz, 1H), 7.86-7.83 (m, 2H), 7.37-7.31 (m, 6H), 7.10-7.04 (m, 2H), 6.08-6.03 (br m, 1H), 5.14 (s, 2H), 4.38 (q, J=7.0 Hz, 2H), 4.09-4.05 (m, 2H), 3.65-3.63 (m, 2H), 2.54-2.51 (m, 2H), 1.50 (s, 9H), 1.38 (t, J=7.0 Hz, 3H).

Step F. tert-Butyl 4-(4-((2-(6-(4-(ethoxycarbonyl)-5-(pentafluoroethyl)-1H-pyrazol-1-yl)pyridin-2-yl) phenoxy)methyl)phenyl)piperidine-1-carboxylate To a degassed solution of the title compound from Example 8 Step E (549 mg, 0.79 mmol) in EtOAc (15 mL) was added platinum(IV) oxide (200 mg). The reaction flask was fitted with a hydrogen balloon attached to a 3-way adapter. The reaction mixture was then evacuated and back-filled with hydrogen. After this process was repeated three times, the reaction mixture was placed under a hydrogen atmosphere, and was stirred vigorously. After 20 min, the reaction mixture was filtered though Celite, rinsing with EtOAc. The filtrate was then concentrated in vacuo. Purification by chromatography on silica gel (0 to 40% EtOAc in hexanes, then 40 to 100% EtOAc in hexanes) provided the title compound: LCMS m/z 700.8 [M+H]⁺; ¹H NMR (500 MHz, CDCl₃) δ 8.21 (s, 1H), 8.13 (d, J=8.0 Hz, 1H), 7.86-7.82 (m, 2H), 7.38-7.35 (m, 2H), 7.30 (d, J=8.0 Hz, 2H), 7.19 (d, J=8.0 Hz, 2H), 7.09-7.06 (m, 2H), 5.12 (s, 2H), 4.37 (q, J=7.0 Hz, 2H), 4.29-4.20 (br m, 2H), 2.83-2.76 (br m, 2H), 2.68-2.63 (m, 1H), 1.84-1.81 (m, 2H), 1.49 (s, 9H), 1.38 (t, J=7.0 Hz, 3H).

Step G. Ethyl 5-(pentafluoroethyl)-1-(6-(2-((4-piperidin-4-ylbenzyl)oxy)phenyl)pyridin-2-O-1H-pyrazole-4-carboxylate To a solution of the title compound from Example 8 Step F (549 mg, 0.78 mmol) in DCM (6 mL) was added TFA (3 mL), and the resulting mixture was stirred at room temperature. After 30 min, the reaction mixture was concentrated in vacuo. The crude TFA salt was used without further purification: LCMS m/z 600.8 [M+H]⁺. A portion of this material was derivatized as described in the following step.

Step. H. 1-(6-(2-((4-(1-(Cyclopropylcarbonyl)piperidin-4-yl)benzyl)oxy)phenyl)pyridin-2-yl)-5-(pentafluoroethyl)-1H-pyrazole-4-carboxylic acid To a solution of the title compound from Example 8 Step G (90 mg, 0.15 mmol) in DCM (1 mL) were added DIEA (262 µL, 1.50 mmol) and cyclopropanecarbonyl chloride (46 µL, 0.45 mmol), and the resulting mixture was allowed to stir at room temperature. After 45 min, the reaction mixture was quenched by addition of sat aq NaHCO₃ and the aqueous phase was extracted with DCM. The organic phase was separated and concentrated in vacuo to provide the unpurified amide, which was used without further purification: LCMS m/z 668.8 [M+H]⁺. To a solution of the carbamate in dioxane (2 mL) was added lithium hydroxide (1 mL, 2N aqueous, 2 mmol), and the mixture was stirred at 50° C. After 1 h, the reaction mixture was rendered acidic by addition of HCl (2N aqueous), then was diluted with acetonitrile and purified by reverse phase HPLC (40 to 100% acetonitrile/water, both 0.1% v/v TFA) to provide the title compound: LCMS m/z 640.9 [M+H]⁺; ¹H NMR (500 MHz, d₆-DMSO) δ 8.34 (s, 1H), 8.14 (d, J=7.5 Hz, 1H), 8.10 (t, J=8.0 Hz, 1H), 7.62 (dd, J=8.0, 2.0 Hz, 1H), 7.61 (d, J=7.0 Hz, 1H), 7.44-7.40 (m, 1H), 7.34 (d, J=8.0 Hz, 2H), 7.26 (d, J=8.0 Hz, 1H), 7.23 (d, J=8.0 Hz, 1H), 7.06 (t, J=8.0 Hz, 2H), 5.20 (s, 2H), 4.54-4.50 (m, 1H), 4.38-4.34 (m, 1H), 3.16-3.14 (m, 1H), 2.81-2.75 (m, 1H), 2.64-2.59 (m, 1H), 2.01-1.96 (m, 1H), 1.83-1.74 (m, 2H), 1.57-1.42 (m, 2 H), 0.75-0.68 (m, 4H).

EXAMPLE 9

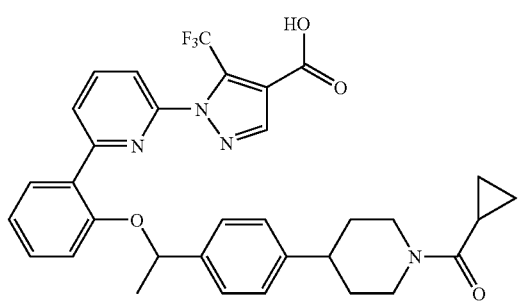 [SMILES: CC(Oc1ccccc1-c1cccc(-n2ncc(C(=O)O)c2C(F)(F)F)n1)c1ccc(C2CCN(C(=O)C3CC3)CC2)cc1]

Step A. tert-Butyl-4-(4-acetylphenyl)-3,6-dihydropyridine-1(2H)-carboxylate

To a flask containing 4-bromoacetophenone (300 mg, 1.51 mmol) were added tert-butyl 4-(4,4,5,5-tetramethyl-1,3,2-dioxaborolan-2-yl)-3,6-dihydropyridine-1(2H)-carboxylate (583 mg, 3.01 mmol; Tetrahedron Lett, 2000, 41, 3705-3708) and trans-dichlorobis(triphenylphosphine)palladium (II) (106 mg, 0.151 mmol). Acetonitrile (6 mL) and sodium carbonate (3.8 mL, 1.0 M aqueous, 3.8 mmol) were added, and the resulting mixture was degassed via nitrogen sparge. The reaction mixture was stirred at 70° C. for 18 h, then was allowed to cool to ambient temperature and was poured into water. The mixture was extracted with EtOAc, and the organic phase was concentrated in vacuo. Purification by chromatography on silica gel (0 to 40% EtOAc in hexanes, then 40 to 100% EtOAc in hexanes) provided the title compound: $^1$H NMR (500 MHz, CDCl$_3$) δ 7.92 (d, J=8.5 Hz, 2H), 7.45 (d, J=8.5 Hz, 2H), 6.21-6.15 (br m, 1H), 4.12-4.10 (m, 2H), 3.65 (t, J=5.5 Hz, 2H), 2.59 (s, 3H), 2.56-2.52 (br m, 2H), 1.49 (s, 9H).

Step B. 1-(4-(1-(Cyclopropylcarbonyl)-1,2,3,6-tetrahydropyridin-4-yl)phenyl)ethanol To a solution of the title compound from Example 9 Step A (301 mg, 1.00 mmol) in DCM (6 mL) was added TFA (3 mL). After 15 min, the reaction mixture was concentrated in vacuo, and the crude TFA salt was used without further purification. To a solution of the crude TFA salt in DCM (5 mL) were added DIEA (263 μL, 15.1 mmol) and cyclopropanecarbonyl chloride (274 μL, 3.01 mmol), and the resulting mixture was allowed to stir at room temperature. After 45 min, the reaction mixture was quenched by addition of sat aq NaHCO$_3$ and the aqueous phase was extracted with DCM. The organic phase was separated and concentrated in vacuo to provide the crude amide, which was used without further purification: LCMS m/z 270.5 [M+H]$^+$. To a solution of the crude amide in MeOH (10 mL) was added NaBH$_4$ (171 mg, 4.52 mmol), and the mixture was stirred at room temperature. After 20 min, the reaction mixture was concentrated in vacuo and was redissolved in EtOAc. The mixture was washed with sat aq NH$_4$Cl, and the organic phase was separated, dried over sodium sulfate, and concentrated in vacuo. The crude alcohol was used without further purification: LCMS m/z 272.5 [M+H]$^+$.

Step C. Ethyl 1-(6 (2 (1-(4 (1 (cyclopropylcarbonyl)-1,2,3,6-tetrahydropyridin-4-yl)phenyl)ethoxy)phenyl)pyridin-2-yl)-5-(trifluoromethyl)-1H-pyrazole-4-carboxylate To a solution of the title compound from Example 1 Step E (189 mg, 0.50 mmol), the title compound from Example 9 Step B (204 mg, 0.75 mmol), and triphenylphosphine (197 mg, 0.75 mmol) in DCM (5 mL) was added diisopropyl azodicarboxylate (0.146 mL, 0.75 mmol), and the resulting mixture was stirred at ambient temperature. After 30 min, the reaction mixture was concentrated in vacuo. Purification by flash chromatography on silica gel (0 to 60% EtOAc in hexanes, then 60 to 100% EtOAc in hexanes) provided the title compound: LCMS m/z 630.8 [M+H]$^+$.

Step D. 1-(6-(2-(1-(4-(1-(c clopropylcarbonyl)piperidin-4-yl)phenyl)ethoxy)phenyl)pyridin-2-yl)-5-(trifluoromethyl)-1H-pyrazole-4-carboxylic acid To a degassed solution of the title compound from Example 9 Step C (100 mg, 0.158 mmol) in EtOAc (10 mL) was added platinum(IV) oxide (47 mg). The reaction flask was fitted with a hydrogen balloon attached to a 3-way adapter. The reaction mixture was then evacuated and back-filled with hydrogen. After this process was repeated three times, the reaction mixture was placed under a hydrogen atmosphere, and was stirred vigorously. After 20 min, the reaction mixture was filtered though Celite, rinsing with EtOAc. The mixture was then concentrated in vacuo to yield a hydrogenation product which was taken forward without further purification: LCMS m/z 630.8 [M+H]$^+$. To a solution of the hydrogenation product in dioxane (2 mL) was added lithium hydroxide (1 mL, 2N aqueous, 2 mmol), and the mixture was stirred at 50° C. After 1 h, the reaction mixture was rendered acidic by addition of HCl (2N aqueous), then was diluted with acetonitrile and purified by reverse phase HPLC (40 to 100% acetonitrile/water, both 0.1% v/v TFA) to provide the title compound: LCMS m/z 604.8 [M+H]$^+$; $^1$H NMR (500 MHz, d$_6$-DMSO) δ 8.32 (s, 1H), 8.28 (d, J=7.5 Hz, 1H), 8.21 (t, J=7.5 Hz, 1H), 7.75 (d, J=7.5 Hz, 1H), 7.72 (dd, J=7.5, 2.0 Hz, 1H), 7.32-7.29 (m, 1H), 7.30 (d, J=8.0 Hz, 2H), 7.20 (d, J=8.0 Hz, 2H), 7.06 (d, J=8.0 Hz, 1H), 7.01 (t, J=7.5 Hz, 1H), 5.61 (q, J=6.5 Hz, 1H), 4.52-4.48 (m, 1H), 4.38-4.32 (m, 1H), 3.14-3.10 (m, 1H), 2.77-2.72 (m, 1H), 2.64-2.58 (m, 1H), 1.99-1.96 (m, 1H), 1.82-1.72 (m, 2H), 1.55 (d, J=6.5 Hz, 3H), 1.55-1.51 (m, 1H), 1.42-1.36 (m, 1H), 0.78-0.68 (m, 4H).

EXAMPLE 10

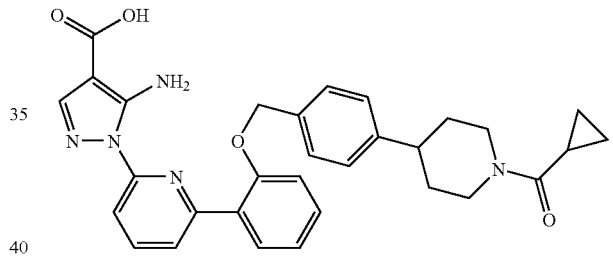

Step A. Ethyl 5-amino-1-(6-chloropyridin-2-yl)-1H-pyrazole-4-carboxylic acid To a mixture of 2-chloro-6-hydrazinopyridine (2.00 g, 13.93 mmol) and ethyl-2-cyano-3-ethoxyacrylate (2.36 g, 13.93 mmol) was added EtOH (14 mL) and the resulting suspension was stirred at room temperature. After 5 min, the mixture was heated at reflux. After 2 h, the reaction mixture was allowed to cool to room temperature. The title compound was isolated as a white solid by filtration, and was used without further purification: LCMS m/z 267.0 [M+I-1]$^+$.

Step B. Ethyl 5-amino-1-(6-(2-hydroxyphenyl)pyridin-2-yl)-1H-pyrazole-4-carboxylate To a vial containing the title compound from Example 10 Step A (200 mg, 0.75 mmol) were added 2-hydroxyphenylboronic acid (125 g, 0.90 mmol) and trans-dichlorobis(triphenylphosphine) palladium (II) (53 mg, 0.075 mmol). Acetonitrile (4 mL) and sodium carbonate (1.9 mL, 1.0 M aqueous, 1.9 mmol) were added, and the resulting mixture was degassed via nitrogen sparge. The reaction vial was capped and the reaction mixture was stirred at 85° C. After 18 h, the reaction mixture was allowed to cool to room temperature and was poured into water. The mixture was extracted with EtOAc, and the organic phase was concentrated in vacuo. Purification by chromatography on silica gel (0 to 75% EtOAc in hexanes, then 75 to 100% EtOAc) provided the title compound: LCMS m/z 324.9 [M+H]$^+$; $^1$H NMR (500 MHz, CDCl$_3$) δ 10.69 (s, 1H), 8.02 (t, J=8.0 Hz, 1H), 7.85 (dd, J=8.0, 3.5 Hz, 1H), 7.83 (s, 1H), 7.72-7.68 (m, 2H), 7.39-7.35 (m, 1H), 7.07-7.05 (m, 1H), 7.02-6.99 (m, 1H), 6.63 (br s, 2H), 4.32 (q, J=7.0 Hz, 2H), 1.37 (t, J=7.0 Hz, 3H).

Step C. tert-Butyl 4-(4-((2-(6-(5-amino-4-(ethoxycarbonyl)-1-pyrazol-1-yl)pyridin-2-yl)phenoxy)methyl)phenyl)piperidine-1-carboxylate To a solution of the title compound from Example 10 Step B (45 mg, 0.14 mmol), the title compound from Example 1 Step C (53 mg, 0.18 mmol), and triphenylphosphine (47 mg, 0.18 mmol) in DCM (1 mL) was added diisopropyl azodicarboxylate (0.035 mL, 0.18 mmol), and the resulting mixture was stirred at ambient temperature. After 30 min, the reaction mixture was concentrated in vacuo. Purification by flash chromatography on silica gel (0 to 80% EtOAc in hexanes, then 80 to 100% EtOAc in hexanes) provided the title compound: LCMS m/z 598.0 [M+H]; (500 MHz, CDCl$_3$) δ 7.85-7.80 (m, 2H), 7.76 (s, 1H), 7.69-7.63 (m, 2H), 7.41-7.38 (m, 1H), 7.27-7.25 (m, 2H), 7.17-7.10 (m, 4H), 6.42-6.35 (br s, 2H), 5.12 (s, 2H), 4.28 (q, J=7.0 Hz, 2H), 4.28-4.16 (br m, 2H), 2.82-2.74 (br m, 2H), 2.65-2.59 (m, 1H), 1.80-1.78 (m, 2H), 1.65-1.55 (m, 2H), 1.48 (s, 9H), 1.35 (t, J=7.0 Hz, 3H).

Step D. 5-Amino-1-(6-(2-((4-(1-(cyclopropylcarbonyl)piperidin-4-yl)benzyl)oxy)phenyl)pyridin-2-yl)-1H-pyrazole-4-carboxylic acid To a solution of the title compound from Example 10 Step C (139 mg, 0.23 mmol) in DCM (3 mL) was added TFA (0.75 mL). After 10 min, the reaction mixture was concentrated in vacuo. The crude TFA salt was used without further purification: LCMS m/z 497.8 [M+H]. To a portion of the crude TFA salt (0.093 mmol) in DCM (1.5 mL) were added DIEA (162 μL, 0.93 mmol) and cyclopropanecarbonyl chloride (11 μL, 0.121 mmol), and the resulting mixture was allowed to stir at room temperature. After 2 h, the reaction mixture was quenched by addition of sat aq NaHCO$_3$ and the aqueous phase was extracted with DCM. The organic phase was separated and concentrated in vacuo to provide the crude amide, which was used without further purification: LCMS m/z 565.9 [M+H]$^+$. To a solution of the amide in dioxane (2 mL) was added lithium hydroxide (1 mL, 2N aqueous, 2 mmol), and the mixture was stirred at 75° C. After 18 h, the reaction mixture was rendered acidic by addition of HCl (2N aqueous), then was diluted with acetonitrile and purified by reverse phase HPLC (40 to 100% acetonitrile/water, both 0.1% v/v TFA) to provide the title compound: LCMS m/z 537.9 [M+H]$^+$; $^1$H NMR (500 MHz, d$_6$-DMSO) δ 8.01 (t, J=8.0 Hz, 1H), 7.94 (t, J=8.0 Hz, 1H), 7.77 (dd, J=8.0, 2.5 Hz, 1H), 7.74 (s, 1H), 7.69 (d, J=7.5 Hz, 1H), 7.65-7.61 (m, 2H), 7.48-7.21 (m, 6H), 7.12-7.09 (m, 1H), 5.18 (app d, J=4.5 Hz, 2H), 4.50-4.48 (m, 1H), 4.35-4.32 (m, 1H), 3.17-3.10 (m, 1 H), 2.77-2.74 (m, 1H), 2.63-2.58 (m, 1H), 1.99-1.96 (m, 2H), 1.80-1.70 (m, 2H), 1.54-1.36 (m, 2H), 0.74-0.67 (m, 4H).

EXAMPLE 11

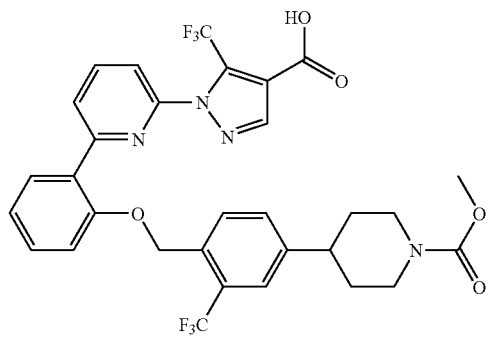 [SMILES: COC(=O)N1CCC(c2ccc(COc3ccccc3-c3cccc(-n4ncc(C(=O)O)c4C(F)(F)F)n3)c(C(F)(F)F)c2)CC1]

Step A. ten-Butyl 4-(4-(methoxycarbonyl)-3-(trifluoromethyl)phenyl)-3,6-dihydropyridine-1-(2H)-carboxylate To a solution of 4-hydroxy-2-(trifluoromethyl)benzoic acid (3.00 g, 14.55 mmol) in DCM (60 mL) and MeOH (15 mL) was added trimethylsilyl diazomethane (8.75 mL, 2.0 M in hexanes, 17.5 mmol). After 1 h, the mixture was quenched by careful addition of acetic acid (5 mL), and the resulting mixture was poured into sat aq NaHCO$_3$ and extracted with EtOAc. The organic phase was concentrated in vacuo to provide the title compound: LCMS m/z 220.9 [M+H]$^+$. To a solution of the methyl ester (1.50 g, 6.81 mmol) in DCM (34 mL) was added pyridine (1.21 mL, 15.0 mmol), followed by triflic anhydride (1.27 mL, 7.5 mmol). After 40 min, the reaction mixture was poured into sat aq NaHCO$_3$. The organic phase was separated, concentrated in vacuo, and filtered though silica to provide the triflate: LCMS m/z 352.7 [M+H]$^+$. To a flask containing the triflate obtained above (300 mg, 0.852 mmol) were added ten-butyl 4-(4,4,5,5-tetramethyl-1,3,2-dioxaborolan-2-yl)-3,6-dihydropyridine-1(2H)-carboxylate (263 mg, 0.852 mmol; Tetrahedron Lett, 2000, 41, 3705-3708) and trans-dichlorobis(triphenylphosphine) palladium (II) (60 mg, 0.085 mmol). Acetonitrile (4 mL) and sodium carbonate (2 mL, 1.0 M aqueous, 2 mmol) were added, and the resulting mixture was degassed via nitrogen sparge. The reaction mixture was stirred at 70° C. for 18 h, then was allowed to cool to ambient temperature and was loaded directly onto a silica gel column. Purification by chromatography on silica gel (0 to 40% EtOAc in hexanes, then 40 to 100% EtOAc in hexanes) provided the title compound: LCMS m/z 220.9 [M+H]$^+$; $^1$H NMR (500 MHz, CDCl$_3$) δ 7.79 (d, J=8.5 Hz, 1H), 7.73 (br s, 1H), 7.57 (dd, J=8.5, 2.0 Hz, 1H), 6.24-6.15 (br s, 1H), 4.12 (br m, 2H), 3.93 (s, 3H), 3.66 (t, J=5.5 Hz, 2H), 2.56-2.52 (br m, 2H), 1.49 (s, 9H).

Step B. tert-Butyl 4-(4-methoxycarbonyl-3-trifluoromethyl)phenyl)piperidine-1-carboxylate To a degassed solution of the title compound from Example 11 Step A (300 mg, 0.778 mmol) in EtOAc (10 mL) was added platinum(IV) oxide (90 mg). The reaction flask was fitted with a hydrogen balloon attached to a 3-way adapter. The reaction mixture was then evacuated and back-filled with hydrogen. After this process was repeated three times, the reaction mixture was placed under a hydrogen atmosphere, and was stirred vigorously. After 35 min, the reaction mixture was filtered though Celite, rinsing with EtOAc. Purification by flash chromatography on silica gel (0 to 60% EtOAc in hexanes, then 60 to 100% EtOAc in hexanes) provided the title compound: $^1$H NMR (500 MHz, CDCl$_3$) δ 7.76 (d, J=8.0 Hz, 1H), 7.57 (s, 1H), 7.43 (d, J=8.0 Hz, 1H), 4.32-4.20 (br s, 2H), 3.92 (s, 3H), 2.83-2.72 (m, 3H), 1.85-1.81 (m, 2H), 1.67-1.59 (m, 2H), 1.48 (s, 9H).

Step C. tert-Butyl 4-(4-((2-(6-(4-(ethoxycarbonyl)-5-(trifluoromethyl)-1H-pyrazol-1-yl)pyridin-2-yl)phenoxy)methyl)-3-(trifluoromethyl)phenyl)piperidine-1-carboxylate To a cooled (−78° C.) solution of the title compound from Example 11 Step B (250 mg, 0.65 mmol) in DCM (5 mL) was added DIBAL-H (1.0 mL, 1.0 M in DCM, 1.0 mmol). After 1 h, the reaction mixture was quenched by addition of MeOH (1 mL). The resulting mixture was diluted with saturated aqueous sodium/potassium tartrate, and the mixture was stirred vigorously until a clear phase separation was achieved. The organic phase was then separated, dried over anhydrous sodium sulfate, and concentrated in vacuo to provide the desired benzylic alcohol, which was used without further purification. To a solution of the title compound from Example 1 Step E (110 mg, 0.292 mmol), the benzylic alcohol obtained above (157 mg, 0.44 mmol), and triphenylphosphine (115 mg, 0.44 mmol) in DCM (2 mL) was added diisopropyl azodicarboxylate (0.085 mL, 0.44 mmol), and the resulting mixture was stirred at ambient temperature. After 1 h, the reaction mixture was concentrated in vacuo. Purification by flash chromatography on silica gel (0 to 50% EtOAc in hexanes, then 50 to 100% EtOAc in hexanes) provided the title compound: LCMS m/z 718.8 [M+H]$^+$.

Step D. 1-(6-(2-((4-(1-(Methoxycarbonyl)piperidin-4-yl)-2-(trifluoromethyl)benzyl)-oxy)phenyl)pyridin-2-yl)-5-(trifluoromethyl)-1H-pyrazole-4-carboxylic acid To a solution of the title compound from Example 11 Step C (200 mg, 0.278 mmol) in DCM (3 mL) was added TFA (1 mL). After 10 min, the reaction mixture was concentrated in vacuo, and the crude TFA salt was used without further purification: LCMS m/z 618.8 [M+H]$^+$. To a portion of the crude TFA salt in DCM (1.5 mL) were added DIEA (486 µL, 2.78 mmol) and methyl chloroformate (65 µL, 0.84 mmol), and the resulting mixture was allowed to stir at room temperature. After 90 min, the reaction mixture was quenched by addition of sat aq NaHCO$_3$ and the aqueous phase was extracted with DCM. The organic phase was separated and concentrated in vacuo to provide the crude carbamate, which was used without further purification: LCMS m/z 676.8 [M+H]$^+$. To a solution of the carbamate in dioxane (3 mL) was added lithium hydroxide (1.5 mL, 2N aqueous, 3 mmol), and the mixture was stirred at 50° C. After 1 h, the reaction mixture was rendered acidic by addition of HCl (2N aqueous), then was diluted with acetonitrile and purified by reverse phase HPLC (30 to 100% acetonitrile/water, both 0.1% v/v TFA) to provide the title compound: LCMS m/z 648.8 [M+H]$^+$; $^1$H NMR (500 MHz, d$_6$-DMSO) δ 8.29 (s, 1H), 8.07 (t, J=8.0 Hz, 1H), 8.03 (d, J=8.0 Hz, 1H), 7.72-7.69 (m, 2H), 7.62-7.61 (m, 2H), 7.54-7.52 (m, 1H), 7.47-7.43 (m, 1H), 7.24 (d, J=8.5 Hz, 1H), 7.13 (t, J=8.5 Hz, 1H), 5.32 (s, 2H), 4.14-4.08 (m, 2H), 3.60 (s, 3H), 2.88-2.80 (m, 3H), 1.78-1.75 (m, 2H), 1.58-1.49 (m, 2H).

EXAMPLE 12

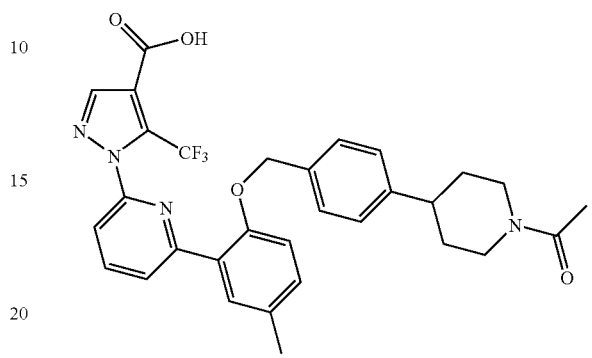

Step A. Ethyl 1-[6-(2-methoxy-5-methylphenyl)pyridin-2-yl]-5-(trifluoromethyl)-1H-pyrazole-4-carboxylate To a flask containing the title compound from Example 1 Step D (1.50 g, 4.69 mmol) were added 2-methoxy-5-methylphenyl boronic acid (0.779 g, 4.69 mmol) and trans-dichlorobis(triphenylphosphine) palladium (II) (329 mg, 0.469 mmol). Acetonitrile (12 mL) and sodium carbonate (11.7 mL, 1.0 M aqueous, 11.7 mmol) were added, and the resulting mixture was degassed via nitrogen sparge. The reaction mixture was stirred at 70° C. for 18 h, then was allowed to cool to room temperature and was poured into water. The mixture was extracted with EtOAc, and the organic phase was concentrated in vacuo. Purification by chromatography on silica gel (0 to 20% EtOAc in hexanes, then 20 to 100% EtOAc in hexanes) provided the title compound: LCMS m/z 406.4 [M+H]$^+$; $^1$H NMR (500 MHz, CDCl$_3$) δ 8.12 (s, 1H), 8.11 (d, J=8.0 Hz, 1H), 7.91 (t, J=8.0 Hz, 1H), 7.77 (d, J=2.0 Hz, 1H), 7.52 (d, J=8.0 Hz, 1H), 7.19 (dd, J=8.0, 2.0 Hz, 1H), 6.91 (d, J=8.0 Hz, 1H), 4.39 (q, J=7.0 Hz, 2H), 3.87 (s, 3H), 2.35 (s, 3H), 1.40 (t, J=7.0 Hz, 3H).

Step B. Ethyl 1-[6-(2-hydroxy-5-methylphenyl)pyridin-2-yl]-5-(trifluoromethyl)-1H-pyrazole-4-carboxylate To a cooled (0° C.) solution of the title compound from Example 12 Step A (1.58 g, 3.90 mmol) in DCM (20 mL) was added boron tribromide (11.7 mL, 1.0 M in DCM, 11.7 mmol). After 15 min, the reaction mixture was allowed to warm to ambient temperature. After an additional 2 h, the reaction mixture was cooled to 0° C., then was quenched by dropwise addition of sat. aq. NaHCO$_3$ (gas evolution) and was extracted with DCM. The organic phase was separated and concentrated in vacuo. Purification by flash chromatography on silica gel (0 to 30% EtOAc in hexanes, then 30 to 100% EtOAc in hexanes) provided the title compound: LCMS m/z 392.6 [M+H]$^+$; $^1$H NMR (500 MHz, CDCl$_3$) δ 11.78 (s, 1H), 8.17 (s, 1H), 8.07-8.03 (m, 2H), 7.60 (d, J=1.5 Hz, 1H), 7.48 (dd, J=7.0, 1.5 Hz, 1H), 7.17 (dd, J=8.0, 2.0 Hz, 1H), 6.94 (d, J=8.0 Hz, 1H), 4.39 (q, J=7.0 Hz, 2H), 2.36 (s, 3H), 1.40 (t, J=7.0 Hz, 3H).

Step C. Ethyl 1-(6-(2-((4-bromobenzyl)oxy)-5-methylphenyl)pyridin-2-yl)-5-(trifluoromethyl)-1H-pyrazole-4-carboxylate To a vial containing the title compound from Example 12 Step B (320 mg, 0.82 mmol) were added 4-bromobenzyl bromide (245 mg, 0.98 mmol), cesium carbonate (533 mg, 1.64 mmol), and DMF (3 mL), and the resulting mixture was stirred at 45° C. After 1 h, the reaction mixture was allowed to cool to ambient temperature, then was loaded directly onto a silica gel column and purified (0 to 30% EtOAc in hexanes, then 30% EtOAc in hexanes) to provide the title compound: LCMS m/z 562.4 [M+H]$^+$; $^1$H NMR (500 MHz, CDCl$_3$) δ 8.13 (s, 1H), 8.08 (d, J=8.0 Hz, 1H), 7.87 (t, J=8.0 Hz, 1H), 7.77 (d, J=3.0 Hz, 1H), 7.53 (d, J=8.0 Hz, 1H), 7.47 (d, J=8.5 Hz, 2H), 7.22 (d, J=8.5 Hz, 2H), 7.16 (dd, J=8.0, 3.0 Hz, 1H), 6.92 (d, J=8.5 Hz, 1H), 5.06 (s, 2H), 4.39 (q, J=7.0 Hz, 2H), 2.35 (s, 3H), 1.40 (t, J=7.0 Hz, 3H).

Step D. tert-Butyl 4-(4-((2-(6-(4-(ethoxycarbonyl)-5-(trifluoromethyl)-1H-pyrazol-1-yl)pyridin-2-yl)-4-methylphenoxy)methyl)phenyl)-3,6-dihydropyridine-1 (2H)-carboxylate A vial was charged with the title compound from Example 12 Step C (375 mg, 0.669 mmol), tert-butyl 4-(4,4,5,5-tetramethyl-1,3,2-dioxaborolan-2-yl)-3,6-dihydropyridine-1 (2H)-carboxylate (310 mg, 1.00 mmol; *Tetrahedron Lett*, 2000, 41, 3705-3708) and trans-dichlorobis(triphenylphosphine)palladium (II) (47 mg, 0.067 mmol). Acetonitrile (2.2 mL) and sodium carbonate (1.7 mL, 1.0 M aqueous, 1.7 mmol) were added, and the resulting mixture was degassed via nitrogen sparge. The reaction mixture was stirred at 70° C. for 15 h, then was allowed to cool to ambient temperature and was loaded directly onto a silica gel column. Purification by chromatography on silica gel (0 to 50% EtOAc in hexanes, then 50 to 100% EtOAc in hexanes) provided the title compound: LCMS m/z 663.0 [M+H]$^+$; $^1$H NMR (500 MHz, CDCl$_3$) δ 8.15 (d, J=8.0 Hz, 1H), 8.12 (s, 1H), 7.86 (t, J=8.0 Hz, 1H), 7.79 (d, J=2.0 Hz, 1H), 7.51 (d, J=8.0 Hz, 1H), 7.36 (d, J=8.5 Hz, 2H), 7.32 (d, J=8.5 Hz, 2H), 7.16 (dd, J=8.5, 2.0 Hz, 1H), 6.95 (d, J=8.0 Hz, 1H), 6.08-6.02 (m, 1H), 5.11 (s, 2H), 4.39 (q, J=7.0 Hz, 2H), 4.08-4.06 (m, 2H), 3.65-3.63 (m, 2H), 2.54-2.50 (m, 2H), 2.35 (s, 3H), 1.49 (s, 9H), 1.41 (q, J=7.0 Hz, 3H).

Step E. tert-Butyl 4-(4-((2-(6-(4-(ethoxycarbonyl)-5-(trifluoromethyl)-1H-pyrazol-1-yl)pyridin-2-yl)-4-methylphenoxy)methyl)phenyl)piperidine-1-carboxylate To a degassed solution of the title compound from Example 12 Step D (365 mg, 0.551 mmol) in EtOAc (10 mL) was added platinum(IV) oxide (125 mg). The reaction flask was fitted with a hydrogen balloon attached to a 3-way adapter. The reaction mixture was then evacuated and back-filled with hydrogen. After this process was repeated three times, the reaction mixture was placed under a hydrogen atmosphere, and was stirred vigorously. After 40 min, the reaction mixture was filtered though Celite, rinsing with EtOAc. Purification by flash chromatography on silica gel (0 to 50% EtOAc in hexanes, then 50 to 100% EtOAc in hexanes) provided the title compound: LCMS m/z 665.0 [M+H]$^+$; $^1$H NMR (500 MHz, CDCl$_3$) δ 8.16 (d, J=8.0 Hz, 1 H), 8.12 (s, 1H), 7.86 (t, J=8.0 Hz, 1H), 7.79 (br s, 1H), 7.51 (d, J=8.0 Hz, 1H), 7.30 (d, J=8.0 Hz, 2H), 7.19-7.16 (m, 3H), 6.97 (d, J=8.5 Hz, 1H), 5.09 (s, 2H), 4.38 (q, J=7.0 Hz, 2H), 4.30-4.18 (m, 2H), 2.82-2.78 (m, 2H), 2.67-2.62 (m, 1H), 2.35 (s, 3H), 1.83-1.80 (m, 2H), 1.66-1.57 (m, 2H), 1.49 (s, 9H), 1.40 (t, J=7.0 Hz, 3H).

Step F. Ethyl 1-(6-(5-methyl-2-((4-piperidin-4-yl-benzyl)oxy)phenyl)pyridin-2-O-5-(trifluoromethyl)-1H-pyrazole-4-carboxylate To a solution of the title compound from Example 12 Step E (200 mg, 0.278 mmol) in DCM (4 mL) was added TFA (2 mL). After 1 h, the reaction mixture was concentrated in vacuo, and the crude TFA salt was used without further purification: LCMS m/z 564.9 [M+1-1]$^+$.

Step G. 1-(6-(2-((4-(1-Acetylpiperidin-4-yl)benzyl) oxy)-5-methylphenyl)pyridin-2-yl)-5-(trifluoromethyl)-1H-pyrazole-4-carboxylic acid To a solution of the title compound from Example 12 Step F (24 mg, 0.035 mmol) in DCM (1 mL) were added DIEA (62 µL, 0.35 mmol) and acetyl chloride (8.3 mg, 0.104 mmol), and the resulting mixture was allowed to stir at room temperature. After 18 h, the reaction mixture was quenched by addition of sat aq NaHCO$_3$ and the aqueous phase was extracted with DCM. The organic phase was separated and concentrated in vacuo to provide the crude amide, which was used without further purification: LCMS m/z 606.9 [M+1-1]$^+$. To a solution of the amide in dioxane (1.5 mL) was added lithium hydroxide (0.75 mL, 2N aqueous, 1.5 mmol), and the mixture was stirred at 50° C. After 1 h, the reaction mixture was rendered acidic by addition of HCl (2N aqueous), then was diluted with acetonitrile and purified by reverse phase HPLC (40 to 100% acetonitrile/water, both 0.1% v/v TFA) to provide the title compound: LCMS m/z 578.9 [M+H]$^+$; $^1$H NMR (500 MHz, d$_6$-DMSO) δ 8.29 (s, 1H), 8.14 (d, J=8.0 Hz, 1H), 8.10 (t, J=8.0 Hz, 1H), 7.69 (d, J=8.0 Hz, 1H), 7.56 (d, J=2.0 Hz, 1H), 7.32 (d, J=8.0 Hz, 2H), 7.23-7.21 (m, 1H), 7.21 (d, J=8.0 Hz, 2H), 7.15 (d, J=8.0 Hz, 1H), 5.16 (s, 2H), 4.52-4.49 (m, 1H), 3.91-3.87 (m, 1H), 3.12-3.07 (m, 1H), 2.77-2.70 (m, 1H), 2.58-2.53 (m, 1H), 2.27 (s, 3H), 2.01 (s, 3H), 1.78-1.72 (m, 2H), 1.59-1.51 (m, 1H), 1.44-1.35 (m, 1H).

EXAMPLE 13

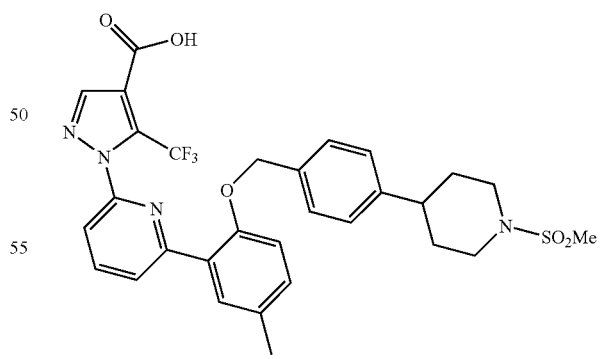

Step A. 1-(6-5-Methyl-2-((4-(1-methylsulfonyl)piperidin-4-yl)benzyl)oxy)phenyl)pyridin-2-yl)-5-(trifluoromethyl)-1H-pyrazole-4-carboxylic acid To a solution of the title compound from Example 12 Step F (24 mg, 0.035 mmol) in DCM (1 mL) were added DIEA (62

μL, 0.35 mmol) and methanesulfonyl chloride (8.3 μL, 0.104 mmol), and the resulting mixture was allowed to stir at room temperature. After 18 h, the reaction mixture was quenched by addition of sat aq NaHCO$_3$ and the aqueous phase was extracted with DCM. The organic phase was separated and concentrated in vacuo to provide the crude sulfonamide, which was used without further purification: LCMS m/z 642.9 [M+H]$^+$. To a solution of the sulfonamide in dioxane (1.5 mL) was added lithium hydroxide (0.75 mL, 2N aqueous, 1.5 mmol), and the mixture was stirred at 50° C. After 1 h, the reaction mixture was rendered acidic by addition of HCl (2N aqueous), then was diluted with acetonitrile and purified by reverse phase HPLC (40 to 100% acetonitrile/water, both 0.1% v/v TFA) to provide the title compound: LCMS m/z 614.8 [M+H]$^+$; $^1$H NMR (500 MHz, d$_6$-DMSO) δ 8.29 (s, 1H), 8.14 (d, J=8.0 Hz, 1H), 8.10 (t, J=8.0 Hz, 1H), 7.69 (d, J=8.0 Hz, 1H), 7.56 (d, J=2.0 Hz, 1H), 7.33 (d, J=8.0 Hz, 2H), 7.25 (d, J=8.0 Hz, 2H), 7.24-7.22 (m, 1H), 7.15 (d, J=8.0 Hz, 1H), 5.17 (s, 2H), 3.66-3.64 (m, 2H), 2.87 (s, 3H), 2.81-2.77 (m, 2H), 2.64-2.59 (m, 1H), 2.27 (s, 3H), 1.85-1.83 (m, 2H), 1.69-1.61 (m, 2H).

EXAMPLE 14

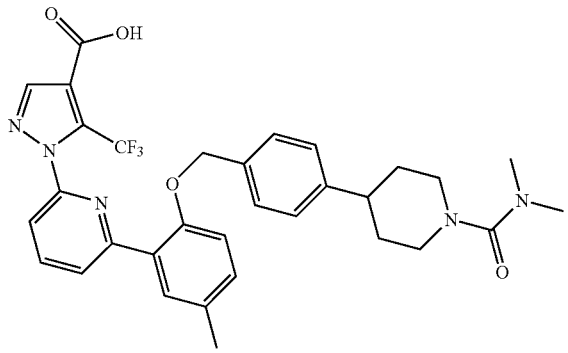 [SMILES: Cc1ccc(OCc2ccc(C3CCN(C(=O)N(C)C)CC3)cc2)c(-c2cccc(-n3ncc(C(=O)O)c3C(F)(F)F)n2)c1]

Step A. 1-(6-(2-((4-(1-((Dimethylamino)carbonyl)piperidin-4-yl)benzyl)oxy)-5-methylphenyl)pyridin-2-yl)-5-(trifluoromethyl)-1H-pyrazole-4-carboxylic acid To a solution of the title compound from Example 12 Step F (48 mg, 0.071 mmol) in DCM (1 mL) were added DIEA (124 μL, 0.708 mmol) and dimethylcarbamyl chloride (20 μL, 0.213 mmol), and the resulting mixture was allowed to stir at room temperature. After 1.5 h, the reaction mixture was quenched by addition of sat aq NaHCO$_3$ and the aqueous phase was extracted with DCM. The organic phase was separated and concentrated in vacuo to provide the crude urea, which was used without further purification: LCMS m/z 635.8 [M+H]$^+$. To a solution of the urea in dioxane (2 mL) was added lithium hydroxide (1 mL, 2N aqueous, 2 mmol), and the mixture was stirred at 50° C. After 1 h, the reaction mixture was rendered acidic by addition of HCl (2N aqueous), then was diluted with acetonitrile and purified by reverse phase HPLC (40 to 100% acetonitrile/water, both 0.1% v/v TFA) to provide the title compound: LCMS m/z 607.8 [M+H]$^+$; $^1$H NMR (500 MHz, d$_6$-DMSO) δ 8.31 (s, 1H), 8.15 (d, J=7.0 Hz, 1H), 8.11 (t, J=8.0 Hz, 1H), 7.70 (d, J=7.0 Hz, 1H), 7.57 (d, J=2.0 Hz, 1H), 7.34 (d, J=8.0 Hz, 2H), 7.23 (d, J=8.0 Hz, 2H), 7.24-7.22 (m, 1H), 7.17 (d, J=8.5 Hz, 1H), 5.17 (s, 2H), 3.65-3.63 (m, 2H), 2.79-2.77 (m, 2H), 2.75 (s, 6H), 2.69-2.64 (m, 1H), 2.28 (s, 3H), 1.75-1.72 (m, 2H), 1.61-1.52 (m, 2H).

The compounds in Table 1 were prepared using chemistry described in Examples 1-14.

TABLE 1

| Example | Structure | IUPAC name | LCMS |
|---|---|---|---|
| 15 | 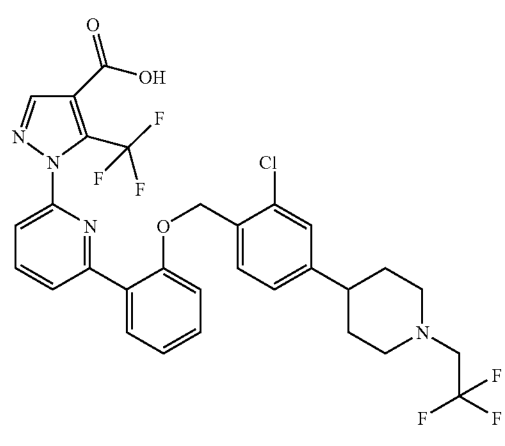 [SMILES: O=C(O)c1cnn(-c2cccc(-c3ccccc3OCc3ccc(C4CCN(CC(F)(F)F)CC4)cc3Cl)n2)c1C(F)(F)F] | 1-(6-(2-((2-chloro-4-(1-(2,2,2-trifluoroethyl)piperidin-4-yl)benzyl)oxy)phenyl)pyridin-2-yl)-5-(trifluoromethyl)-1H-pyrazole-4-carboxylic acid | 639.7 |

TABLE 1-continued

| Example | Structure | IUPAC name | LCMS |
|---|---|---|---|
| 16 | 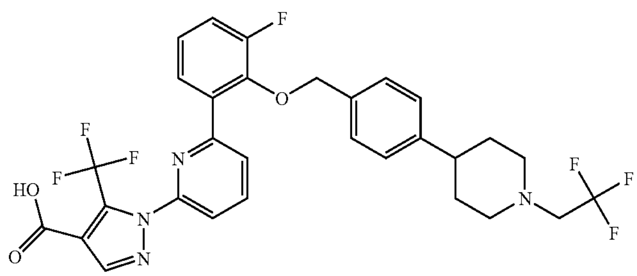 [SMILES: O=C(O)c1cnn(-c2cccc(-c3cccc(F)c3OCc3ccc(C4CCN(CC(F)(F)F)CC4)cc3)n2)c1C(F)(F)F] | 1-(6-(3-fluoro-2-((4-(1-(2,2,2-trifluoroethyl)piperidin-4-yl)benzyl)oxy)phenyl)pyridin-2-yl)-5-(trifluoromethyl)-1H-pyrazole-4-carboxylic acid | 622.8 |
| 17 | 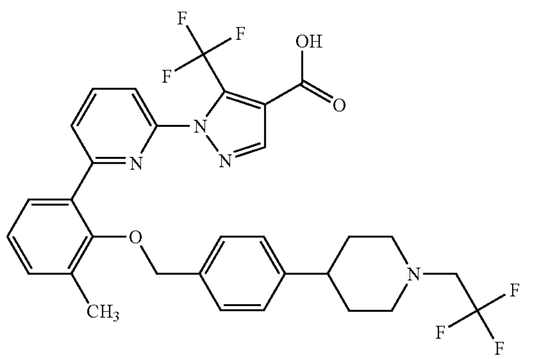 [SMILES: Cc1cccc(-c2cccc(-n3ncc(C(=O)O)c3C(F)(F)F)n2)c1OCc1ccc(C2CCN(CC(F)(F)F)CC2)cc1] | 1-(6-(3-methyl-2-((4-(1-(2,2,2-trifluoroethyl)piperidin-4-yl)benzyl)oxy)phenyl)pyridin-2-yl)-5-(trifluoromethyl)-1H-pyrazole-4-carboxylic acid | 618.8 |
| 18 | 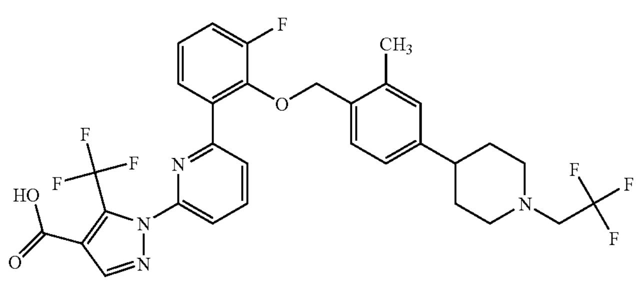 [SMILES: Cc1cc(C2CCN(CC(F)(F)F)CC2)ccc1COc1c(F)cccc1-c1cccc(-n2ncc(C(=O)O)c2C(F)(F)F)n1] | 1-(6-(3-fluoro-2-((2-methyl-4-(1-(2,2,2-trifluoroethyl)piperidin-4-yl)benzyl)oxy)phenyl)pyridin-2-yl)-5-(trifluoromethyl)-1H-pyrazole-4-carboxylic acid | 636.9 |
| 19 | 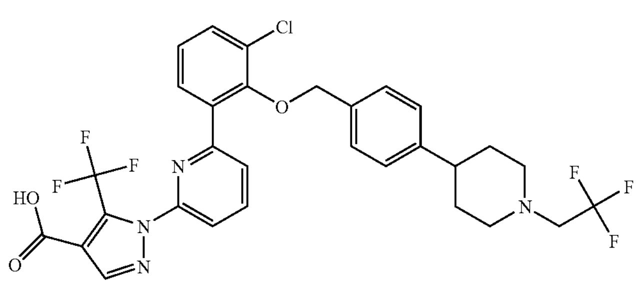 | 1-(6-(3-chloro-2-((4-(1-(2,2,2-trifluoroethyl)piperidin-4-yl)benzyl)oxy)phenyl)pyridin-2-yl)-5-(trifluoromethyl)-1H-pyrazole-4-carboxylic acid | 638.9 |
| 20 | 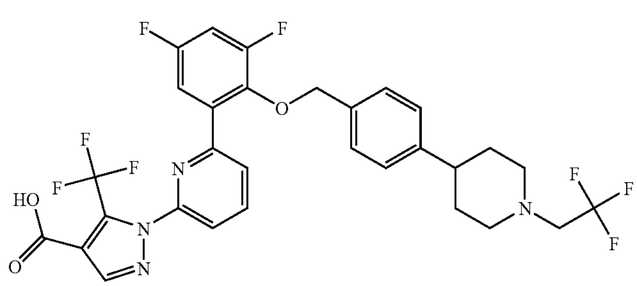 [SMILES: O=C(O)c1cnn(-c2cccc(-c3cc(F)cc(F)c3OCc3ccc(C4CCN(CC(F)(F)F)CC4)cc3)n2)c1C(F)(F)F] | 1-(6-(3,5-difluoro-2-((4-(1-(2,2,2-trifluoroethyl)piperidin-4-yl)benzyl)oxy)phenyl)pyridin-2-yl)-5-(trifluoromethyl)-1H-pyrazole-4-carboxylic acid | 640.8 |

TABLE 1-continued

| Example | Structure | IUPAC name | LCMS |
|---------|-----------|------------|------|
| 21 | 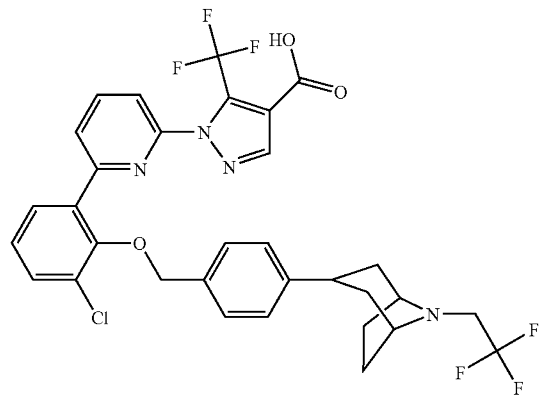 [SMILES: O=C(O)c1cnn(-c2cccc(-c3cccc(Cl)c3OCc3ccc(C4CC5CCC(C4)N5CC(F)(F)F)cc3)n2)c1C(F)(F)F] | 1-(6-(3-chloro-2-((4-(8-(2,2,2-trifluoroethyl)-8-azabicyclo[3.2.1]oct-3-yl)benzyl)oxy)phenyl)pyridin-2-yl)-5-(trifluoromethyl)-1H-pyrazole-4-carboxylic acid | 665.0 |
| 22 | 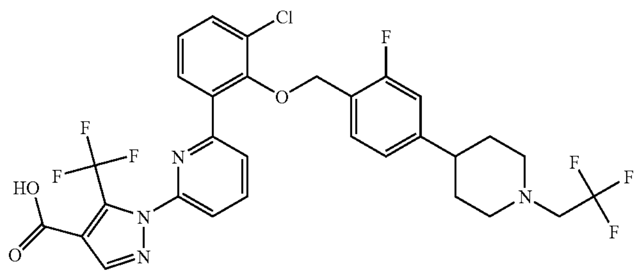 [SMILES: O=C(O)c1cnn(-c2cccc(-c3cccc(Cl)c3OCc3ccc(C4CCN(CC(F)(F)F)CC4)cc3F)n2)c1C(F)(F)F] | 1-(6-(3-chloro-2-((2-fluoro-4-(1-(2,2,2-trifluoroethyl)piperidin-4-yl)benzyl)oxy)phenyl)pyridin-2-yl)-5-(trifluoromethyl)-1H-pyrazole-4-carboxylic acid | 656.9 |
| 23 | 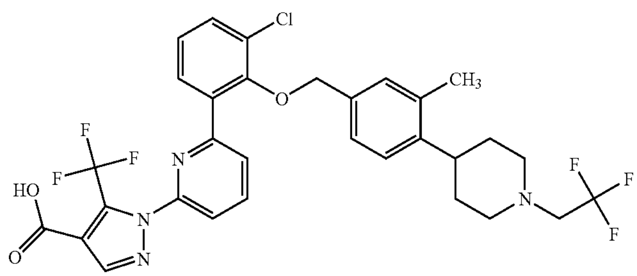 [SMILES: Cc1cc(COc2c(Cl)cccc2-c2cccc(-n3ncc(C(=O)O)c3C(F)(F)F)n2)ccc1C1CCN(CC(F)(F)F)CC1] | 1-(6-(3-chloro-2-((3-methyl-4-(1-(2,2,2-trifluoroethyl)piperidin-4-yl)benzyl)oxy)phenyl)pyridin-2-yl)-5-(trifluoromethyl)-1H-pyrazole-4-carboxylic acid | 653.0 |
| 24 | 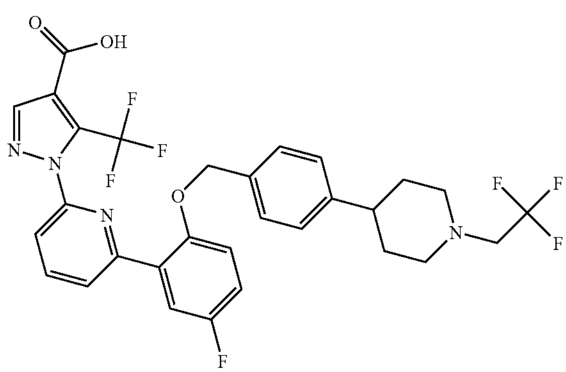 [SMILES: O=C(O)c1cnn(-c2cccc(-c3cc(F)ccc3OCc3ccc(C4CCN(CC(F)(F)F)CC4)cc3)n2)c1C(F)(F)F] | 1-(6-(5-fluoro-2-((4-(1-(2,2,2-trifluoroethyl)piperidin-4-yl)benzyl)oxy)phenyl)pyridin-2-yl)-5-(trifluoromethyl)-1H-pyrazole-4-carboxylic acid | 623.0 |
| 25 | 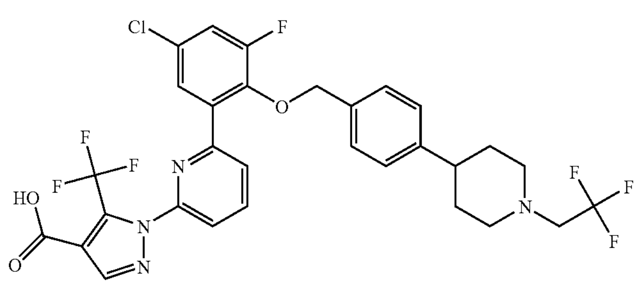 [SMILES: O=C(O)c1cnn(-c2cccc(-c3cc(Cl)cc(F)c3OCc3ccc(C4CCN(CC(F)(F)F)CC4)cc3)n2)c1C(F)(F)F] | 1-(6-(5-chloro-3-fluoro-2-((4-(1-(2,2,2-trifluoroethyl)piperidin-4-yl)benzyl)oxy)phenyl)pyridin-2-yl)-5-(trifluoromethyl)-1H-pyrazole-4-carboxylic acid | 657.0 |

TABLE 1-continued

| Example | Structure | IUPAC name | LCMS |
|---|---|---|---|
| 26 | 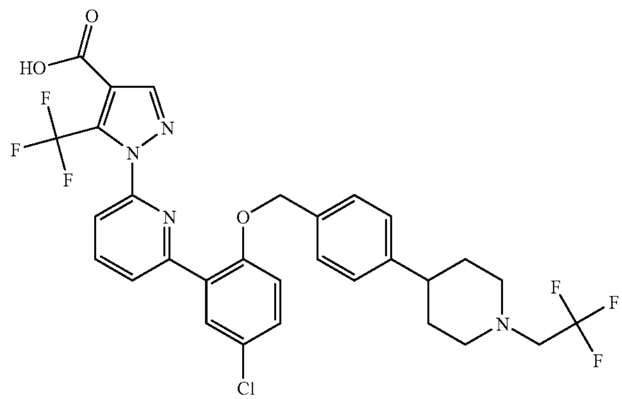 [SMILES: O=C(O)c1cnn(-c2cccc(-c3cc(Cl)ccc3OCc3ccc(C4CCN(CC(F)(F)F)CC4)cc3)n2)c1C(F)(F)F] | 1-(6-(5-chloro-2-((4-(1-(2,2,2-trifluoroethyl)piperidin-4-yl)benzyl)oxy)phenyl)pyridin-2-yl)-5-(trifluoromethyl)-1H-pyrazole-4-carboxylic acid | 638.9 |
| 27 | 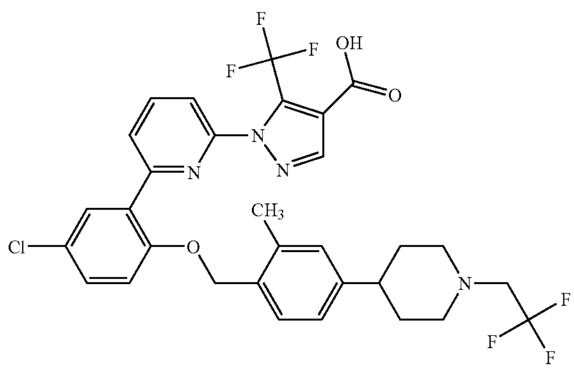 [SMILES: Cc1cc(C2CCN(CC(F)(F)F)CC2)ccc1COc1ccc(Cl)cc1-c1cccc(-n2ncc(C(=O)O)c2C(F)(F)F)n1] | 1-(6-(5-chloro-2-((2-methyl-4-(1-(2,2,2-trifluoroethyl)piperidin-4-yl)benzyl)oxy)phenyl)pyridin-2-yl)-5-(trifluoromethyl)-1H-pyrazole-4-carboxylic acid | 653.0 |
| 28 | 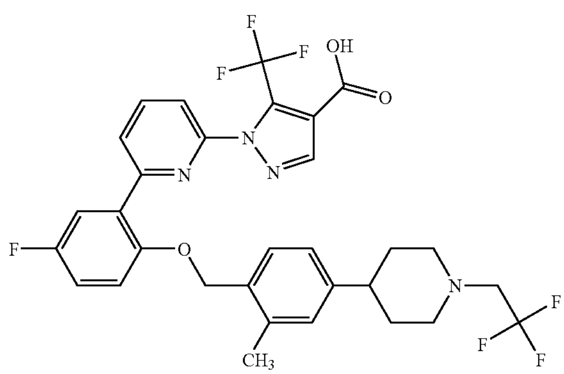 [SMILES: Cc1cc(C2CCN(CC(F)(F)F)CC2)ccc1COc1ccc(F)cc1-c1cccc(-n2ncc(C(=O)O)c2C(F)(F)F)n1] | 1-(6-(5-fluoro-2-((2-methyl-4-(1-(2,2,2-trifluoroethyl)piperidin-4-yl)benzyl)oxy)phenyl)pyridin-2-yl)-5-(trifluoromethyl)-1H-pyrazole-4-carboxylic acid | 637.0 |
| 29 | 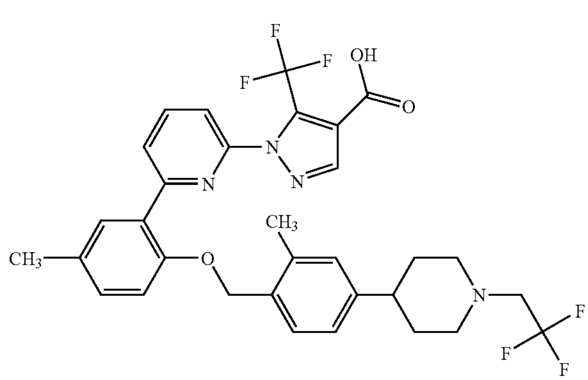 [SMILES: Cc1ccc(OCc2ccc(C3CCN(CC(F)(F)F)CC3)cc2C)c(-c2cccc(-n3ncc(C(=O)O)c3C(F)(F)F)n2)c1] | 1-(6-(5-methyl-2-((2-methyl-4-(1-(2,2,2-trifluoroethyl)piperidin-4-yl)benzyl)oxy)phenyl)pyridin-2-yl)-5-(trifluoromethyl)-1H-pyrazole-4-carboxylic acid | 633.0 |

TABLE 1-continued

| Example | Structure | IUPAC name | LCMS |
|---|---|---|---|
| 30 | 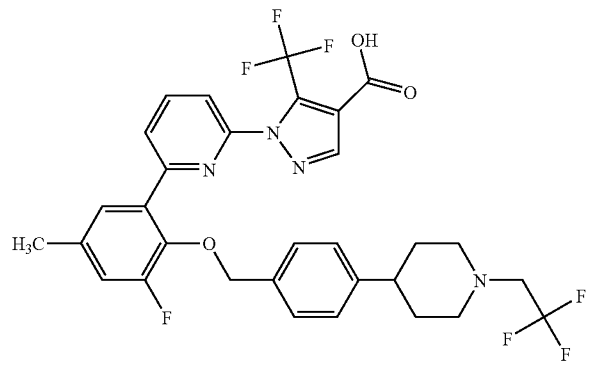 [SMILES: Cc1cc(F)c(OCc2ccc(C3CCN(CC(F)(F)F)CC3)cc2)c(-c2cccc(-n3ncc(C(=O)O)c3C(F)(F)F)n2)c1] | 1-(6-(3-fluoro-5-methyl-2-((4-(1-(2,2,2-trifluoroethyl)piperidin-4-yl)benzyl)oxy)phenyl)pyridin-2-yl)-5-(trifluoromethyl)-1H-pyrazole-4-carboxylic acid | 637.0 |
| 31 | 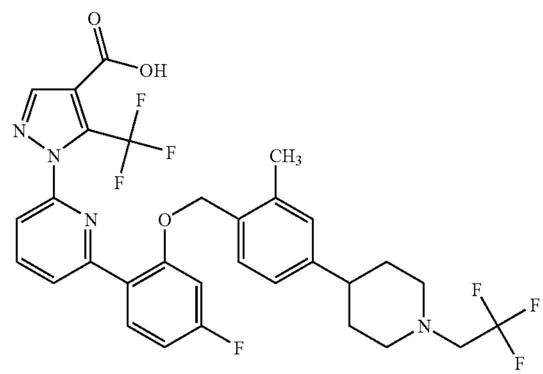 [SMILES: Cc1cc(C2CCN(CC(F)(F)F)CC2)ccc1COc1cc(F)ccc1-c1cccc(-n2ncc(C(=O)O)c2C(F)(F)F)n1] | 1-(6-(4-fluoro-2-((2-methyl-4-(1-(2,2,2-trifluoroethyl)piperidin-4-yl)benzyl)oxy)phenyl)pyridin-2-yl)-5-(trifluoromethyl)-1H-pyrazole-4-carboxylic acid | 637.0 |
| 32 | 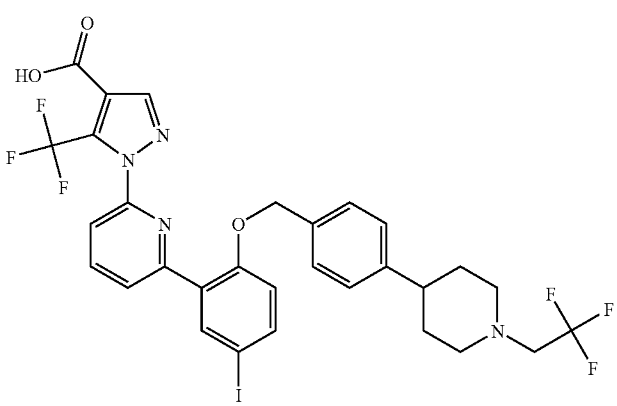 | 1-(6-(5-iodo-2-((4-(1-(2,2,2-trifluoroethyl)piperidin-4-yl)benzyl)oxy)phenyl)pyridin-2-yl)-5-(trifluoromethyl)-1H-pyrazole-4-carboxylic acid | 731.0 |
| 33 | 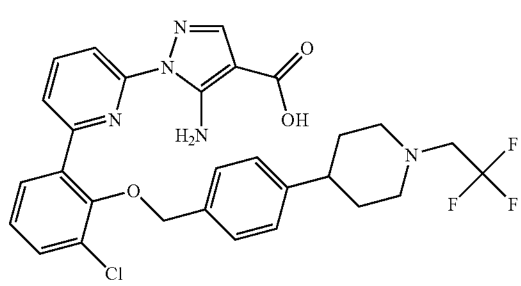 [SMILES: Nc1c(C(=O)O)cnn1-c1cccc(-c2cccc(Cl)c2OCc2ccc(C3CCN(CC(F)(F)F)CC3)cc2)n1] | 5-amino-1-(6-(3-chloro-2-((4-(1-(2,2,2-trifluoroethyl)piperidin-4-yl)benzyl)oxy)phenyl)pyridin-2-yl)-1H-pyrazole-4-carboxylic acid | 586.0 |

TABLE 1-continued

| Example | Structure | IUPAC name | LCMS |
|---|---|---|---|
| 34 | 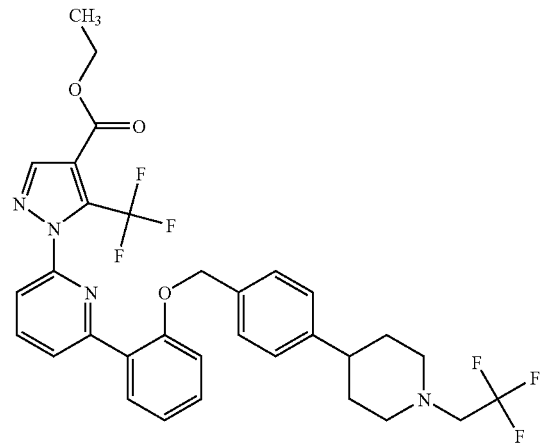 [SMILES: CCOC(=O)c1cnn(-c2cccc(-c3ccccc3OCc3ccc(C4CCN(CC(F)(F)F)CC4)cc3)n2)c1C(F)(F)F] | ethyl 1-(6-(2-((4-(1-(2,2,2-trifluoroethyl)piperidin-4-yl)benzyl)oxy)phenyl)pyridin-2-yl)-5-(trifluoromethyl)-1H-pyrazole-4-carboxylate | 633.0 |
| 35 | 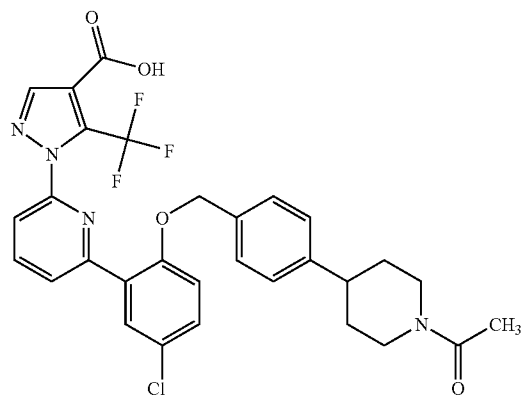 [SMILES: CC(=O)N1CCC(c2ccc(COc3ccc(Cl)cc3-c3cccc(-n4ncc(C(=O)O)c4C(F)(F)F)n3)cc2)CC1] | 1-(6-(2-((4-(1-acetylpiperidin-4-yl)benzyl)oxy)-5-chlorophenyl)pyridin-2-yl)-5-(trifluoromethyl)-1H-pyrazole-4-carboxylic acid | 598.8 |
| 36 | 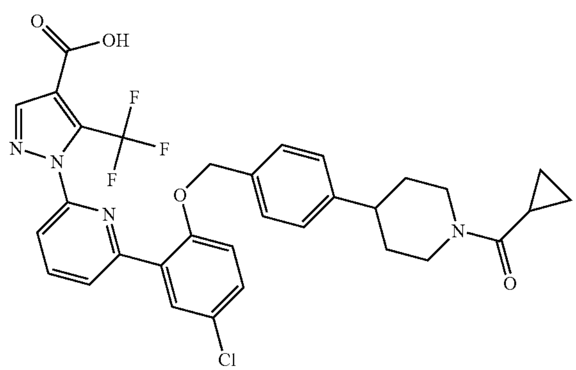 [SMILES: O=C(O)c1cnn(-c2cccc(-c3cc(Cl)ccc3OCc3ccc(C4CCN(C(=O)C5CC5)CC4)cc3)n2)c1C(F)(F)F] | 1-(6-(5-chloro-2-((4-(1-(cyclopropylcarbonyl)piperidin-4-yl)benzyl)oxy)phenyl)pyridin-2-yl)-5-(trifluoromethyl)-1H-pyrazole-4-carboxylic acid | 624.8 |
| 37 | 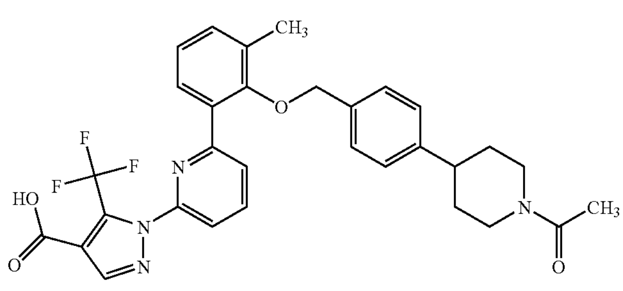 [SMILES: CC(=O)N1CCC(c2ccc(COc3c(C)cccc3-c3cccc(-n4ncc(C(=O)O)c4C(F)(F)F)n3)cc2)CC1] | 1-(6-(2-((4-(1-acetylpiperidin-4-yl)benzyl)oxy)-3-methylphenyl)pyridin-2-yl)-5-(trifluoromethyl)-1H-pyrazole-4-carboxylic acid | 578.9 |

TABLE 1-continued

| Example | Structure | IUPAC name | LCMS |
|---|---|---|---|
| 38 | 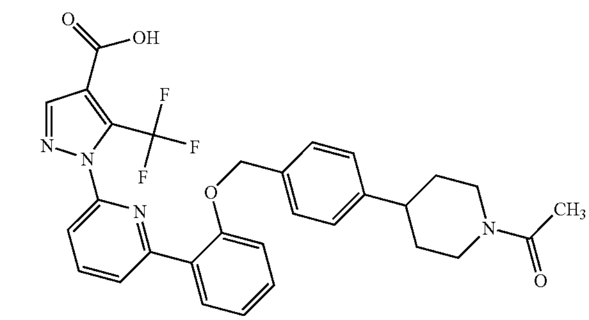 [SMILES: CC(=O)N1CCC(c2ccc(COc3ccccc3-c3cccc(-n4ncc(C(=O)O)c4C(F)(F)F)n3)cc2)CC1] | 1-(6-(2-((4-(1-acetylpiperidin-4-yl)benzyl)oxy)phenyl)pyridin-2-yl)-5-(trifluoromethyl)-1H-pyrazole-4-carboxylic acid | 564.9 |
| 39 | 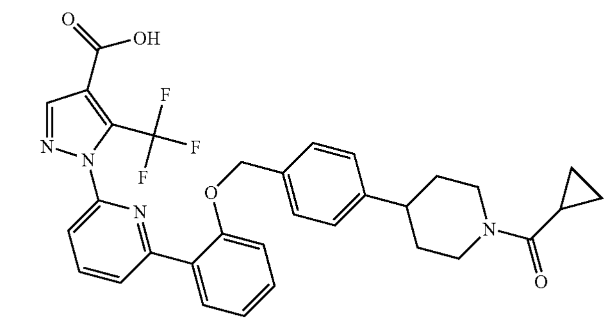 [SMILES: O=C(O)c1cnn(-c2cccc(-c3ccccc3OCc3ccc(C4CCN(C(=O)C5CC5)CC4)cc3)n2)c1C(F)(F)F] | 1-(6-(2-((4-(1-(cyclopropylcarbonyl)piperidin-4-yl)benzyl)oxy)phenyl)pyridin-2-yl)-5-(trifluoromethyl)-1H-pyrazole-4-carboxylic acid | 590.9 |
| 40 | 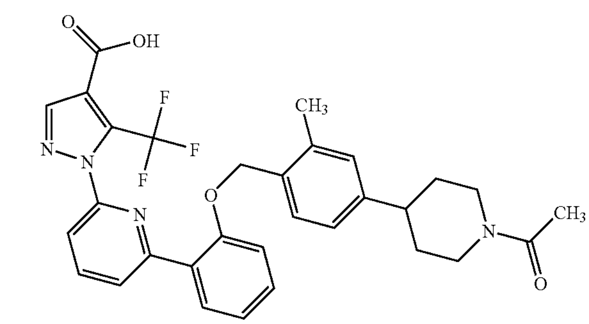 [SMILES: CC(=O)N1CCC(c2ccc(COc3ccccc3-c3cccc(-n4ncc(C(=O)O)c4C(F)(F)F)n3)c(C)c2)CC1] | 1-(6-(2-((4-(1-acetylpiperidin-4-yl)-2-methylbenzyl)oxy)phenyl)pyridin-2-yl)-5-(trifluoromethyl)-1H-pyrazole-4-carboxylic acid | 579.0 |
| 41 | 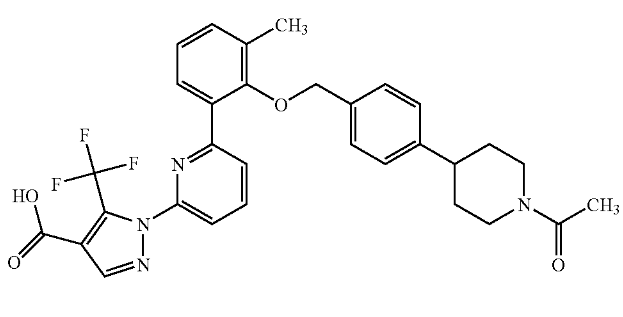 [SMILES: CC(=O)N1CCC(c2ccc(COc3c(C)cccc3-c3cccc(-n4ncc(C(=O)O)c4C(F)(F)F)n3)cc2)CC1] | 1-(6-(2-((4-(1-acetylpiperidin-4-yl)benzyl)oxy)-3-methylphenyl)pyridin-2-yl)-5-(trifluoromethyl)-1H-pyrazole-4-carboxylic acid | 578.9 |
| 42 | 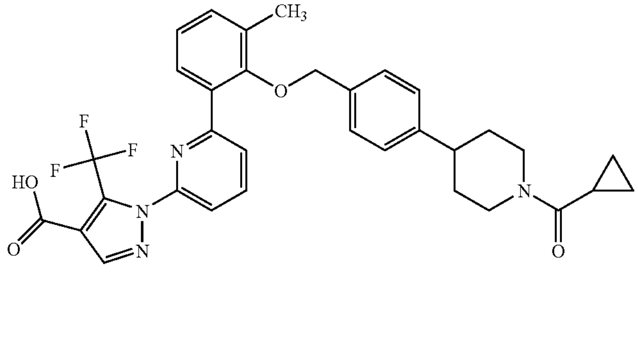 [SMILES: Cc1cccc(-c2cccc(-n3ncc(C(=O)O)c3C(F)(F)F)n2)c1OCc1ccc(C2CCN(C(=O)C3CC3)CC2)cc1] | 1-(6-(2-((4-(1-(cyclopropylcarbonyl)piperidin-4-yl)benzyl)oxy)-3-methylphenyl)pyridin-2-yl)-5-(trifluoromethyl)-1H-pyrazole-4-carboxylic acid | 604.9 |

TABLE 1-continued

| Example | Structure | IUPAC name | LCMS |
|---|---|---|---|
| 43 | 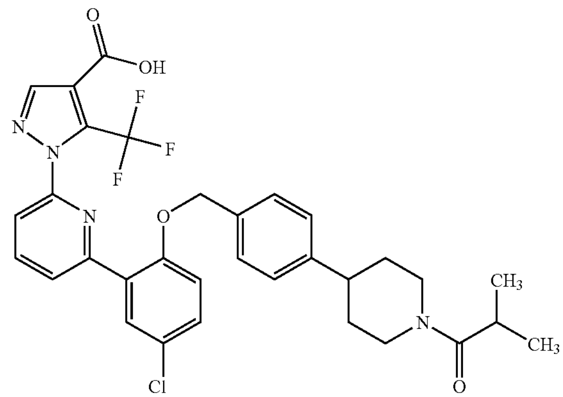 [SMILES: CC(C)C(=O)N1CCC(c2ccc(COc3ccc(Cl)cc3-c3cccc(-n4ncc(C(=O)O)c4C(F)(F)F)n3)cc2)CC1] | 1-(6-(5-chloro-2-((4-(1-isobutyrylpiperidin-4-yl)benzyl)oxy)phenyl)pyridin-2-yl)-5-(trifluoromethyl)-1H-pyrazole-4-carboxylic acid | 626.8 |
| 44 | 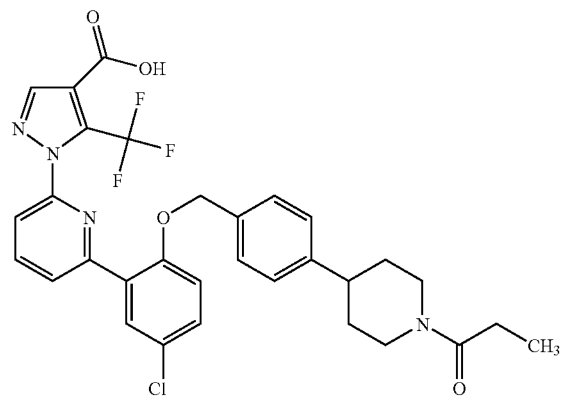 [SMILES: CCC(=O)N1CCC(c2ccc(COc3ccc(Cl)cc3-c3cccc(-n4ncc(C(=O)O)c4C(F)(F)F)n3)cc2)CC1] | 1-(6-(5-chloro-2-((4-(1-propionylpiperidin-4-yl)benzyl)oxy)phenyl)pyridin-2-yl)-5-(trifluoromethyl)-1H-pyrazole-4-carboxylic acid | 612.8 |
| 45 | 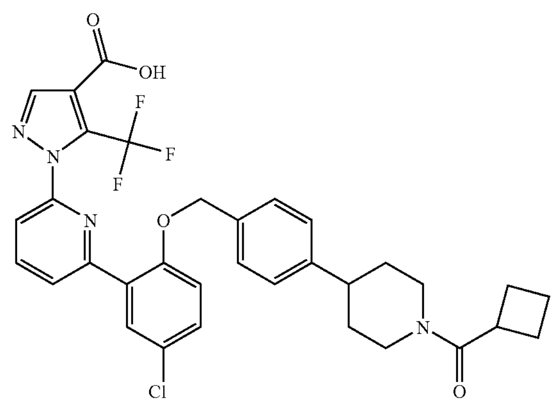 [SMILES: O=C(O)c1cnn(-c2cccc(-c3cc(Cl)ccc3OCc3ccc(C4CCN(C(=O)C5CCC5)CC4)cc3)n2)c1C(F)(F)F] | 1-(6-(5-chloro-2-((4-(1-(cyclobutylcarbonyl)piperidin-4-yl)benzyl)oxy)phenyl)pyridin-2-yl)-5-(trifluoromethyl)-1H-pyrazole-4-carboxylic acid | 638.8 |
| 46 | 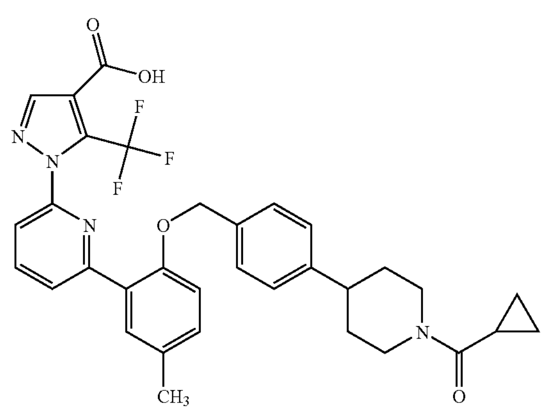 [SMILES: Cc1ccc(OCc2ccc(C3CCN(C(=O)C4CC4)CC3)cc2)c(-c2cccc(-n3ncc(C(=O)O)c3C(F)(F)F)n2)c1] | 1-(6-(2-((4-(1-(cyclopropylcarbonyl)piperidin-4-yl)benzyl)oxy)-5-methylphenyl)pyridin-2-yl)-5-(trifluoromethyl)-1H-pyrazole-4-carboxylic acid | 604.9 |

TABLE 1-continued

| Example | Structure | IUPAC name | LCMS |
|---|---|---|---|
| 47 | 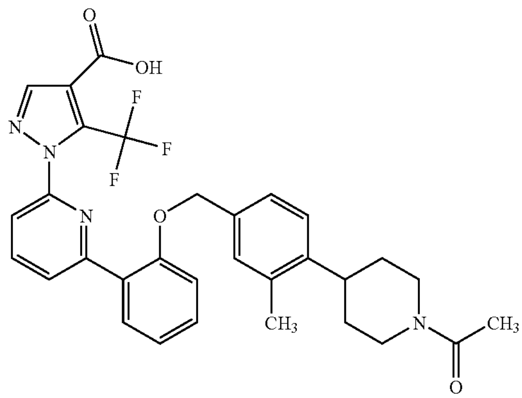 [SMILES: CC(=O)N1CCC(c2ccc(COc3ccccc3-c3cccc(-n4ncc(C(=O)O)c4C(F)(F)F)n3)cc2C)CC1] | 1-(6-(2-((4-(1-acetylpiperidin-4-yl)-3-methylbenzyl)oxy)phenyl)pyridin-2-yl)-5-(trifluoromethyl)-1H-pyrazole-4-carboxylic acid | 580.2 |
| 48 | 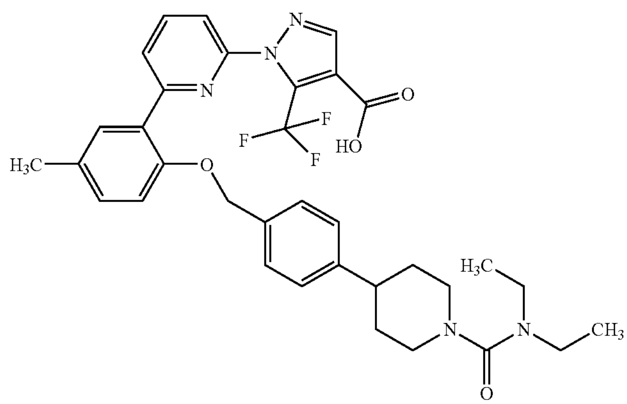 [SMILES: CCN(CC)C(=O)N1CCC(c2ccc(COc3ccc(C)cc3-c3cccc(-n4ncc(C(=O)O)c4C(F)(F)F)n3)cc2)CC1] | 1-(6-(2-((4-(1-((diethylamino)carbonyl)piperidin-4-yl)benzyl)oxy)-5-methylphenyl)pyridin-2-yl)-5-(trifluoromethyl)-1H-pyrazole-4-carboxylic acid | 635.9 |
| 49 | 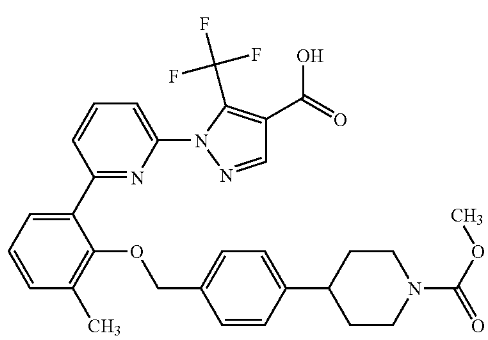 [SMILES: COC(=O)N1CCC(c2ccc(COc3c(C)cccc3-c3cccc(-n4ncc(C(=O)O)c4C(F)(F)F)n3)cc2)CC1] | 1-(6-(2-((4-(1-(methoxycarbonyl)piperidin-4-yl)benzyl)oxy)-3-methylphenyl)pyridin-2-yl)-5-(trifluoromethyl)-1H-pyrazole-4-carboxylic acid | 594.8 |
| 50 | 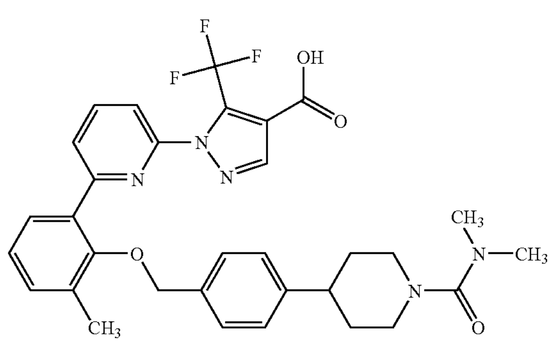 [SMILES: Cc1cccc(-c2cccc(-n3ncc(C(=O)O)c3C(F)(F)F)n2)c1OCc1ccc(C2CCN(C(=O)N(C)C)CC2)cc1] | 1-(6-(2-((4-(1-((dimethylamino)carbonyl)piperidin-4-yl)benzyl)oxy)-3-methylphenyl)pyridin-2-yl)-5-(trifluoromethyl)-1H-pyrazole-4-carboxylic acid | 607.9 |

TABLE 1-continued

| Example | Structure | IUPAC name | LCMS |
|---|---|---|---|
| 51 | 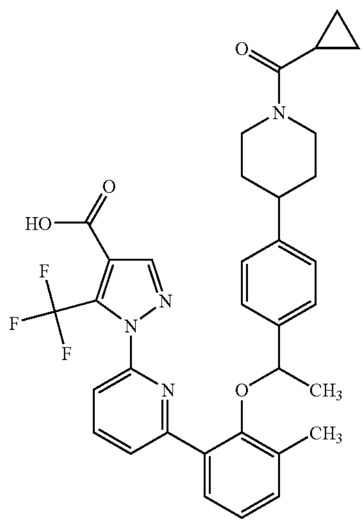 [SMILES: Cc1cccc(-c2cccc(-n3ncc(C(=O)O)c3C(F)(F)F)n2)c1OC(C)c1ccc(C2CCN(C(=O)C3CC3)CC2)cc1] | 1-(6-(2-(1-(4-(1-(cyclopropylcarbonyl)piperidin-4-yl)phenyl)ethoxy)-3-methylphenyl)pyridin-2-yl)-5-(trifluoromethyl)-1H-pyrazole-4-carboxylic acid | 618.9 |
| 52 | 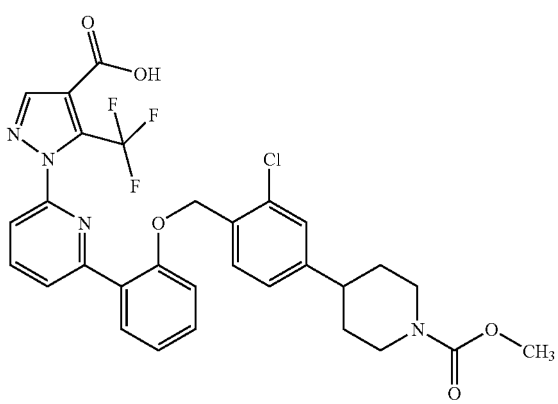 [SMILES: COC(=O)N1CCC(c2ccc(COc3ccccc3-c3cccc(-n4ncc(C(=O)O)c4C(F)(F)F)n3)c(Cl)c2)CC1] | 1-(6-(2-((2-chloro-4-(1-(methoxycarbonyl)piperidin-4-yl)benzyl)oxy)phenyl)pyridin-2-yl)-5-(trifluoromethyl)-1H-pyrazole-4-carboxylic acid | 614.7 |
| 53 | 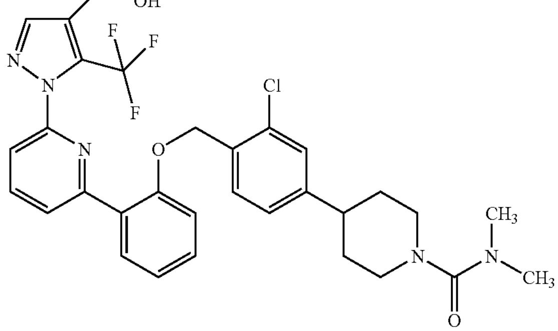 | 1-(6-(2-((2-chloro-4-(1-((dimethylamino)carbonyl)piperidin-4-yl)benzyl)oxy)phenyl)pyridin-2-yl)-5-(trifluoromethyl)-1H-pyrazole-4-carboxylic acid | 627.8 |

TABLE 1-continued

| Example | Structure | IUPAC name | LCMS |
|---|---|---|---|
| 54 | 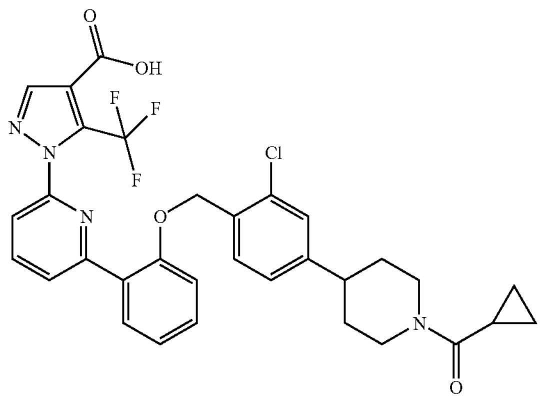 [SMILES: O=C(O)c1cnn(-c2cccc(-c3ccccc3OCc3ccc(C4CCN(C(=O)C5CC5)CC4)cc3Cl)n2)c1C(F)(F)F] | 1-(6-(2-((2-chloro-4-(1-(cyclopropylcarbonyl)piperidin-4-yl)benzyl)oxy)phenyl)pyridin-2-yl)-5-(trifluoromethyl)-1H-pyrazole-4-carboxylic acid | 624.8 |
| 55 | 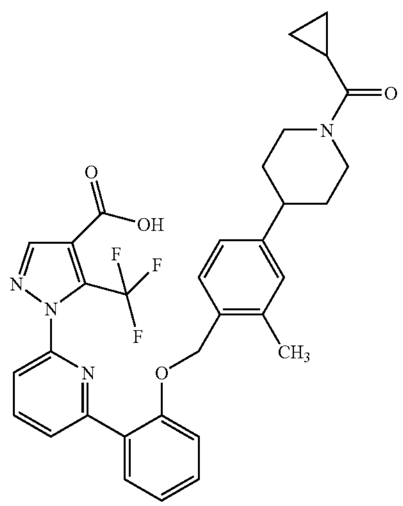 [SMILES: Cc1cc(C2CCN(C(=O)C3CC3)CC2)ccc1COc1ccccc1-c1cccc(-n2ncc(C(=O)O)c2C(F)(F)F)n1] | 1-(6-(2-((4-(1-(cyclopropylcarbonyl)piperidin-4-yl)-2-methylbenzyl)oxy)phenyl)pyridin-2-yl)-5-(trifluoromethyl)-1H-pyrazole-4-carboxylic acid | 604.8 |
| 56 | 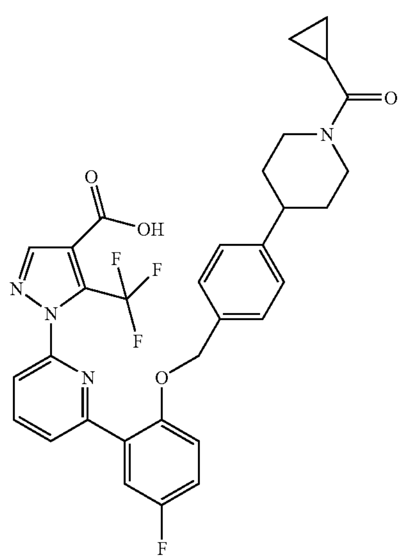 [SMILES: O=C(O)c1cnn(-c2cccc(-c3cc(F)ccc3OCc3ccc(C4CCN(C(=O)C5CC5)CC4)cc3)n2)c1C(F)(F)F] | 1-(6-(2-((4-(1-(cyclopropylcarbonyl)piperidin-4-yl)benzyl)oxy)-5-fluorophenyl)pyridin-2-yl)-5-(trifluoromethyl)-1H-pyrazole-4-carboxylic acid | 608.8 |

TABLE 1-continued

| Example | Structure | IUPAC name | LCMS |
|---|---|---|---|
| 57 | 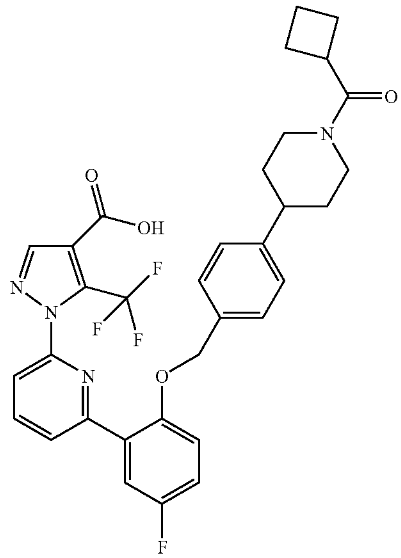 [SMILES: O=C(O)c1cnn(-c2cccc(-c3cc(F)ccc3OCc3ccc(C4CCN(C(=O)C5CCC5)CC4)cc3)n2)c1C(F)(F)F] | 1-(6-(2-((4-(1-(cyclobutylcarbonyl)piperidin-4-yl)benzyl)oxy)-5-fluorophenyl)pyridin-2-yl)-5-(trifluoromethyl)-1H-pyrazole-4-carboxylic acid | 622.8 |
| 58 | 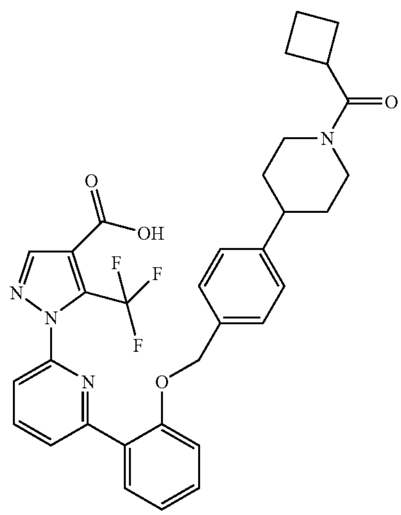 [SMILES: O=C(O)c1cnn(-c2cccc(-c3ccccc3OCc3ccc(C4CCN(C(=O)C5CCC5)CC4)cc3)n2)c1C(F)(F)F] | 1-(6-(2-((4-(1-(cyclobutylcarbonyl)piperidin-4-yl)benzyl)oxy)phenyl)pyridin-2-yl)-5-(trifluoromethyl)-1H-pyrazole-4-carboxylic acid | 604.8 |
| 59 | 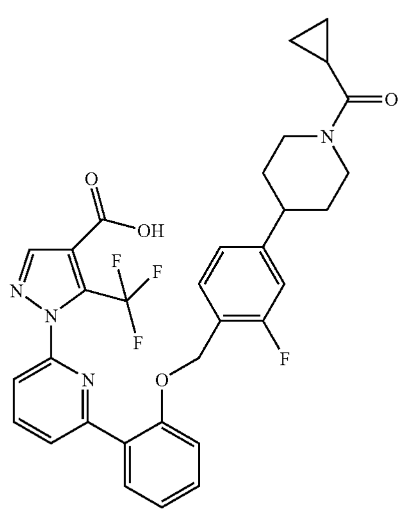 [SMILES: O=C(O)c1cnn(-c2cccc(-c3ccccc3OCc3ccc(C4CCN(C(=O)C5CC5)CC4)cc3F)n2)c1C(F)(F)F] | 1-(6-(2-((4-(1-(cyclopropylcarbonyl)piperidin-4-yl)-2-fluorobenzyl)oxy)phenyl)pyridin-2-yl)-5-(trifluoromethyl)-1H-pyrazole-4-carboxylic acid | 608.8 |

TABLE 1-continued

| Example | Structure | IUPAC name | LCMS |
|---|---|---|---|
| 60 | 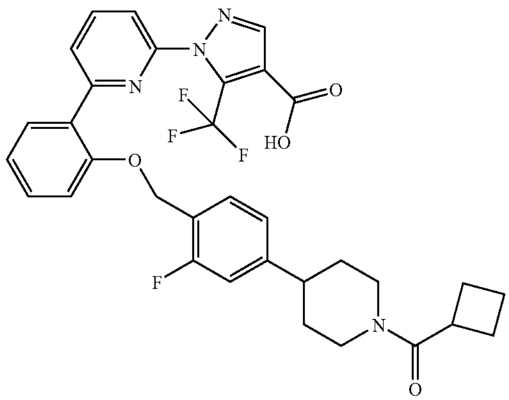 [SMILES: O=C(O)c1cnn(-c2cccc(-c3ccccc3OCc3ccc(C4CCN(C(=O)C5CCC5)CC4)cc3F)n2)c1C(F)(F)F] | 1-(6-(2-((4-(1-(cyclobutylcarbonyl)piperidin-4-yl)-2-fluorobenzyl)oxy)phenyl)pyridin-2-yl)-5-(trifluoromethyl)-1H-pyrazole-4-carboxylic acid | 622.9 |
| 61 | 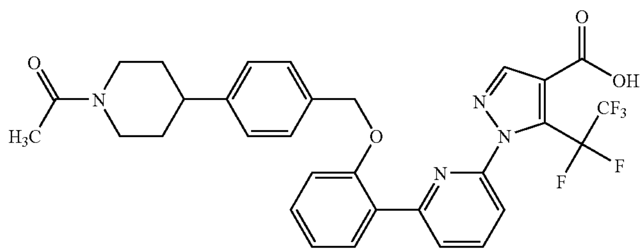 [SMILES: CC(=O)N1CCC(c2ccc(COc3ccccc3-c3cccc(-n4ncc(C(=O)O)c4C(F)(F)C(F)(F)F)n3)cc2)CC1] | 1-(6-(2-((4-(1-acetylpiperidin-4-yl)benzyl)oxy)phenyl)pyridin-2-yl)-5-(pentafluoroethyl)-1H-pyrazole-4-carboxylic acid | 614.9 |
| 62 | 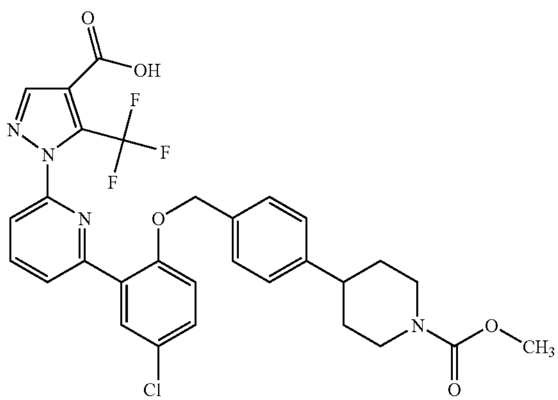 [SMILES: COC(=O)N1CCC(c2ccc(COc3ccc(Cl)cc3-c3cccc(-n4ncc(C(=O)O)c4C(F)(F)F)n3)cc2)CC1] | 1-(6-(5-chloro-2-((4-(1-(methoxycarbonyl)piperidin-4-yl)benzyl)oxy)phenyl)pyridin-2-yl)-5-(trifluoromethyl)-1H-pyrazole-4-carboxylic acid | 614.8 |
| 63 | 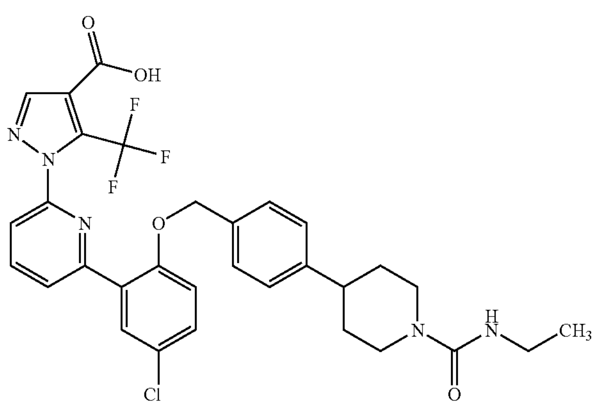 [SMILES: CCNC(=O)N1CCC(c2ccc(COc3ccc(Cl)cc3-c3cccc(-n4ncc(C(=O)O)c4C(F)(F)F)n3)cc2)CC1] | 1-(6-(5-chloro-2-((4-(1-((ethylamino)carbonyl)piperidin-4-yl)benzyl)oxy)phenyl)pyridin-2-yl)-5-(trifluoromethyl)-1H-pyrazole-4-carboxylic acid | 627.8 |

TABLE 1-continued

| Example | Structure | IUPAC name | LCMS |
|---|---|---|---|
| 64 | 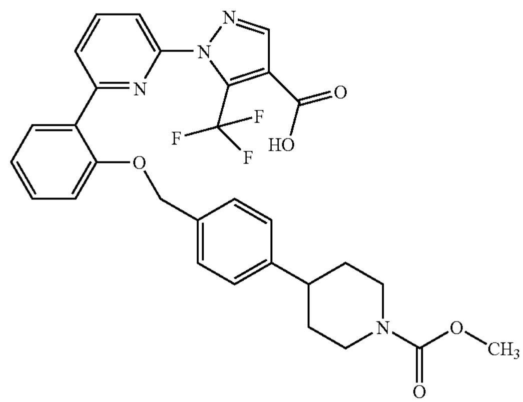 [SMILES: COC(=O)N1CCC(c2ccc(COc3ccccc3-c3cccc(-n4ncc(C(=O)O)c4C(F)(F)F)n3)cc2)CC1] | 1-(6-(2-((4-(1-(methoxycarbonyl)piperidin-4-yl)benzyl)oxy)phenyl)pyridin-2-yl)-5-(trifluoromethyl)-1H-pyrazole-4-carboxylic acid | 580.8 |
| 65 | 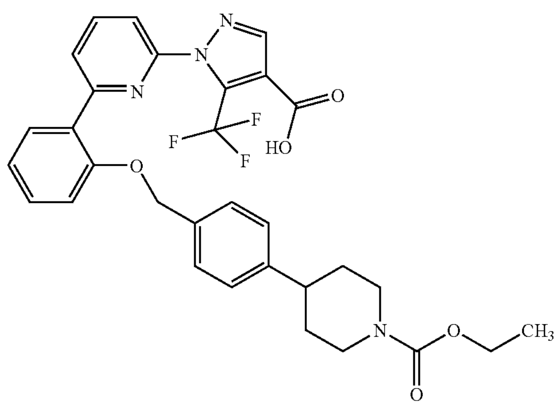 [SMILES: CCOC(=O)N1CCC(c2ccc(COc3ccccc3-c3cccc(-n4ncc(C(=O)O)c4C(F)(F)F)n3)cc2)CC1] | 1-(6-(2-((4-(1-(ethoxycarbonyl)piperidin-4-yl)benzyl)oxy)phenyl)pyridin-2-yl)-5-(trifluoromethyl)-1H-pyrazole-4-carboxylic acid | 594.8 |
| 66 | 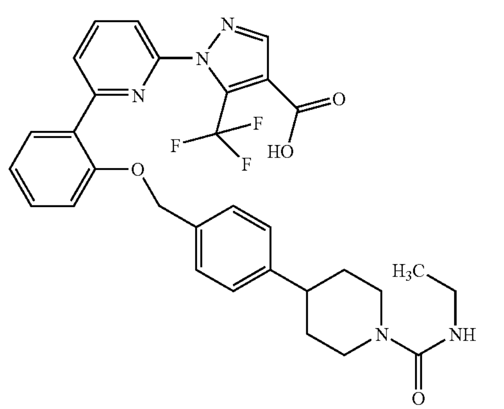 [SMILES: CCNC(=O)N1CCC(c2ccc(COc3ccccc3-c3cccc(-n4ncc(C(=O)O)c4C(F)(F)F)n3)cc2)CC1] | 1-(6-(2-((4-(1-((ethylamino)carbonyl)piperidin-4-yl)benzyl)oxy)phenyl)pyridin-2-yl)-5-(trifluoromethyl)-1H-pyrazole-4-carboxylic acid | 593.8 |
| 67 | 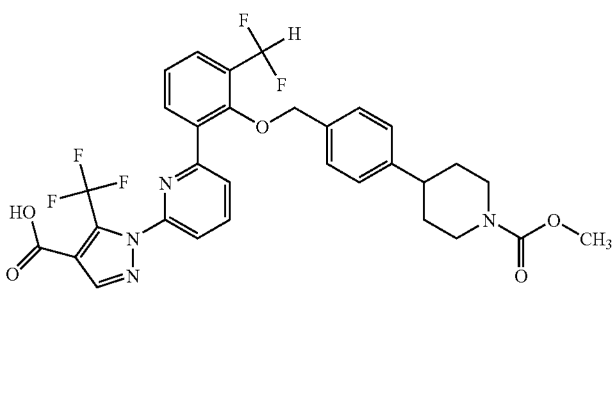 | 1-(6-(3-(difluoromethyl)-2-((4-(1-(methoxycarbonyl)piperidin-4-yl)benzyl)oxy)phenyl)pyridin-2-yl)-5-(trifluoromethyl)-1H-pyrazole-4-carboxylic acid | 630.8 |

TABLE 1-continued

| Example | Structure | IUPAC name | LCMS |
|---|---|---|---|
| 68 | 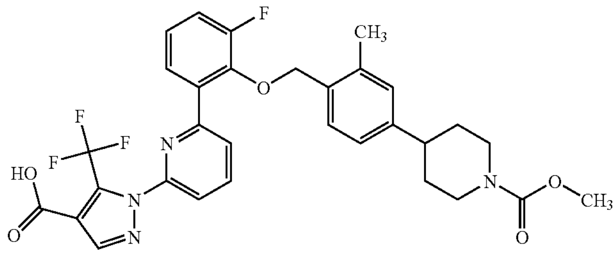 [SMILES: COC(=O)N1CCC(c2ccc(COc3c(F)cccc3-c3cccc(-n4ncc(C(=O)O)c4C(F)(F)F)n3)c(C)c2)CC1] | 1-(6-(3-fluoro-2-((4-(1-(methoxycarbonyl)piperidin-4-yl)-2-methylbenzyl)oxy)phenyl)pyridin-2-yl)-5-(trifluoromethyl)-1H-pyrazole-4-carboxylic acid | 612.9 |
| 69 | 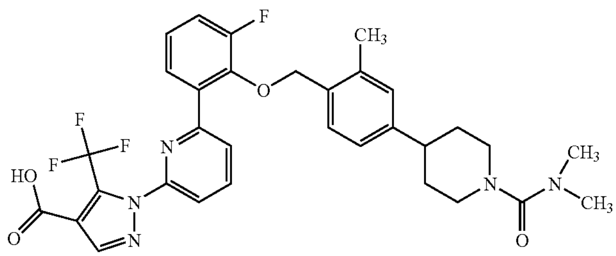 [SMILES: Cc1cc(C2CCN(C(=O)N(C)C)CC2)ccc1COc1c(F)cccc1-c1cccc(-n2ncc(C(=O)O)c2C(F)(F)F)n1] | 1-(6-(2-((4-(1-((dimethylamino)carbonyl)piperidin-4-yl)-2-methylbenzyl)oxy)-3-fluorophenyl)pyridin-2-yl)-5-(trifluoromethyl)-1H-pyrazole-4-carboxylic acid | 625.9 |
| 70 | 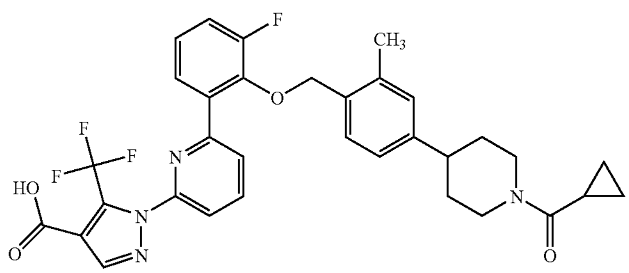 [SMILES: Cc1cc(C2CCN(C(=O)C3CC3)CC2)ccc1COc1c(F)cccc1-c1cccc(-n2ncc(C(=O)O)c2C(F)(F)F)n1] | 1-(6-(2-((4-(1-(cyclopropylcarbonyl)piperidin-4-yl)-2-methylbenzyl)oxy)-3-fluorophenyl)pyridin-2-yl)-5-(trifluoromethyl)-1H-pyrazole-4-carboxylic acid | 622.9 |
| 71 | 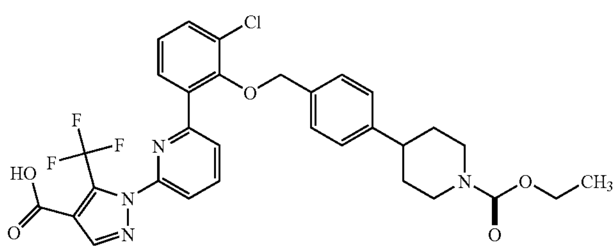 [SMILES: CCO[C@@H](O)N1CCC(c2ccc(COc3c(Cl)cccc3-c3cccc(-n4ncc(C(=O)O)c4C(F)(F)F)n3)cc2)CC1] | 1-(6-(3-chloro-2-((4-(1-(ethoxycarbonyl)piperidin-4-yl)benzyl)oxy)phenyl)pyridin-2-yl)-5-(trifluoromethyl)-1H-pyrazole-4-carboxylic acid | 628.2 |
| 72 | 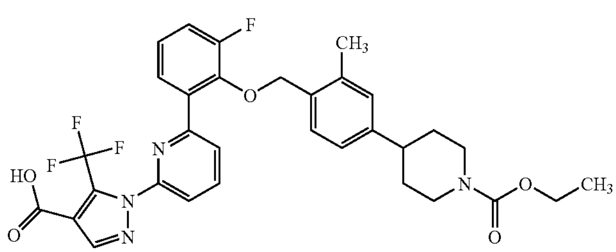 [SMILES: CCOC(=O)N1CCC(c2ccc(COc3c(F)cccc3-c3cccc(-n4ncc(C(=O)O)c4C(F)(F)F)n3)c(C)c2)CC1] | 1-(6-(2-((4-(1-(ethoxycarbonyl)piperidin-4-yl)-2-methylbenzyl)oxy)-3-fluorophenyl)pyridin-2-yl)-5-(trifluoromethyl)-1H-pyrazole-4-carboxylic acid | 626.9 |
| 73 | 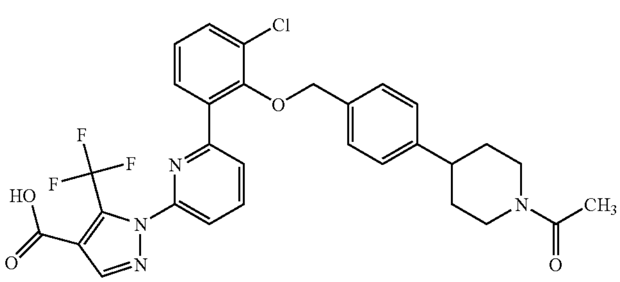 [SMILES: CC(=O)N1CCC(c2ccc(COc3c(Cl)cccc3-c3cccc(-n4ncc(C(=O)O)c4C(F)(F)F)n3)cc2)CC1] | 1-(6-(2-((4-(1-acetylpiperidin-4-yl)benzyl)oxy)-3-chlorophenyl)pyridin-2-yl)-5-(trifluoromethyl)-1H-pyrazole-4-carboxylic acid | 598.9 |

TABLE 1-continued

| Example | Structure | IUPAC name | LCMS |
|---|---|---|---|
| 74 | 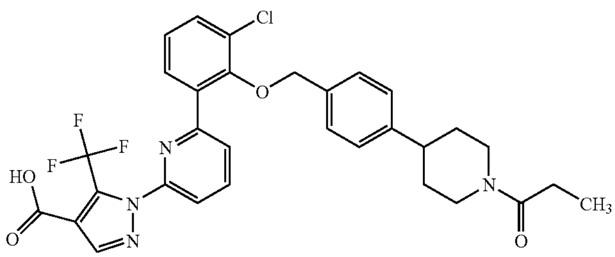 [SMILES: CCC(=O)N1CCC(c2ccc(COc3c(Cl)cccc3-c3cccc(-n4ncc(C(=O)O)c4C(F)(F)F)n3)cc2)CC1] | 1-(6-(3-chloro-2-((4-(1-propionylpiperidin-4-yl)benzyl)oxy)phenyl)pyridin-2-yl)-5-(trifluoromethyl)-1H-pyrazole-4-carboxylic acid | 612.9 |
| 75 | 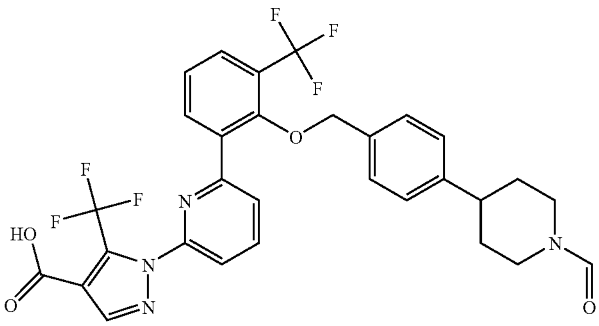 [SMILES: O=CN1CCC(c2ccc(COc3c(-c4cccc(-n5ncc(C(=O)O)c5C(F)(F)F)n4)cccc3C(F)(F)F)cc2)CC1] | 1-(6-(2-((4-(1-formylpiperidin-4-yl)benzyl)oxy)-3-(trifluoromethyl)phenyl)pyridin-2-yl)-5-(trifluoromethyl)-1H-pyrazole-4-carboxylic acid | 619.0 |
| 76 | 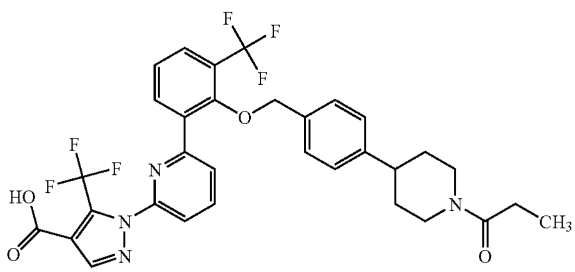 [SMILES: CCC(=O)N1CCC(c2ccc(COc3c(-c4cccc(-n5ncc(C(=O)O)c5C(F)(F)F)n4)cccc3C(F)(F)F)cc2)CC1] | 1-(6-(2-((4-(1-propionylpiperidin-4-yl)benzyl)oxy)-3-(trifluoromethyl)phenyl)pyridin-2-yl)-5-(trifluoromethyl)-1H-pyrazole-4-carboxylic acid | 647.0 |
| 77 | 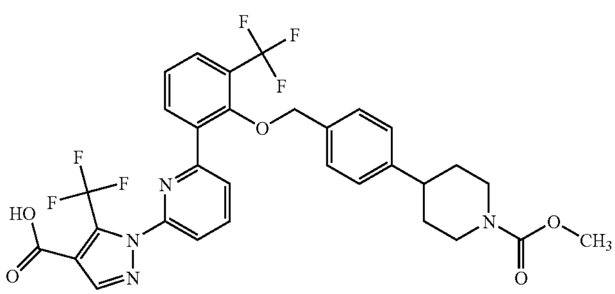 [SMILES: COC(=O)N1CCC(c2ccc(COc3c(-c4cccc(-n5ncc(C(=O)O)c5C(F)(F)F)n4)cccc3C(F)(F)F)cc2)CC1] | 1-(6-(2-((4-(1-(methoxycarbonyl)piperidin-4-yl)benzyl)oxy)-3-(trifluoromethyl)phenyl)pyridin-2-yl)-5-(trifluoromethyl)-1H-pyrazole-4-carboxylic acid | 648.9 |
| 78 | 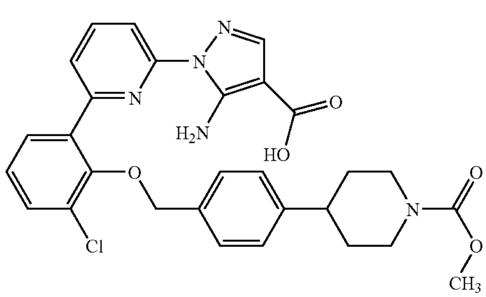 [SMILES: COC(=O)N1CCC(c2ccc(COc3c(Cl)cccc3-c3cccc(-n4ncc(C(=O)O)c4N)n3)cc2)CC1] | 5-amino-1-(6-(3-chloro-2-((4-(1-(methoxycarbonyl)piperidin-4-yl)benzyl)oxy)phenyl)pyridin-2-yl)-1H-pyrazole-4-carboxylic acid | 560 (M − H) |

TABLE 1-continued

| Example | Structure | IUPAC name | LCMS |
|---|---|---|---|
| 79 | 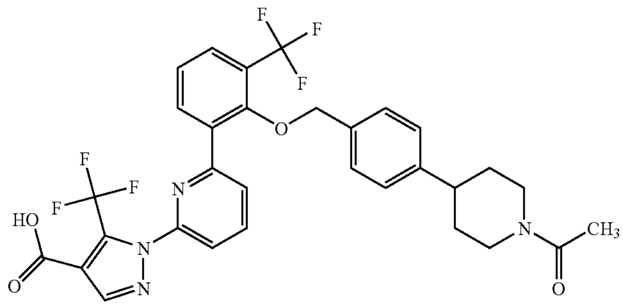 [SMILES: CC(=O)N1CCC(c2ccc(COc3c(-c4cccc(-n5ncc(C(=O)O)c5C(F)(F)F)n4)cccc3C(F)(F)F)cc2)CC1] | 1-(6-(2-((4-(1-acetylpiperidin-4-yl)benzyl)oxy)-3-(trifluoromethyl)phenyl)pyridin-2-yl)-5-(trifluoromethyl)-1H-pyrazole-4-carboxylic acid | 632.9 |
| 80 | 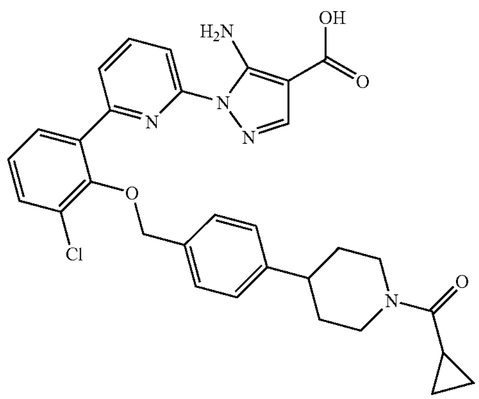 [SMILES: Nc1c(C(=O)O)cnn1-c1cccc(-c2cccc(Cl)c2OCc2ccc(C3CCN(C(=O)C4CC4)CC3)cc2)n1] | 5-amino-1-(6-(3-chloro-2-((4-(1-cyclopropylcarbonyl)piperidin-4-yl)benzyl)oxy)phenyl)pyridin-2-yl)-1H-pyrazole-4-carboxylic acid | 570.0 (M − H) |
| 81 | 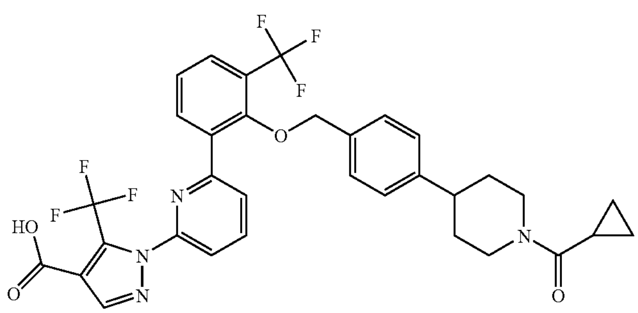 [SMILES: O=C(O)c1cnn(-c2cccc(-c3cccc(C(F)(F)F)c3OCc3ccc(C4CCN(C(=O)C5CC5)CC4)cc3)n2)c1C(F)(F)F] | 1-(6-(2-((4-(1-cyclopropylcarbonyl)piperidin-4-yl)benzyl)oxy)-3-(trifluoromethyl)phenyl)pyridin-2-yl)-5-(trifluoromethyl)-1H-pyrazole-4-carboxylic acid | 658.9 |
| 82 | 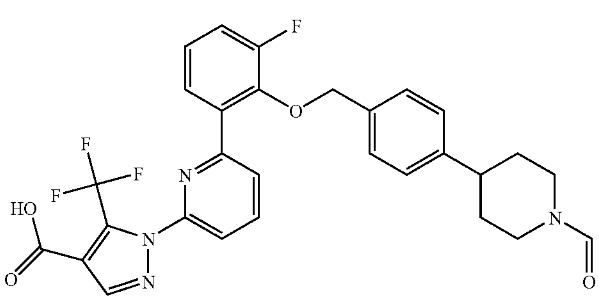 | 1-(6-(3-fluoro-2-((4-(1-formylpiperidin-4-yl)benzyl)oxy)phenyl)pyridin-2-yl)-5-(trifluoromethyl)-1H-pyrazole-4-carboxylic acid | 568.9 |

TABLE 1-continued

| Example | Structure | IUPAC name | LCMS |
|---|---|---|---|
| 83 | 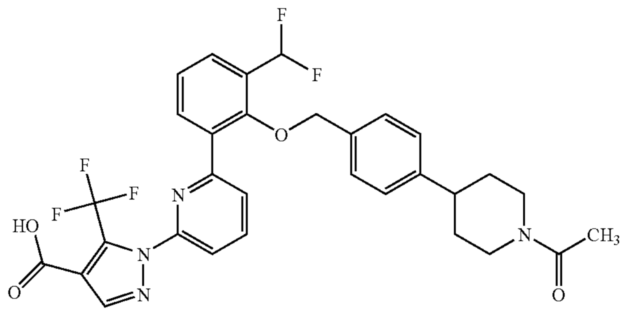 [SMILES: CC(=O)N1CCC(c2ccc(COc3c(-c4cccc(-n5ncc(C(=O)O)c5C(F)(F)F)n4)cccc3C(F)F)cc2)CC1] | 1-(6-(2-((4-(1-acetylpiperidin-4-yl)benzyl)oxy)-3-(difluoromethyl)phenyl)pyridin-2-yl)-5-(trifluoromethyl)-1H-pyrazole-4-carboxylic acid | 615.0 |
| 84 | 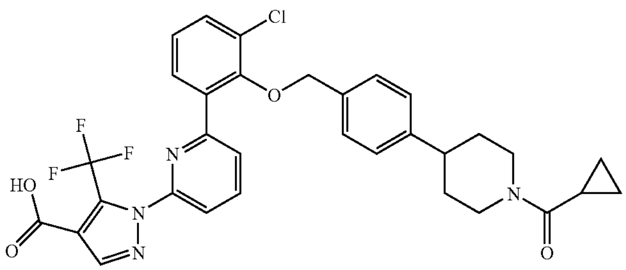 | 1-(6-(3-chloro-2-((4-(1-(cyclopropylcarbonyl)piperidin-4-yl)benzyl)oxy)phenyl)pyridin-2-yl)-5-(trifluoromethyl)-1H-pyrazole-4-carboxylic acid | 624.9 |
| 85 | 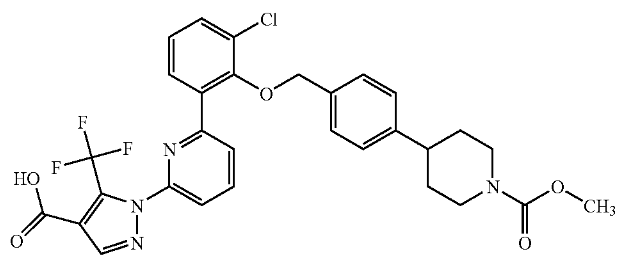 [SMILES: COC(=O)N1CCC(c2ccc(COc3c(Cl)cccc3-c3cccc(-n4ncc(C(=O)O)c4C(F)(F)F)n3)cc2)CC1] | 1-(6-(3-chloro-2-((4-(1-(methoxycarbonyl)piperidin-4-yl)benzyl)oxy)phenyl)pyridin-2-yl)-5-(trifluoromethyl)-1H-pyrazole-4-carboxylic acid | 614.9 |
| 86 | 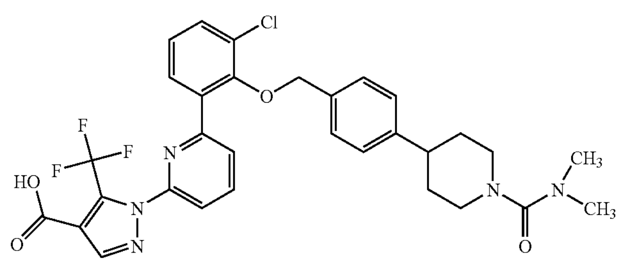 [SMILES: CN(C)C(=O)N1CCC(c2ccc(COc3c(Cl)cccc3-c3cccc(-n4ncc(C(=O)O)c4C(F)(F)F)n3)cc2)CC1] | 1-(6-(3-chloro-2-((4-(1-((dimethylamino)carbonyl)piperidin-4-yl)benzyl)oxy)phenyl)pyridin-2-yl)-5-(trifluoromethyl)-1H-pyrazole-4-carboxylic acid | 627.9 |
| 87 | 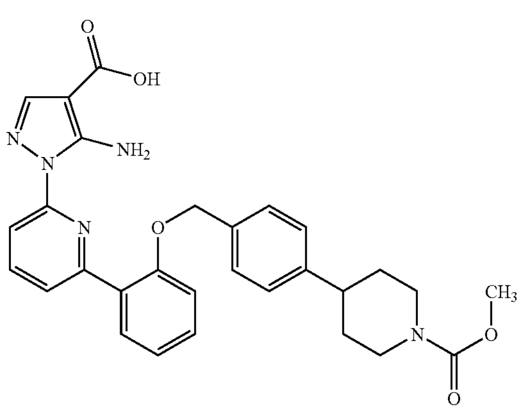 [SMILES: COC(=O)N1CCC(c2ccc(COc3ccccc3-c3cccc(-n4ncc(C(=O)O)c4N)n3)cc2)CC1] | 5-amino-1-(6-(2-((4-(1-(methoxycarbonyl)piperidin-4-yl)benzyl)oxy)phenyl)pyridin-2-yl)-1H-pyrazole-4-carboxylic acid | 527.9 |

TABLE 1-continued

| Example | Structure | IUPAC name | LCMS |
|---|---|---|---|
| 88 | 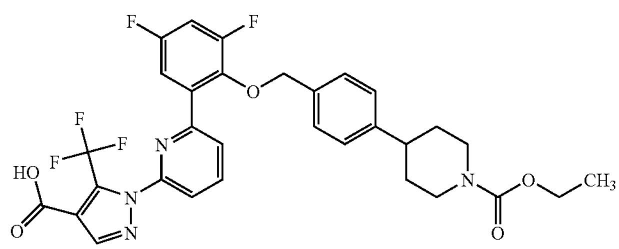 [SMILES: CCOC(=O)N1CCC(c2ccc(COc3c(F)cc(F)cc3-c3cccc(-n4ncc(C(=O)O)c4C(F)(F)F)n3)cc2)CC1] | 1-(6-(2-((4-(1-(ethoxycarbonyl)piperidin-4-yl)benzyl)oxy)-3,5-difluorophenyl)pyridin-2-yl)-5-(trifluoromethyl)-1H-pyrazole-4-carboxylic acid | 630.9 |
| 89 | 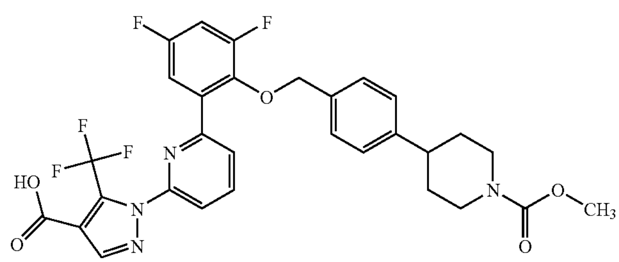 [SMILES: COC(=O)N1CCC(c2ccc(COc3c(F)cc(F)cc3-c3cccc(-n4ncc(C(=O)O)c4C(F)(F)F)n3)cc2)CC1] | 1-(6-(2-((4-(1-(methoxycarbonyl)piperidin-4-yl)benzyl)oxy)-3,5-difluorophenyl)pyridin-2-yl)-5-(trifluoromethyl)-1H-pyrazole-4-carboxylic acid | 616.8 |
| 90 | 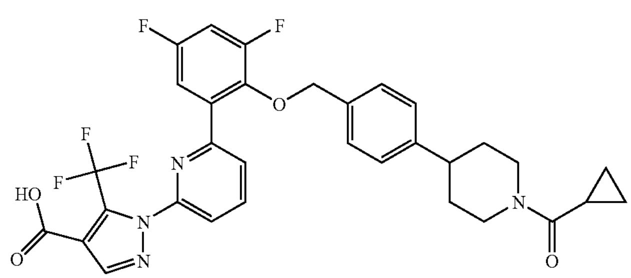 [SMILES: O=C(O)c1cnn(-c2cccc(-c3cc(F)cc(F)c3OCc3ccc(C4CCN(C(=O)C5CC5)CC4)cc3)n2)c1C(F)(F)F] | 1-(6-(2-((4-(1-(cyclopropylcarbonyl)piperidin-4-yl)benzyl)oxy)-3,5-difluorophenyl)pyridin-2-yl)-5-(trifluoromethyl)-1H-pyrazole-4-carboxylic acid | 626.9 |
| 91 | 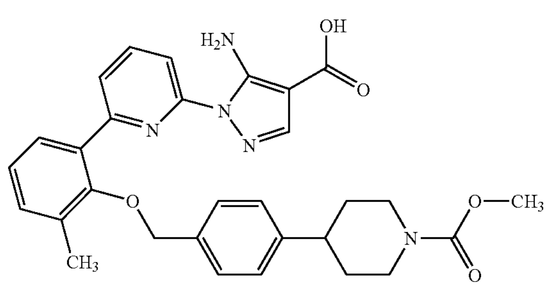 [SMILES: COC(=O)N1CCC(c2ccc(COc3c(C)cccc3-c3cccc(-n4ncc(C(=O)O)c4N)n3)cc2)CC1] | 5-amino-1-(6-(2-((4-(1-(methoxycarbonyl)piperidin-4-yl)benzyl)oxy)-3-methylphenyl)pyridin-2-yl)-1H-pyrazole-4-carboxylic acid | 542.0 |
| 92 | 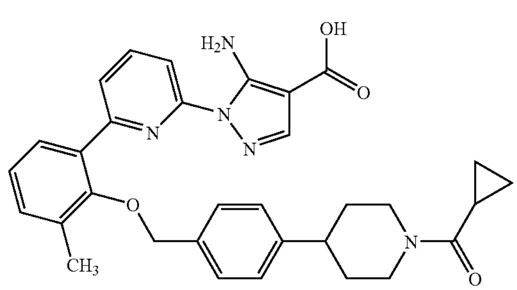 [SMILES: Cc1cccc(-c2cccc(-n3ncc(C(=O)O)c3N)n2)c1OCc1ccc(C2CCN(C(=O)C3CC3)CC2)cc1] | 5-amino-1-(6-(2-((4-(1-(cyclopropylcarbonyl)piperidin-4-yl)benzyl)oxy)-3-methylphenyl)pyridin-2-yl)-1H-pyrazole-4-carboxylic acid | 552.0 |

TABLE 1-continued

| Example | Structure | IUPAC name | LCMS |
|---|---|---|---|
| 93 | 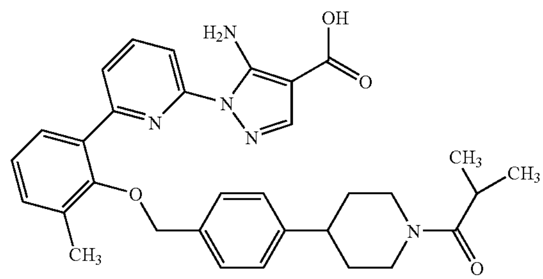 [SMILES: Cc1cccc(-c2cccc(-n3ncc(C(=O)O)c3N)n2)c1OCc1ccc(C2CCN(C(=O)C(C)C)CC2)cc1] | 5-amino-1-(6-(2-((4-(1-isobutyrylpiperidin-4-yl)benzyl)oxy)-3-methylphenyl)pyridin-2-yl)-1H-pyrazole-4-carboxylic acid | 554.1 |
| 94 | 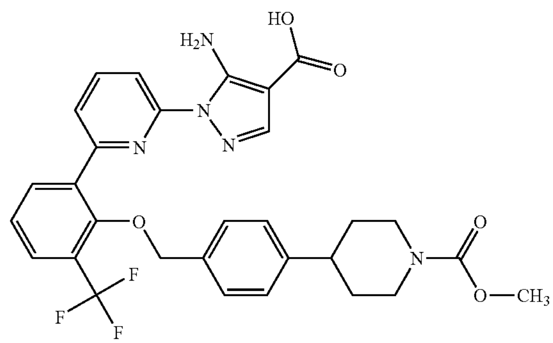 [SMILES: COC(=O)N1CCC(c2ccc(COc3c(-c4cccc(-n5ncc(C(=O)O)c5N)n4)cccc3C(F)(F)F)cc2)CC1] | 5-amino-1-(6-(2-((4-(1-(methoxycarbonyl)piperidin-4-yl)benzyl)oxy)-3-(trifluoromethyl)phenyl)pyridin-2-yl)-1H-pyrazole-4-carboxylic acid | 596.0 |
| 95 | 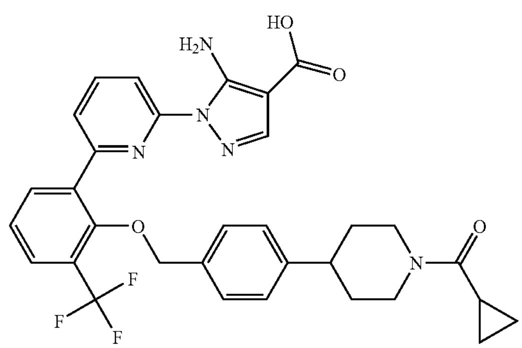 [SMILES: Nc1c(C(=O)O)cnn1-c1cccc(-c2cccc(C(F)(F)F)c2OCc2ccc(C3CCN(C(=O)C4CC4)CC3)cc2)n1] | 5-amino-1-(6-(2-((4-(1-(cyclopropylcarbonyl)piperidin-4-yl)benzyl)oxy)-3-(trifluoromethyl)phenyl)pyridin-2-yl)-1H-pyrazole-4-carboxylic acid | 606.0 |
| 96 | 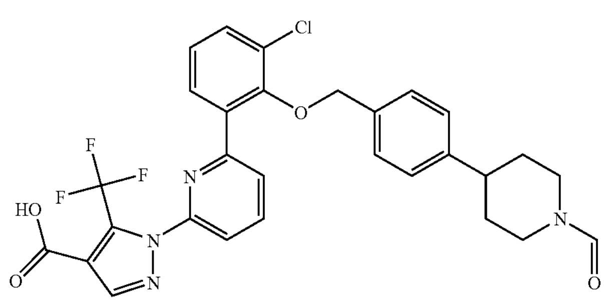 [SMILES: O=CN1CCC(c2ccc(COc3c(Cl)cccc3-c3cccc(-n4ncc(C(=O)O)c4C(F)(F)F)n3)cc2)CC1] | 1-(6-(3-chloro-2-((4-(1-formylpiperidin-4-yl)benzyl)oxy)phenyl)pyridin-2-yl)-5-(trifluoromethyl)-1H-pyrazole-4-carboxylic acid | 584.9 |

TABLE 1-continued

| Example | Structure | IUPAC name | LCMS |
|---|---|---|---|
| 97 | 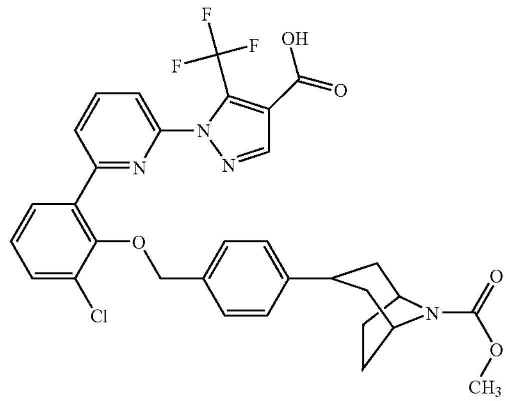 [SMILES: COC(=O)N1C2CCC1CC(c1ccc(COc3c(Cl)cccc3-c3cccc(-n4ncc(C(=O)O)c4C(F)(F)F)n3)cc1)C2] | 1-(6-(3-chloro-2-((4-(8-(methoxycarbonyl)-8-azabicyclo[3.2.1]oct-3-yl)benzyl)oxy)phenyl)pyridin-2-yl)-5-(trifluoromethyl)-1H-pyrazole-4-carboxylic acid | 641.0 |
| 98 | 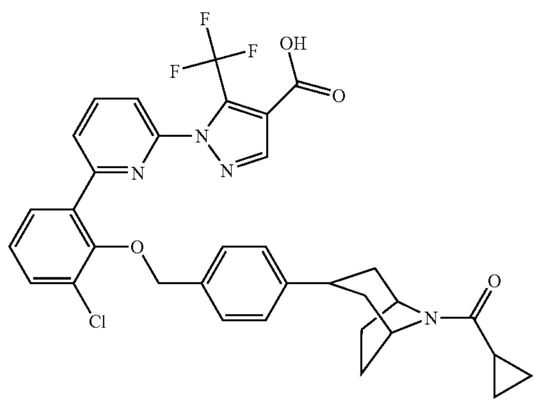 [SMILES: O=C(O)c1cnn(-c2cccc(-c3cccc(Cl)c3OCc3ccc(C4CC5CCC(C4)N5C(=O)C4CC4)cc3)n2)c1C(F)(F)F] | 1-(6-(3-chloro-2-((4-(8-(cyclopropylcarbonyl)-8-azabicyclo[3.2.1]oct-3-yl)benzyl)oxy)phenyl)pyridin-2-yl)-5-(trifluoromethyl)-1H-pyrazole-4-carboxylic acid | 651.0 |
| 99 | 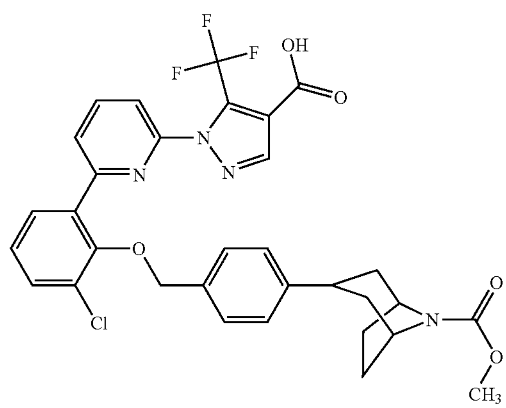 [SMILES: COC(=O)N1C2CCC1CC(c1ccc(COc3c(Cl)cccc3-c3cccc(-n4ncc(C(=O)O)c4C(F)(F)F)n3)cc1)C2] | 1-(6-(2-((4-(8-(methoxycarbonyl)-8-azabicyclo[3.2.1]oct-3-yl)benzyl)oxy)-3-methylphenyl)pyridin-2-yl)-5-(trifluoromethyl)-1H-pyrazole-4-carboxylic acid | 621.1 |
| 100 | 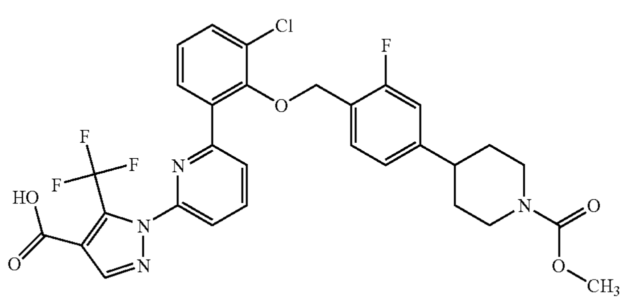 [SMILES: COC(=O)N1CCC(c2ccc(COc3c(Cl)cccc3-c3cccc(-n4ncc(C(=O)O)c4C(F)(F)F)n3)c(F)c2)CC1] | 1-(6-(3-chloro-2-((2-fluoro-4-(1-(methoxycarbonyl)piperidin-4-yl)benzyl)oxy)phenyl)pyridin-2-yl)-5-(trifluoromethyl)-1H-pyrazole-4-carboxylic acid | 633.0 |

TABLE 1-continued

| Example | Structure | IUPAC name | LCMS |
|---|---|---|---|
| 101 | 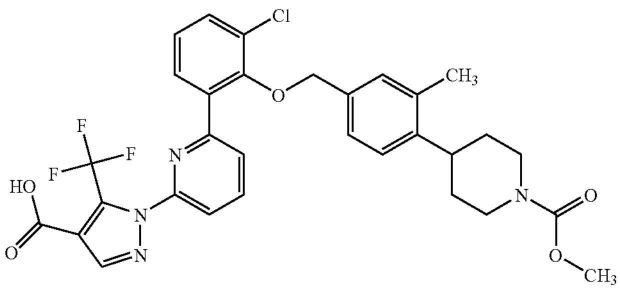 [SMILES: COC(=O)N1CCC(c2ccc(COc3c(Cl)cccc3-c3cccc(-n4ncc(C(=O)O)c4C(F)(F)F)n3)cc2C)CC1] | 1-(6-(3-chloro-2-((4-(1-(methoxycarbonyl)piperidin-4-yl)-3-methylbenzyl)oxy)phenyl)pyridin-2-yl)-5-(trifluoromethyl)-1H-pyrazole-4-carboxylic acid | 629.0 |
| 102 | 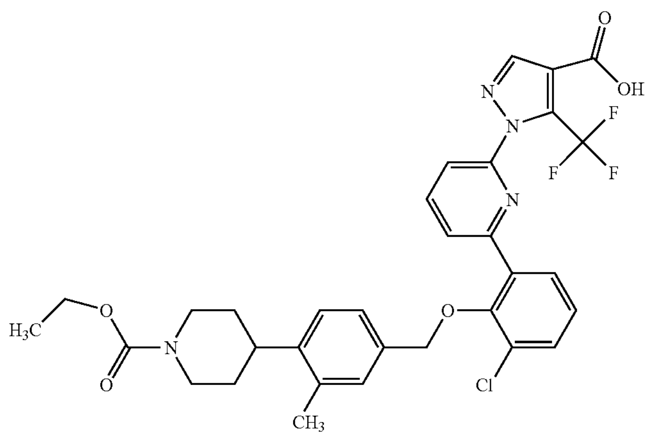 [SMILES: CCOC(=O)N1CCC(c2ccc(COc3c(Cl)cccc3-c3cccc(-n4ncc(C(=O)O)c4C(F)(F)F)n3)cc2C)CC1] | 1-(6-(3-chloro-2-((4-(1-(ethoxycarbonyl)piperidin-4-yl)-3-methylbenzyl)oxy)phenyl)pyridin-2-yl)-5-(trifluoromethyl)-1H-pyrazole-4-carboxylic acid | 643.0 |
| 103 | 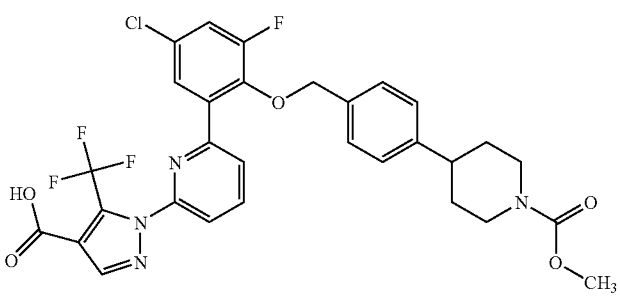 [SMILES: COC(=O)N1CCC(c2ccc(COc3c(F)cc(Cl)cc3-c3cccc(-n4ncc(C(=O)O)c4C(F)(F)F)n3)cc2)CC1] | 1-(6-(5-chloro-3-fluoro-2-((4-(1-(methoxycarbonyl)piperidin-4-yl)benzyl)oxy)phenyl)pyridin-2-yl)-5-(trifluoromethyl)-1H-pyrazole-4-carboxylic acid | 633.0 |
| 104 | 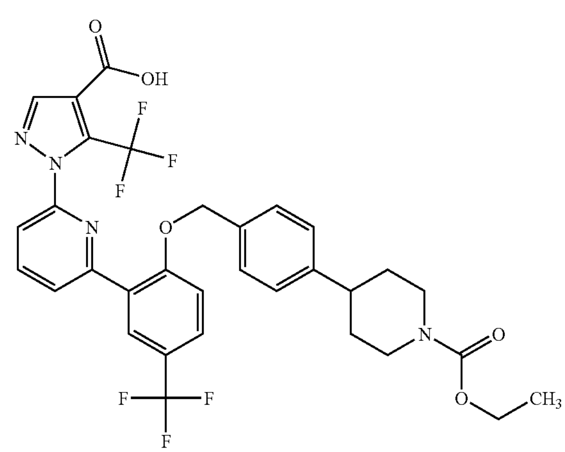 [SMILES: CCOC(=O)N1CCC(c2ccc(COc3ccc(C(F)(F)F)cc3-c3cccc(-n4ncc(C(=O)O)c4C(F)(F)F)n3)cc2)CC1] | 1-(6-(2-((4-(1-(ethoxycarbonyl)piperidin-4-yl)benzyl)oxy)-5-(trifluoromethyl)phenyl)pyridin-2-yl)-5-(trifluoromethyl)-1H-pyrazole-4-carboxylic acid | 663.0 |

TABLE 1-continued

| Example | Structure | IUPAC name | LCMS |
|---|---|---|---|
| 105 | 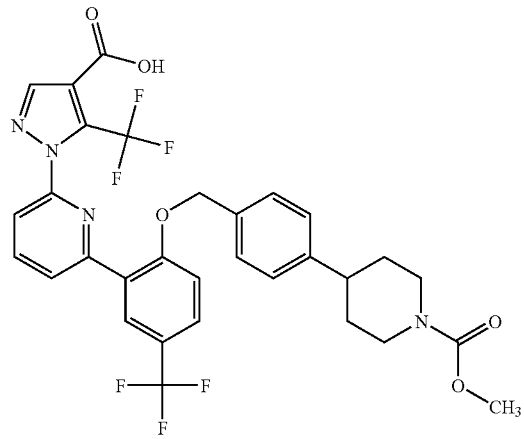 [SMILES: COC(=O)N1CCC(c2ccc(COc3ccc(C(F)(F)F)cc3-c3cccc(-n4ncc(C(=O)O)c4C(F)(F)F)n3)cc2)CC1] | 1-(6-(2-((4-(1-(methoxycarbonyl)piperidin-4-yl)benzyl)oxy)-5-(trifluoromethyl)phenyl)pyridin-2-yl)-5-(trifluoromethyl)-1H-pyrazole-4-carboxylic acid | 649.1 |
| 106 | 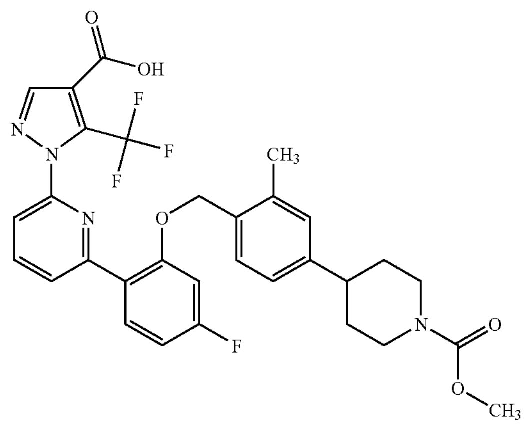 [SMILES: COC(=O)N1CCC(c2ccc(COc3cc(F)ccc3-c3cccc(-n4ncc(C(=O)O)c4C(F)(F)F)n3)c(C)c2)CC1] | 1-(6-(4-fluoro-2-((4-(1-(methoxycarbonyl)piperidin-4-yl)-2-methylbenzyl)oxy)phenyl)pyridin-2-yl)-5-(trifluoromethyl)-1H-pyrazole-4-carboxylic acid | 613.1 |
| 107 | 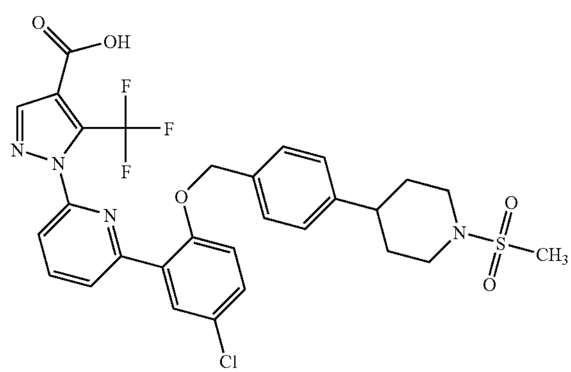 [SMILES: CS(=O)(=O)N1CCC(c2ccc(COc3ccc(Cl)cc3-c3cccc(-n4ncc(C(=O)O)c4C(F)(F)F)n3)cc2)CC1] | 1-(6-(5-chloro-2-((4-(1-(methylsulfonyl)piperidin-4-yl)benzyl)oxy)phenyl)pyridin-2-yl)-5-(trifluoromethyl)-1H-pyrazole-4-carboxylic acid | 634.8 |
| 108 | 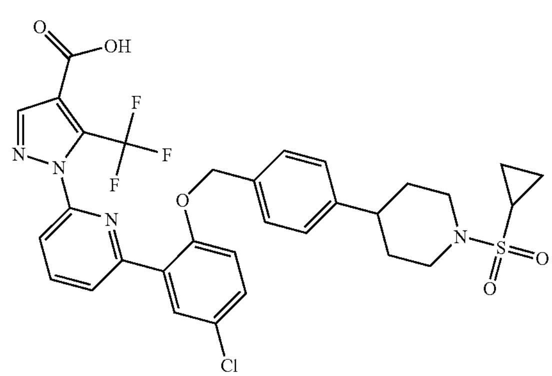 [SMILES: O=C(O)c1cnn(-c2cccc(-c3cc(Cl)ccc3OCc3ccc(C4CCN(S(=O)(=O)C5CC5)CC4)cc3)n2)c1C(F)(F)F] | 1-(6-(5-chloro-2-((4-(1-(cyclopropylsulfonyl)piperidin-4-yl)benzyl)oxy)phenyl)pyridin-2-yl)-5-(trifluoromethyl)-1H-pyrazole-4-carboxylic acid | 660.8 |

TABLE 1-continued

| Example | Structure | IUPAC name | LCMS |
|---|---|---|---|
| 109 | 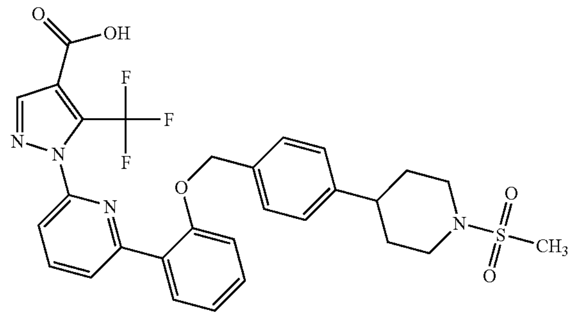 [SMILES: CS(=O)(=O)N1CCC(c2ccc(COc3ccccc3-c3cccc(-n4ncc(C(=O)O)c4C(F)(F)F)n3)cc2)CC1] | 1-(6-(2-((4-(1-(methylsulfonyl)piperidin-4-yl)benzyl)oxy)phenyl)pyridin-2-yl)-5-(trifluoromethyl)-1H-pyrazole-4-carboxylic acid | 600.9 |
| 110 | 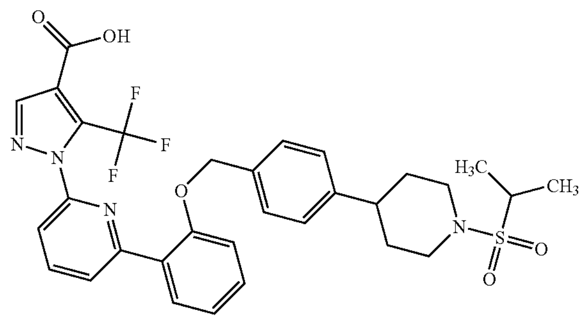 [SMILES: CC(C)S(=O)(=O)N1CCC(c2ccc(COc3ccccc3-c3cccc(-n4ncc(C(=O)O)c4C(F)(F)F)n3)cc2)CC1] | 1-(6-(2-((4-(1-(isopropylsulfonyl)piperidin-4-yl)benzyl)oxy)phenyl)pyridin-2-yl)-5-(trifluoromethyl)-1H-pyrazole-4-carboxylic acid | 628.9 |
| 111 | 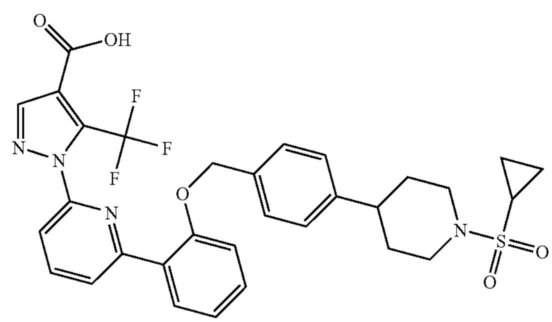 [SMILES: O=C(O)c1cnn(-c2cccc(-c3ccccc3OCc3ccc(C4CCN(S(=O)(=O)C5CC5)CC4)cc3)n2)c1C(F)(F)F] | 1-(6-(2-((4-(1-(cyclopropylsulfonyl)piperidin-4-yl)benzyl)oxy)phenyl)pyridin-2-yl)-5-(trifluoromethyl)-1H-pyrazole-4-carboxylic acid | 626.9 |
| 112 | 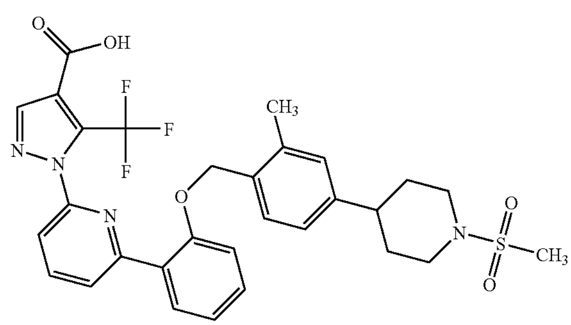 [SMILES: Cc1cc(C2CCN(S(C)(=O)=O)CC2)ccc1COc1ccccc1-c1cccc(-n2ncc(C(=O)O)c2C(F)(F)F)n1] | 1-(6-(2-((2-methyl-4-(1-(methylsulfonyl)piperidin-4-yl)benzyl)oxy)phenyl)pyridin-2-yl)-5-(trifluoromethyl)-1H-pyrazole-4-carboxylic acid | 615.0 |
| 113 | 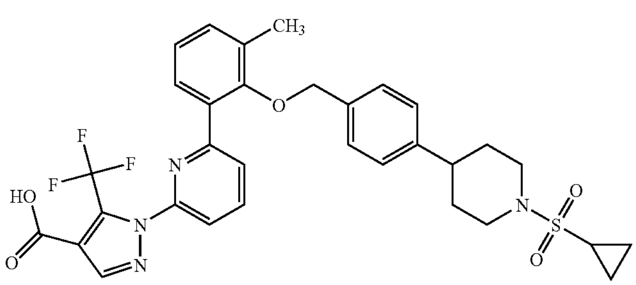 [SMILES: Cc1cccc(-c2cccc(-n3ncc(C(=O)O)c3C(F)(F)F)n2)c1OCc1ccc(C2CCN(S(=O)(=O)C3CC3)CC2)cc1] | 1-(6-(2-((4-(1-(cyclopropylsulfonyl)piperidin-4-yl)benzyl)oxy)-3-methylphenyl)pyridin-2-yl)-5-(trifluoromethyl)-1H-pyrazole-4-carboxylic acid | 641.7 |

TABLE 1-continued

| Example | Structure | IUPAC name | LCMS |
|---|---|---|---|
| 114 | 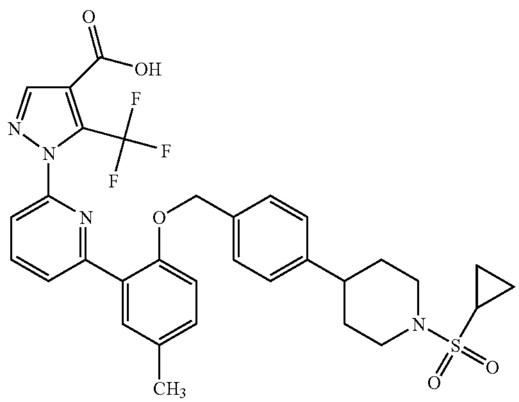 [SMILES: Cc1ccc(OCc2ccc(C3CCN(S(=O)(=O)C4CC4)CC3)cc2)c(-c2cccc(-n3ncc(C(=O)O)c3C(F)(F)F)n2)c1] | 1-(6-(2-((4-(1-(cyclopropylsulfonyl)piperidin-4-yl)benzyl)oxy)-5-methylphenyl)pyridin-2-yl)-5-(trifluoromethyl)-1H-pyrazole-4-carboxylic acid | 640.9 |
| 115 | 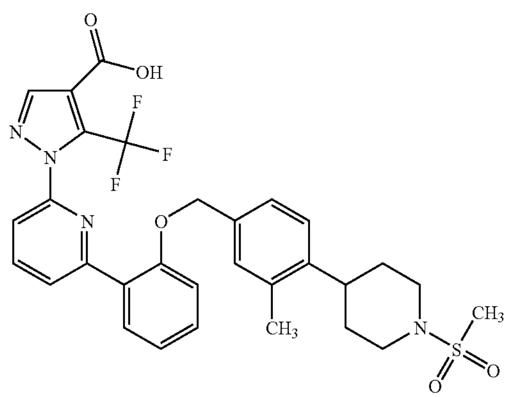 [SMILES: Cc1cc(COc2ccccc2-c2cccc(-n3ncc(C(=O)O)c3C(F)(F)F)n2)ccc1C1CCN(S(C)(=O)=O)CC1] | 1-(6-(2-((3-methyl-4-(1-(methylsulfonyl)piperidin-4-yl)benzyl)oxy)phenyl)pyridin-2-yl)-5-(trifluoromethyl)-1H-pyrazole-4-carboxylic acid | 616.2 |
| 116 | 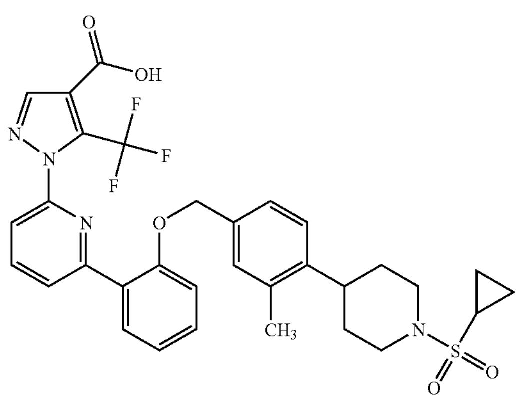 [SMILES: Cc1cc(COc2ccccc2-c2cccc(-n3ncc(C(=O)O)c3C(F)(F)F)n2)ccc1C1CCN(S(=O)(=O)C2CC2)CC1] | 1-(6-(2-((4-(1-(cyclopropylsulfonyl)piperidin-4-yl)-3-methylbenzyl)oxy)phenyl)pyridin-2-yl)-5-(trifluoromethyl)-1H-pyrazole-4-carboxylic acid | 642.3 |
| 117 | 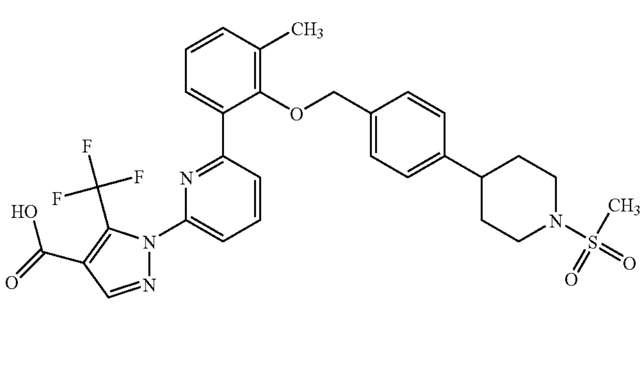 [SMILES: Cc1cccc(-c2cccc(-n3ncc(C(=O)O)c3C(F)(F)F)n2)c1OCc1ccc(C2CCN(S(C)(=O)=O)CC2)cc1] | 1-(6-(3-methyl-2-((4-(1-(methylsulfonyl)piperidin-4-yl)benzyl)oxy)phenyl)pyridin-2-yl)-5-(trifluoromethyl)-1H-pyrazole-4-carboxylic acid | 614.8 |

TABLE 1-continued

| Example | Structure | IUPAC name | LCMS |
|---|---|---|---|
| 118 | 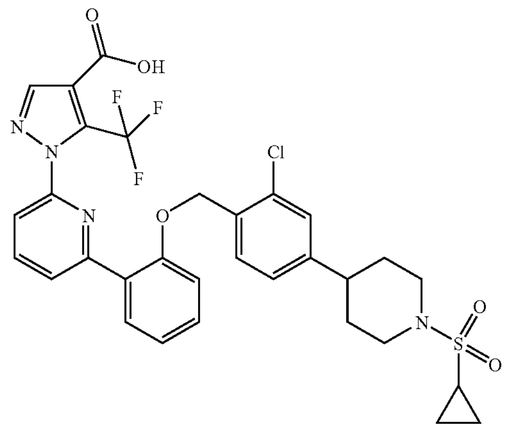 [SMILES: O=C(O)c1cnn(-c2cccc(-c3ccccc3OCc3ccc(C4CCN(S(=O)(=O)C5CC5)CC4)cc3Cl)n2)c1C(F)(F)F] | 1-(6-(2-((2-chloro-4-(1-(cyclopropylsulfonyl)piperidin-4-yl)benzyl)oxy)phenyl)pyridin-2-yl)-5-(trifluoromethyl)-1H-pyrazole-4-carboxylic acid | 660.7 |
| 119 | 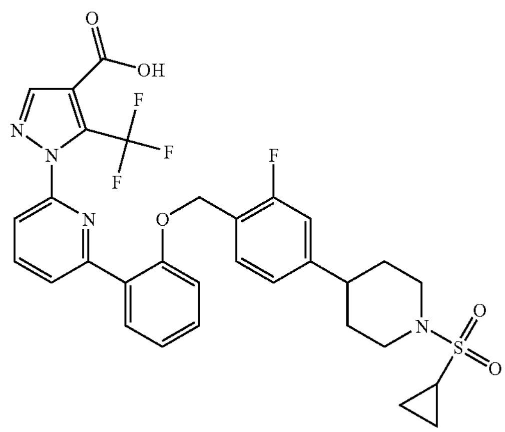 [SMILES: O=C(O)c1cnn(-c2cccc(-c3ccccc3OCc3ccc(C4CCN(S(=O)(=O)C5CC5)CC4)cc3F)n2)c1C(F)(F)F] | 1-(6-(2-((4-(1-(cyclopropylsulfonyl)piperidin-4-yl)-2-fluorobenzyl)oxy)phenyl)pyridin-2-yl)-5-(trifluoromethyl)-1H-pyrazole-4-carboxylic acid | 644.7 |
| 120 | 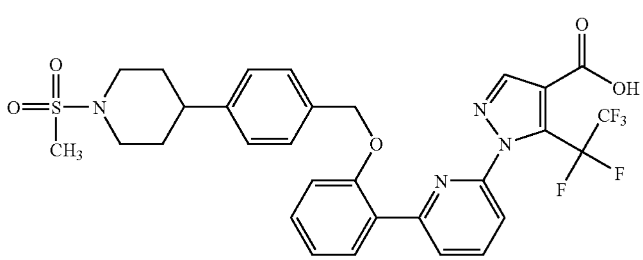 [SMILES: CS(=O)(=O)N1CCC(c2ccc(COc3ccccc3-c3cccc(-n4ncc(C(=O)O)c4C(F)(F)C(F)(F)F)n3)cc2)CC1] | 1-(6-(2-((4-(1-(methylsulfonyl)piperidin-4-yl)benzyl)oxy)phenyl)pyridin-2-yl)-5-(pentafluoroethyl)-1H-pyrazole-4-carboxylic acid | 650.8 |
| 121 | 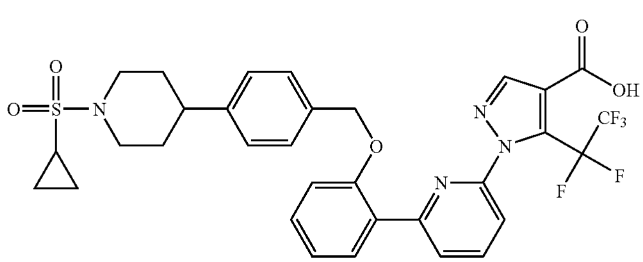 [SMILES: O=C(O)c1cnn(-c2cccc(-c3ccccc3OCc3ccc(C4CCN(S(=O)(=O)C5CC5)CC4)cc3)n2)c1C(F)(F)C(F)(F)F] | 1-(6-(2-((4-(1-(cyclopropylsulfonyl)piperidin-4-yl)benzyl)oxy)phenyl)pyridin-2-yl)-5-(pentafluoroethyl)-1H-pyrazole-4-carboxylic acid | 676.8 |

TABLE 1-continued

| Example | Structure | IUPAC name | LCMS |
|---|---|---|---|
| 122 | 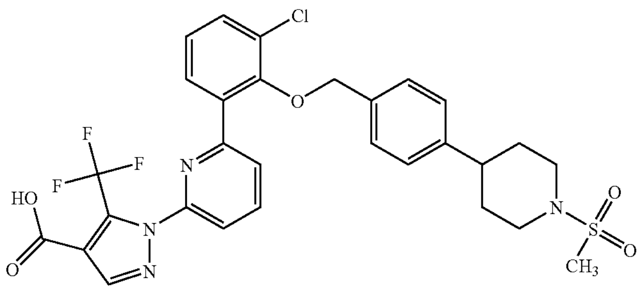 [SMILES: CS(=O)(=O)N1CCC(c2ccc(COc3c(Cl)cccc3-c3cccc(-n4ncc(C(=O)O)c4C(F)(F)F)n3)cc2)CC1] | 1-(6-(3-chloro-2-((4-(1-(methylsulfonyl)piperidin-4-yl)benzyl)oxy)phenyl)pyridin-2-yl)-5-(trifluoromethyl)-1H-pyrazole-4-carboxylic acid | 658.0 (M + Na) |
| 123 | 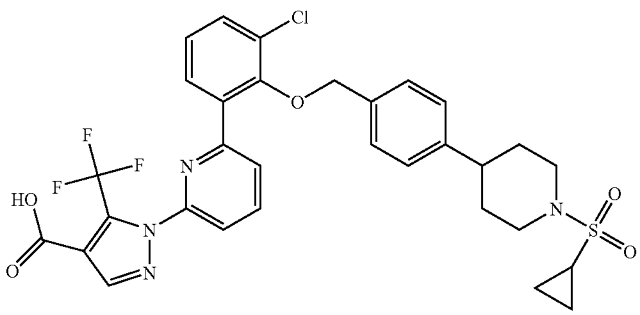 [SMILES: O=C(O)c1cnn(-c2cccc(-c3cccc(Cl)c3OCc3ccc(C4CCN(S(=O)(=O)C5CC5)CC4)cc3)n2)c1C(F)(F)F] | 1-(6-(3-chloro-2-((4-(1-(cyclopropylsulfonyl)piperidin-4-yl)benzyl)oxy)phenyl)pyridin-2-yl)-5-(trifluoromethyl)-1H-pyrazole-4-carboxylic acid | 660.9 |
| 124 | 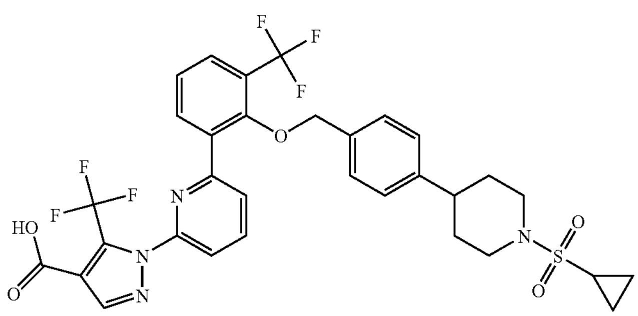 [SMILES: O=C(O)c1cnn(-c2cccc(-c3cccc(C(F)(F)F)c3OCc3ccc(C4CCN(S(=O)(=O)C5CC5)CC4)cc3)n2)c1C(F)(F)F] | 1-(6-(2-((4-(1-(cyclopropylsulfonyl)piperidin-4-yl)benzyl)oxy)-3-(trifluoromethyl)phenyl)pyridin-2-yl)-5-(trifluoromethyl)-1H-pyrazole-4-carboxylic acid | 695.0 |
| 125 | 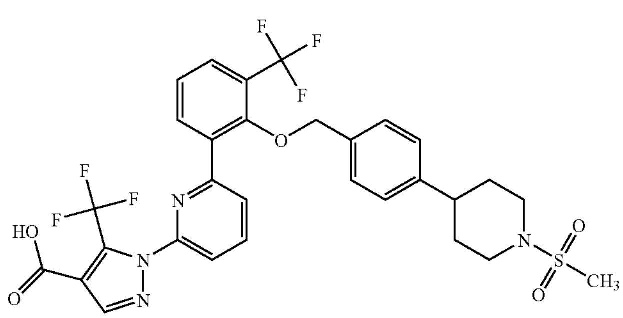 [SMILES: CS(=O)(=O)N1CCC(c2ccc(COc3c(-c4cccc(-n5ncc(C(=O)O)c5C(F)(F)F)n4)cccc3C(F)(F)F)cc2)CC1] | 1-(6-(2-((4-(1-(methylsulfonyl)piperidin-4-yl)benzyl)oxy)-3-(trifluoromethyl)phenyl)pyridin-2-yl)-5-(trifluoromethyl)-1H-pyrazole-4-carboxylic acid | 690.8 (M + Na) |
| 126 | 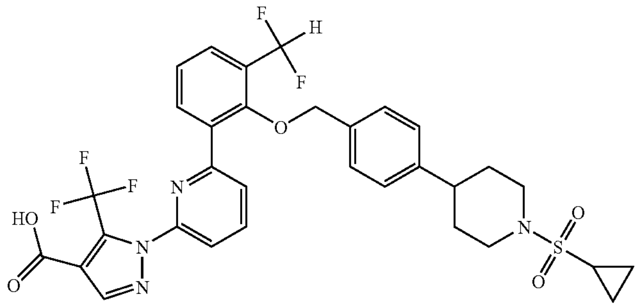 | 1-(6-(2-((4-(1-(cyclopropylsulfonyl)piperidin-4-yl)benzyl)oxy)-3-(difluoromethyl)phenyl)pyridin-2-yl)-5-(trifluoromethyl)-1H-pyrazole-4-carboxylic acid | 676.9 |

TABLE 1-continued

| Example | Structure | IUPAC name | LCMS |
|---|---|---|---|
| 127 | 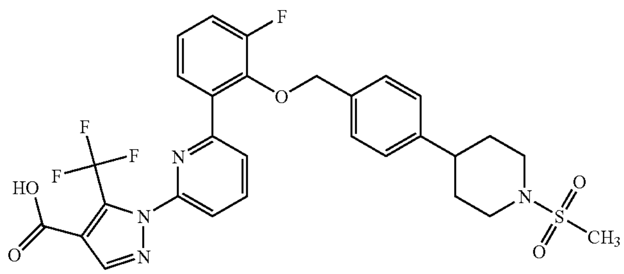 [SMILES: CS(=O)(=O)N1CCC(c2ccc(COc3c(F)cccc3-c3cccc(-n4ncc(C(=O)O)c4C(F)(F)F)n3)cc2)CC1] | 1-(6-(3-fluoro-2-((4-(1-(methylsulfonyl)piperidin-4-yl)benzyl)oxy)phenyl)pyridin-2-yl)-5-(trifluoromethyl)-1H-pyrazole-4-carboxylic acid | 620.0 |
| 128 | 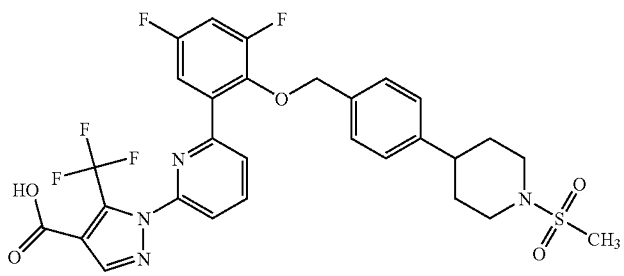 [SMILES: CS(=O)(=O)N1CCC(c2ccc(COc3c(F)cc(F)cc3-c3cccc(-n4ncc(C(=O)O)c4C(F)(F)F)n3)cc2)CC1] | 1-(6-(3,5-difluoro-2-((4-(1-(methylsulfonyl)piperidin-4-henyl)pyridin-2-yl)-5-(trifluoromethyl)-1H-pyrazole-4-carboxylic acid | 637.0 |
| 129 | 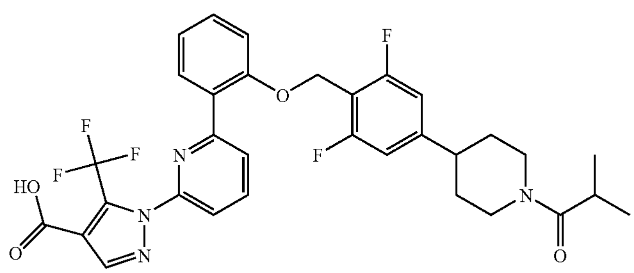 [SMILES: CC(C)C(=O)N1CCC(c2cc(F)c(COc3ccccc3-c3cccc(-n4ncc(C(=O)O)c4C(F)(F)F)n3)c(F)c2)CC1] | 1-(6-(2-((2,6-difluoro-4-(1-isobutyrylpiperidin-4-yl)benzyl)oxy)phenyl)pyridin-2-yl)-5-(trifluoromethyl)-1H-pyrazole-4-carboxylic acid | 629.0 |
| 130 | 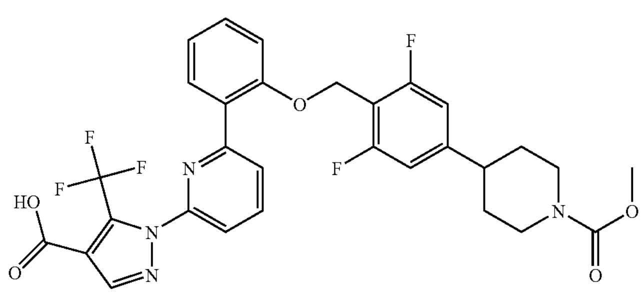 [SMILES: COC(=O)N1CCC(c2cc(F)c(COc3ccccc3-c3cccc(-n4ncc(C(=O)O)c4C(F)(F)F)n3)c(F)c2)CC1] | 1-(6-(2-((2,6-difluoro-4-(1-(methoxycarbonyl)piperidin-4-yl)benzyl)oxy)phenyl)pyridin-2-yl)-5-(trifluoromethyl)-1H-pyrazole-4-carboxylic acid | 616.9 |
| 131 | 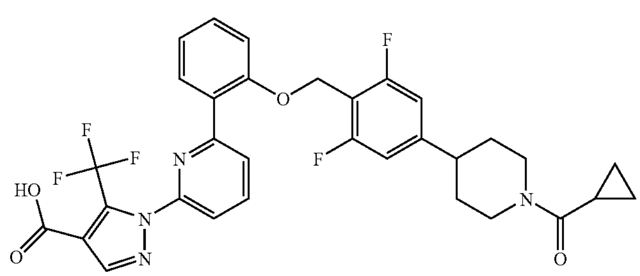 [SMILES: O=C(O)c1cnn(-c2cccc(-c3ccccc3OCc3c(F)cc(C4CCN(C(=O)C5CC5)CC4)cc3F)n2)c1C(F)(F)F] | 1-(6-(2-((4-(1-(cyclopropylcarbonyl)piperidin-4-yl)-2,6-difluorobenzyl)oxy)phenyl)pyridin-2-yl)-5-(trifluoromethyl)-1H-pyrazole-4-carboxylic acid | 626.9 |

TABLE 1-continued

| Example | Structure | IUPAC name | LCMS |
|---|---|---|---|
| 132 | 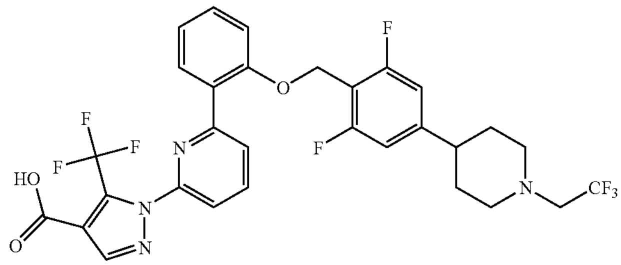 [SMILES: O=C(O)c1cnn(-c2cccc(-c3ccccc3OCc3c(F)cc(C4CCN(CC(F)(F)F)CC4)cc3F)n2)c1C(F)(F)F] | 1-(6-(2-((2,6-difluoro-4-(1-(2,2,2-trifluoroethyl)piperidin-4-yl)benzyl)oxy)phenyl)pyridin-2-yl)-5-(trifluoromethyl)-1H-pyrazole-4-carboxylic acid | 641.0 |
| 133 | 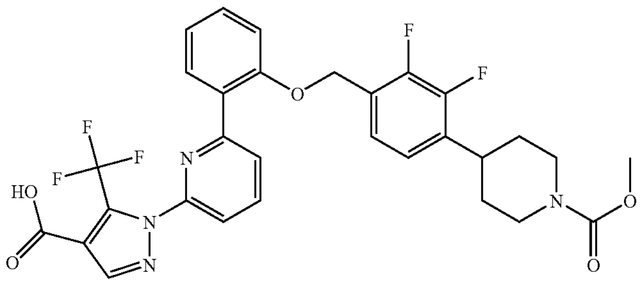 [SMILES: COC(=O)N1CCC(c2ccc(COc3ccccc3-c3cccc(-n4ncc(C(=O)O)c4C(F)(F)F)n3)c(F)c2F)CC1] | 1-(6-(2-((2,3-difluoro-4-(1-(methoxycarbonyl)piperidin-4-yl)benzyl)oxy)phenyl)pyridin-2-yl)-5-(trifluoromethyl)-1H-pyrazole-4-carboxylic acid | 617.1 |
| 134 | 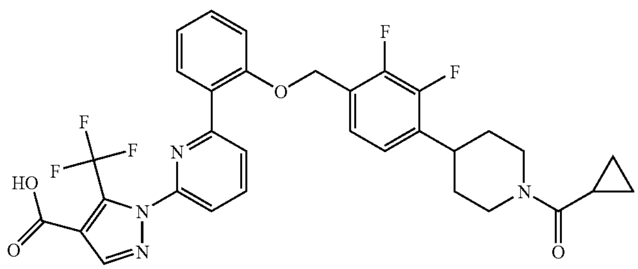 [SMILES: O=C(O)c1cnn(-c2cccc(-c3ccccc3OCc3ccc(C4CCN(C(=O)C5CC5)CC4)c(F)c3F)n2)c1C(F)(F)F] | 1-(6-(2-((4-(1-(cyclopropylcarbonyl)piperidin-4-yl)-2,3-difluorobenzyl)oxy)phenyl)pyridin-2-yl)-5-(trifluoromethyl)-1H-pyrazole-4-carboxylic acid | 627.1 |
| 135 | 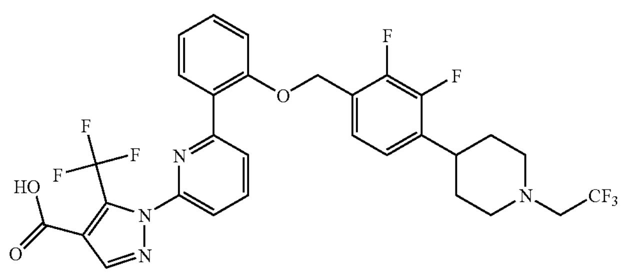 [SMILES: O=C(O)c1cnn(-c2cccc(-c3ccccc3OCc3ccc(C4CCN(CC(F)(F)F)CC4)c(F)c3F)n2)c1C(F)(F)F] | 1-(6-(2-((2,3-difluoro-4-(1-(2,2,2-trifluoroethyl)piperidin-4-yl)benzyl)oxy)phenyl)pyridin-2-yl)-5-(trifluoromethyl)-1H-pyrazole-4-carboxylic acid | 641.1 |

EXAMPLE 136

-continued

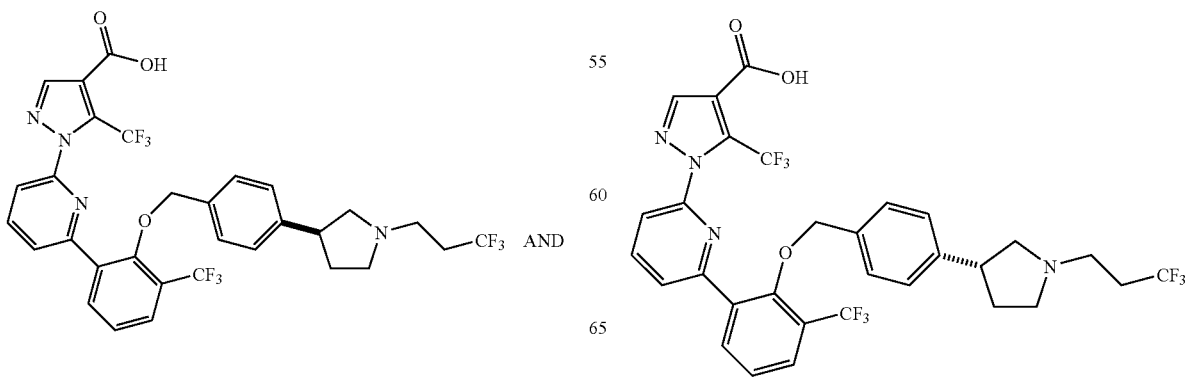

Step A. tert-Butyl 3-[4-(ethoxycarbonyl)phenyl]-2,5-dihydro-1H-pyrrole-1-carboxylate To a cooled (−78° C.) solution of 1-Boc-3-pyrollidinone (8.00 grams, 43.2 mmol) in anhydrous THF (70 mL) was added lithium bis(trimethylsilyl)amide (49.7 mL, 1.0 M in THF, 49.7 mmol) dropwise. After 45 min, a solution of 2-[N, N-bis(trifluoromethylsulfonyl)amino]5-chloropyridine (17.81 g, 45.4 mmol) in THF (65 mL) was added, and the resulting mixture was allowed to warm slowly to ambient temperature overnight, at which point it was quenched by pouring into brine. The mixture was extracted with EtOAc. The organic phase was separated, dried over anhydrous sodium sulfate, and concentrated in vacuo. The resulting enol triflate was filtered though silica gel, concentrated in vacuo, and used without further purification. To a flask containing the enol triflate obtained above (4.94 g, 15.6 mmol) were added 4-ethoxycarbonylphenylboronic acid (3.32 g, 17.1 mmol) and trans-dichlorobis(triphenylphosphine) palladium (II) (1.09 g, 1.56 mmol). Acetonitrile (78 mL) and sodium carbonate (39 mL, 1.0 M aqueous, 39 mmol) were added, and the resulting mixture was degassed via nitrogen sparge. The reaction mixture was stirred at 70° C. for 3 h, then was allowed to cool to room temperature and was poured into water. The mixture was extracted with EtOAc, and the organic phase was concentrated in vacuo. Purification by chromatography on silica gel (0 to 25% EtOAc in hexanes, then 25 to 100% EtOAc in hexanes) provided the title compound: LCMS m/z 261.9 [M-t-Boc]$^+$; $^1$H NMR (500 MHz, CDCl$_3$) δ 8.03 (d, J=8.0 Hz, 2H), 7.44 (d, J=8.5 Hz, 2H), 6.29 (ddd, J=25.0, 4, 4 Hz, 1H), 4.58-4.46 (m, 2H), 4.41-4.28 (m, 2H), 4.38 (q, J=7.0 Hz, 2H), 1.53 and 1.51 (s, doubled (rotamers) 9H), 1.40 (t, doubled (rotamers) J=7.0 Hz, 1.5H), 1.39 (t, doubled (rotamers) J=7.0 Hz, 1.5H).

Step B. tert-Butyl 3-[4-(ethoxycarbonyl)phenyl]pyrrolidine-1-carboxylate

To a degassed solution of the title compound from Example 136 Step A (3.17 g, 9.99 mmol) in EtOAc (50 mL) was added platinum oxide (0.68 g, 3.00 mmol). The reaction flask was fitted with a hydrogen balloon attached to a 3-way adapter. The reaction mixture was then evacuated and back-filled with hydrogen. After this process was repeated three times, the reaction mixture was placed under a hydrogen atmosphere, and was stirred vigorously. After 45 min, the reaction mixture was filtered though Celite, rinsing with EtOAc. The mixture was dried over anhydrous sodium sulfate, filtered, and concentrated in vacuo. Purification by chromatography on silica gel (0 to 8% EtOAc in hexanes, 8% EtOAc in hexanes, then 8 to 100% EtOAc in hexanes) provided the title compound: LCMS m/z 264.0 [M-t-Boc]$^+$; $^1$H NMR (500 MHz, CDCl$_3$) δ 7.99 (d, J=8.5 Hz, 2H), 7.30 (d, J=8.0 Hz, 2H), 4.37 (q, J=7.0 Hz, 2H), 3.92-3.76 (br m, 1H), 3.70-3.52 (br m, 1H), 3.48-3.34 (br m, 2H), 3.30 (t, J=10.0 Hz, 1H), 2.34-2.24 (br m, 1H), 1.99 (q, J=10.0 Hz, 1H), 1.48 (s, doubled (rotamers), 9H), 1.39 (t, J=7.0 Hz, 3H).

Step C. tert-Butyl 3-[4-(ethoxycarbonyl)phenyl]pyrrolidine-1-carboxylate

The title compound from Example 136 Step B (3.28 g, 10.27 mmol) was dissolved in benzene (50 mL) and concentrated in vacuo. This process was repeated, and the resulting azeotropically dried oil was dissolved in THF (100 mL) and was cooled to 0° C. To the cooled reaction mixture was added DIBAL-H (30.8 mL, 1.0 M in hexanes, 30.80 mmol) After 1 h, the reaction mixture was quenched by addition of MeOH (10 mL). The resulting mixture was diluted with EtOAc and saturated aqueous sodium/potassium tartrate, and the mixture was stirred vigorously until a clear phase separation was achieved. The organic phase was then separated, dried over anhydrous sodium sulfate, and concentrated in vacuo to provide the title compound as an off-white oil, which was used without further purification: LCMS m/z 278.0 [M+H]$^+$; $^1$H NMR (500 MHz, CDCl$_3$) δ 7.33 (d, J=8.0 Hz, 2H), 7.23 (d, J=6.5 Hz, 2H), 4.67 (s, 2H), 3.88-3.72 (m, 1H), 3.66-3.50 (m, 1H), 3.43-3.22 (m, 2H), 2.29-2.20 (br m, 1H), 2.08-1.92 (m, 2H), 1.47 (s, doubled (rotamers), 9H).

Step D. Ethyl 1-[6-[2-hydroxy-3-(trifluoromethyl)phenyl]pyridin-2-yl]-5-(trifluoromethyl)-1H-pyrazole-4-carboxylate To a flask containing the title compound from the Example 1 Step D (1.13 g, 3.52 mmol) were added [2-hydroxy-3-(trifluoromethyl)phenyl]boronic acid (0.80 g, 3.87 mmol) and trans-dichlorobis(triphenylphosphine)palladium (II) (0.25 g, 0.35 mmol). Acetonitrile (17 mL) and sodium carbonate (8.80 mL, 1.0 M aqueous, 8.80 mmol) were added, and the resulting mixture was degassed via nitrogen sparge. The reaction mixture was stirred at 70° C. for 3 h, then was allowed to cool to ambient temperature and was poured into water. The mixture was extracted with EtOAc, and the organic phase was concentrated in vacuo. Purification by chromatography on silica gel (0 to 30% EtOAc in hexanes, then 30 to 100% EtOAc in hexanes), provided the title compound: LCMS m/z 445.8 [M+H]$^+$; $^1$H NMR (500 MHz, CDCl$_3$) δ 13.05 (s, 1H), 8.18 (s, 1H), 8.13 (t, J=8.0 Hz, 1H), 8.07 (d, J=8.0 Hz, 1H), 8.01 (d, J=8.0 Hz, 1H), 7.66 (d, J=7.5 Hz, 1H), 7.55 (d, J=8.0, 1H), 7.03 (t, J=8.0 Hz, 1H), 4.40 (q, J=7.5 Hz, 2H), 1.33 (t, J=7.5 Hz, 3H).

Step E. Ethyl 1-{6-[2-({4-[(3S)-1-(tert-butoxycarbonyl)pyrrolidin-3-yl]benzyl}oxy)-3-(trifluoromethyl)phenyl]pyridin-2-yl}-5-(trifluoromethyl)-1H-pyrazole-4-carboxylate and ethyl 1-{6-[2-({4-[(3R)-1-(tert-butoxycarbonyl)pyrrolidin-3-yl]benzyl}oxy)-3-(trifluoromethyl)phenyl]pyridin-2-yl}-5-(trifluoromethyl)-1H-pyrazole-4-carboxylate To a solution of the title compound from Example 136 Step C (530 mg, 1.34 mmol), the title compound from Example 136 Step D (508 mg, 1.74 mmol), and triphenylphosphine (527 mg, 2.01 mmol) in DCM (7 mL) was added diisopropyl azodicarboxylate (0.39 mL, 2.01 mmol), and the resulting mixture was stirred at ambient temperature. After 2 h, the reaction mixture was concentrated in vacuo. Purification by flash chromatography on silica gel (0 to 40% EtOAc in hexanes, then 40 to 100% EtOAc in hexanes), followed by chiral separation of the racemic mixture (chiral column ChiralPak AD-H 2 cm×25 cm, 10% EtOH in heptane, retention time 20 and 22 min, detector wavelength 234 nm), provided two enantiomers which were carried through the next three steps separately. Characterization of the first eluted enantiomer (enantiomer A): LCMS m/z 705.0 [M+H]$^+$; $^1$H NMR (500 MHz, CDCl$_3$) δ 8.16 (s, 1H), 8.10 (d, J=8.0, 1H), 8.05 (d, J=8.0, 1H), 7.94-7.88 (br m, 1H), 7.73 (d, J=7.5 Hz, 1H), 7.67 (d, J=8.0, 1H), 7.39 (t, J=8.0 Hz, 1H), 7.24-7.12 (br m, 4H), 4.58 (s, 2H), 4.42 (q, J=7.0 Hz, 2H), 3.92-3.72 (m, 1H), 3.70-3.50 (m, 1H), 3.48-3.22 (m, 3H), 2.32-2.20 (m, 1H), 2.04-1.90 (m, 1H), 1.49 and 1.48 (s, doubled (rotamers) 9H), 1.40 (t, J=7.0 Hz, 3H).

The enantiomeric title compounds from Example 136 Step E were taken forward separately in the following Steps F-H. The details of the experimental procedure involving the first eluting enantiomer (enantiomer A) from Step E are described in Steps F-H, but substantially the same procedural steps were followed using the second eluting enantiomer (enantiomer B) from Step E. Therefore, both the S and R chiral intermediates and final products were prepared in Steps F-H, although the absolute stereochemistry of enantiomer A and enantiomer B have not been determined.

Step F. Ethyl 1-{6-[2-{[4-(3 (S)-pyrrolidin-3-yl)benzyl]oxy]-3-(trifluoromethyl)phenyl]pyridin-2-yl}-5-(trifluoromethyl)-1H-pyrazole-4-carboxylate and ethyl 1-{6-[2-{[4-(3 (R)-pyrrolidin-3-yl)benzyl]oxy}-3-(trifluoromethyl)phenyl]pyridin-2-yl}-5-(trifluoromethyl)-1H-pyrazole-4-carboxylate A solution of the title compound from Example 136 Step E (150 mg, 0.21 mmol) in acetic acid (2 mL) and water (0.5 mL) was stirred at 90° C. for 14 h. The reaction mixture was allowed to cool to ambient temperature and evaporated in vacuo. The product was used in the subsequent step without further purification: LCMS m/z 605.0 [M+H]⁺.

Step G. Ethyl 5-(trifluoromethyl)-1-{6-[3-(trifluoromethyl)-2-({4-[(3S)-1-(3,3,3-trifluoropropyl)pyrrolidin-3-yl]benzyl}oxy)phenyl]pyridin-2-yl}-1H-pyrazole-4-carboxylate and ethyl 5-(trifluoromethyl)-1-{6-[3-(trifluoromethyl)-2-({4-[(3R)-1-(3,3,3-trifluoropropyl)pyrrolidin-3-yl]benzyl}oxy)phenyl]pyridin-2-yl}-1H-pyrazole-4-carboxylate To a solution of the title compound from Example 136 Step F (65 mg, 0.11 mmol) in acetonitrile (1 mL) were added DIEA (0.11 mL, 0.65 mmol) and 3-bromo-1,1,1-trifluoropropane (57 mg, 0.32 mmol). The reaction mixture was stirred for 12 h at ambient temperature, then was diluted with sat. aq. NaHCO₃ and extracted with EtOAc. The organic phase was separated, dried over sodium sulfate, filtered, and concentrated in vacuo. The product was used in the subsequent step without further purification: LCMS m/z 701.4 [M+H]⁺.

Step H. 5-(Trifluoromethyl)-1-{6-[3-(trifluoromethyl)-2-({4-[3(S)-1-(3,3,3-trifluoropropyl)pyrrolidin-3-yl]benzyl}oxy)phenyl]pyridin-2-yl}-1H-pyrazole-4-carboxylic acid and 5-(Trifluoromethyl)-1-{6-[3-(trifluoromethyl)-2-(14-13(R)-1-(3,3,3-trifluoropropyl)pyrrolidin-3-yl]benzyl}oxy)phenyl]pyridin-2-yl}-1H-pyrazole-4-carboxylic acid To a solution of the title compound from Example 136 Step G (75 mg, 0.11 mmol) in 1,4-dioxane (2 mL) was added lithium hydroxide (1.0 mL, 2.0 M in water, 2.00 mmol), and the resulting mixture was stirred at 50° C. After 2 h, the reaction mixture was rendered acidic by addition of aqueous hydrochloric acid (1.5 mL), then was diluted with 1,4-dioxane and passed though a 0.45 micron syringe filter. Purification by reverse phase HPLC (40 to 100% acetonitrile in water, each with 0.1% v/v TFA) provided the title compound (enantiomer A): LCMS m/z 673.2 [M+H]⁺; ¹H NMR (500 MHz, d₆-DMSO) δ 8.35 (s, 1H), 8.21 (t, J=8.0 Hz, 1H), 8.07 (d, J=7.5 Hz, 1H), 7.96 (d, J=7.5 Hz, 1H), 7.88 (t, J=9.0 Hz, 2H), 7.54 (t, J=8.0 Hz, 1H), 7.33 (d, J=7.5 Hz, 2H), 7.15 (d, J=8.5, 2H), 4.55 (s, 2H), 4.02-3.36 (br m, 7 H), 2.94-2.78 (m, 2H), 2.48-2.36 (br m, 1H), 2.16-1.96 (br m, 1H). The product derived from enantiomer B was also obtained and had essentially the same LCMS and ¹H NMR characterization data.

The compounds in Table 2 were prepared using chemistry described in Example 136, or by analogy to chemistry described in Examples 1-14.

TABLE 2

| Example | Structure | IUPAC | LCMS |
| --- | --- | --- | --- |
| 137 | 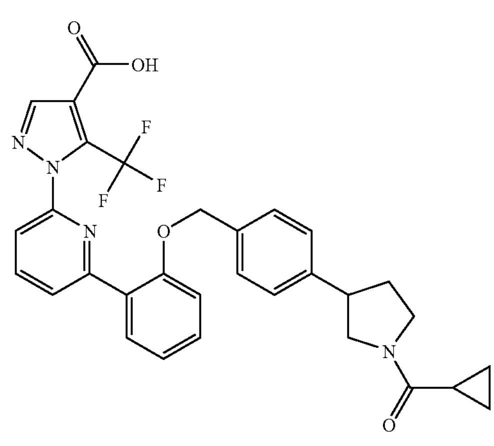 [SMILES: O=C(O)c1cnn(-c2cccc(-c3ccccc3OCc3ccc(C4CCN(C(=O)C5CC5)C4)cc3)n2)c1C(F)(F)F] | 1-(6-(2-((4-(1-(cyclopropylcarbonyl)pyrrolidin-3-yl)benzyl)oxy)phenyl)pyridin-2-yl)-5-(trifluoromethyl)-1H-pyrazole-4-carboxylic acid | 577.7 (rac) |

TABLE 2-continued

| Example | Structure | IUPAC | LCMS |
|---|---|---|---|
| 138, 139 | 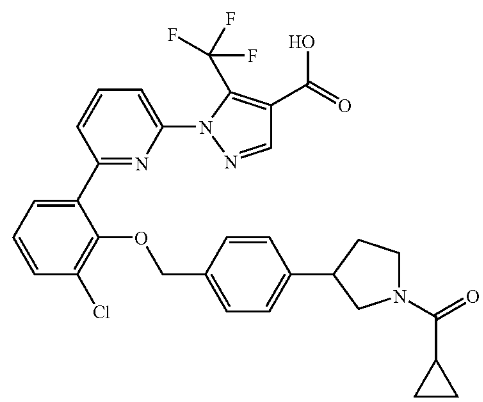 [SMILES: O=C(O)c1cnn(-c2cccc(-c3cccc(Cl)c3OCc3ccc(C4CCN(C(=O)C5CC5)C4)cc3)n2)c1C(F)(F)F] | 1-(6-(3-chloro-2-((4-((3R)-1-(cyclopropylcarbonyl)pyrrolidin-3-yl)benzyl)oxy)phenyl)pyridin-2-yl)-5-(trifluoromethyl)-1H-pyrazole-4-carboxylic acid And 1-(6-(3-chloro-2-((4-((3S)-1-(cyclopropylcarbonyl)pyrrolidin-3-yl)benzyl)oxy)phenyl)pyridin-2-yl)-5-(trifluoromethyl)-1H-pyrazole-4-carboxylic acid | 611.0 (ent A) 611.0 (ent B) |
| 140, 141 | 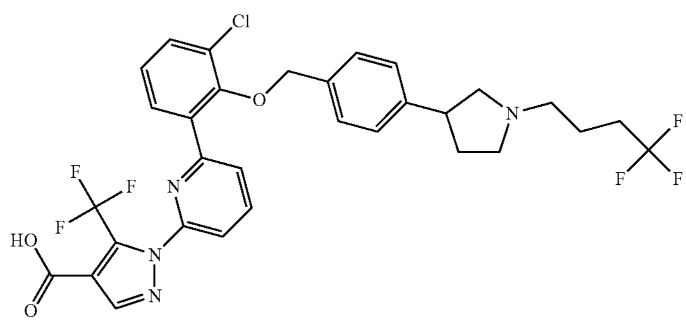 [SMILES: O=C(O)c1cnn(-c2cccc(-c3cccc(Cl)c3OCc3ccc(C4CCN(CCCC(F)(F)F)C4)cc3)n2)c1C(F)(F)F] | 1-(6-(3-chloro-2-((4-(3R)-(1-(4,4,4-trifluorobutyl)pyrrolidin-3-yl)benzyl)oxy)phenyl)pyridin-2-yl)-5-(trifluoromethyl)-1H-pyrazole-4-carboxylic acid And 1-(6-(3-chloro-2-((4-(3S)-(1-(4,4,4-trifluorobutyl)pyrrolidin-3-yl)benzyl)oxy)phenyl)pyridin-2-yl)-5-(trifluoromethyl)-1H-pyrazole-4-carboxylic acid | 653.2 (ent A) 652.9 (ent B) |
| 142 | 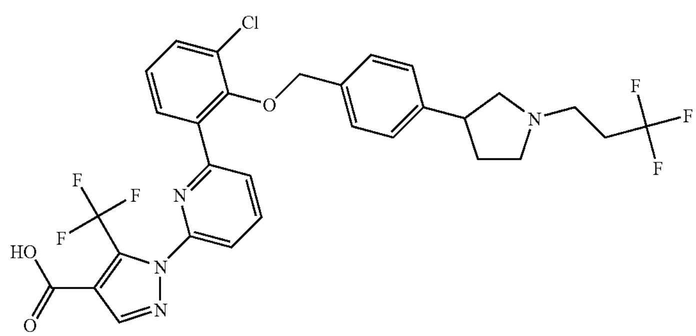 [SMILES: O=C(O)c1cnn(-c2cccc(-c3cccc(Cl)c3OCc3ccc(C4CCN(CCC(F)(F)F)C4)cc3)n2)c1C(F)(F)F] | 1-(6-(3-chloro-2-((4-(1-(3,3,3-trifluoropropyl)pyrrolidin-3-yl)benzyl)oxy)phenyl)pyridin-2-yl)-5-(trifluoromethyl)-1H-pyrazole-4-carboxylic acid | 639.2 (ent A) 652.9 (ent B) |
| 143, 144 | 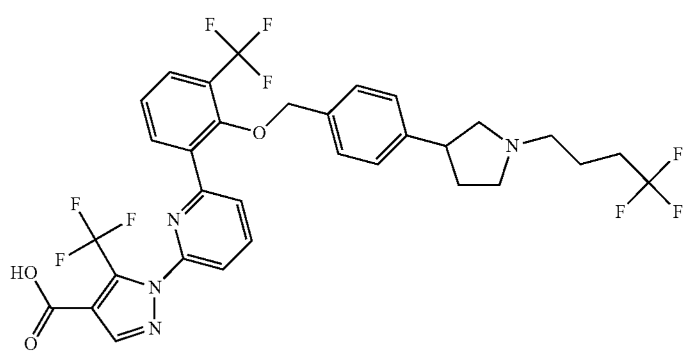 [SMILES: O=C(O)c1cnn(-c2cccc(-c3cccc(C(F)(F)F)c3OCc3ccc(C4CCN(CCCC(F)(F)F)C4)cc3)n2)c1C(F)(F)F] | 1-(6-(2-((4-(3R)-(1-(4,4,4-trifluorobutyl)pyrrolidin-3-yl)benzyl)oxy)-3-(trifluoromethyl)phenyl)pyridin-2-yl)-5-(trifluoromethyl)-1H-pyrazole-4-carboxylic acid AND 1-(6-(2-((4-(3S)-(1-(4,4,4-trifluorobutyl)pyrrolidin-3-yl)benzyl)oxy)-3-(trifluoromethyl)phenyl)pyridin-2-yl)-5-(trifluoromethyl)-1H-pyrazole-4-carboxylic acid | 687.1 (ent A) 687.1 (ent B) |

TABLE 2-continued

| Example | Structure | IUPAC | LCMS |
|---|---|---|---|
| 145 | 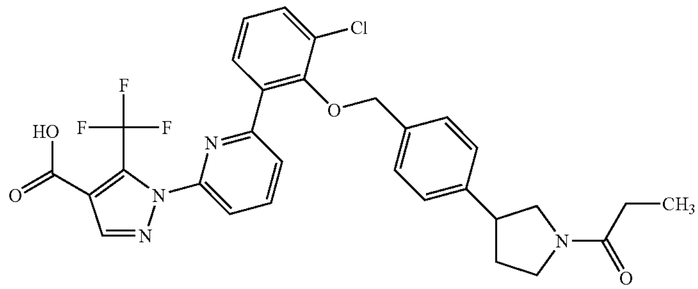 [SMILES: CCC(=O)N1CCC(c2ccc(COc3c(Cl)cccc3-c3cccc(-n4ncc(C(=O)O)c4C(F)(F)F)n3)cc2)C1] | 1-(6-(3-chloro-2-((4-(1-propionylpyrrolidin-3-yl)benzyl)oxy)phenyl)pyridin-2-yl)-5-(trifluoromethyl)-1H-pyrazole-4-carboxylic acid | 600.0 (rac) |
| 146 | 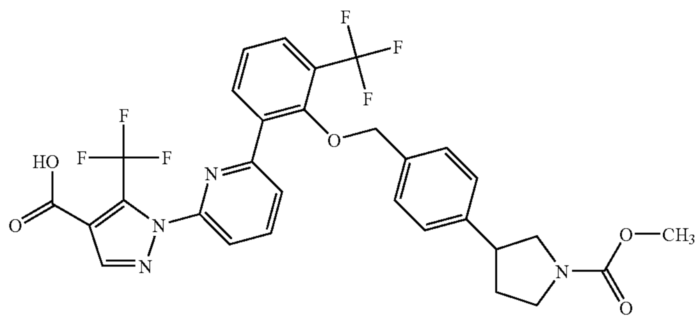 [SMILES: COC(=O)N1CCC(c2ccc(COc3c(-c4cccc(-n5ncc(C(=O)O)c5C(F)(F)F)n4)cccc3C(F)(F)F)cc2)C1] | 1-(6-(2-((4-(1-(methoxycarbonyl)pyrrolidin-3-yl)benzyl)oxy)-3-(trifluoromethyl)phenyl)pyridin-2-yl)-5-(trifluoromethyl)-1H-pyrazole-4-carboxylic acid | 635.0 (rac) |
| 147 | 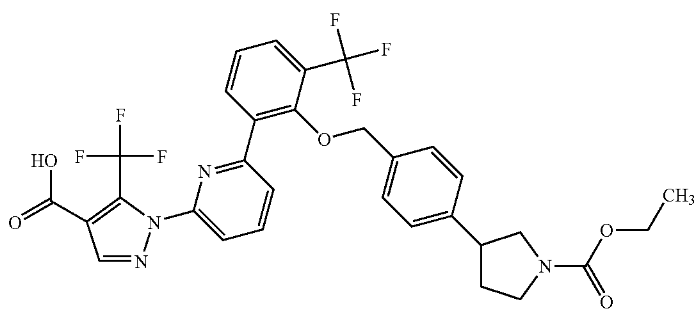 [SMILES: CCOC(=O)N1CCC(c2ccc(COc3c(-c4cccc(-n5ncc(C(=O)O)c5C(F)(F)F)n4)cccc3C(F)(F)F)cc2)C1] | 1-(6-(2-((4-(1-(ethoxycarbonyl)pyrrolidin-3-yl)benzyl)oxy)-3-(trifluoromethyl)phenyl)pyridin-2-yl)-5-(trifluoromethyl)-1H-pyrazole-4-carboxylic acid | 649.0 (rac) |

EXAMPLE 148

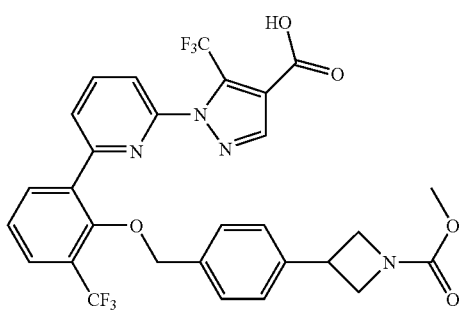 [SMILES: COC(=O)N1CC(c2ccc(COc3c(-c4cccc(-n5ncc(C(=O)O)c5C(F)(F)F)n4)cccc3C(F)(F)F)cc2)C1]

Step A. ten-Butyl 3-(4-(methoxycarbonyl)phenyl)azetidine-1-carboxylate

An oven dried glass vial was charged with zinc powder (120 mg, 1.837 mmol). THF (0.5 mL) was added, followed by 1,2-dibromoethane (15 μL, 0.17 mmol), and the resulting mixture was placed in a pre-heated (65° C.) oil bath. After 10 min, the mixture was allowed to cool to room temperature, TMSCl (18 μL, 0.141 mmol) was added, and the resulting mixture was stirred at room temperature. After 30 min, a solution of tent-butyl 3-iodoazetidine-1-carboxylate (400 mg, 1.41 mmol) in THF (1 mL) was added, and the mixture was stirred at room temperature. After 45 min, a solution of tris(dibenzylideneacetone)dipalladium (65 mg, 0.071 mmol) and tri(2-furyl)phosphine (66 mg, 0.283 mmol) in THF (1 mL) was added, followed by a solution of methyl 4-iodobenzoate (444 mg, 1.70 mmol) in THF (1 mL). The septum and nitrogen inlet were quickly replaced with a teflon cap, and the reaction mixture was heated at 65° C. After 18 h, the mixture was allowed to cool to room temperature, then was diluted with EtOAc and poured in sat aq NaHCO$_3$. The organic phase was separated and concentrated in vacuo. Purification by flash chromatography on silica gel (0 to 25% EtOAc in hexanes, then 25 to 100% EtOAc in hexanes) provided the title compound: LCMS m/z 235.9 [M-tBu]$^+$; $^1$H NMR (500 MHz, CDCl$_3$) δ 8.02 (d, J=8.5 Hz, 2H), 7.39 (d, J=8.5 Hz, 2H), 4.35 (t, J=7.5 Hz, 2H), 3.99-3.95 (m, 2H), 3.92 (s, 3H), 3.81-3.76 (m, 1H), 1.47 (s, 9H).

Step B. ten-Butyl 3-(4-(hydroxymethyl)phenyl)azetidine-1-carboxylate

To a cooled (0° C.) solution of the title compound from Example 148 Step A (160 mg, 0.55 mmol) in THF (5 mL) was added DIBAL-H (1.7 mL, 1.0 M in DCM, 8.0 mmol). After 1 h, the reaction mixture was quenched by addition of MeOH (1 mL). The resulting mixture was diluted with ether and saturated aqueous sodium/potassium tartrate, and the mixture was stirred vigorously until a clear phase separation was achieved. The organic phase was then separated, dried over anhydrous sodium sulfate, and concentrated in vacuo to provide the title compound, which was used without further purification: $^1$H NMR (500 MHz, CDCl$_3$) δ 7.35 (d, J=8.0 Hz, 2H), 7.29 (d, J=8.0 Hz, 2H), 4.68 (s, 2H), 4.32 (t, J=8.5 Hz, 2H), 3.97-3.91 (m, 2H), 3.74-3.71 (m, 1H), 1.46 (s, 9H).

Step C. Ethyl 1-(6-(2-((4-(1-(tert-butoxycarbonyl)azetidin-3-yl)benzyl)oxy)-3-(trifluoromethyl)phenyl)pyridin-2-yl)-5-(trifluoromethyl)-1H-pyrazole-4-carboxylate To a solution of the title compound from Example 136 Step D (147 mg, 0.33 mmol), the title compound from Example 148 Step B (130 mg, 0.50 mmol), and triphenylphosphine (87 mg, 0.33 mmol) in DCM (3 mL) was added diisopropyl azodicarboxylate (0.064 mL, 0.33 mmol), and the resulting mixture was stirred at ambient temperature. After 2 h, the reaction mixture was concentrated in vacuo. Purification by flash chromatography on silica gel (0 to 35% EtOAc in hexanes, then 35 to 100% EtOAc in hexanes) provided the title compound: LCMS m/z 690.9 [M+H]$^+$; $^1$H NMR (500 MHz, CDCl$_3$) δ 8.16 (s, 1H), 8.10 (d, J=7.5 Hz, 1H), 8.02 (d, J=7.5 Hz, 1H), 7.91 (t, J=8.0 Hz, 1H), 7.75-7.73 (m, 1H), 7.67 (d, J=8.0 Hz, 1H), 7.40-7.38 (m, 1H), 7.28 (d, J=8.0 Hz, 2H), 7.19 (d, J=8.0 Hz, 2H), 4.59 (s, 2H), 4.39 (q, J=7.0 Hz, 2H), 4.35-4.31 (m, 2H), 4.00-3.95 (m, 2H), 3.75-3.71 (m, 1H), 1.47 (s, 9H), 1.40 (t, J=7.0 Hz, 3H).

Step D. 1-(6-(2-((4-(1-(Methoxycarbonyl)azetidin-3-yl)benzyl)oxy)-3-(trifluoromethyl)phenyl)pyridin-2-yl)-5-(trifluoromethyl)-1H-pyrazole-4-carboxylic acid To a solution of the title compound from Example 148 Step C (170 mg, 0.246 mmol) in DCM (3 mL) was added TFA (1 mL). After 3 min, the reaction mixture was concentrated in vacuo to provide the crude TFA-salt, which was used without further purification: LCMS m/z 590.9 [M+1-1]$^+$. A portion of the unpurified TFA salt (0.08 mmol) was dissolved in DCM (1 mL), and DIEA (130 μL, 0.74 mmol) was added, followed by methyl chloroformate (19 μL, 0.25 mmol). After 20 min, the reaction mixture was quenched by addition of sat aq NaHCO$_3$ and the aqueous phase was extracted with DCM. The organic phase was separated and concentrated in vacuo to provide the unpurified carbamate, which was used without further purification: LCMS m/z 648.9 [M+H]$^+$. To a solution of the carbamate in dioxane (2 mL) was added lithium hydroxide (1 mL, 2N aqueous, 2 mmol), and the mixture was stirred at 50° C. for 1 h, then at ambient temperature. After 15 h, the reaction mixture was rendered acidic by addition of HCl (2N aqueous), then was diluted with acetonitrile and purified by reverse phase HPLC (30 to 100% acetonitrile/water, both 0.1% v/v TFA) to provide the title compound: LCMS m/z 620.9 [M+H]$^+$; $^1$H NMR (500 MHz, d$_6$-DMSO) δ 8.34 (s, 1H), 8.22 (t, J=8.0 Hz, 1H), 8.07 (d, J=8.0 Hz, 1H), 7.95 (d, J=8.0 Hz, 1H), 7.88-7.86 (m, 2H), 7.54 (t, J=8.0 Hz, 1H), 7.32 (d, J=8.0 Hz, 2H), 7.13 (d, J=8.0 Hz, 2H), 4.54 (s, 2H), 4.33-4.26 (m, 2H), 3.90-3.81 (m, 3H), 3.59 (s, 3H).

The compounds listed in Table 3 were prepared using chemistry described in Example 148, and/or by analogy to chemistry described in Examples 1-14 and Example 136.

TABLE 3

| Example | Structure | IUPAC | LCMS |
|---|---|---|---|
| 149 | 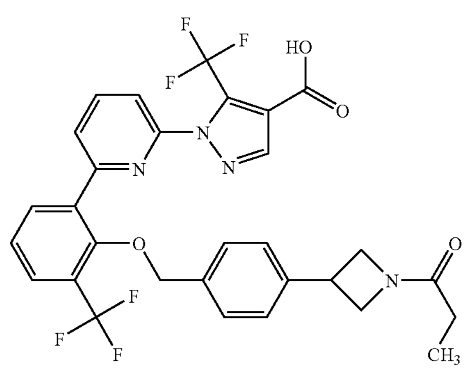 [SMILES: CCC(=O)N1CC(c2ccc(COc3c(-c4cccc(-n5ncc(C(=O)O)c5C(F)(F)F)n4)cccc3C(F)(F)F)cc2)C1] | 1-(6-(2-((4-(1-propionylazetidin-3-yl)benzyl)oxy)-3-(trifluoromethyl)phenyl)pyridin-2-yl)-5-(trifluoromethyl)-1H-pyrazole-4-carboxylic acid | 619.0 |

TABLE 3-continued

| Example | Structure | IUPAC | LCMS |
|---|---|---|---|
| 150 | 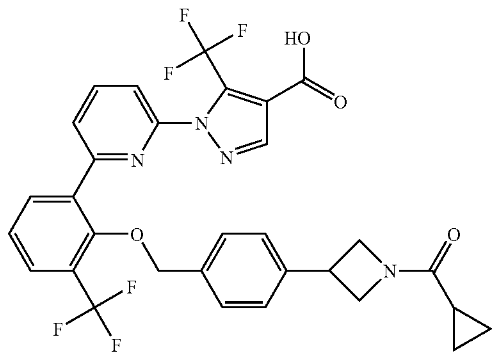 [SMILES: O=C(O)c1cnn(-c2cccc(-c3cccc(C(F)(F)F)c3OCc3ccc(C4CN(C(=O)C5CC5)C4)cc3)n2)c1C(F)(F)F] | 1-(6-(2-((4-(1-(cyclopropylcarbonyl)azetidin-3-yl)benzyl)oxy)-3-(trifluoromethyl)phenyl)pyridin-2-yl)-5-(trifluoromethyl)-1H-pyrazole-4-carboxylic acid | 631.0 |
| 151 | 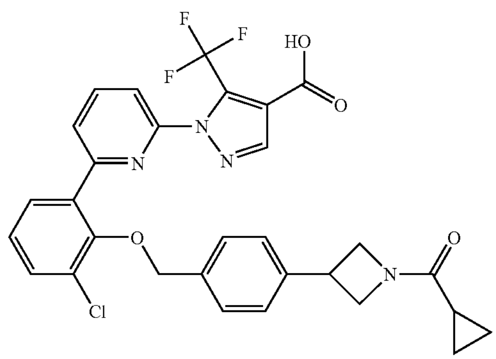 [SMILES: O=C(O)c1cnn(-c2cccc(-c3cccc(Cl)c3OCc3ccc(C4CN(C(=O)C5CC5)C4)cc3)n2)c1C(F)(F)F] | 1-(6-(3-chloro-2-((4-(1-(cyclopropylcarbonyl)azetidin-3-yl)benzyl)oxy)phenyl)pyridin-2-yl)-5-(trifluoromethyl)-1H-pyrazole-4-carboxylic acid | 596.9 |
| 152 | 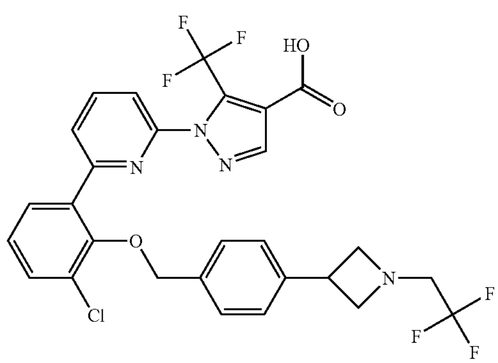 [SMILES: O=C(O)c1cnn(-c2cccc(-c3cccc(Cl)c3OCc3ccc(C4CN(CC(F)(F)F)C4)cc3)n2)c1C(F)(F)F] | 1-(6-(3-chloro-2-((4-(1-(2,2,2-trifluoroethyl)azetidin-3-yl)benzyl)oxy)phenyl)pyridin-2-yl)-5-(trifluoromethyl)-1H-pyrazole-4-carboxylic acid | 610.9 |
| 153 | 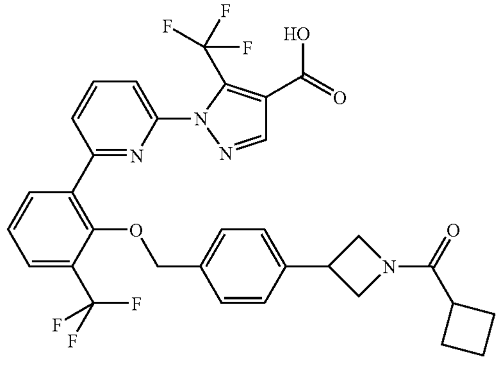 [SMILES: O=C(O)c1cnn(-c2cccc(-c3cccc(C(F)(F)F)c3OCc3ccc(C4CN(C(=O)C5CCC5)C4)cc3)n2)c1C(F)(F)F] | 1-(6-(2-((4-(1-(cyclobutylcarbonyl)azetidin-3-yl)benzyl)oxy)-3-(trifluoromethyl)phenyl)pyridin-2-yl)-5-(trifluoromethyl)-1H-pyrazole-4-carboxylic acid | 645.0 |

TABLE 3-continued

| Example | Structure | IUPAC | LCMS |
|---|---|---|---|
| 154 | 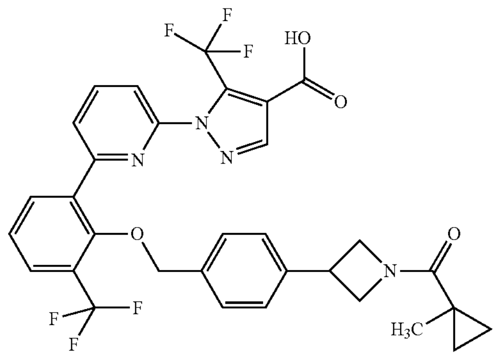 [SMILES: CC1(C(=O)N2CC(c3ccc(COc4c(-c5cccc(-n6ncc(C(=O)O)c6C(F)(F)F)n5)cccc4C(F)(F)F)cc3)C2)CC1] | 1-(6-(2-((4-(1-((1-methylcyclopropyl)carbonyl)azetidin-3-yl)benzyl)oxy)-3-(trifluoromethyl)phenyl)pyridin-2-yl)-5-(trifluoromethyl)-1H-pyrazole-4-carboxylic acid | 645.0 |
| 155 | 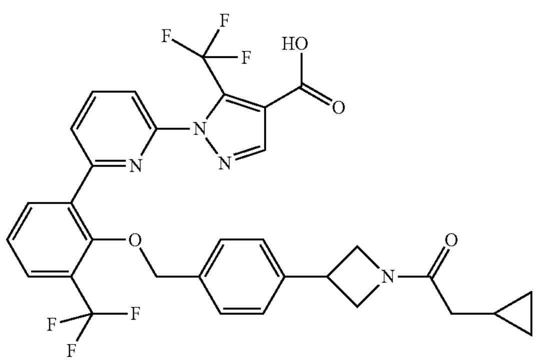 [SMILES: O=C(O)c1cnn(-c2cccc(-c3cccc(C(F)(F)F)c3OCc3ccc(C4CN(C(=O)CC5CC5)C4)cc3)n2)c1C(F)(F)F] | 1-(6-(2-((4-(1-(cyclopropylacetyl)azetidin-3-yl)benzyl)oxy)-3-(trifluoromethyl)phenyl)pyridin-2-yl)-5-(trifluoromethyl)-1H-pyrazole-4-carboxylic acid | 645.0 |
| 156 | 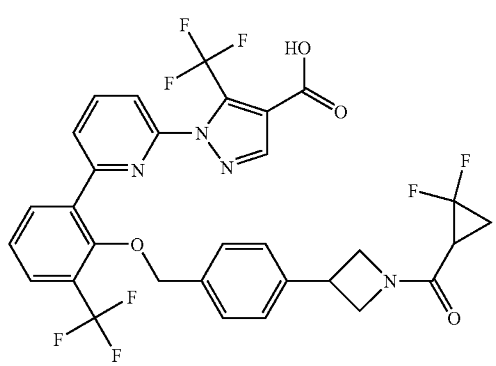 [SMILES: O=C(O)c1cnn(-c2cccc(-c3cccc(C(F)(F)F)c3OCc3ccc(C4CN(C(=O)C5CC5(F)F)C4)cc3)n2)c1C(F)(F)F] | 1-(6-(2-((4-(1-((2,2-difluorocyclopropyl)carbonyl)azetidin-3-yl)benzyl)oxy)-3-(trifluoromethyl)phenyl)pyridin-2-yl)-5-(trifluoromethyl)-1H-pyrazole-4-carboxylic acid | 666.9 (rac) |
| 157 | 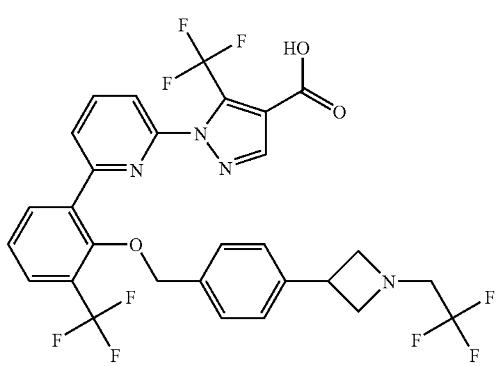 [SMILES: O=C(O)c1cnn(-c2cccc(-c3cccc(C(F)(F)F)c3OCc3ccc(C4CN(CC(F)(F)F)C4)cc3)n2)c1C(F)(F)F] | 1-(6-(2-((4-(1-(2,2,2-trifluoroethyl)azetidin-3-yl)benzyl)oxy)-3-(trifluoromethyl)phenyl)pyridin-2-yl)-5-(trifluoromethyl)-1H-pyrazole-4-carboxylic acid | 645.0 |

TABLE 3-continued

| Example | Structure | IUPAC | LCMS |
|---|---|---|---|
| 158 | 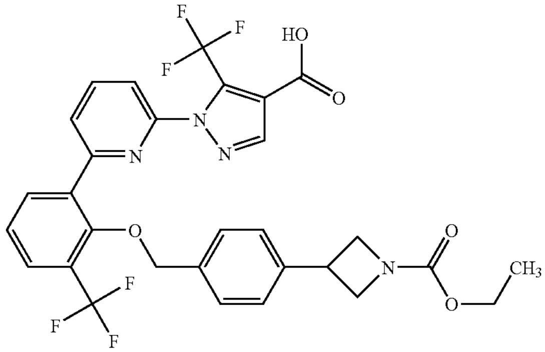 [SMILES: CCOC(=O)N1CC(c2ccc(COc3c(-c4cccc(-n5ncc(C(=O)O)c5C(F)(F)F)n4)cccc3C(F)(F)F)cc2)C1] | 1-(6-(2-((4-(1-(ethoxycarbonyl)azetidin-3-yl)benzyl)oxy)-3-(trifluoromethyl)phenyl)pyridin-2-yl)-5-(trifluoromethyl)-1H-pyrazole-4-carboxylic acid | 634.9 |
| 159 | 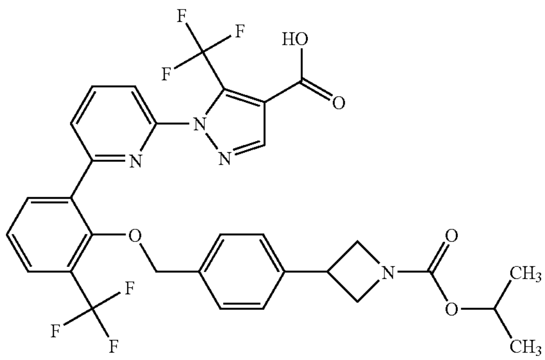 [SMILES: CC(C)OC(=O)N1CC(c2ccc(COc3c(-c4cccc(-n5ncc(C(=O)O)c5C(F)(F)F)n4)cccc3C(F)(F)F)cc2)C1] | 1-(6-(2-((4-(1-(isopropoxycarbonyl)azetidin-3-yl)benzyl)oxy)-3-(trifluoromethyl)phenyl)pyridin-2-yl)-5-(trifluoromethyl)-1H-pyrazole-4-carboxylic acid | 648.9 |
| 160 | 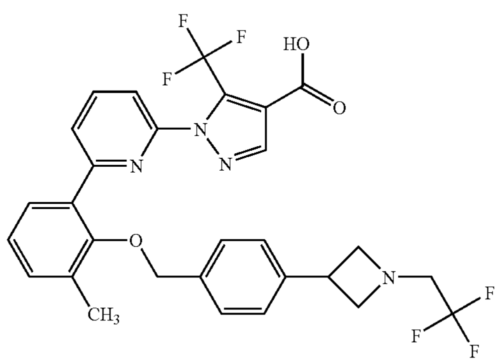 | 1-(6-(3-methyl-2-((4-(1-(2,2,2-trifluoroethyl)azetidin-3-yl)benzyl)oxy)phenyl)pyridin-2-yl)-5-(trifluoromethyl)-1H-pyrazole-4-carboxylic acid | 591.1 |
| 161 | 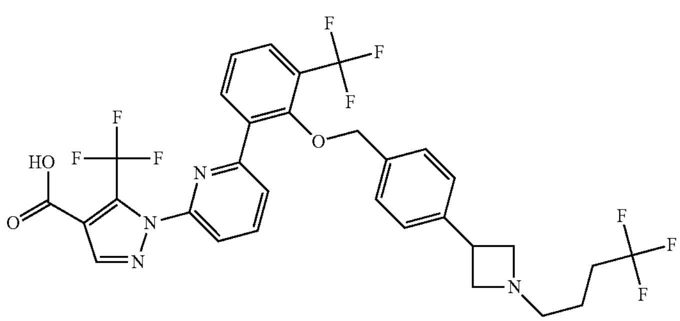 [SMILES: O=C(O)c1cnn(-c2cccc(-c3cccc(C(F)(F)F)c3OCc3ccc(C4CN(CCCC(F)(F)F)C4)cc3)n2)c1C(F)(F)F] | 1-(6-(2-((4-(1-(4,4,4-trifluorobutyl)azetidin-3-yl)benzyl)oxy)-3-(trifluoromethyl)phenyl)pyridin-2-yl)-5-(trifluoromethyl)-1H-pyrazole-4-carboxylic acid | 673.0 |

EXAMPLE 162

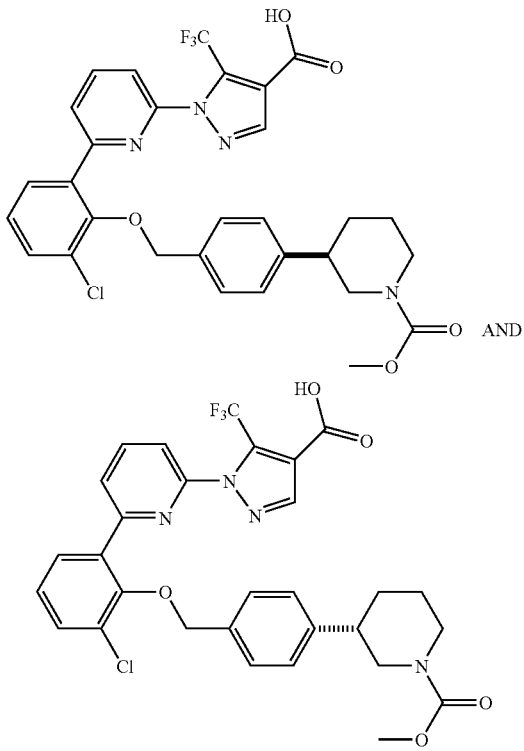

Step A. Ethyl 1-(6-(3-chloro-2-hydroxyphenyl)pyridin-2-yl)-5-(trifluoromethyl)-1H-pyrazole-4-carboxylate To a flask containing the title compound from the Example 1 Step D (2.50 g, 7.82 mmol) were added 2-hydroxy-3-chloro-phenylboronic acid (1.75 g, 10.2 mmol) and trans-dichlorobis(triphenylphosphine)palladium (II) (548 mg, 0.782 mmol). Acetonitrile (25 mL) and sodium carbonate (19.6 mL, 1.0 M aqueous, 19.6 mmol) were added, and the resulting mixture was degassed via nitrogen sparge. The reaction mixture was stirred at 70° C. for 18 h, then was allowed to cool to ambient temperature and was poured into water. The mixture was extracted with EtOAc, and the organic phase was concentrated in vacuo. Purification by chromatography on silica gel (0 to 40% EtOAc in hexanes, then 40 to 100% EtOAc in hexanes) provided the title compound: LCMS m/z 411.8 [M+H]$^+$; $^1$H NMR (500 MHz, CDCl$_3$) δ 12.79 (s, 1H), 8.18 (s, 1H), 8.11 (t, J=7.5 Hz, 1H), 8.06 (d, J=8.0 Hz, 1H), 7.75 (dd, J=8.0, 1.0 Hz, 1H), 7.54 (d, J=8.0 Hz, 1H), 7.46 (dd, J=8.0, 1.5 Hz, 1H), 6.92 (t, J=8.0 Hz, 1H), 4.40 (q, J=7.0 Hz, 2 H), 1.40 (t, J=7.0 Hz, 3H).

Step B. tert-Butyl-5-(4-(ethoxycarbonyl)phenyl)-3,6-dihydropyridine-1(2H)-carboxylate To a cooled (−78° C.) solution of tert-butyl 3-oxopiperidine-1-carboxylate (5.00 grams, 25.1 mmol) in anhydrous THF (40 mL) was added lithium bis(trimethylsilyl)amide (28.9 mL, 1.0 M in THF, 28.9 mmol) dropwise. After 90 min, a solution of 2-[N,N-bis(trifluoromethylsulfonyl)amino]5-chloropyridine (10.35 g, 26.3 mmol) in THF (20 mL) was added, and the resulting mixture was allowed to warm slowly to ambient temperature overnight, at which point it was quenched by pouring into sat aq NaHCO$_3$. The mixture was extracted with EtOAc. The organic phase was separated, dried over anhydrous sodium sulfate, and concentrated in vacuo. The resulting enol triflate was filtered though silica gel, concentrated in vacuo, and used without further purification. To a flask containing the unpurified enol triflate were added 4-ethoxycarbonylphenylboronic acid (6.33 g, 32.6 mmol) and trans-dichlorobis(triphenylphosphine) palladium (II) (890 mg, 1.26 mmol). Acetonitrile (90 mL) and sodium carbonate (63 mL, 1.0 M aqueous, 63.0 mmol) were added, and the resulting mixture was degassed via nitrogen sparge. The reaction mixture was stirred at 70° C. for 3 h, then was allowed to cool to room temperature and was poured into water. The mixture was extracted with EtOAc, and the organic phase was concentrated in vacuo. Purification by chromatography on silica gel (0 to 10% EtOAc in hexanes, then 10 to 100% EtOAc) provided the title compound: LCMS m/z 276.0 [M-tBu]$^+$; $^1$H NMR (500 MHz, CDCl$_3$) δ 8.00 (d, J=8.0 Hz, 2H), 7.42 (d, J=8.0 Hz, 2H), 6.34-6.32 (m, 1H), 4.37 (q, J=7.0 Hz, 2H), 4.30-4.24 (br m, 2H), 3.58-3.54 (m, 2H), 2.34 (br m, 2H), 1.50 (s, 9H), 1.39 (t, J=7.0 Hz, 3H).

Step C. tert-Butyl 3-(4-(ethoxycarbonyl)phenyl)piperidine-1-carboxylate

To a degassed solution of the title compound from Example 162 Step B (660 mg, 1.99 mmol) in EtOAc (15 mL) was added platinum(IV) oxide (140 mg). The reaction flask was fitted with a hydrogen balloon attached to a 3-way adapter. The reaction mixture was then evacuated and back-filled with hydrogen. After this process was repeated three times, the reaction mixture was placed under a hydrogen atmosphere, and was stirred vigorously. After 15 min, the reaction mixture was filtered though Celite, rinsing with EtOAc. The mixture was dried over sodium sulfate, filtered, concentrated in vacuo, and taken forward without further purification: $^1$H NMR (500 MHz, CDCl$_3$) δ 7.99 (d, J=8.0 Hz, 2H), 7.29 (d, J=8.0 Hz, 2H), 4.36 (q, J=7.0 Hz, 2H), 4.30-4.10 (br m, 2H), 2.79-2.70 (br m, 2H), 1.98-1.50 (m, 5H), 1.47 (s, 9H), 1.38 (t, J=7.0 Hz, 3H).

Step D. tert-Butyl 3-(4-(hydroxymethyl)phenyl)piperidine-1-carboxylate

To a cooled (0° C.) solution of the title compound from Example 162 Step C (664 mg, 1.99 mmol) in THF (15 mL) was added DIBAL-H (8.0 mL, 1.0 M in hexanes, 8.0 mmol). After 1 h, the reaction mixture was quenched by addition of MeOH (3.0 mL). The resulting mixture was diluted with ether and saturated aqueous sodium/potassium tartrate, and the mixture was stirred vigorously until a clear phase separation was achieved. The organic phase was then separated, dried over anhydrous sodium sulfate, and concentrated in vacuo to provide the title compound, which was used without further purification.

Step E. tert-Butyl-(3R)-3-(4-((2-chloro-6-(6-(4-(ethoxycarbonyl)-5-(trifluoromethyl)-1H-pyrazol-1-yl)pyridin-2-yl)phenoxy)methyl)phenyl)piperidine-1-carboxylate and tert-Butyl-(3S)-3-(4-((2-chloro-6-(6-(4-(ethoxycarbonyl)-5-(trifluoromethyl)-1H-pyrazol-1-yl)pyridin-2-yl)phenoxy)methyl)phenyl)piperidine-1-carboxylate To a solution of the title compound from Example 162 Step A (500 mg, 1.21 mmol), the title compound from Example 162 Step D (531 mg, 1.82 mmol), and triphenylphosphine (478 mg, 1.82 mmol) in DCM (5 mL) was added diisopropyl azodicarboxylate (0.354 mL, 1.82 mmol), and the resulting mixture was stirred at ambient temperature. After 1 h, the reaction mixture was concentrated in vacuo. Purification by flash chromatography on silica gel (0 to 35% EtOAc in hexanes, then 35 to 100% EtOAc in hexanes) provided the title compound as a racemic mixture. Chiral separation (ChiralCel AD-H column, 10% IPA/heptane isocratic) provided the two enantiomers of the title compound, which were taken forward separately. Data for the first eluting enantiomer ("enantiomer A"): LCMS m/z 685.1 [M+H]+; $^1$H NMR (500 MHz, CDCl$_3$) δ 8.14 (s, 1H), 8.09 (d, J=8.0 Hz, 1H), 7.89 (t, J=8.0 Hz, 1H), 7.78 (dd, J=8.0 Hz, 2.0 Hz, 1H), 7.61 (d, J=7.0 Hz, 1H), 7.50 (dd, J=8.0 Hz, 2.0 Hz, 1H), 7.23-7.15 (m, 5H), 4.70 (s, 2H), 4.40 (q, J=7.0 Hz, 2H), 4.22-4.17 (m, 2H), 2.78-2.62 (m, 3H), 2.04-1.97 (m, 1H), 1.76-1.74 (m, 1H), 1.60-1.57 (m, 2H), 1.47 (s, 9H), 1.40 (t, J=7.0 Hz, 3H).

The enantiomeric title compounds from Example 162 Step E were taken forward separately in the following Step F. The experimental procedure using the first eluting enantiomer (enantiomer A) from Step E is described in Step F, but substantially the same procedure was followed using the second eluting enantiomer (enantiomer B) from Step E. Therefore, both the S and R chiral compounds were prepared in Step F, although the absolute stereochemistry of enantiomer A and enantiomer B have not been determined Step F. 1-(6-(3-Chloro-2-((4-((3S)-1-(methoxycarbonyl)piperidin-3-yl)benzyl)oxy)phenyl)pyridin-2-yl)-5-(trifluoromethyl)-1H-pyrazole-4-carboxylic acid and 1-(6-(3-Chloro-2-((4-((3R)-1-(methoxycarbonyl)piperidin-3-yl)benzyl)oxy)phenyl)pyridin-2-yl)-5-(trifluoromethyl)-1H-pyrazole-4-carboxylic acid A solution of the title compound from Example 162 Step E (enantiomer A, 189 mgs, 0.276 mmol) in acetic acid (4 mL) and water (1 mL) was heated at 90° C. After 15 h, the mixture was allowed to cool to ambient temperature and was concentrated in vacuo. The resulting crude oil was azeotropically dried from benzene (2×10 mL), and was used without further purification: LCMS m/z 584.9 [M+H]+. To a solution of the unpurified acetic acid salt (50.0 mg, 0.085 mmol) in DCM (1 mL) was added DIEA (149 μL, 0.855 mmol), followed by methyl chloroformate (20 μL, 0.256 mmol), and the resulting mixture was stirred at ambient temperature. After 20 min, the reaction mixture was poured into sat aq NaHCO$_3$ and brine, then was extracted with DCM. The organic phase was separated and concentrated in vacuo, and the crude carbamate was used without further purification: LCMS m/z 643.0 [M+H]+. To a solution of the alkylation product obtained above in 1,4-dioxane (2 mL) was added lithium hydroxide (1 mL, 2N aqueous, 2 mmol), and the resulting mixture was stirred at 50° C. After 1 h, the reaction mixture was rendered acidic by addition of 2N HCl, then was diluted with acetonitrile and purified by reverse phase HPLC (20 to 100% acetonitrile/water, both 0.1% v/v TFA). Enantiomer A: LCMS m/z 614.9 [M+H]+; $^1$H NMR (500 MHz, d$_6$-DMSO) δ 13.30 (br s, 1H), 8.31 (s, 1H), 8.16 (t, J=8.0 Hz, 1H), 8.01 (d, J=8.0 Hz, 1H), 7.80 (d, J=8.0 Hz, 1H), 7.65 (t, J=8.0 Hz, 1H), 7.33 (t, J=8.0 Hz, 1H), 7.14 (d, J=8.0 Hz, 2H), 7.09 (d, J=8.0 Hz, 2H), 4.72 (app t, J=11.0 Hz, 2H), 4.02-3-88 (br m, 2H), 3.58 (s, 3H), 2.88-2.70 (m, 2H), 2.59-2.54 (m, 1H), 1.82-1.79 (m, 1H), 1.70-1.67 (m, 1H), 1.63-1.54 (m, 1H), 1.47-1.39 (m, 1H). The product derived from enantiomer B was also obtained and had essentially the same LCMS and $^1$H NMR characterization data.

The compounds listed in Table 4 were prepared using chemistry described in Example 162, and/or by analogy to chemistry described in Examples 1-14, Example 136, and Example 148.

TABLE 4

| Example | Structure | IUPAC | LCMS |
|---------|-----------|-------|------|
| 163, 164 | 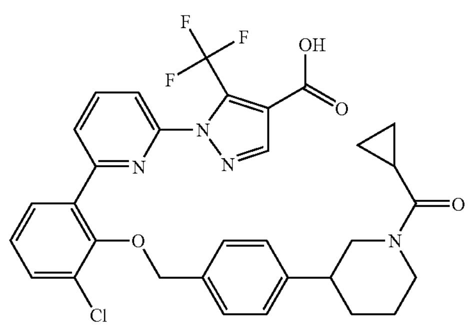 [SMILES: O=C(O)c1cnn(-c2cccc(-c3cccc(Cl)c3OCc3ccc(C4CCCN(C(=O)C5CC5)C4)cc3)n2)c1C(F)(F)F] | 1-(6-(3-chloro-2-((4-(3R)-(1-(cyclopropylcarbonyl)piperidin-3-yl)benzyl)oxy)phenyl)pyridin-2-yl)-5-(trifluoromethyl)-1H-pyrazole-4-carboxylic acid AND 1-(6-(3-chloro-2-((4-(3S)-(1-(cyclopropylcarbonyl)piperidin-3-yl)benzyl)oxy)phenyl)pyridin-2-yl)-5-(trifluoromethyl)-1H-pyrazole-4-carboxylic acid | 624.9 (ent A) 625.0 (ent B) |
| 165, 166 | 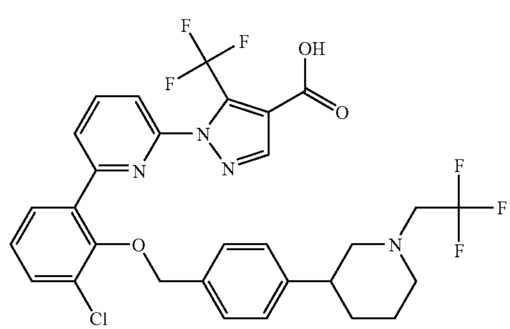 [SMILES: O=C(O)c1cnn(-c2cccc(-c3cccc(Cl)c3OCc3ccc(C4CCCN(CC(F)(F)F)C4)cc3)n2)c1C(F)(F)F] | 1-(6-(3-chloro-2-((4-(3R)-(1-(2,2,2-trifluoroethyl)piperidin-3-yl)benzyl)oxy)phenyl)pyridin-2-yl)-5-(trifluoromethyl)-1H-pyrazole-4-carboxylic acid AND 1-(6-(3-chloro-2-((4-(3S)-(1-(2,2,2-trifluoroethyl)piperidin-3-yl)benzyl)oxy)phenyl)pyridin-2-yl)-5-(trifluoromethyl)-1H-pyrazole-4-carboxylic acid | 638.9 (ent A) 638.9 (ent B) |

EXAMPLE 167

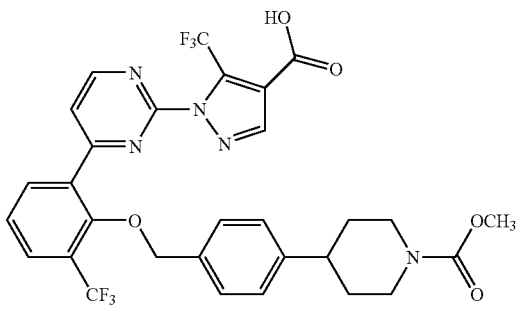 [SMILES: COC(=O)N1CCC(c2ccc(COc3c(-c4ccnc(-n5ncc(C(=O)O)c5C(F)(F)F)n4)cccc3C(F)(F)F)cc2)CC1]

Step A. 2-(2-Chloropyrimidin-4-yl)-6-(trifluoromethyl)phenol

A vial was charged with 2,4-dichloropyrimidine (362 mg, 2.43 mmol), 2-hydroxy-3-trifluoromethylphenylboronic acid (250 mg, 1.21 mmol) and trans-dichlorobis(triphenylphosphine)palladium (II) (42.6 mg, 0.061 mmol). Acetonitrile (6 mL) and sodium carbonate (3.0 mL, 1.0 M aqueous, 3.0 mmol) were added, and the resulting mixture was degassed via nitrogen sparge. The reaction mixture was stirred at 70° C. for 6 h, then was allowed to cool to ambient temperature and was poured into water. The mixture was extracted with EtOAc, and the organic phase was concentrated in vacuo. Purification by chromatography on silica gel (0 to 25% EtOAc in hexanes, then 25 to 100% EtOAc in hexanes) provided the title compound: LCMS m/z 275.0 [M+H]$^+$; $^1$H NMR (500 MHz, CDCl$_3$) δ 13.43 (s, 1H), 8.74 (d, J=5.5 Hz, 1H), 7.98 (d, J=8.0 Hz, 1H), 7.76 (app d, J=5.5 Hz, 2H), 7.06 (t, J=8.0 Hz, 1H).

Step B. tert-Butyl 4-(4-((2-(2-chloropyrimidin-4-O-6-(trifluoromethyl)phenoxy)methyl)phenyl)piperidine-1-carboxylate To a solution of the title compound from Example 167 Step A (110 mg, 0.40 mmol), the title compound from Example 1 Step C (175 mg, 0.60 mmol), and triphenylphosphine (158 mg, 0.60 mmol) in DCM (2 mL) was added diisopropyl azodicarboxylate (0.117 mL, 0.60 mmol), and the resulting mixture was stirred at ambient temperature. After 1 h, the reaction mixture was concentrated in vacuo. Purification by flash chromatography on silica gel (0 to 50% EtOAc in hexanes, then 50 to 100% EtOAc in hexanes) provided the title compound: LCMS m/z 547.91 [M+H]$^+$; $^1$H NMR (500 MHz, CDCl$_3$) δ 8.51 (d, J=5.5 Hz, 1H), 8.13-8.11 (m, 1H), 7.88 (d, J=5.5 Hz, 1H), 7.81 (d, J=7.5 Hz, 1H), 7.42 (d, J=7.5 Hz, 1H), 7.18-7.14 (m, 4H), 4.67 (s, 2H), 4.32-4.18 (m, 2H), 2.83-2.78 (m, 2H), 2.69-2.62 (m, 1H), 1.84-1.81 (m, 2H), 1.66-1.59 (m, 2H), 1.49 (s, 9H).

Step C. tert-Butyl 4-(4-((2-(2-(4-(ethoxycarbonyl)-5-(trifluoromethyl)-1H-pyrazol-1-yl)pyrimidin-4-yl)-6-(trifluoromethyl)phenoxy)methyl)phenyl)piperidine-1-carboxylate To a solution of the title compound from Example 167 Step B (198 mg, 0.361 mmol) in EtOH (3 mL) was added hydrazine hydrate (213 µL 0.542 mmol). The reaction flask was equipped with a reflux condenser and heated at 80° C. After 45 min, the mixture was allowed to cool to room temperature, then was concentrated in vacuo. The resulting mixture was dissolved in EtOAc, then was washed with brine, dried over sodium sulfate, and concentrated in vacuo. The crude hydrazine adduct was used without further purification: LCMS m/z 543.9 [M+H]$^+$. To a solution of the hydrazine adduct obtained above in acetonitrile (3 mL) were added triethylamine (76 µL 0.54 mmol) and ethyl-2-(ethoxymethylene)-4,4,4-trifluoro-3-oxobutanoate (105 µL 0.54 mmol), and the resulting mixture was stirred at 60° C. After 10 min, the mixture was allowed to cool to room temperature then was concentrated in vacuo. Purification by flash chromatography on silica gel (0 to 50% EtOAc in hexanes, then 50 to 100% EtOAc in hexanes) provided the title compound: LCMS m/z 720.0 [M+H]$^+$; $^1$H NMR (500 MHz, CDCl$_3$) δ 8.77 (d, J=5.5 Hz, 1H), 8.21 (s, 1H), 8.18 (dd, J=8.0, 1.5 Hz, 1H), 8.09 (d, J=5.5 Hz, 1H), 7.83 (dd, J=8.0, 1.5 Hz, 1H), 7.44 (t, J=8.0 Hz, 1H), 7.19-7.15 (m, 4H), 4.67 (s, 2H), 4.40 (q, J=7.0 Hz, 2H), 4.28-4.20 (m, 2H), 2.83-2.76 (m, 2H), 2.64 (dddd, J=12.0, 12.0, 3.5, 3.5 Hz, 1H), 1.82-1.80 (m, 2H), 1.65-1.58 (m, 2H), 1.49 (s, 9H), 1.41 (t, J=7.0 Hz, 3H).

Step D. 1-(4-(2-((4-(1-(Methoxycarbonyl)piperidin-4-yl)benzyl)oxy)-3-(trifluoromethyl)phenyl)pyrimidin-2-yl)-5-(trifluoromethyl)-1H-pyrazole-4-carboxylic acid To a solution of the title compound from Example 167 Step C (198 mg, 0.30 mmol) in DCM (3 mL) was added TFA (0.5 mL). After 3 min, the reaction mixture was concentrated in vacuo, and the crude TFA salt was used without further purification: LCMS m/z 619.9 [M+1-1]$^+$. To a portion of the crude TFA salt (~0.15 mmol) in DCM (1.5 mL) were added DIEA (262 µL, 1.50 mmol) and methyl chloroformate (34 µL, 0.45 mmol), and the resulting mixture was allowed to stir at room temperature. After 90 min, the reaction mixture was quenched by addition of sat aq NaHCO$_3$ and the aqueous phase was extracted with DCM. The organic phase was separated and concentrated in vacuo to provide the crude carbamate, which was used without further purification: LCMS m/z 677.9 [M+H]$^+$. To a solution of the carbamate in dioxane (2 mL) was added lithium hydroxide (1 mL, 2N aqueous, 2 mmol), and the mixture was stirred at 50° C. After 1 h, the reaction mixture was rendered acidic by addition of HCl (2N aqueous), then was diluted with acetonitrile and purified by reverse phase HPLC (30 to 100% acetonitrile/water, both 0.1% v/v TFA) to provide the title compound: LCMS m/z 649.9 [M+H]$^+$; $^1$H NMR (500 MHz, d$_6$-DMSO) δ 9.07 (d, J=5.5 Hz, 1H), 8.35 (s, 1H), 8.16 (d, J=5.5 Hz, 1H), 8.07 (dd, J=8.0, 1.5 Hz, 1H), 7.96 (dd, J=8.0, 1.5 Hz, 1H), 7.58 (t, J=8.0 Hz, 1H), 7.17 (d, J=8.5 Hz, 2H), 7.09 (d, J=8.5 Hz, 2H), 4.63 (s, 2H), 4.10-4.04 (m, 2H), 3.58 (s, 3H), 2.88-2.62 (m, 3H), 1.72-1.68 (m, 2H), 1.50-1.42 (m, 2H).

The compounds listed in Table 5 were prepared using chemistry described in Example 167, and/or by analogy to chemistry described in Examples 1-14, Examples 136, 148, and 162.

TABLE 5

| Example | Structure | IUPAC | LCMS |
| --- | --- | --- | --- |
| 168 | 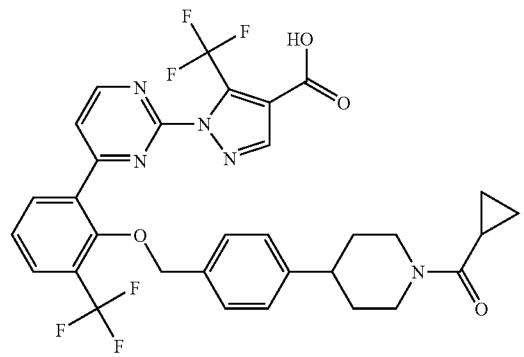 [SMILES: O=C(O)c1cnn(-c2nccc(-c3cccc(C(F)(F)F)c3OCc3ccc(C4CCN(C(=O)C5CC5)CC4)cc3)n2)c1C(F)(F)F] | 1-(4-(2-((4-(1-(cyclopropylcarbonyl)piperidin-4-yl)benzyl)oxy)-3-(trifluoromethyl)phenyl)pyrimidin-2-yl)-5-(trifluoromethyl)-1H-pyrazole-4-carboxylic acid | 659.9 |
| 169 | 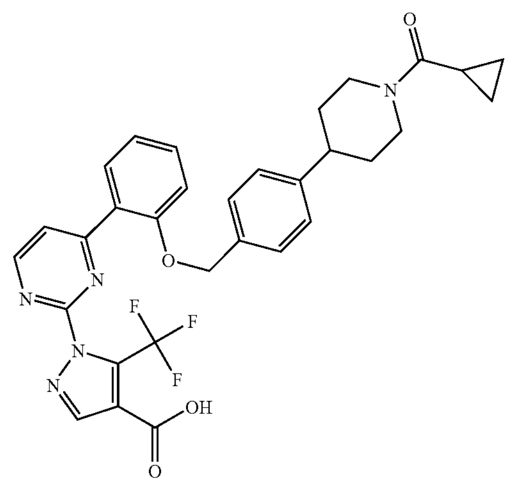 [SMILES: O=C(O)c1cnn(-c2nccc(-c3ccccc3OCc3ccc(C4CCN(C(=O)C5CC5)CC4)cc3)n2)c1C(F)(F)F] | 1-(4-(2-((4-(1-(cyclopropylcarbonyl)piperidin-4-yl)benzyl)oxy)phenyl)pyrimidin-2-yl)-5-(trifluoromethyl)-1H-pyrazole-4-carboxylic acid | 591.8 |
| 170 | 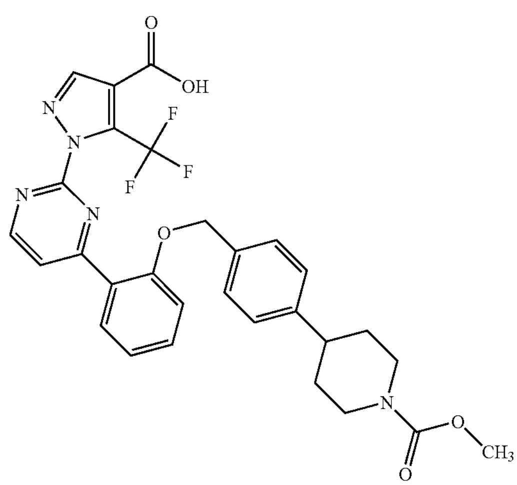 [SMILES: COC(=O)N1CCC(c2ccc(COc3ccccc3-c3ccnc(-n4ncc(C(=O)O)c4C(F)(F)F)n3)cc2)CC1] | 1-(4-(2-((4-(1-(methoxycarbonyl)piperidin-4-yl)benzyl)oxy)phenyl)pyrimidin-2-yl)-5-(trifluoromethyl)-1H-pyrazole-4-carboxylic acid | 581.8 |
| 171 | 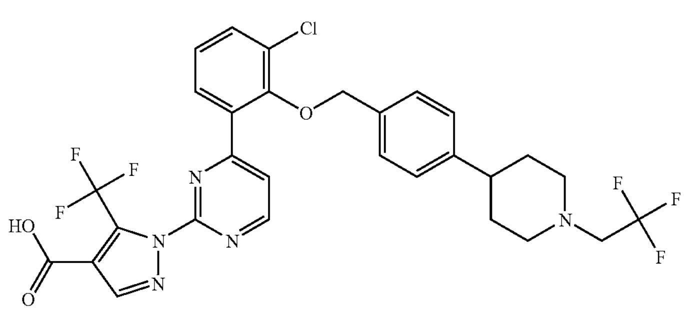 [SMILES: O=C(O)c1cnn(-c2nccc(-c3cccc(Cl)c3OCc3ccc(C4CCN(CC(F)(F)F)CC4)cc3)n2)c1C(F)(F)F] | 1-(4-(3-chloro-2-((4-(1-(2,2,2-trifluoroethyl)piperidin-4-yl)benzyl)oxy)phenyl)pyrimidin-2-yl)-5-(trifluoromethyl)-1H-pyrazole-4-carboxylic acid | 639.9 |

TABLE 5-continued

| Example | Structure | IUPAC | LCMS |
|---|---|---|---|
| 172 | 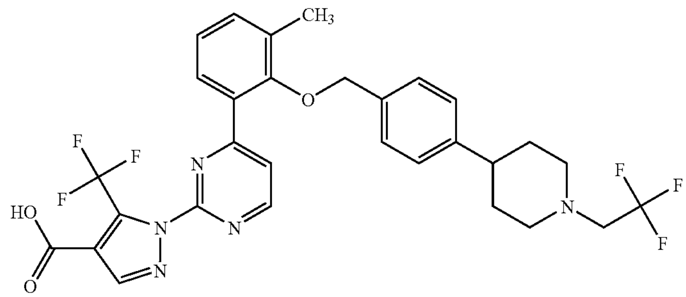 [SMILES: Cc1cccc(-c2ccnc(-n3ncc(C(=O)O)c3C(F)(F)F)n2)c1OCc1ccc(C2CCN(CC(F)(F)F)CC2)cc1] | 1-(4-(3-methyl-2-((4-(1-(2,2,2-trifluoroethyl)piperidin-4-yl)benzyl)oxy)phenyl)pyrimidin-2-yl)-5-(trifluoromethyl)-1H-pyrazole-4-carboxylic acid | 619.9 |
| 173 | 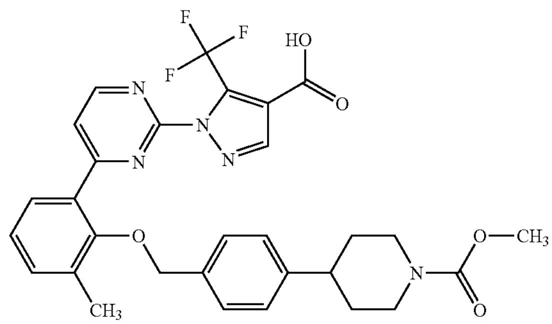 [SMILES: COC(=O)N1CCC(c2ccc(COc3c(C)cccc3-c3ccnc(-n4ncc(C(=O)O)c4C(F)(F)F)n3)cc2)CC1] | 1-(4-(2-((4-(1-(methoxycarbonyl)piperidin-4-yl)benzyl)oxy)-3-methylphenyl)pyrimidin-2-yl)-5-(trifluoromethyl)-1H-pyrazole-4-carboxylic acid | 595.9 |
| 174 | 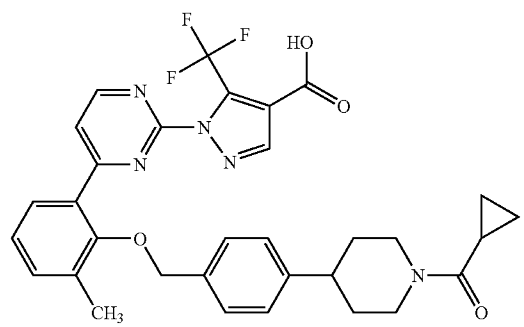 [SMILES: Cc1cccc(-c2ccnc(-n3ncc(C(=O)O)c3C(F)(F)F)n2)c1OCc1ccc(C2CCN(C(=O)C3CC3)CC2)cc1] | 1-(4-(2-((4-(1-(cyclopropylcarbonyl)piperidin-4-yl)benzyl)oxy)-3-methylphenyl)pyrimidin-2-yl)-5-(trifluoromethyl)-1H-pyrazole-4-carboxylic acid | 605.9 |
| 175 | 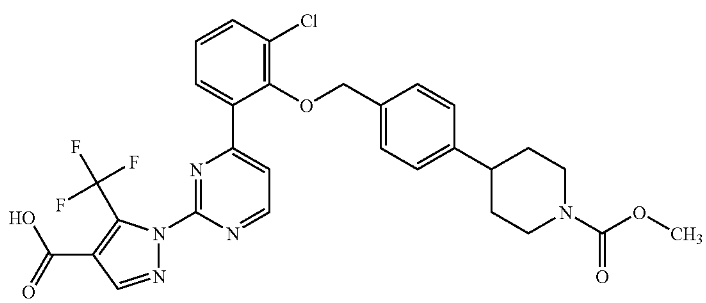 [SMILES: COC(=O)N1CCC(c2ccc(COc3c(Cl)cccc3-c3ccnc(-n4ncc(C(=O)O)c4C(F)(F)F)n3)cc2)CC1] | 1-(4-(3-chloro-2-((4-(1-(methoxycarbonyl)piperidin-4-yl)benzyl)oxy)phenyl)pyrimidin-2-yl)-5-(trifluoromethyl)-1H-pyrazole-4-carboxylic acid | 616.1 |
| 176 | 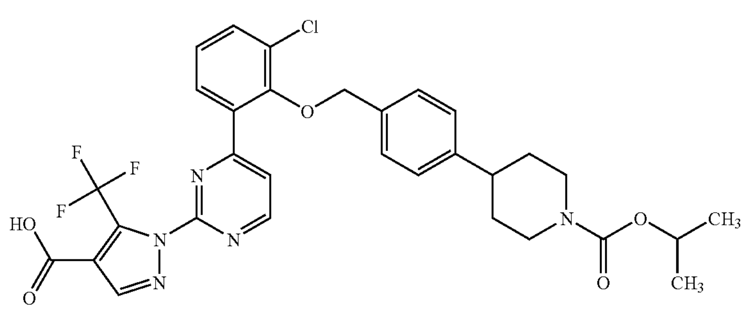 [SMILES: CC(C)OC(=O)N1CCC(c2ccc(COc3c(Cl)cccc3-c3ccnc(-n4ncc(C(=O)O)c4C(F)(F)F)n3)cc2)CC1] | 1-(4-(3-chloro-2-((4-(1-(isopropoxycarbonyl)piperidin-4-yl)benzyl)oxy)phenyl)pyrimidin-2-yl)-5-(trifluoromethyl)-1H-pyrazole-4-carboxylic acid | 644.1 |

TABLE 5-continued

| Example | Structure | IUPAC | LCMS |
|---|---|---|---|
| 177 | 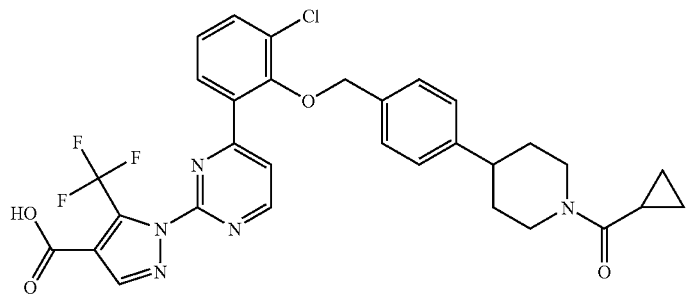 [SMILES: O=C(O)c1cnn(-c2nccc(-c3cccc(Cl)c3OCc3ccc(C4CCN(C(=O)C5CC5)CC4)cc3)n2)c1C(F)(F)F] | 1-(4-(3-chloro-2-((4-(1-(cyclopropylcarbonyl)piperidin-4-yl)benzyl)oxy)phenyl)pyrimidin-2-yl)-5-(trifluoromethyl)-1H-pyrazole-4-carboxylic acid | 626.1 |
| 178 | 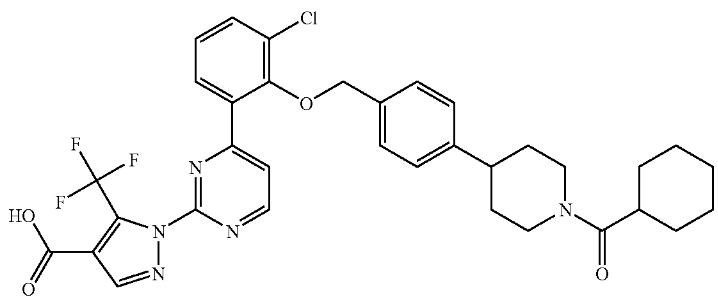 [SMILES: O=C(O)c1cnn(-c2nccc(-c3cccc(Cl)c3OCc3ccc(C4CCN(C(=O)C5CCCCC5)CC4)cc3)n2)c1C(F)(F)F] | 1-(4-(3-chloro-2-((4-(1-(cyclohexylcarbonyl)piperidin-4-yl)benzyl)oxy)phenyl)pyrimidin-2-yl)-5-(trifluoromethyl)-1H-pyrazole-4-carboxylic acid | 668.2 |
| 179 | 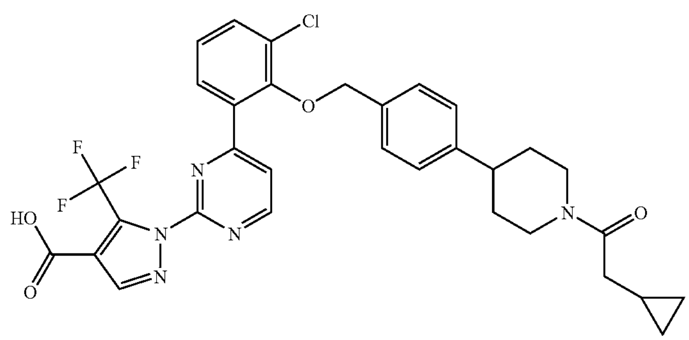 [SMILES: O=C(O)c1cnn(-c2nccc(-c3cccc(Cl)c3OCc3ccc(C4CCN(C(=O)CC5CC5)CC4)cc3)n2)c1C(F)(F)F] | 1-(4-(3-chloro-2-((4-(1-(cyclopropylacetyl)piperidin-4-yl)benzyl)oxy)phenyl)pyrimidin-2-yl)-5-(trifluoromethyl)-1H-pyrazole-4-carboxylic acid | 640.1 |

EXAMPLE 180

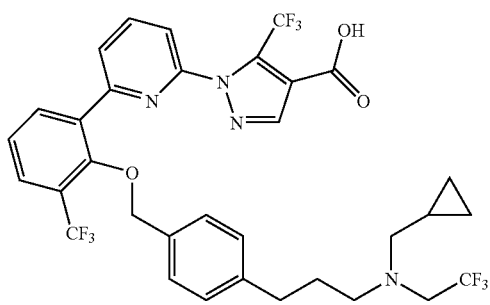 [SMILES: O=C(O)c1cnn(-c2cccc(-c3cccc(C(F)(F)F)c3OCc3ccc(CCCN(CC4CC4)CC(F)(F)F)cc3)n2)c1C(F)(F)F]

Step A. Ethyl 1-(6-[2-1(4-bromobenzyl)oxy-1-3-(trifluoromethyl)phenyl]pyridin-2-yl)-5-(trifluoromethyl)-1H-pyrazole-4-carboxylate To a solution of the title compound from the Example 136 Step D (2.26 g, 5.06 mmol) in DMF (25 mL), were added 1-bromo-4-(bromomethyl)benzene (1.65 g, 6.60 mmol) and cesium carbonate (3.31 g, 10.15 mmol). The reaction mixture was stirred at 40° C. for 2 h, then was diluted with water and extracted with EtOAc. The organic phase was dried over $Na_2SO_4$ and concentrated in vacuo. Purification by chromatography on silica gel (0 to 15% EtOAc in hexanes, then 15 to 100% EtOAc in hexanes) provided the title compound: LCMS m/z 615.7 [M+H]$^+$; $^1$H NMR (500 MHz, CDCl$_3$) δ 8.17 (s, 1H), 8.07-8.01 (m, 2H), 7.89 (t, J=8.0 Hz, 1H), 7.73 (d, J=8.0 Hz, 1H), 7.67 (d, J=8.0 Hz, 1H), 7.45 (d, J=8.5 Hz, 2H), 7.39 (t, J=8.0 Hz, 1H), 7.07 (d, J=8.5 Hz, 2H), 4.56 (s, 2H), 4.40 (q, J=7.0 Hz, 2H), 1.40 (t, J=7.0 Hz, 3H).

Step B. Ethyl 1-6-{2-4-1-3-tert-butoxycarbonyl amino]prop-1-en-1-yl}benzyl)oxy]-3-(trifluoromethyl)phenyl}pyridin-2-yl)-5-(trifluoromethyl)-1H-pyrazole-4-carboxylate To a flask containing the title compound from the Example 180 Step A (1.70 g, 2.77 mmol) were added tert-butyl [(2E)-3-(4,4,5,5-tetramethyl-1,3,2-dioxaborolan-2-yl)prop-2-en-1-yl]carbamate (1.02 g, 3.60 mmol, Tetrahedron Lett., 2002, 43, 4935-4938) and trans-dichlorobis(triphenylphosphine) palladium (II) (194 mg, 0.28 mmol). Acetonitrile (15 mL) and sodium carbonate (6.92 mL, 1.0 M aqueous, 6.92 mmol) were added, and the resulting mixture was degassed via nitrogen sparge. The reaction mixture was stirred at 70° C. for 3 h, then was allowed to cool to ambient temperature and was poured into water. The mixture was extracted with EtOAc, and the organic phase was concentrated in vacuo. Purification by chromatography on silica gel (0 to 20% EtOAc in hexanes, then 20 to 100% EtOAc in hexanes) provided the title compound: LCMS m/z 691.0 [M+H]$^+$; $^1$H NMR (500 MHz, CDCl$_3$) δ 8.16 (s, 1H), 8.08 (d, J=7.5 Hz, 1H), 8.04 (d, J=7.5 Hz, 1H), 7.88 (t, J=8.0 Hz, 1H), 7.73 (d, J=8.0 Hz, 1H), 7.66 (d, J=8.0 Hz, 1H), 7.38 (t, J=7.5 Hz, 1H), 7.31 (d, J=8.0 Hz, 2H), 7.14 (d, J=8.0 Hz, 2 H), 6.49 (d, J=16.0 Hz, 1H), 6.24-6.16 (m, 1H), 4.70-4.62 (br m, 1H), 4.58 (s, 2H), 4.40 (q, J=7.0 Hz, 2H), 3.96-3.88 (br m, 2H), 1.47 (s, 9H), 1.40 (t, J=7.0 Hz, 3H).

Step C. Ethyl 1-(6-{2-[(4-{3-1(tert-butoxycarbonyl)amino]propyl}benzyl)oxy]-3-(trifluoromethyl)phenyl}pyridin-2-yl)-5-(trifluoromethyl)-1H-pyrazole-4-carboxylate To a degassed solution of the title compound from Example 180 Step B (1030 mg, 1.49 mmol) in EtOAc (10 mL) was added platinum oxide (102 mg, 0.45 mmol). The reaction flask was fitted with a hydrogen balloon attached to a 3-way adapter. The reaction mixture was then evacuated and backfilled with hydrogen. After this process was repeated three times, the reaction mixture was placed under a hydrogen atmosphere, and was stirred vigorously. After 45 min, the reaction mixture was filtered though Celite, rinsing with EtOAc. The mixture was dried over anhydrous sodium sulfate, filtered, and concentrated in vacuo. Purification by chromatography on silica gel (0 to 20% EtOAc in hexanes, 20 to 100% EtOAc in hexanes) provided the title compound: LCMS m/z 693.0 [M+H]$^+$; $^1$H NMR (500 MHz, CDCl$_3$) δ 8.16 (s, 1H), 8.11 (d, J=8.0 Hz, 1H), 8.05 (d, J=8.0 Hz, 1H), 7.91 (t, J=8.0 Hz, 1H), 7.72 (d, J=8.0 Hz, 1H), 7.67 (d, J=7.5 Hz, 1H), 7.38 (t, J=8.0 Hz, 1H), 7.14 (d, J=8.5 Hz, 2H), 7.11 (d, J=8.5 Hz, 2H), 4.59-4.53 (br m, 1H), 4.57 (s, 2H), 4.40 (q, J=7.0 Hz, 2H), 3.22-3.12 (br m, 2H), 2.63 (t, J=7.5 Hz, 2H), 1.80 (q, J=7.5 Hz, 2H), 1.45 (s, 9H), 1.40 (t, J=7.5 Hz, 3 H).

Step D. Ethyl 1-{6-[2-{[4-(3-aminopropyl)benzyl]oxy}-3-(trifluoromethyl)phenyl]pyridin-2-yl}-5-(trifluoromethyl)-1H-pyrazole-4-carboxylate A solution of the title compound from Example 180 Step C (850 mg, 1.23 mmol) in acetic acid (4 mL) and water (1 mL) was stirred at 90° C. for 14 h. The reaction mixture was allowed to cool to ambient temperature and was concentrated in vacuo. The product was used in the subsequent step without further purification: LCMS m/z 593.0 [M+H]$^+$.

Step E. Ethyl 1-(6-{2-[(4-{3-[(2,2,2-trifluoroethyl)amino]propyl}benzyl)oxy]-3-(trifluoromethyl)phenyl]pyridin-2-yl)-5-(trifluoromethyl)-1H-pyrazole-4-carboxylate To a solution of the title compound from the Example 180 Step D (500 mg, 0.84 mmol) in DCM (5 mL), were added 2,2,2-trifluoroethyl trifluoromethanesulfonate (0.42 mL, 2.53 mmol) and cesium carbonate (1.65 g, 5.06 mmol). The reaction mixture was stirred at ambient temperature for 6 h, then was diluted with saturated aq. NaHCO$_3$ and extracted with DCM. The organic phase was dried over Na$_2$SO$_4$ and concentrated in vacuo. The product was used in the subsequent step without further purification: LCMS m/z 675.1 [M+H]$^+$.

Step F. Ethyl 1-(6-{2-[(4-{3-[(cyclopropylmethyl)(2,2,2-trifluoroethyl)amino]propyl}benzyl)oxy-1-3-(trifluoromethyl)phenyl}pyridin-2-O-5-(trifluoromethyl)-1H-pyrazole-4-carboxylate To a solution of the title compound from the Example 180 Step E (80 mg, 0.12 mmol) in DCM (2 mL), were added cyclopropanecarbaldehyde (0.01 mL, 0.12 mmol), acetic acid (0.02 mL, 0.36 mmol) and sodium triacetoxyborohydride (33 mg, 0.15 mmol). The reaction mixture was stirred at ambient temperature for 12 h, then was diluted with saturated aq. NaHCO$_3$ and extracted with DCM. The organic phase was dried over Na$_2$SO$_4$ and concentrated in vacuo. The product was used in the subsequent step without further purification: LCMS m/z 729.1 [M+H]$^+$.

Step G. 1-(6-{2-[(4-{3-[(Cyclopropylmethyl)(2,2,2-trifluoroethyl)amino]propyl}benzyl)oxy]-1-3-(trifluoromethyl)phenyl}pyridin-2-yl)-5-(trifluoromethyl)-1H-pyrazole-4-carboxylic acid To a solution of the title compound from Example 180 Step F (86 mg, 0.12 mmol) in 1,4-dioxane (2 mL) was added lithium hydroxide (1.0 mL, 2.0 M in water, 2.00 mmol), and the resulting mixture was stirred at 50° C. After 2 h, the reaction mixture was rendered acidic by addition of aqueous hydrochloric acid (1.5 mL), then was diluted with 1,4-dioxane and passed though a 0.45 micron syringe filter. Purification by reverse phase HPLC (40 to 100% acetonitrile in water, each with 0.1% v/v TFA) provided the title compound: LCMS m/z 701.0 [M+H]$^+$; $^1$H NMR (500 MHz, d$_6$-DMSO) δ 8.32 (s, 1H), 8.21 (t, J=8.0 Hz, 1H), 8.06 (d, J=8.0 Hz, 1H), 7.94 (d, J=8.0 Hz, 1H), 7.87 (d, J=8.0 Hz, 1H), 7.84 (d, J=8.0 Hz, 1H), 7.52 (t, J=8.0 Hz, 1H), 7.15 (d, J=8.0 Hz, 2H), 7.03 (d, J=8.0, 2H), 4.49 (s, 2H), 2.76-2.68 (m, 2H), 2.58-2.52 (m, 4H), 1.78-1.68 (m, 2H), 0.90-0.78 (m, 1H), 0.48-0.40 (m, 2H), 0.14-0.06 (m, 2H).

The compounds listed in Table 6 were prepared using chemistry described in Example 180, and/or by analogy to chemistry described in Examples 1-14, 136, 148, 162, and 167.

TABLE 6

| Example | Structure | IUPAC | LCMS |
|---|---|---|---|
| 181 | 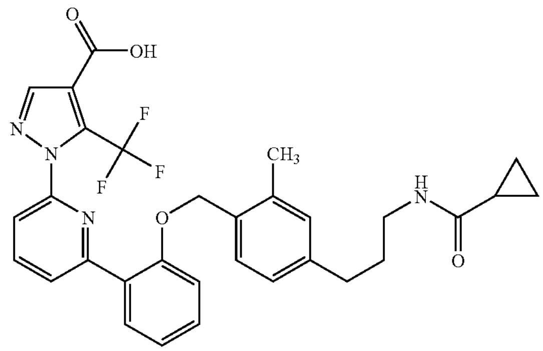 [SMILES: Cc1cc(CCCNC(=O)C2CC2)ccc1COc1ccccc1-c1cccc(-n2ncc(C(=O)O)c2C(F)(F)F)n1] | 1-(6-(2-((4-(3-((cyclopropylcarbonyl)amino)propyl)-2-methylbenzyl)oxy)phenyl)pyridin-2-yl)-5-(trifluoromethyl)-1H-pyrazole-4-carboxylic acid | 578.8 |
| 182 | 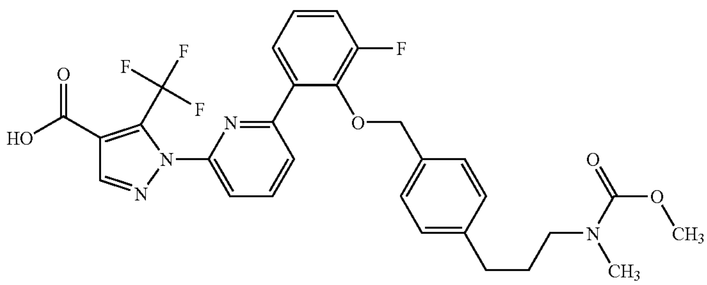 [SMILES: COC(=O)N(C)CCCc1ccc(COc2c(F)cccc2-c2cccc(-n3ncc(C(=O)O)c3C(F)(F)F)n2)cc1] | 1-(6-(3-fluoro-2-((4-(3-((methoxycarbonyl)(methyl)amino)propyl)benzyl)oxy)phenyl)pyridin-2-yl)-5-(trifluoromethyl)-pyrazole-4-carboxylic acid | 586.8 |
| 183 | 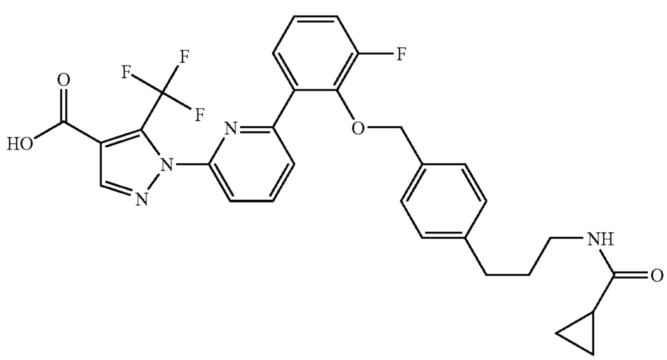 [SMILES: O=C(O)c1cnn(-c2cccc(-c3cccc(F)c3OCc3ccc(CCCNC(=O)C4CC4)cc3)n2)c1C(F)(F)F] | 1-(6-(2-((4-(3-((cyclopropylcarbonyl)amino)propyl)benzyl)oxy)-3-fluorophenyl)pyridin-2-yl)-5-(trifluoromethyl)-1H-pyrazole-4-carboxylic acid | 582.8 |
| 184 | 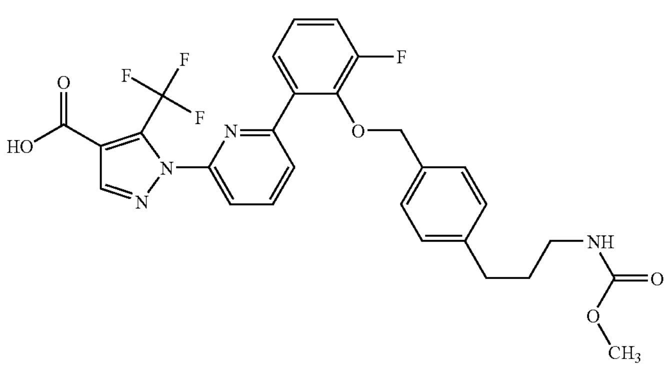 [SMILES: COC(=O)NCCCc1ccc(COc2c(F)cccc2-c2cccc(-n3ncc(C(=O)O)c3C(F)(F)F)n2)cc1] | 1-(6-(3-fluoro-2-((4-(3-((methoxycarbonyl)amino)propyl)benzyl)oxy)phenyl)pyridin-2-yl)-5-(trifluoromethyl)-1H-pyrazole-4-carboxylic acid | 572.8 |

TABLE 6-continued

| Example | Structure | IUPAC | LCMS |
|---|---|---|---|
| 185 | 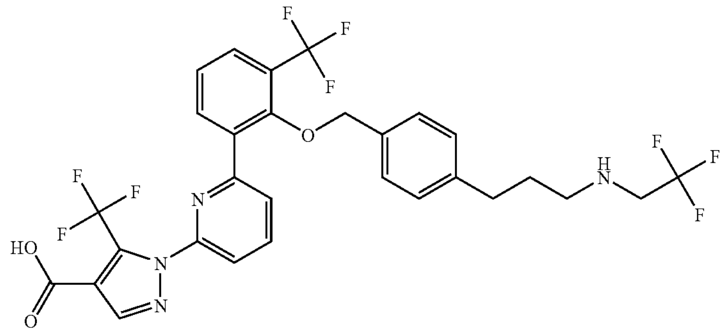 [SMILES: O=C(O)c1cnn(-c2cccc(-c3cccc(C(F)(F)F)c3OCc3ccc(CCCNCC(F)(F)F)cc3)n2)c1C(F)(F)F] | 1-(6-(2-((4-(3-((2,2,2-trifluoroethyl)amino)propyl)benzyl)oxy)-3-(trifluoromethyl)phenyl)pyridin-2-yl)-5-(trifluoromethyl)-1H-pyrazole-4-carboxylic acid | 647.0 |
| 186 | 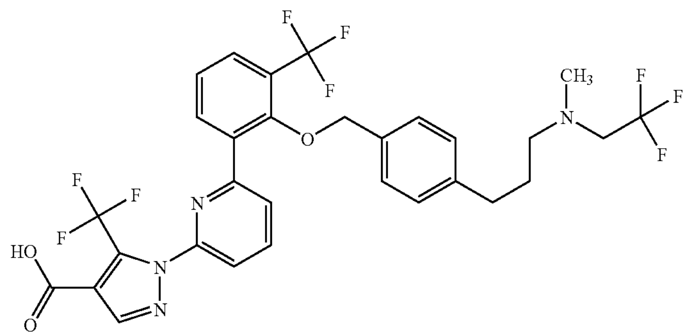 [SMILES: CN(CCCc1ccc(COc2c(-c3cccc(-n4ncc(C(=O)O)c4C(F)(F)F)n3)cccc2C(F)(F)F)cc1)CC(F)(F)F] | 1-(6-(2-((4-(3-(methyl(2,2,2-trifluoroethyl)amino)propyl)benzyl)oxy)-3-(trifluoromethyl)phenyl)pyridin-2-yl)-5-(trifluoromethyl)-1H-pyrazole-4-carboxylic acid | 661.0 |

Cell-Based sGC Functional Assay (CASA Assay)

Rationale: sGC is a heme-containing enzyme that converts GTP (guanosine 5'-triphosphate) to secondary messenger cGMP. Increases in cGMP levels affect several physiological processes including vasorelaxation through multiple downstream pathways. The rate by which sGC catalyzes cGMP formation is greatly increased by NO and by recently discovered NO-independent activators and stimulators. Heme-independent activators (HIAs) preferentially activate sGC containing a ferric heme group, which can be generated upon incubation with 1H-(1,2,4)oxadiazolo(4,3-a) quinoxalin-1-one (ODQ). To determine the effect of sGC activators on enzyme activity, the CASA assay was developed to monitor the generation of cGMP in a cell line that stably expresses the heterodimeric sGC protein.

Methods: A CHO-K1 cell line stably expressing the sGC α1/β1 heterodimer was generated using a standard transfection protocol. CHO-K1 cells were transfected with plasmids pIREShyghsGCα1 and pIRESneo-hsGCβ1 simultaneously using FUGENE reagent. Clones that stably express both subunits were selected with hygromycin and neomycin for ~2 weeks. Clone #7 was chosen for the assay and was designated CHO-K1/sGC. CHO-K1/sGC cells were maintained in F-K12 medium containing 10% heat-inactivated Fetal Bovine Serum (FBS), 100 μg/mL penicillin/streptomycin, 0.5 mg/mL hygromycin and 0.25 mg/mL G418. On the day of the assay, cells were harvested in EBSS (Earle's balanced salt solution) Assay Buffer (EAB) containing 5 mM $MgCl_2$, 10 mM HEPES (4-(2-hydroxyethyl)piperazine-1-ethanesulfonic acid) and 0.05% BSA (bovine serum albumin) and cell density was adjusted to $2\times10^6$/mL with EAB. IBMX (3-isobutyl-1-methylxanthin, 0.5 mM) was added to inhibit degradation of cGMP. Compounds were diluted from DMSO stock solutions and added to the assay at a final DMSO concentration of 1%. Cells were incubated with compounds in the presence and absence of 10 μM of 1H-(1,2,4)oxadiazolo(4,3-a) quinoxalin-1-one (ODQ) for 1 hr at 37° C. At the end of the incubation period, the reaction was terminated and the cells were lysed. The level of intracellular cGMP was determined using an HTRF-based assay kit (CisBio, 62GM2PEC), which detects the displacement of a fluorescence labeled cGMP from its specific antibody. The amount of cGMP was plotted against compound concentration in PRISM software and the inflection point (IP) and maximum fold induction over DMSO control were derived from the plot.

The compounds of the instant invention had inflection points (IP) less than or equal to 10 μM and a maximum fold induction over DMSO control of at least 4-fold in the cell based assay described above (with ODQ incubation), and more particularly less than or equal to about 200 nM/equal to or greater than about 20-fold. Preferred compounds had an IP of less than or equal to about 100 nM and a maximum fold induction over DMSO control of at least 50-fold.

Cell-based assay results (with ODQ incubation) for the following representative compounds are provided. Data are listed as inflection points (IP) and the maximal fold induction over DMSO control:

| Example # | IUPAC | IP (nM) (maximum fold induction) |
|---|---|---|
| 1 | 1-[6-[2-[[4-[1-(2,2,2-Trifluoroethyl)-4-piperidinyl]phenyl]methoxy]phenyl]-2-pyridinyl]-5-(trifluoromethyl)-1H-pyrazole-4-carboxylic acid | 51.5 nM (281-fold) |
| 2 | 1-(6-(3-Chloro-5-fluoro-2-((4-(1-(2,2,2-trifluoroethyl)piperidin-4-yl)benzyl)oxy)phenyl)pyridin-2-yl)-5-(trifluoromethyl)-1H-pyrazole-4-carboxylic acid | 2.4 nM (189-fold) |
| 3 | 1-(6-(2-((2-Methyl-4-(1-(2,2,2-trifluoroethyl)piperidin-4-yl)benzyl)oxy)phenyl)pyridin-2-yl)-5-(trifluoromethyl)-1H-pyrazole-4-carboxylic acid | 10.4 nM (127-fold) |
| 5 | 1-{6-[3-fluoro-2-({4-[1-(methoxycarbonyl)piperidin-4-yl]benzyl}oxy)phenyl]pyridin-2-yl}-5-(trifluoromethyl)-1H-pyrazole-4-carboxylic acid | 26.9 nM (244-fold) |
| 77 | 1-(6-(2-((4-(1-(methoxycarbonyl)piperidin-4-yl)benzyl)oxy)-3-(trifluoromethyl)phenyl)pyridin-2-yl)-5-(trifluoromethyl)-1H-pyrazole-4-carboxylic acid | 1.5 nM (151-fold) |
| 81 | 1-(6-(2-((4-(1-(cyclopropylcarbonyl)piperidin-4-yl)benzyl)oxy)-3-(trifluoromethyl)phenyl)pyridin-2-yl)-5-(trifluoromethyl)-1H-pyrazole-4-carboxylic acid | 2.6 nM (170-fold) |
| 76 | 1-(6-(2-((4-(1-propionylpiperidin-4-yl)benzyl)oxy)-3-(trifluoromethyl)phenyl)pyridin-2-yl)-5-(trifluoromethyl)-1H-pyrazole-4-carboxylic acid | <0.5 nM (216-fold) |
| 84 | 1-(6-(3-chloro-2-((4-(1-(cyclopropylcarbonyl)piperidin-4-yl)benzyl)oxy)phenyl)pyridin-2-yl)-5-(trifluoromethyl)-1H-pyrazole-4-carboxylic acid | 5.4 nM (50-fold) |

While the invention has been described with reference to certain particular embodiments thereof, numerous alternative embodiments will be apparent to those skilled in the art from the teachings described herein. Recitation of a specific compound in the claims (i.e., a species) without a chiral designation is intended to encompass the racemate, racemic mixtures, each individual enantiomer, a diastereoisomeric mixture and each individual diastereomer of the compound where such forms are possible due to the presence of one or more asymmetric centers. All patents, patent applications and publications cited herein are incorporated by reference in their entirety.

What is claimed is:

1. A compound of structural Formula I:

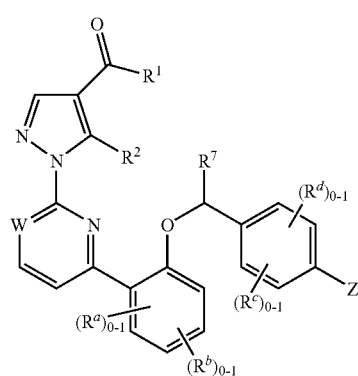

I or a pharmaceutically acceptable salt thereof, wherein:

W is selected from the group consisting of CH and N;

Z is selected from the group consisting of:

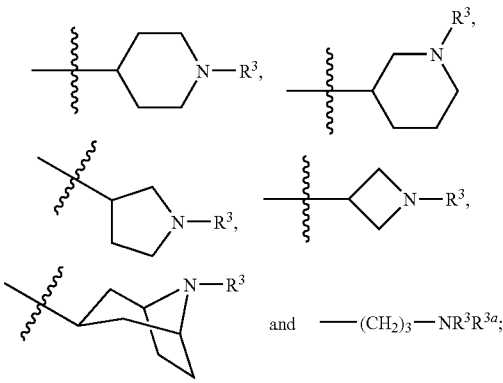

and $-(CH_2)_3-NR^3R^{3a}$;

$R^1$ is selected from the group consisting of —OH, —OC$_{1-6}$ alkyl and —N(R$^5$)$_2$;

$R^2$ is selected from the group consisting of —C$_{1-2}$ perfluoroalkyl and —NH$_2$;

$R^3$ is selected from the group consisting of:
 1) —C$_{1-6}$ alkyl substituted with 1-3 of —F,
 2) —COR$^4$ and
 3) —SO$_2$R$^6$;

$R^{3a}$ is selected from the group consisting of —H; —C$_{1-3}$ alkyl; C$_{3-6}$ cycloalkyl optionally mono- or di-substituted with one or more substituents selected from the group consisting of —CH$_3$ and —F; and —CH$_2$—C$_{3-6}$cycloalkyl optionally mono- or di-substituted with one or more substituents selected from the group consisting of —CH$_3$ and —F;

$R^4$ is selected from the group consisting of:
 1) —H,
 2) —C$_{1-3}$ alkyl,
 3) —OC$_{1-3}$ alkyl
 4) —C$_{3-6}$ cycloalkyl optionally mono- or di-substituted with one or more substituents selected from the group consisting of —CH$_3$ and —F, 5) —CH₂—C₃₋₆cycloalkyl optionally mono- or di-substituted with one or more substituents selected from the group consisting of —CH₃ and —F,
6) —OC₃₋₆ cycloalkyl optionally mono- or di-substituted with one or more substituents selected from the group consisting of —CH₃ and —F, and
7) —N(R⁵)₂;

R⁵ is independently selected at each occurrence from —H and —C₁₋₃ alkyl;

R⁶ is selected from the group consisting of —C₁₋₃alkyl; —C₃₋₆cycloalkyl optionally mono- or di- substituted with one or more substituents selected from the group consisting of —CH₃ and —F; and —CH₂—C₃₋₆cycloalkyl optionally mono- or di-substituted with one or more substituents selected from the group consisting of —CH₃ and —F;

R⁷ is selected from the group consisting of —H and —CH₃;

Rᵃ and Rᵇ are independently selected at each occurrence from —F, —Cl and —C₁₋₃ alkyl optionally substituted with 1-3 of —F; and Rᶜ and Rᵈ are independently selected at each occurrence from —F, —Cl and —C₁₋₃ alkyl optionally substituted with 1-3 of —F.

2. The compound of claim 1 wherein W is N or a pharmaceutically acceptable salts thereof.

3. The compound of claim 1 wherein W is CH or a pharmaceutically acceptable salts thereof.

4. The compound of claim 1 wherein Z is selected from the group consisting of:

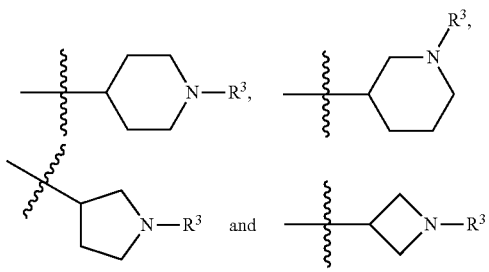

or a pharmaceutically acceptable salts thereof.

5. The compound of claim 1 wherein Z is

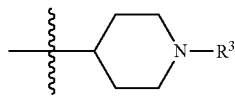

or a pharmaceutically acceptable salts thereof.

6. The compound of claim 1 wherein R¹ is —OH and R² is —C₁₋₂ perfluoroalkyl or a pharmaceutically acceptable salt thereof.

7. The compound of claim 6 wherein R³ is selected from the group consisting of:
(a) —C₁₋₄ alkyl substituted with 1-3 of —F;
(b) —COR⁴ wherein R⁴ is selected from the group consisting of —C₁₋₃ alkyl; —OC₁₋₃ alkyl; —C₃₋₄ cycloalkyl optionally mono- or di-substituted with one or more substituents selected from the group consisting of —CH₃ and —F; and —N(R⁵)₂ wherein R⁵ is independently selected each occurrence from —H, —CH₃ and —CH₂CH₃; and
(c) —SO₂R⁶ and R⁶ is selected from the group consisting of —C₁₋₃ alkyl, and cyclopropyl;

or a pharmaceutically acceptable salt thereof.

8. The compound of claim 1 wherein R³ᵃ is selected from the group consisting of —H, —CH₃ and —CH₂-cyclopropyl or a pharmaceutically acceptable salt thereof.

9. The compound of claim 1 having a structural Formula selected from the group consisting of:

II

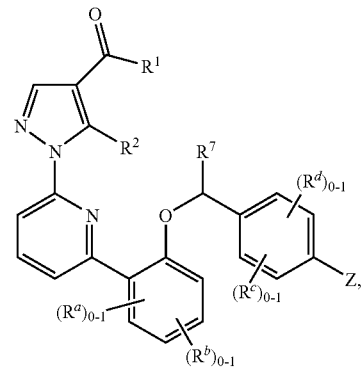

III

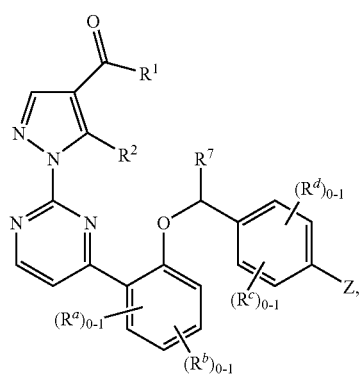

IV

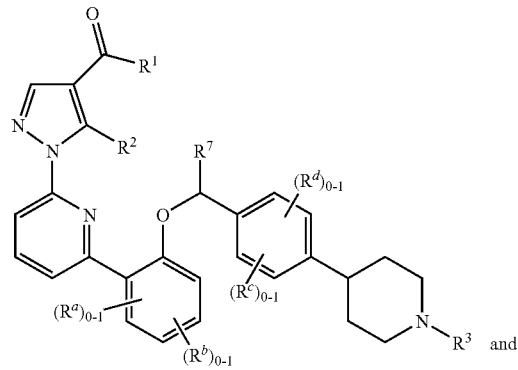

and

-continued

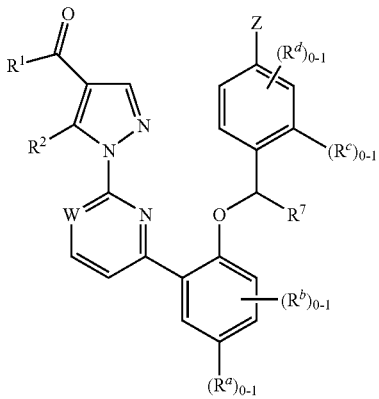

VI or a pharmaceutically acceptable salt thereof wherein:
$R^1$ is —OH;
$R^2$ is —$C_{1-2}$ perfluoroalkyl;
$R^3$ is selected from the group consisting of:
 (a) —$C_{1-4}$ alkyl substituted with 1-3 of —F;
 (b) —$COR^4$ wherein $R^4$ is selected from the group consisting of —$C_{1-3}$ alkyl; —$OC_{1-3}$ alkyl; —$C_{3-4}$ cycloalkyl optionally mono- or di-substituted with one or more substituents selected from the group consisting of —$CH_3$ and —F; and —$N(R^5)_2$ wherein $R^5$ is independently selected each occurrence from —H, —$CH_3$ and —$CH_2CH_3$; and
 (c) —$SO_2R^6$ wherein $R^6$ is selected from the group consisting of —$C_{1-3}$ alkyl and cyclopropyl;
$R^{3a}$ when present is selected from the group consisting of —H, —$CH_3$ and —$CH_2$-cyclopropyl; and $R^7$ is —H.

10. The compound of claim 1 having a structural Formula V:

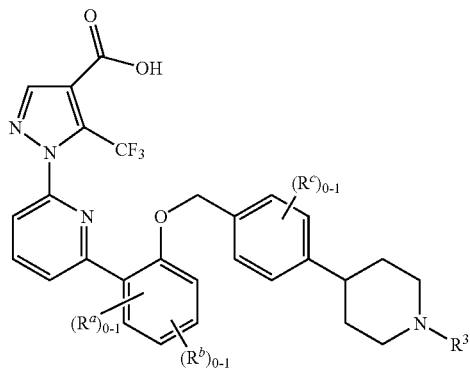

V or a pharmaceutically acceptable salt thereof.

11. The compound f claim 10 wherein $R^3$ is selected from the group consisting of:
 (a) —$C_{1-4}$ alkyl substituted with 1-3 of —F;
 (b) —$COR^4$ wherein $R^4$ is selected from the group consisting of —$C_{1-3}$ alkyl; —$OC_{1-3}$ alkyl; —$C_{3-4}$ cycloalkyl optionally mono- or di-substituted with one or more substituents selected from the group consisting of —$CH_3$ and —F; and —$N(R^5)_2$ wherein $R^5$ is independently selected each occurrence from —H, —$CH_3$ and —$CH_2CH_3$; and
 (c) —$SO_2R^6$ wherein $R^6$ is selected from the group consisting of —$C_{1-3}$ alkyl and cyclopropyl;
or a pharmaceutically acceptable salt thereof.

12. The compound of claim 9 having a structural Formula selected from the group consisting of Formula II, III and IV or a pharmaceutically acceptable salt thereof wherein the substituents $R^a$, $R^b$, $R^c$ and $R^d$ are optionally present at the positions on the rings as shown in Formula VIa:

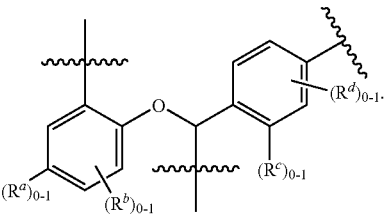

VIa

13. The compound of claim 10 or a pharmaceutically acceptable salt thereof wherein the substituents $R^a$, $R^b$, $R^c$ and $R^d$ are optionally present at the positions on the rings as shown in Formula VIa:

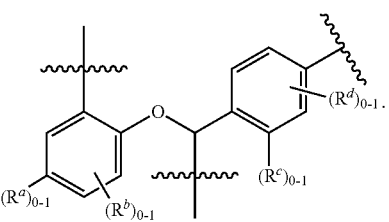

VIa

14. The compound of claim 1 selected from the group consisting of:
 1-[6-[2-[[4-[1-(2,2,2-Trifluoroethyl)-4-piperidinyl]phenyl]methoxy]phenyl]-2-pyridinyl]-5-(trifluoromethyl)-1H-pyrazole-4-carboxylic acid;
 1-(6-(3-Chloro-5-fluoro-2-((4-(1-(2,2,2-trifluoroethyl)piperidin-4-yl)benzyl)oxy)-phenyl)pyridin-2-yl)-5-(trifluoromethyl)-1H-pyrazole-4-carboxylic acid;
 1-(6-(2-((2-Methyl-4-(1-(2,2,2-trifluoroethyl)piperidin-4-yl)benzyl)oxy)phenyl)pyridin-2-yl)-5-(trifluoromethyl)-1H-pyrazole-4-carboxylic acid;
 1-{6-[3-fluoro-2-({4-[1-(methoxycarbonyl)piperidin-4 yl]benzyl}oxy)phenyl]pyridin-2-yl}-5-(trifluoromethyl)-1H-pyrazole-4-carboxylic acid;
 1-(6-(2-((4-(1-(methoxycarbonyl)piperidin-4-yl)benzyl)oxy)-3-(trifluoromethyl)-phenyl)pyridin-2-yl)-5-(trifluoromethyl)-1H-pyrazole-4-carboxylic acid;
 1-(6-(2-((4-(1-(cyclopropylcarbonyl)piperidin-4-yl)benzyl)oxy)-3-(trifluoromethyl)-phenyl)pyridin-2-yl)-5-(trifluoromethyl)-1H-pyrazole-4-carboxylic acid;
 1-(6-(2-((4-(1-propionylpiperidin-4-yl)benzyl)oxy)-3-(trifluoromethyl)phenyl)pyridin-2-yl)-5-(trifluoromethyl)-1H-pyrazole-4-carboxylic acid;
 1-(6-(3-chloro-2-((4-(1-(cyclopropylcarbonyl)piperidin-4-yl)benzyl)oxy)phenyl)pyridin-2-yl)-5-(trifluoromethyl)-1H-pyrazole-4-carboxylic acid;
 1-{6-2-({4-[1-(Cyclopropylcarbonyl)piperidin-4-yl]benzyl}oxy)-3-(difluoromethyl)phenyl]pyridin-2-yl}-5-(trifluoromethyl)-1H-pyrazole-4-carboxylic acid;
 1-(6-(3-methyl-2-((4-(1-(2,2,2-trifluoroethyl)piperidin-4-yl)benzyl)oxy)phenyl)pyridin-2-yl)-5-(trifluoromethyl)-1H-pyrazole-4-carboxylic acid;

1-(6-(3,5-difluoro-2-((4-(1-(2,2,2-trifluoroethyl)piperidin-4-yl)benzyl)oxy)phenyl)pyridin-2-yl)-5-(trifluoromethyl)-1H-pyrazole-4-carboxylic acid;

5-(Trifluoromethyl)-1-{6-[3-(trifluoromethyl)-2-({4-1-(3,3,3-trifluoropropyl)pyrrolidin-3-yl]benzyl}oxy)phenyl]pyridin-2-yl}-1H-pyrazole-4-carboxylic acid (enantiomer A);

1-(6-(5-fluoro-2-((2-methyl-4-(1-(2,2,2-trifluoroethyl)piperidin-4-yl)benzyl)oxy)-phenyl)pyridin-2-yl)-5-(trifluoromethyl)-1H-pyrazole-4-carboxylic acid;

1-(6-(4-fluoro-2-((2-methyl-4-(1-(2,2,2-trifluoroethyl)piperidin-4-yl)benzyl)-oxy)phenyl)pyridin-2-yl)-5-(trifluoromethyl)-1H-pyrazole-4-carboxylic acid;

1-(6-(2-((4-(1-(methoxycarbonyl)piperidin-4-yl)benzyl)oxy)-3-methylphenyl)pyridin-2-yl)-5-(trifluoromethyl)-1H-pyrazole-4-carboxylic acid;

1-(6-(3-(difluoromethyl)-2-((4-(1-(methoxycarbonyl)piperidin-4-yl)benzyl)oxy)-phenyl)pyridin-2-yl)-5-(trifluoromethyl)-1H-pyrazole-4-carboxylic acid;

1-(6-(2-((4-(1-(Methoxycarbonyl)azetidin-3-yl)benzyl)oxy)-3-(trifluoromethyl)-phenyl)pyridin-2-yl)-5-(trifluoromethyl)-1H-pyrazole-4-carboxylic acid;

or a pharmaceutically acceptable salts thereof.

15. A method for activating soluble guanylate cyclase comprising the step of administering an amount efficacious therefore of a compound of claim 1 to a patient in need thereof.

16. A method for the treatment of hypertension, comprising administering a therapeutically effective amount of a compound of claim 1 to a patient in need thereof.

17. A method for the treatment of pulmonary hypertension comprising administering a therapeutically effective amount of a compound of claim 1 to a patient in need thereof.

18. A method for the treatment of heart failure comprising administering a therapeutically effective amount of a compound of claim 1 to a patient in need thereof.

19. A pharmaceutical composition comprised of a compound of claim 1 and a pharmaceutically acceptable carrier.

20. The composition of claim 19 additionally comprising one or more active agents selected from the group consisting of an angiotensin converting enzyme inhibitor, an angiotensin II receptor antagonist, a neutral endopeptidase inhibitor, an aldosterone antagonist, a renin inhibitor, an endothelin receptors antagonist, a vasodilator, a calcium channel blocker, a potassium channel activators, a diuretic, a sympatholitic, a beta-adrenergic blocking drug, an alpha adrenergic blocking drug, a central alpha adrenergic agonist, a peripheral vasodilator, a lipid lowering agent, and a metabolic altering agent.

21. The compound of claim 1 that is 1-[6-[2-[[4-[1-(2,2,2-Trifluoroethyl)-4-piperidinyl]phenyl]methoxy]phenyl]-2-pyridinyl]-5-(trifluoromethyl)-1H-pyrazole-4-carboxylic acid,

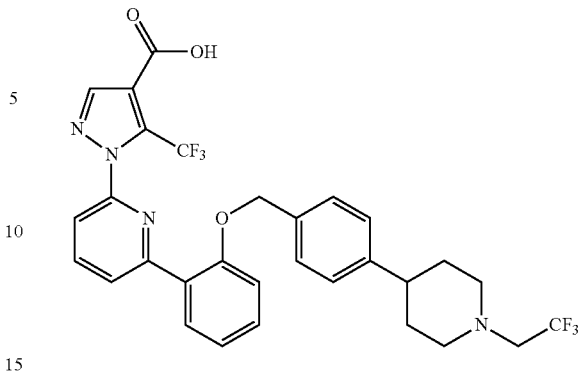

or a pharmaceutically acceptable salt thereof.

22. The compound of claim 1 that is 1-(6-(3-Chloro-5-fluoro-2-((4-(1-(2,2,2-trifluoroethyl)piperidin-4-yl)benzyl)oxy)phenyl)pyridin-2-yl)-5-(trifluoromethyl)-1H-pyrazole-4-carboxylic acid,

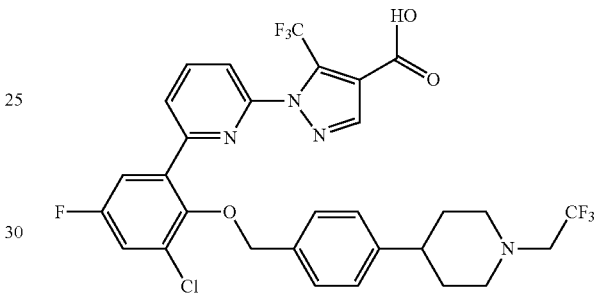

or a pharmaceutically acceptable salt thereof.

23. The compound of claim 1 that is 1-(6-((2-Methyl-4-(1-(2,2,2-trifluoroethyl)piperidin-4-yl)benzyl)oxy)phenyl)pyridine-2-yl)-5-trifluoromethyl)-1H-pyrazole-4-carboxylic acid,

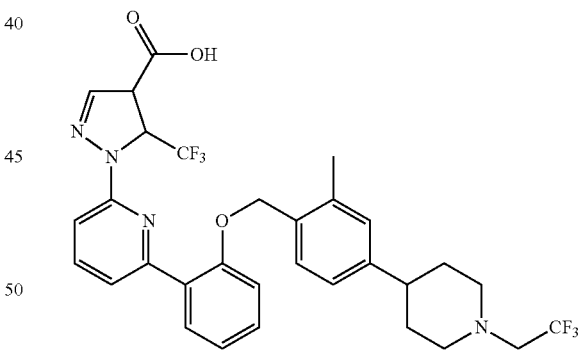

or a pharmaceutically acceptable salt thereof.

* * * * *